US011085030B2

(12) United States Patent
Mijts et al.

(10) Patent No.: US 11,085,030 B2
(45) Date of Patent: Aug. 10, 2021

(54) MAD NUCLEASES

(71) Applicant: Inscripta, Inc., Boulder, CO (US)

(72) Inventors: Benjamin Mijts, Boulder, CO (US); Juhan Kim, Boulder, CO (US); Aamir Mir, Boulder, CO (US); Andrew Garst, Boulder, CO (US); Kyle Seamon, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/200,074

(22) Filed: Mar. 12, 2021

(65) Prior Publication Data

US 2021/0198641 A1 Jul. 1, 2021

Related U.S. Application Data

(63) Continuation of application No. 17/084,522, filed on Oct. 29, 2020, now Pat. No. 11,053,485, which is a continuation of application No. 16/837,212, filed on Apr. 1, 2020, now Pat. No. 10,883,095.

(60) Provisional application No. 62/946,282, filed on Dec. 10, 2019.

(51) Int. Cl.
*C12N 9/22* (2006.01)
*C12N 15/113* (2010.01)

(52) U.S. Cl.
CPC .............. *C12N 9/22* (2013.01); *C12N 15/113* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,266,851 B2 | 4/2019 | Chen |
| 2002/0139741 A1 | 10/2002 | Kopf |
| 2004/0110253 A1 | 6/2004 | Kappler et al. |
| 2010/0076057 A1 | 3/2010 | Sontheimer et al. |
| 2014/0068797 A1 | 3/2014 | Doudna et al. |
| 2014/0199767 A1 | 7/2014 | Barrangou et al. |
| 2014/0234972 A1 | 8/2014 | Zhang |
| 2014/0273226 A1 | 9/2014 | Wu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0200342 A1 | 7/2018 | Bikard et al. |
| 2018/0230460 A1 | 8/2018 | Gill et al. |
| 2019/0017072 A1 | 1/2019 | Ditommaso et al. |

(Continued)

FOREIGN PATENT DOCUMENTS

| | | |
|---|---|---|
| EP | 2395087 | 12/2011 |
| EP | 3199632 | 8/2017 |
| WO | WO2002/010183 | 2/2002 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).

(Continued)

*Primary Examiner* — Nancy J Leith
(74) *Attorney, Agent, or Firm* — Sarah Brashears; Dianna L. DeVore

(57) ABSTRACT

The present disclosure provides new RNA-guided nucleases for making rational, direct edits to nucleic acids in live cells.

6 Claims, 9 Drawing Sheets

Specification includes a Sequence Listing.

(56) References Cited

U.S. PATENT DOCUMENTS

2019/0169605 A1  6/2019  Masquelier et al.

FOREIGN PATENT DOCUMENTS

| WO | WO 2003/087341 | 10/2003 |
|---|---|---|
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO 2015123339 | 8/2015 |
| WO | WO 2016/110453 | 7/2016 |
| WO | WO 2017/053902 | 3/2017 |
| WO | WO 2017/078631 | 5/2017 |
| WO | WO 2017/083722 | 5/2017 |
| WO | WO 2017/106414 | 6/2017 |
| WO | WO 2017/161371 | 9/2017 |
| WO | WO 2017/174329 | 10/2017 |
| WO | WO 2017/186718 | 11/2017 |
| WO | WO 2017/216392 | 12/2017 |
| WO | WO 2017/223330 | 12/2017 |
| WO | WO 2018/031950 | 2/2018 |
| WO | WO 2018/071672 | 4/2018 |
| WO | WO 2018071672 | 4/2018 |
| WO | WO 2018/083339 | 5/2018 |
| WO | WO 2018/191715 | 10/2018 |
| WO | WO 2018236548 | 12/2018 |
| WO | WO2019/006436 | 1/2019 |

OTHER PUBLICATIONS

Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpfl enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962, 2003.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29(2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.

(56) References Cited

OTHER PUBLICATIONS

International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd.,. doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2020/026095, dated Jul. 17, 2020, p. 1-10.
Seamon, et al., "SAMHD1 is a single-stranded nucleic acid binding protein with no active site-associated nuclease activity,"Nucleic Acids Research, Jun. 22, 2015, vol. 43, Issue 13, pp. 6486-6499.

_US 11,085,030 B2_

SEQUENCE LISTING

<160> NUMBER OF SEQ ID NOS: 144

<210> SEQ ID NO 1
<211> LENGTH: 1322
<212> TYPE: PRT
<213> ORGANISM: Eubacterium rectale

<400> SEQUENCE: 1

Met Lys Asn Thr Asn Glu Asp Tyr Tyr Leu Gly Leu Asp Ile Gly Thr
1               5                   10                  15

Asp Ser Val Gly Trp Ala Val Thr Asp Lys Glu Tyr Asn Ile Leu Glu
            20                  25                  30

```
Phe Arg Arg Lys Pro Met Trp Gly Ile His Leu Phe Glu Gly Gly Ser
     35                  40                  45

Thr Ala Gln Lys Thr Arg Val Tyr Arg Thr Ser Arg Arg Leu Lys
 50                  55                  60

Arg Arg Ala Glu Arg Ile Ala Leu Leu Arg Asp Ile Phe Ser Glu Glu
 65                  70                  75                  80

Ile Gly Lys Val Asp Pro Gly Phe Phe Glu Arg Leu Asp Glu Ser Asp
                     85                  90                  95

Leu His Leu Glu Asp Arg Val Thr Ser Gln Lys Asn Ser Leu Phe Asp
             100                 105                 110

Asp Pro Glu Phe Asn Asp Lys Asp Leu His Lys Arg Phe Pro Thr Ile
             115                 120                 125

Tyr His Leu Arg Arg His Leu Met His Ser Asn Arg Lys Glu Asp Ile
 130                 135                 140

Arg Leu Ile Tyr Leu Ala Ala His His Ile Ile Lys Phe Arg Gly His
 145                 150                 155                 160

Phe Leu Tyr Lys Gly Ile Gly Asp Glu Glu Ile Pro Ser Phe Glu Ile
                     165                 170                 175

Val Leu Asn Ser Leu Ile Asp Asn Leu Arg Asp Glu Tyr Gly Met Glu
             180                 185                 190

Leu Glu Val Ser Asp Arg Asp Leu Val Lys Ala Leu Leu Ser Asp Phe
             195                 200                 205

Ser Ile Gly Ile Arg Glu Lys Ser Arg Glu Leu Ser Ser Cys Leu Asn
 210                 215                 220

Ala Glu Ser Glu Asn Glu Lys Ala Leu Val Asp Phe Ile Ser Gly Lys
 225                 230                 235                 240

Lys Thr Asn Met Lys Lys Leu Phe Asp Asp Glu Ala Leu Asp Lys Met
                     245                 250                 255

Ser Phe Ser Leu Arg Asp Ser Gly Phe Glu Asp Gln Leu Arg Glu Asn
             260                 265                 270

Glu Gly Val Leu Gly Pro Glu Arg Val His Thr Leu Glu Leu Ser Arg
             275                 280                 285

Gln Ile Phe Glu Trp Ala Arg Leu Ser Ser Ile Leu Lys Asp Ser Asp
 290                 295                 300

Ser Ile Ser Glu Ala Lys Ile Lys Asp Tyr Asp Gln His Arg Glu Asp
 305                 310                 315                 320

Leu Arg Met Leu Lys Arg Ala Val Lys Lys Tyr Ala Pro Asp Lys Tyr
                     325                 330                 335

Ser Glu Val Phe Lys Ser Lys Glu His Thr Gly Asn Tyr Cys Ser Tyr
             340                 345                 350

Val Tyr Val Cys Gly Lys Gly Leu Pro Asp Lys Lys Cys Ser Thr Glu
             355                 360                 365

Glu Phe Gln Lys Tyr Leu Lys Lys Ile Leu Asp Asp Ser Gly Val Arg
 370                 375                 380

Asp Asp Glu Glu Phe Lys Thr Leu Ile Gln Arg Leu Asp Ala Gly Ile
 385                 390                 395                 400

Leu Cys Pro Lys Gln Arg Thr Gly Glu Asn Ser Val Ile Pro Tyr Ser
                     405                 410                 415

Val His Arg Lys Glu Leu Ile Gly Ile Leu Asn Asn Ala Ala Glu His
             420                 425                 430

Tyr Pro Ser Leu Ser Arg Lys Gly Glu Asp Gly Phe Ser Ser Ile Asp
             435                 440                 445

Lys Ile Leu Met Leu Glu Glu Phe Arg Ile Pro Tyr Tyr Val Gly Pro
```

```
                450             455             460
Leu Asp Asp Arg Ser Ser Arg Ser Trp Leu Ile Arg Asn Ser Phe Glu
465                 470                 475                 480

Ala Ile Thr Pro Trp Asn Phe Asn Glu Ile Val Asp Glu Asp Glu Thr
                485                 490                 495

Ser Glu Arg Phe Ile Gly Asn Leu Thr Ser Met Cys Thr Tyr Leu Gly
                500                 505                 510

Gly Glu Lys Val Leu Pro Lys Asn Ser Leu Leu Tyr Ser Arg Phe Met
                515                 520                 525

Leu Tyr Asn Glu Ile Asn Asn Leu Arg Val Gly Gly Glu Lys Ile Pro
530                 535                 540

Ala Ala Leu Lys Asn Lys Met Val Ser Glu Leu Phe Ala Asn Arg Ala
545                 550                 555                 560

Thr Ser Ser Lys Val Thr Leu Lys Glu Leu Lys Ala Phe Leu Lys Gly
                565                 570                 575

Glu Gly Val Leu Thr Asp Ala Asp Glu Ile Ser Gly Ile Asp Asp Gly
                580                 585                 590

Val Lys Ser Thr Leu Arg Ser Glu Ile Leu Ile Arg Lys Ile Ile Gly
                595                 600                 605

Asp Lys Ile Ser Asp Arg Glu Met Ala Glu Ile Val Arg Ile Leu
610                 615                 620

Thr Val Phe Gly Asp Glu Arg Arg Ser Lys Ala Lys Leu Lys Lys
625                 630                 635                 640

Glu Phe Ser Asp Lys Leu Thr Glu Lys Glu Ile Glu Lys Leu Ser Ser
                645                 650                 655

Leu Lys Phe Asp Gly Trp Gly Arg Leu Ser Glu Lys Phe Leu Thr Gly
                660                 665                 670

Leu Arg Gln Glu Val Asn Gly Arg Ser Met Ser Ile Ile Glu Ile Leu
                675                 680                 685

Glu Asp Thr Asn Tyr Asn Leu Gln Glu Thr Leu Ser Lys Tyr Ser Phe
690                 695                 700

Asn Glu Ile Ile Asp Ser Tyr Asn Glu Val Leu Thr Ser Gly Pro Arg
705                 710                 715                 720

Ser Ile Ser Tyr Asp Ile Leu Lys Asp Ser Tyr Leu Ser Pro Ala Val
                725                 730                 735

Lys Arg Gly Val Trp Arg Ala Leu Ser Val Val Lys Asp Ile Leu Lys
                740                 745                 750

Ala Val Gly Arg Pro Pro Lys Lys Ile Phe Val Glu Thr Thr Arg Glu
                755                 760                 765

Glu Arg Glu Lys Lys Arg Thr Glu Ser Arg Lys Asp Ala Leu Met Tyr
                770                 775                 780

Leu Tyr Lys Ser Cys Lys Glu Thr Glu Trp Lys Arg Leu Asp Ser
785                 790                 795                 800

Val Glu Glu Ser Ser Leu Arg Asn Arg Ser Leu Tyr Leu Tyr Thr
                805                 810                 815

Gln Leu Gly Lys Cys Met Tyr Cys Gly Lys Asn Ile Asp Ile Gly Glu
                820                 825                 830

Leu Asn Thr Asp Leu Ala Asp Arg Asp His Ile Tyr Pro Gln Ser Lys
                835                 840                 845

Thr Lys Asp Asp Ser Ile Arg Asn Asn Leu Val Leu Val Cys Arg Gly
850                 855                 860

Cys Asn Gln Ala Lys Gly Asp Arg Tyr Pro Leu Pro Gln Glu Trp Val
865                 870                 875                 880
```

-continued

```
Ser Arg Met His Ala Phe Trp Thr Met Leu Lys Asp Lys Gly Tyr Ile
            885                 890                 895

Ser Ser Glu Lys Tyr Arg Arg Leu Thr Arg Arg Gly Glu Leu Thr Glu
        900                 905                 910

Glu Glu Phe Gly Ala Phe Ile Asn Arg Gln Leu Val Glu Thr Ser Gln
            915                 920                 925

Ser Ala Lys Ala Val Ile Thr Val Leu Lys Asn Ala Phe Lys Asp Ser
    930                 935                 940

Asp Ile Val Tyr Val Lys Gly Ser Asn Val Ser Asp Phe Arg Ser Ser
945                 950                 955                 960

Tyr Asn Phe Ile Lys Cys Arg Ser Val Asn Asp Tyr His His Ala Lys
                965                 970                 975

Asp Ala Tyr Leu Asn Ile Val Val Gly Asn Val Leu Asp Thr Lys Phe
            980                 985                 990

Thr Lys Asn Pro Ser Tyr Val Leu Lys Asn Arg Glu Gln Tyr Asn Ile
        995                 1000                1005

Gly Arg Met Tyr Asp Arg Asn Val Ser Arg Phe Gly Val Asp Ala
    1010                1015                1020

Trp Val Ala Gly Asp Arg Gly Ser Ile Ala Thr Val Arg Lys Tyr
    1025                1030                1035

Met Arg Arg Asn Asn Ile Leu Phe Thr Arg Tyr Ala Thr Lys Ser
    1040                1045                1050

Lys Gly Ala Leu Phe Lys Glu Thr Val His Arg Lys Lys Glu Gly
    1055                1060                1065

Leu Phe Glu Arg Lys Lys Gly Leu Glu Thr Glu Lys Tyr Gly Gly
    1070                1075                1080

Tyr Ser Asp Ile Ser Thr Ser Tyr Leu Thr Leu Leu Glu Tyr Asp
    1085                1090                1095

Lys Gly Lys Lys Arg Ile Arg Ser Leu Glu Ile Val Pro Thr Tyr
    1100                1105                1110

Phe Ala Asn Thr Arg Pro Lys Glu Glu Asp Val Ile Arg Phe Phe
    1115                1120                1125

Ser Glu Thr Arg Gly Leu Ala Asn Val Arg Val Val Met Pro Glu
    1130                1135                1140

Val Arg Met Lys Ser Leu Phe Glu Tyr Arg Gly Phe Arg Phe His
    1145                1150                1155

Val Thr Gly Ser Asn Gly Lys Gly Arg Phe Trp Ile Ser Ser Ala
    1160                1165                1170

Ile Gln Leu Leu Leu Pro Glu Asn Leu Tyr Ala Tyr Cys Lys Ser
    1175                1180                1185

Ile Glu Asn Asn Glu Lys Asp Ser Gln Arg Arg Ser Glu Lys Pro
    1190                1195                1200

Leu Gln Asn Tyr Gly Phe Ser Ser Glu Met Asn Ile Glu Leu Phe
    1205                1210                1215

Lys Cys Leu Met Asp Lys Ala Ala Lys Pro Pro Tyr Asp Val Lys
    1220                1225                1230

Leu Ser Thr Leu Ser Lys Asn Leu Glu Glu Gly Phe Glu Lys Phe
    1235                1240                1245

Lys Ala Leu Glu Leu Gly Pro Gln Val Lys Val Leu Gln Gln Ile
    1250                1255                1260

Leu Asp Ile Tyr Ser Cys Asp Arg Lys Ser Gly Asp Leu Ser Val
    1265                1270                1275
```

-continued

```
Leu Gly Ser Ala Arg Asn Ala Gly Arg Leu Asp Met Asn Gly Val
    1280                1285                1290

Leu Ser Glu Ala Asp Gly Glu Gln Val Thr Met Ile Cys Gln Ser
    1295                1300                1305

Pro Ser Gly Leu Phe Glu Lys Arg Val Pro Met Asn Glu Lys
    1310                1315                1320

<210> SEQ ID NO 2
<211> LENGTH: 997
<212> TYPE: PRT
<213> ORGANISM: Eubacterium rectale

<400> SEQUENCE: 2

Met Lys Lys Arg Ile Phe Gly Phe Asp Ile Gly Ile Ala Ser Leu Gly
  1               5                  10                  15

Trp Ala Val Val Asp Phe Asp Asp Thr Ala Asp Pro Glu Asn Asp Ile
             20                  25                  30

Tyr Pro Thr Gly Glu Ile Val Lys Ser Gly Val Arg Cys Phe Pro Val
         35                  40                  45

Ala Glu Asn Pro Lys Asp Gly Ser Ser Leu Ala Gln Pro Arg Arg Gln
     50                  55                  60

Lys Arg Leu Leu Arg Arg Leu Cys Arg Arg Lys Ala Arg Arg Met Ala
 65                  70                  75                  80

Gly Ile Lys Asn Leu Phe Val Ala Asn Gly Leu Ile Gly Lys Asp Ala
                 85                  90                  95

Leu Phe Asn Glu Lys Ser Asn Ile Tyr Lys Ala Arg Asp Asn Ala Asp
            100                 105                 110

Val Trp Asp Leu Arg Val Lys Ala Leu Thr Asp Lys Leu Thr Thr Ile
        115                 120                 125

Glu Phe Ile Arg Val Leu Thr His Leu Ala Lys His Arg Gly Phe Lys
    130                 135                 140

Ser Tyr Arg Ile Ala Ala Glu Lys Ala Asp Ala Glu Ser Gly Lys Val
145                 150                 155                 160

Leu Glu Ala Val Lys Ala Asn Arg Ala Leu Leu Glu Asn Gly Lys Thr
                165                 170                 175

Leu Ala Gln Ile Ile Val Glu Lys Gly Gly Gln Lys Arg Asn Arg Glu
            180                 185                 190

Lys Met Ile Val Lys Asn Gly Lys Thr Glu Lys Gln Ala Ser Tyr Glu
        195                 200                 205

Asn Ser Ile Pro Arg Asp Glu Ile Glu Arg Glu Thr Arg Leu Ile Phe
    210                 215                 220

Glu Lys Gln Arg Ala Phe Gly Leu Glu Ala Ala Asn Glu Lys Leu Gln
225                 230                 235                 240

Arg Asp Phe Glu Lys Ile Ala Phe Arg Phe Arg Glu Ile Lys Ser Lys
                245                 250                 255

Asn Ile Glu Lys Met Ile Gly Lys Cys Glu Phe Glu Lys Asp Glu Pro
            260                 265                 270

Arg Ala Pro Lys Asn Ala Pro Ser Ala Glu Phe Phe Val Ala Trp Thr
        275                 280                 285

Lys Ile Asn Asn Cys Arg Val Arg Glu Pro Asp Gly Lys Ile Arg Phe
    290                 295                 300

Leu Thr Gln Glu Glu Lys Glu Asn Val Phe Asn Leu Leu Lys Asp Gln
305                 310                 315                 320

Lys Glu Val Lys Tyr Ser Ala Leu Lys Lys Ala Leu Phe Ala Lys Arg
                325                 330                 335
```

Pro Asp Val Gln Phe Thr Asp Ile Glu Tyr Asn Pro Lys Pro Val Tyr
            340                 345                 350

Asp Lys Lys Thr Gly Glu Ile Ile Glu Lys Thr Glu Asn Pro Glu Asn
            355                 360                 365

Gln Lys Phe Phe Ser Leu Lys Gly Trp His Asp Leu Lys Ser Val Ile
            370                 375                 380

Asp Val Ser Ser Tyr Pro Val Glu Thr Leu Asp Lys Ile Ala Thr Val
385                     390                 395                 400

Ile Ala Thr Lys Lys Asn Asp Thr Asp Ile Ala Lys Gly Leu Lys Glu
                405                 410                 415

Leu Asn Leu Pro Asp Ala Glu Ile Glu Lys Leu Thr Ser Leu Ser Phe
            420                 425                 430

Ser Lys Phe Ile Arg Leu Ser Leu Lys Ala Leu Tyr Lys Ile Leu Pro
            435                 440                 445

Glu Met Gln Lys Gly Met Lys Tyr Asn Glu Ala Cys Asp Ala Val Gly
            450                 455                 460

Tyr Asp Phe Lys Ser Thr Gly Glu Ser Phe Ala Ala Gln Lys Gly Lys
465                     470                 475                 480

Phe Leu Pro Pro Ile Pro Glu Ala Leu Ala Thr Thr Val Pro Val Val
                485                 490                 495

Asn Arg Ala Met Thr Gln Phe Arg Lys Val Tyr Asn Ala Leu Ala Arg
            500                 505                 510

Glu Tyr Gly Thr Pro Asp Gln Ile Asn Ile Glu Leu Ala Arg Asp Val
            515                 520                 525

Tyr Asn Thr His Asp Glu Arg Lys Lys Ile Ala Asp Lys Gln Lys Glu
            530                 535                 540

Tyr Gly Glu Glu Arg Lys Lys Ala Arg Asp Leu Ala Gln Glu Lys Met
545                     550                 555                 560

Glu Ile Glu Asn Ile Ser Gly Arg Asp Leu Leu Lys Phe Arg Leu Tyr
                565                 570                 575

Glu Gln Gln Asp Gly Lys Cys Ile Tyr Ser Gly Glu Thr Leu Asp Leu
            580                 585                 590

Arg Arg Leu Thr Glu Gln Asp Tyr Cys Asp Val Asp His Ile Ile Pro
            595                 600                 605

Tyr Ser Arg Ser Leu Asp Asn Ser Gln Asn Asn Lys Val Leu Cys Leu
            610                 615                 620

Ser Arg Glu Asn Arg Arg Lys Ser Asp Lys Thr Pro Leu Glu Tyr Ile
625                     630                 635                 640

Ile Asp Pro Val Lys Gln Ala Glu Phe Ile Ala Arg Val Lys Ser Met
                645                 650                 655

Lys Gly Leu Ser Ala Pro Lys Arg Asp Arg Leu Leu Ile Arg Asp Phe
            660                 665                 670

Lys Glu Lys Glu Leu Glu Phe Arg Asp Arg Asn Ile Asn Asp Thr Arg
            675                 680                 685

Tyr Met Ala Arg Tyr Ile Met Lys Tyr Leu Asp Asp Cys Ile Asp Phe
            690                 695                 700

Ser Gly Ser Gln Thr Asp Ile Lys Asp His Val Gln Ser Arg Ile Gly
705                     710                 715                 720

Ser Leu Thr Asp Phe Leu Arg His Gln Trp Gly Leu His Lys Asp Arg
                725                 730                 735

Asn Glu Asn Asp Arg His His Ala Gln Asp Ala Ile Val Ile Ala Cys
            740                 745                 750

```
Ala Thr Asn Gly Tyr Thr Gln Tyr Leu Ala His Leu Ser Lys Ile Phe
        755                 760                 765

Glu Asn Lys Gln Ala Tyr Ala Asn Lys Tyr Gly Gln Pro Trp Tyr Lys
770                 775                 780

Ala Phe Lys Gln His Val Lys Gln Pro Trp Asp Gly Phe Tyr Gln Asp
785                 790                 795                 800

Val Gln Ala Ser Leu Ala Glu Ile Phe Val Ser Arg Pro Pro Arg Lys
                805                 810                 815

Asn Ala Thr Gly Glu Val His Gln Asp Thr Ile Arg Thr Leu Asn Pro
            820                 825                 830

Asn Lys Pro Gln Tyr Ser Glu Lys Asp Val Lys Ser Gly Ile Lys Leu
        835                 840                 845

Arg Gly Gly Leu Ala Asn Asn Gly Asp Met Leu Arg Val Asp Val Phe
    850                 855                 860

Ser Lys Lys Asn Ala Lys Gly Lys Glu Gln Phe Tyr Leu Val Pro Ile
865                 870                 875                 880

Tyr Leu Ala Asp Arg Ile Lys Pro Glu Leu Pro Asn Lys Ala Ile Val
                885                 890                 895

Ala Asn Lys Ser Glu Ser Glu Trp Ile Ile Met Asp Ala Thr Tyr Ser
            900                 905                 910

Phe Lys Phe Ser Leu Tyr Met Asp Asp Leu Val Ser Val Ile Lys Gly
        915                 920                 925

Asp Lys Lys Ile Phe Gly Tyr Tyr Lys Gly Thr Ser Arg Ser Thr Ala
    930                 935                 940

Ser Ile Thr Ile Glu Gly His Asp Arg Asn Phe Ile Gln Pro Ser Ile
945                 950                 955                 960

Gly Val Lys Thr Val Asp Asn Ile Lys Lys Tyr Gln Ile Asp Pro Leu
                965                 970                 975

Gly Arg Tyr Val Glu Val Lys Ser Glu Ile Arg Leu Pro Leu Asn Ile
            980                 985                 990

Lys Lys Arg Lys Ser
        995

<210> SEQ ID NO 3
<211> LENGTH: 1392
<212> TYPE: PRT
<213> ORGANISM: Eubacterium rectale

<400> SEQUENCE: 3

Met Lys Lys Val Leu Gly Leu Asp Leu Gly Ser Ser Ile Gly Trp
1               5                   10                  15

Ala Tyr Val His Glu Ala Glu Asn Glu Ala Glu Leu Gly Ser Ser Lys
                20                  25                  30

Ile Ile Lys Leu Gly Val Arg Val Asn Pro Leu Thr Val Asp Glu Gln
            35                  40                  45

Arg Asn Phe Glu Gln Gly Lys Ser Ile Thr Thr Asn Ala Ser Arg Thr
        50                  55                  60

Leu Lys Arg Cys Met Arg Arg Asn Leu Gln Arg Tyr Lys Leu Arg Arg
65                  70                  75                  80

Glu Asn Leu Ile Glu Val Leu Lys Lys His Gly Phe Ile Ser Asp Ala
                85                  90                  95

Ser Ile Leu Ser Glu Gln Gly Asn Tyr Thr Thr Phe Glu Thr Tyr Arg
            100                 105                 110

Leu Arg Ala Lys Ala Ala Val Ala Glu Ile Ser Leu Glu Glu Leu Ala
        115                 120                 125
```

```
Arg Val Leu Leu Met Ile Asn Lys Lys Arg Gly Tyr Lys Ser Ser Arg
    130                 135                 140

Lys Asn Arg Gly Gly Asp Glu Gly Lys Phe Ile Asp Gly Ile Ser Val
145                 150                 155                 160

Ala Lys Gln Leu Tyr Asp Arg Gly Ile Thr Pro Gly Gln Phe Ser Leu
                165                 170                 175

Glu Leu Leu Lys Glu Gly Lys Arg His Leu Pro Asp Tyr Tyr Arg Ser
            180                 185                 190

Asp Leu Gln Asn Glu Leu Asp Arg Ile Trp Asn Phe Gln Gln Ser Phe
        195                 200                 205

Tyr Pro Glu Ile Leu Thr Gln Asn Phe Arg Glu Gln Ile Arg Asp Lys
    210                 215                 220

Gly Gln Lys Asn Thr Ser Gln Ile Phe Leu Arg Glu Tyr Gln Ile Tyr
225                 230                 235                 240

Thr Ala Asp Asn Lys Gly Ala Asp Lys Leu Ser Arg Ala Leu Gln Trp
                245                 250                 255

Arg Val Glu Gly Leu Ser Arg Lys Leu Ser Val Glu Leu Ala Phe
            260                 265                 270

Val Met Ser Asp Leu Asn Gly Ser Ile Ser Gly Ser Gly Tyr Leu
    275                 280                 285

Gly Ala Ile Gly Asp Arg Ser Lys Glu Leu Tyr Leu Gly Lys Gln Thr
290                 295                 300

Val Gly Gln Tyr Leu Met Glu Lys Leu Asn Thr Asn Pro Asn Gly Ser
305                 310                 315                 320

Leu Lys Ser Lys Val Phe Tyr Arg Gln Asp Tyr Leu Asp Glu Phe Glu
                325                 330                 335

Arg Ile Trp Glu Thr Gln Ala Gly Phe His Lys Glu Leu Thr Leu Glu
            340                 345                 350

Leu Lys Lys Glu Ile Arg Asp Ile Ile Phe Tyr Gln Arg Ser Leu
        355                 360                 365

Lys Ser Gln Lys Gly Leu Ile Ser Phe Cys Glu Leu Glu Ser Lys Leu
    370                 375                 380

Val Glu Ile Glu Val Asn Gly Lys Met Arg Arg Lys Val Val Gly Ser
385                 390                 395                 400

Arg Val Cys Pro Lys Ser Ser Pro Leu Phe Gln Glu Phe Lys Ile Trp
                405                 410                 415

Ser Ile Leu Asn Asn Ile Cys Val Trp Ser Val Asp Lys Ser Lys Ser
            420                 425                 430

Ser Glu Ala Arg Lys Met Asp Glu Arg Asp Lys Glu Pro Asn Leu Asn
        435                 440                 445

Gln Glu Glu Lys Glu Ile Leu Phe Lys Glu Leu Ser Leu Lys Glu Lys
    450                 455                 460

Leu Ser Lys Arg Asp Val Leu Glu Leu Leu Phe Glu Asp Ala Arg Lys
465                 470                 475                 480

Leu Asp Met Asn Tyr Glu Lys Val Glu Gly Asn Arg Thr Gln Ala Thr
                485                 490                 495

Leu Phe Lys Ala Tyr Gln Glu Ile Ile Ala Arg Ser Gly His Gly Glu
            500                 505                 510

Tyr Asp Phe Thr Arg Met Leu Ser Ser Glu Ile Leu Glu Ile Val Ser
        515                 520                 525

Gly Val Phe Asp Gly Leu Gly Tyr Asn Thr Asp Ile Leu Tyr Phe Asn
530                 535                 540
```

```
Ser Glu Gly Glu Leu Asp Gln Gln Pro Leu Tyr Arg Leu Trp His Leu
545                 550                 555                 560
Leu Tyr Ser Phe Glu Gly Asp Lys Ser Asn Ser Gly Asn Glu Asn Leu
                565                 570                 575
Ile Asn Lys Ile Thr Asn Leu Tyr Gly Phe Asp Arg Glu Tyr Ala Val
            580                 585                 590
Ile Leu Ala Asp Val Val Phe Pro Asp Tyr Gly Asn Leu Ser Ala
        595                 600                 605
Lys Ala Ile His Lys Ile Leu Pro Tyr Leu Lys Asp Gly Asn Lys Tyr
    610                 615                 620
Ser Leu Ala Cys Glu Tyr Ala Gly Phe Arg His Ser Lys Asn Ser Leu
625                 630                 635                 640
Thr Lys Glu Glu Arg Glu Lys Arg Val Leu Lys Glu Arg Leu Asp Ile
                645                 650                 655
Leu Pro Lys Asn Thr Leu Arg Asn Pro Val Val Glu Lys Ile Leu Asn
                660                 665                 670
Gln Met Val His Val Val Asn Gly Val Ile Asn Lys Tyr Gly Lys Pro
            675                 680                 685
Asp Glu Ile Arg Ile Glu Leu Ala Arg Glu Leu Lys Lys Asn Ala Lys
    690                 695                 700
Glu Arg Glu Glu Trp Thr Arg Ala Ile Asn Lys Ser Thr Ile Glu Asn
705                 710                 715                 720
Glu Lys Leu Arg Ser Val Leu Lys Lys Glu Phe Gly Phe Thr Gln Val
                725                 730                 735
Ser Arg Asn Asp Ile Val Arg Tyr Lys Leu Tyr Leu Glu Leu Glu Ser
            740                 745                 750
Arg Gly Phe Lys Thr Leu Tyr Ser Asn Thr Tyr Ile Pro Leu Glu Lys
        755                 760                 765
Leu Phe Phe Lys Glu Phe Asp Ile Glu His Ile Ile Pro Gln Ser Arg
    770                 775                 780
Leu Phe Asp Asp Ser Phe Ser Asn Lys Thr Ile Glu Leu Arg Ser Val
785                 790                 795                 800
Asn Gln Glu Lys Asp Asn Gln Thr Ala Tyr Asp Tyr Val Ser Gly Lys
                805                 810                 815
Gly Gly Glu Ala Gly Leu Gln Glu Tyr Leu Glu Arg Val Glu Asp Leu
            820                 825                 830
Phe Lys Gly Gly Tyr Ile Asn Lys Ala Lys Tyr Asn Lys Leu Arg Met
        835                 840                 845
Thr Gly Lys Asp Ile Pro Asp Asp Phe Ile Asp Arg Asp Leu Arg Asp
    850                 855                 860
Thr Gln Tyr Ile Ala Arg Arg Ala Lys Ala Met Leu Glu Glu Val Val
865                 870                 875                 880
Gly Asn Val Val Ser Thr Ser Gly Ala Val Thr Asp Arg Leu Arg Glu
                885                 890                 895
Asp Trp Gln Leu Val Asp Val Met Lys Glu Leu Asn Trp Asn Lys Tyr
            900                 905                 910
Glu Arg Leu Gly Leu Thr Glu Ile Val Glu Asp Arg Asp Gly Arg Lys
        915                 920                 925
Ile Arg Arg Ile Lys Gly Trp Thr Lys Arg Asn Asp His Arg His
    930                 935                 940
Ala Met Asp Ala Leu Thr Ile Ala Phe Thr Lys Pro Lys Tyr Val Gln
945                 950                 955                 960
Tyr Leu Asn Asn Leu Asn Ala Arg Gly Asp Lys Ser Ser Ser Val Tyr
```

-continued

```
              965                 970                 975
Gly Ile Glu Arg Asp Glu Leu Ser Arg Asp Ser Lys Gly Lys Leu Arg
              980                 985                 990
Phe Asn Ser Pro Met Pro Leu Lys Glu Phe Arg Met Glu Ala Lys Leu
              995                1000                1005
His Leu Glu Asn Val Leu Val Ser Thr Lys Ala Lys Asn Lys Val
             1010                1015                1020
Ile Thr Pro Asn Val Asn Lys Ser Lys Lys Arg Gly Gly Met Asn
             1025                1030                1035
Gln Lys Val Gln Leu Thr Pro Arg Gly Gln Leu His Gln Glu Thr
             1040                1045                1050
Ile Tyr Gly Ser Ile Lys Gln Tyr Val Thr Lys Glu Val Lys Val
             1055                1060                1065
Gly Ser Ala Phe Asn Met Glu Met Ile Leu Lys Val Ala Asn Lys
             1070                1075                1080
Ala Tyr Arg Glu Ala Leu Leu Lys Arg Leu Asn Ala Phe Asp Gln
             1085                1090                1095
Asp Ala Lys Lys Ala Phe Thr Gly Lys Asn Ser Leu Glu Lys Asn
             1100                1105                1110
Pro Ile Phe Ile Asn Asp Ser His Thr Cys Lys Val Pro Glu Lys
             1115                1120                1125
Val Lys Val Val Ser Phe Glu Thr Val Tyr Thr Ile Arg Lys Glu
             1130                1135                1140
Ile Gly Pro Asp Leu Lys Val Asp Lys Val Ile Asp Lys Arg Val
             1145                1150                1155
Arg Asp Ile Leu Glu Thr Arg Leu Val Glu Phe Gly Gly Asp Ser
             1160                1165                1170
Lys Leu Ala Phe Thr Asn Leu Asp Glu Asn Pro Ile Trp Leu Asn
             1175                1180                1185
Lys Glu Lys Gly Ile Asp Ile Lys Arg Val Thr Ile Ser Gly Val
             1190                1195                1200
Ser Asn Val Ile Ala Leu His Asp Lys Leu Asp Lys Asp Gly Lys
             1205                1210                1215
Leu Val Leu Asp Glu His Gly Gln Pro Gln Pro Val Asp Phe Val
             1220                1225                1230
Cys Ser Gly Asn Asn His His Val Val Tyr Arg Asp Pro Glu
             1235                1240                1245
Gly Lys Ile Gln Asp Asp Val Val Ser Phe Phe Glu Ala Thr Val
             1250                1255                1260
Arg Ala Lys Glu Gly Leu Pro Val Ile Asp Arg Glu Tyr Lys Lys
             1265                1270                1275
Gln Glu Gly Trp Glu Phe Leu Phe Ser Met Lys Gln Asn Glu Tyr
             1280                1285                1290
Phe Val Phe Pro Asn Glu Glu Thr Gly Phe Asp Pro Lys Glu Val
             1295                1300                1305
Asp Leu Met Asn Pro Asp Asn Tyr Ala Leu Ile Ser Pro Asn Leu
             1310                1315                1320
Phe Arg Val Gln Thr Met Ser Arg Val Met Tyr Gly Asn Gln Val
             1325                1330                1335
Val Arg Asp Tyr Lys Phe Arg His His Leu Glu Thr Thr Val Lys
             1340                1345                1350
Asp Cys Lys Glu Leu Lys Asp Ile Ala Tyr Lys Gln Tyr Lys Ser
             1355                1360                1365
```

-continued

Leu Asp Phe Ala Ser Gln Ile Val Lys Val Arg Ile Asp His Ile
1370                1375                1380

Gly Gln Ile Val His Val Gly Glu Tyr
        1385                1390

<210> SEQ ID NO 4
<211> LENGTH: 1133
<212> TYPE: PRT
<213> ORGANISM: Eubacterium rectale

<400> SEQUENCE: 4

Met Ala Asp Lys Glu Lys Leu Lys Glu Thr Tyr Thr Ile Gly Leu Asp
1               5                   10                  15

Ile Gly Ile Ala Ser Val Gly Trp Ala Ile Leu Gly Glu Asn Arg Ile
            20                  25                  30

Ile Asp Leu Gly Val Arg Cys Phe Asp Lys Ala Glu Thr Ala Lys Glu
        35                  40                  45

Gly Glu Ser Leu Asn Leu Ser Arg Arg Met Ala Arg Leu Met Arg Arg
    50                  55                  60

Arg Leu Arg Arg Arg Ala Trp Arg Leu Thr Lys Leu Ala Arg Leu Leu
65                  70                  75                  80

Lys Arg Val Gly Leu Ile Ala Asp Val Gly Val Leu Lys Gln Pro Pro
                85                  90                  95

Ser Lys Gly Phe Gln Thr Pro Asn Leu Trp Gln Leu Arg Val Glu Gly
            100                 105                 110

Leu Asp Arg Lys Leu Gly Asp Asp Glu Trp Ala Arg Val Ile Tyr His
        115                 120                 125

Leu Cys Lys His Arg Gly Phe His Trp Ile Ser Lys Ala Glu Ala Lys
    130                 135                 140

Ala Ala Asp Ser Asp Lys Glu Gly Gly Lys Val Lys Gln Gly Leu Ala
145                 150                 155                 160

Gly Thr Lys Arg Leu Met Gln Glu Lys Ser Tyr Arg Thr Ala Ala Glu
                165                 170                 175

Met Val Leu Ala Glu Phe Pro Asp Ala Gln Arg Asn Lys Gln Gly Glu
            180                 185                 190

Tyr Ser Lys Ala Leu Ser Arg Glu Leu Leu Cys Glu Glu Leu Lys Glu
        195                 200                 205

Leu Phe Lys Gln Gln Arg Ala Phe Gly His Thr His Ala Asp Asp Lys
    210                 215                 220

Leu Glu Thr Asn Ile Leu Gly Asn Gly Asp Lys Lys Ser Gly Leu Phe
225                 230                 235                 240

Trp Val Gln Lys Pro Ser Leu Ser Gly Glu Ala Leu Leu Lys Met Leu
                245                 250                 255

Gly Lys Cys Thr Phe Glu Lys Asp Glu Tyr Arg Ala Ala Lys Ala Cys
            260                 265                 270

Phe Thr Ala Glu Arg His Val Leu Leu Thr Arg Ile Asn Asn Leu Arg
        275                 280                 285

Ile Val Glu Asn Gly Lys Met Arg Gly Leu Thr Ala Asp Glu Arg Arg
    290                 295                 300

Ile Ala Leu Trp Gln Pro Tyr Gln Gln Ala Gly Asp Phe Thr Phe Lys
305                 310                 315                 320

Gln Leu Gly Ser Ala Leu Glu Lys His Gly Ser Leu Leu Lys Gly Gly
                325                 330                 335

Tyr Lys Phe Ala Gly Leu Thr Tyr Pro Arg Glu Thr Asp Glu Lys Ala

```
              340                 345                 350
Lys Asn Pro Glu Thr Ala Thr Leu Val Lys Ile Pro Ala Trp Gln Glu
            355                 360                 365

Leu Lys Lys Thr Leu Ile Gly Val Gly Leu Glu Arg Glu Trp Gln Gly
        370                 375                 380

Met Ala Asp Ala Ala Leu Asn Gly Lys Pro Asp Leu Leu Asp Lys Ile
385                 390                 395                 400

Gly Trp Val Leu Ser Val Tyr Lys Glu Asp Glu Val Glu Leu Glu
                405                 410                 415

Leu Gly Lys Leu Gln Leu Ala Ala Asn Val Ile His Ala Leu Gln Thr
                420                 425                 430

Val Arg Phe Asp Lys Phe Ser Asn Leu Ser Leu Leu Ala Leu Cys Lys
            435                 440                 445

Ile Leu Pro Gln Met Glu Asn Gly Met Arg Tyr Asp Glu Ala Cys Lys
        450                 455                 460

Glu Ala Gly Tyr Gln His Ser Met Pro Asp Met Gln Asp Leu Glu Ala
465                 470                 475                 480

Lys Val Arg Tyr Leu Pro Pro Phe Tyr Ser Gly Arg Glu Lys Asp Gly
                485                 490                 495

Arg Leu Lys Phe Asn Glu Asp Met Asp Ile Pro Arg Asn Pro Val Val
                500                 505                 510

Leu Arg Ala Leu Asn Gln Ala Arg Lys Val Val Asn Ala Leu Ile Arg
            515                 520                 525

Lys Tyr Gly Ser Pro His Ala Val His Ile Glu Met Ala Arg Asp Leu
        530                 535                 540

Ser Arg Pro Ile Asp Glu Arg Lys Ile Glu Arg Asp Gln Ala Asp
545                 550                 555                 560

Tyr Arg Thr Lys Asn Glu Asp Ala Arg Lys Ala Phe Ala Ser Asp Phe
                565                 570                 575

Gly Phe Glu Pro Lys Gly Arg Gln Phe Glu Lys Tyr Met Leu Tyr Arg
                580                 585                 590

Glu Gln Gln Ala Lys Cys Ala Tyr Ser Leu Ala Pro Leu Asp Leu Asn
            595                 600                 605

Arg Val Leu Asn Asp Gln Gly Tyr Ala Glu Val Asp His Ala Leu Pro
        610                 615                 620

Tyr Ser Arg Ser Phe Asp Asp Gly Lys Asn Asn Arg Val Leu Val Leu
625                 630                 635                 640

Thr Ser Glu Asn Arg Asn Lys Gly Asn Gln Thr Pro Tyr Glu Tyr Leu
                645                 650                 655

Asp Gly Thr Ser Asp Ser Glu Lys Trp Arg Leu Phe Glu Ser Phe Val
                660                 665                 670

Ser Gly Asn Lys Ala Tyr Ser Gln Ala Lys Arg Asn Arg Leu Leu Lys
            675                 680                 685

Lys Asp Phe Gly Val Lys Glu Thr Gln Asp Phe Lys Glu Arg Asn Leu
        690                 695                 700

Asn Asp Thr Arg Tyr Ile Cys Arg Phe Phe Lys Asn Tyr Val Glu Gln
705                 710                 715                 720

Tyr Leu Gln Leu His Glu Glu Ser Asp Ala Lys Arg Cys Val Val
                725                 730                 735

Ser Gly Gln Leu Thr Ser Leu Leu Arg Phe Arg Trp Gly Ile Asn Lys
            740                 745                 750

Ile Arg Ser Glu Ser Asp Arg His His Ala Leu Asp Ala Val Val
        755                 760                 765
```

-continued

```
Ala Ala Cys Ser His Gly Leu Val Lys Arg Met Ser Asp Tyr Ser Arg
        770                 775                 780

Arg Lys Glu Leu Gly Gln Val Arg Asp Arg Ile Glu Lys Val Asp Lys
785                 790                 795                 800

Lys Thr Gly Glu Ile Ile Asp His Phe Pro Ser Pro Trp Ala His Phe
                805                 810                 815

Arg Gln Glu Leu Leu Ala Arg Leu His Ile Asp Asp Ala Asn Glu Leu
            820                 825                 830

Arg Ala Val Val Glu Asn Leu Gly Thr Tyr Pro Pro Glu Ala Leu Glu
        835                 840                 845

Ser Leu Thr Pro Leu Phe Val Ser Arg Ala Pro Gln Arg Arg Asn Ser
850                 855                 860

Gly Ala Ala His Lys Glu Thr Ile Tyr Ala Gln Pro Glu Ala Met Lys
865                 870                 875                 880

Glu Lys Gly Ser Val Thr Gln Lys Val Ala Val Thr Ser Leu Lys Pro
                885                 890                 895

Ala Asp Val Asp Lys Leu Ile Asp Pro Glu Arg Asn Val Lys Leu Tyr
            900                 905                 910

Ala Tyr Leu Arg Lys Trp Leu Ala Gly Lys Asp Glu Arg Glu Lys Arg
        915                 920                 925

Ala Lys Ala Ile Glu Ala Ser Ala Gly Arg Gly Lys Glu Lys Arg Asp
    930                 935                 940

Leu Thr Pro Glu Glu Lys Ile Glu Ile Glu Arg Leu Arg Ala Leu Pro
945                 950                 955                 960

Gln Lys Pro Asp Lys Gln Gly Lys Pro Thr Gly Pro Ile Val Arg Ala
                965                 970                 975

Val Thr Met Val Ile Asp Lys Leu Ser Gly Ile Pro Val Arg Gly Gly
            980                 985                 990

Ile Ala Lys Asn Asp Thr Met Leu Arg Val Asp Met Phe Ser Lys Ala
        995                 1000                1005

Lys Arg Tyr Tyr Leu Val Thr Val Tyr Val Phe His Ser Val Ala
    1010                1015                1020

Lys Glu Leu Pro Ser Arg Ala Ile Val Ala His Lys Asp Glu Asp
    1025                1030                1035

Asp Trp Thr Val Ile Ser Glu Asp Phe Glu Phe Cys Phe Ser Met
    1040                1045                1050

Tyr Pro Asn Asp Phe Ile Arg Ile Ser Gln Lys Lys Glu Thr Phe
    1055                1060                1065

Met Gly Tyr Tyr Ala Gly Cys Asp Arg Gly Ser Gly Asn Val Asn
    1070                1075                1080

Leu Trp Ser His Asp Arg Asn Ser Gln Ile Gly Lys Ser Gly Met
    1085                1090                1095

Ile Arg Gly Ile Gly Val Lys Thr Ala Val Asn Val Glu Lys Phe
    1100                1105                1110

Asn Val Asp Val Leu Gly Asn Ile Tyr Pro Ala Pro Pro Glu Ile
    1115                1120                1125

Arg Arg Glu Leu Ala
    1130

<210> SEQ ID NO 5
<211> LENGTH: 1049
<212> TYPE: PRT
<213> ORGANISM: Eubacterium rectale
```

<400> SEQUENCE: 5

```
Met Gly Tyr Ile Leu Gly Ile Asp Ile Gly Ile Ala Ser Ile Gly Phe
1               5                   10                  15

Ala Gly Val Asn His Asp Leu Lys Lys Ile Leu Phe Ser Gly Val His
            20                  25                  30

Ile Phe Glu Ala Ala Glu Asn Pro Lys Thr Gly Ala Ser Leu Ala Glu
        35                  40                  45

Pro Arg Arg Thr Ala Arg Gly Gln Arg Val Ile His Arg Arg Ala
50                  55                  60

Gln Arg Lys Asn Ala Ile Arg Gln Leu Leu Arg His Gly Leu Asn
65                  70                  75                  80

Cys Leu Ser Val Val Asp Lys Lys Tyr Glu Pro Thr Gly Lys Asn Thr
                85                  90                  95

Pro Pro Ile Ser Pro Trp Asp Leu Arg Arg Thr Ala Leu Asp Arg Lys
            100                 105                 110

Leu Thr Asp Glu Glu Leu Val Arg Ile Leu Phe His Ile Gly Lys His
        115                 120                 125

Arg Gly Phe Gln Ser Asn Lys Lys Ser Gln Ser Asn Glu Gly Asp Asp
130                 135                 140

Gly Lys Ala Leu Lys Gly Ala Gly Asp Leu Glu Gln Lys Trp Ile Gln
145                 150                 155                 160

Ser Gly Glu Lys Thr Ile Gly Ala Tyr Leu Ser Thr Gln Ser Lys Lys
                165                 170                 175

Arg Asn Gly Asn Glu Ser Tyr Asp Asn Phe Ile Lys Arg Asp Trp Leu
            180                 185                 190

Arg Glu Glu Ile Lys Val Ile Phe Glu Ala Gln Arg Lys Phe Asn Gln
        195                 200                 205

Ile Lys Ala Thr Glu Val Leu Arg Leu Glu Tyr Ala Gly Thr Gly Glu
210                 215                 220

Lys Ala Lys Arg Asn Thr Pro Glu Gly Asp Gly Ile Ala Phe Tyr Gln
225                 230                 235                 240

Arg Pro Leu Gln Ser Ser Glu Lys Leu Ile Gly Asp Cys Thr Phe Glu
                245                 250                 255

Lys Gly Glu Lys Arg Ala Pro Lys Phe Ser Tyr Thr Ala Glu Leu Phe
            260                 265                 270

Val Leu Trp Ser Arg Leu Asn Asn Thr Lys Ile Lys Ile Gln Asn Gly
        275                 280                 285

Asp Glu Arg Phe Leu Thr Gln Asp Glu Lys Asn Lys Leu Val Asn Leu
290                 295                 300

Ala His Lys Asn Lys Gly Gly Val Ser Tyr Thr Gln Ala Arg Lys Glu
305                 310                 315                 320

Ile Gly Leu Asn Glu Ser Glu Arg Phe Asn Ile Ser Tyr Arg Gln Leu
                325                 330                 335

Asp Lys Gly Asp Asn Ser Trp Glu Lys Ile Arg Asn Glu Ala Glu Lys
            340                 345                 350

Ser Asn Phe Leu Lys Leu Ser Gly Phe His Ala Leu His Glu Ala Leu
        355                 360                 365

Asp Thr Gly Ser Ala Thr Asp Trp Gln Lys Trp Ile Gly Ser Asp Arg
370                 375                 380

Asp Lys Leu Asp Glu Val Ala Tyr Ile Thr Ser Phe Ile Glu Asp Gly
385                 390                 395                 400

Lys Ile Ile Arg Glu Lys Tyr Gln Lys Leu Gly Leu Asn Glu Asp Gln
                405                 410                 415
```

```
Ile Lys Lys Leu Cys Glu Ile Lys Asn Phe Ser Lys Thr Val Asp Leu
        420                 425                 430

Ser Leu Lys Ala Leu Arg Asn Ile Leu Pro Glu Leu Glu Lys Gly Leu
        435                 440                 445

Arg Tyr Asp Glu Ala Cys Lys Ala Leu Asn Tyr Asn Asn Gln Pro Glu
        450                 455                 460

Asn Lys Gly Leu Ser Lys Val Pro Lys Phe Glu Asp Val Arg Asn Pro
465                 470                 475                 480

Val Val Asn Arg Ala Leu Gly Gln Thr Arg Lys Val Ile Asn Ala Cys
                485                 490                 495

Ile Arg Glu Tyr Gly Leu Pro Asp Thr Ile Val Glu Leu Ala Arg
        500                 505                 510

Glu Val Gly Lys Asn Phe Arg Asp Arg Lys Asp Ile Glu Lys Glu Gln
        515                 520                 525

Lys Thr Asn Glu Ala Arg Arg Asn Thr Ala Lys Thr His Ile Ala Glu
        530                 535                 540

Ile Leu Gly Ile Ile Glu Asp Asn Val Thr Gly Glu Asp Ile Leu Lys
545                 550                 555                 560

Tyr Arg Leu Trp Lys Glu Gln Asp Cys Phe Cys Pro Tyr Ser Gly Ala
                565                 570                 575

Tyr Ile Thr Pro Glu Met Leu Arg Asp Ser Thr Ser Val Gln Ile Asp
        580                 585                 590

His Ile Pro Tyr Ser Arg Ser Trp Asp Asn Ser Tyr Met Asn Lys
        595                 600                 605

Val Leu Val Leu Thr Thr Glu Asn Gln Lys Lys Lys Asn Asp Thr Pro
        610                 615                 620

Phe Glu Tyr Leu Gly Lys Thr Asn Arg Trp Glu Ala Leu Glu Val Phe
625                 630                 635                 640

Ala Arg Gln Leu Pro Pro Lys Lys Ala Glu Arg Leu Leu Thr Glu Asn
                645                 650                 655

Phe Asp Asp Lys Lys Ala Gly Glu Trp Lys Asp Arg Ala Leu Asn Asp
                660                 665                 670

Thr Arg Tyr Met Ala Arg Leu Leu Lys Thr His Leu Glu Gln Ser Leu
        675                 680                 685

Asp Leu Gly Lys Gly Asn Arg Val Gln Thr Arg Asn Gly Ser Leu Thr
        690                 695                 700

Ala His Leu Arg Gly Ala Trp Gly Phe Pro Asp Lys Asn Arg Arg Asn
705                 710                 715                 720

Asp Arg His His Ala Leu Asp Ala Ile Val Ile Ala Cys Ser Thr Gln
                725                 730                 735

Ser Met Val Gln Gly Leu Thr Asn Trp Asn Lys Tyr Glu Ala Arg Arg
        740                 745                 750

Lys Asn Pro Ala Glu Arg Pro Leu Pro Pro Lys Pro Trp Glu Ser Phe
        755                 760                 765

Arg Glu Asp Ala Lys Glu Ser Val Asn Ser Ile Phe Val Ser Arg Met
        770                 775                 780

Pro Val Arg Thr Ile Ser Gly Ala Ala His Glu Asp Thr Ile Arg Ser
785                 790                 795                 800

Ile Arg Lys Ser Asp Gly Lys Ile Ile Gln Arg Ile Lys Leu Lys Asp
                805                 810                 815

Phe Lys Lys Asp Thr Leu Glu Asn Met Val Asp Lys Ala Arg Asn Ile
        820                 825                 830
```

-continued

Lys Leu Tyr Asp Ile Leu Lys Glu Arg Leu Asp Ala His Gly Gly Asp
            835                 840                 845

Ala Lys Lys Ala Phe Ala Thr Pro Val Tyr Met Pro Val Asn Asp Pro
    850                 855                 860

Ser Lys Pro Ala Pro Arg Ile Asn Ser Val Arg Ile Leu Thr Asn Glu
865                 870                 875                 880

Lys Ser Gly Ile Glu Ile Asn His Gly Leu Ala Ser Asn Gly Asp Met
                885                 890                 895

Val Arg Val Asp Val Phe Lys Lys Asp Asn Lys Phe Trp Leu Val Pro
            900                 905                 910

Ile Tyr Val His His Phe Ala Glu Asp Lys Leu Pro Asn Lys Ala Ile
            915                 920                 925

Met Gln Gly Lys Asp Glu Arg Glu Trp Glu Met Asn Asp Asp
            930                 935                 940

Phe Met Phe Ser Leu Tyr Arg Asn Asp Leu Ile Lys Val Thr Thr Lys
945                 950                 955                 960

Lys Glu Thr Met Leu Val Tyr Phe Gly Gly Leu Asp Arg Ala Thr Gly
                965                 970                 975

Asn Ile Ser Ile Lys Ala His Asp Arg Asp Pro Ser Phe Gly Thr Asn
            980                 985                 990

Gly Glu Asn Arg Thr Gly Val Lys  Thr Ala Ile Asn Phe  Glu Lys Phe
            995                 1000                1005

Ser Val  Asn Tyr Phe Gly Arg  Lys His Lys Ile Glu  Lys Glu Lys
    1010                1015                1020

Arg Leu  Gly Val Ala His Ser  Asp Asp Ser Glu Arg  Gly Ala Ala
    1025                1030                1035

Ile Pro  Glu Gln Gly Thr Gly  Ala Ala Ala Glu
    1040                1045

<210> SEQ ID NO 6
<211> LENGTH: 1501
<212> TYPE: PRT
<213> ORGANISM: Eubacterium rectale

<400> SEQUENCE: 6

Met Lys Arg Ile Leu Gly Leu Asp Leu Gly Thr Asn Ser Ile Gly Trp
1               5                   10                  15

Ala Val Ile Asn Gln Asp Asn Ile Asn Asp Lys Asp Ile Leu Thr Gly
            20                  25                  30

Ile Glu Cys Thr Gly Ser Arg Ile Ile Pro Met Asp Ala Ala Thr Leu
        35                  40                  45

Gly Asp Phe Asp Arg Gly Asn Ala Gln Ser Gln Thr Ala Asp Arg Thr
    50                  55                  60

Lys Arg Arg Ser Ala Arg Leu Ile Glu Arg Ser His Ile Arg Arg
65                  70                  75                  80

Glu Arg Leu Asn Arg Val Leu Met Thr Met Gly Trp Leu Pro Glu His
                85                  90                  95

Tyr Ser Asp Ser Leu Asp Arg Tyr Gly Lys Leu Ser Lys Gly Thr Glu
            100                 105                 110

Gln Lys Ile Ala Trp Lys Lys Ser Gly Asn Gly Asn Tyr Glu Phe Ile
        115                 120                 125

Phe Lys Asp Ser Phe Asn Glu Met Leu Asp Asp Phe Lys Asn Glu His
    130                 135                 140

Pro Asp Phe Ala Gln Arg Gly Leu Lys Ile Pro Tyr Asp Trp Thr Ile
145                 150                 155                 160

```
Tyr Tyr Leu Arg Lys Lys Ala Leu Thr His Pro Val Thr Asn Gln Glu
            165                 170                 175

Leu Ala Trp Ile Leu His Ser Phe Asn Gln Lys Arg Gly Tyr Tyr Gln
        180                 185                 190

Arg Gly Glu Glu Glu Gln Gln Pro Asp Lys Ile Glu Tyr Ile
    195                 200                 205

Pro Leu Lys Val Lys Glu Ile Arg Glu Thr Gly Glu Thr Lys Gly Ala
    210                 215                 220

Asp Lys Trp Phe Glu Leu Ile Leu Glu Asn Asp Leu Val Tyr Lys Arg
225                 230                 235                 240

Thr Phe Lys Glu Met Pro Asp Trp Lys Gly Lys Thr Leu Glu Leu Ile
            245                 250                 255

Val Thr Thr Asp Leu Asp Lys Asp Gly Asn Pro Val Ile Lys Asp Gly
            260                 265                 270

Lys Ala Lys Tyr Ser Ile Arg Ala Pro Lys Glu Asp Asp Trp Thr Leu
    275                 280                 285

Val Lys Val Arg Thr Gln Ser Asp Ile Arg Lys Ser Gly Lys Thr Val
    290                 295                 300

Gly Cys Tyr Ile Tyr Asp Ala Leu Ile Arg Lys Pro Asp Ile Lys Ile
305                 310                 315                 320

Arg Gly Lys Leu Val Arg Thr Ile Glu Arg Glu Phe Tyr Arg Glu
            325                 330                 335

Leu Glu Gln Ile Leu Lys Lys Gln Lys Glu Phe Asn Gln Asp Leu Arg
            340                 345                 350

Asp Lys Glu Leu Tyr Asn Glu Cys Ile Gly Val Leu Tyr Pro Asn Asn
            355                 360                 365

Asp Thr His Arg Lys Glu Ile Ala Asn Arg Asp Asp Phe Ala Tyr Leu
            370                 375                 380

Phe Ile Asn Asp Ile Ile Phe Tyr Gln Arg Pro Leu Lys Ser Lys Lys
385                 390                 395                 400

Ser Leu Ile Ser Asp Cys Pro Tyr Glu Glu Arg Ile Tyr Lys Asp Lys
                405                 410                 415

Ser Thr Gly Gln Lys Leu Thr Ser Ala Ile Lys Cys Ile Pro Lys Ser
            420                 425                 430

His Pro Thr Tyr Gln Glu Phe Arg Leu Trp Gln Phe Leu Ser Tyr Leu
            435                 440                 445

Lys Ile Tyr Glu Lys Glu Arg Thr Glu Ile Gly Lys Ile Gln Thr Asp
    450                 455                 460

Ile Asp Ile Thr Asp Ile Leu Pro Asp Asn Glu Ser Tyr Ala Ala
465                 470                 475                 480

Leu Phe Lys Lys Leu Asn Asp Glu Ala Glu Ile Lys Gln Asp Lys Ile
                485                 490                 495

Leu Lys Tyr Phe Pro Gln Leu Lys Lys Asn Ile Lys Asn Phe Arg Trp
            500                 505                 510

Asn Tyr Pro Glu Asp Lys Thr Tyr Pro Gly Asn Thr Thr Arg Ala Glu
            515                 520                 525

Met Leu Lys Arg Leu Lys Ala Asn Ile Gly Ser Asp Phe Leu Thr
530                 535                 540

Thr Glu Gln Glu Thr Ala Leu Trp His Ile Leu Tyr Ser Val Asn Asp
545                 550                 555                 560

Lys Ala Glu Leu Glu Lys Ala Leu Ser Thr Phe Ala Asn Lys His Gly
                565                 570                 575
```

-continued

```
Ile Glu Glu Glu Pro Phe Leu Asn Glu Phe Val Lys Phe Pro Pro Phe
            580                 585                 590

Lys Ser Asp Tyr Gly Ala Tyr Ser Phe Lys Ala Thr Asn Lys Leu Leu
        595                 600                 605

Ser Leu Met Arg Arg Gly Cys Tyr Trp Asp Glu Glu Asn Ile Asp Cys
        610                 615                 620

Asn Thr Lys Glu Arg Ile Glu Lys Ile Ile Ser Gly Glu Tyr Asp Pro
625                 630                 635                 640

Glu Ile Asn Asp Arg Val Arg Glu Lys Thr Ile Asn Leu Asn Gly Ile
                645                 650                 655

Ser Asp Phe Gln Gly Leu Pro Thr Trp Leu Ala Cys Tyr Val Val Tyr
            660                 665                 670

Gly Arg His Ser Glu Ile Lys Asp Ile Thr Lys Trp Glu Lys Pro Ser
        675                 680                 685

Asp Ile Asp Asn Tyr Leu Lys Leu Phe Lys Gln His Ser Leu Arg Asn
        690                 695                 700

Pro Ile Val Glu Gln Val Val Leu Glu Thr Leu Arg Thr Val Arg Asp
705                 710                 715                 720

Ile Trp Lys Gln Val Gly Arg Ile Asp Glu Ile His Ile Glu Leu Gly
                725                 730                 735

Arg Glu Met Lys Asn Ser Ala Ser Glu Arg Lys Arg Ile Ala Glu Gln
            740                 745                 750

Ile Ser Lys Asn Glu Asn Thr Asn Leu Arg Ile Lys Ala Met Leu Thr
        755                 760                 765

Glu Phe Leu Asn Pro Glu Phe Glu Ile Asp Asn Val Arg Pro Tyr Ser
770                 775                 780

Pro Thr Gln Gln Glu Ile Leu Lys Ile Tyr Glu Glu Gly Val Leu Asn
785                 790                 795                 800

Ser Gly Ile Glu Ile Asp Glu Lys Val Lys Asn Phe Leu Lys Ser Phe
                805                 810                 815

Asp Lys Ala Glu Asn Arg Pro Thr Arg Ala Glu Phe Leu Lys Tyr Lys
            820                 825                 830

Leu Trp Leu Asp Gln Lys Tyr Ile Ser Pro Tyr Thr Gly Gln Pro Ile
        835                 840                 845

Pro Leu Ser Lys Leu Phe Thr Ser Glu Tyr Glu Ile Glu His Ile Ile
850                 855                 860

Pro Gln Ser Arg Phe Phe Asp Asp Ser Leu Ser Asn Lys Val Ile Cys
865                 870                 875                 880

Glu Ala Lys Val Asn Ser Glu Lys Gly Ala Arg Leu Gly His Glu Phe
                885                 890                 895

Ile Lys Gly Cys His Glu Gln Ile Ile Asp Leu Gly Phe Gly Lys Thr
            900                 905                 910

Val Lys Ile Leu Ser Ile Glu Ala Tyr Glu Glu His Val Arg Lys Asn
        915                 920                 925

Tyr Gly His Asn Lys Ala Lys Gln Lys Leu Met Leu Asp Glu Ile
        930                 935                 940

Pro Asp Thr Phe Ile Glu Arg Gln Leu Asn Asp Ser Arg Tyr Ile Ser
945                 950                 955                 960

Lys Leu Val Lys Thr Leu Leu Ser Asn Ile Val Arg Glu Asp Asp Glu
                965                 970                 975

Ala Glu Ala Ile Ser Lys Asn Val Ile Thr Cys Thr Gly Gln Ile Thr
            980                 985                 990

Asp Arg Leu Lys His Asp Trp Gly  Val Asn Asp Val Trp  Asn Gly Ile
```

-continued

```
                995                1000              1005
Ile Leu Pro Arg Phe Gln Arg Met Glu Lys Leu Gln Pro Gly Lys
    1010                1015              1020

Arg Phe Thr Ala Thr Asn Thr Asn Gly Lys Leu Ile Pro Tyr Met
    1025                1030              1035

Pro Leu Glu Tyr Gln Lys Gly Phe Ser Ser Lys Arg Ile Asp His
    1040                1045              1050

Arg His His Ala Met Asp Ala Ile Val Ile Ala Cys Ala Asn Arg
    1055                1060              1065

Asn Ile Val Asn Tyr Leu Asn Asn Glu Ser Ala Arg Ser Asp Ala
    1070                1075              1080

Lys Ile Ser Arg Tyr Asp Leu Arg Asn Leu Leu Cys Asp Lys Lys
    1085                1090              1095

Lys Gln Asp Asp Ala Gly Asn His Thr Trp Thr Met Lys Ile Pro
    1100                1105              1110

Trp Asn Thr Phe Ile Arg Asp Met Arg Lys Ala Leu Glu Gly Ile
    1115                1120              1125

Ile Val Ser Phe Lys Gln Asn Leu Arg Val Ile Asn Lys Ser Ser
    1130                1135              1140

Asn His Ile Thr Lys Tyr Val Asp Gly Gln Lys Lys Arg Val Pro
    1145                1150              1155

Gln Ser Glu Gly Asp Asn Arg Ser Ile Arg Lys Ser Leu His Lys
    1160                1165              1170

Asp Thr Val Phe Gly Leu Val Asn Leu Arg Glu Lys Lys Thr Val
    1175                1180              1185

Ser Leu Ser Glu Ala Leu Lys Lys Pro Asp Arg Ile Val Asp Lys
    1190                1195              1200

Ala Leu Lys His Arg Ile Lys Glu Phe Lys Thr Ala Gly Lys Thr
    1205                1210              1215

Asp Thr Asp Ile Lys Lys Leu Leu Lys Asn Gly Pro Asp Lys Val
    1220                1225              1230

Glu Ile Tyr Tyr Phe Ser Glu Glu Lys Ser Ile Gly Lys Asp Lys
    1235                1240              1245

Ala Arg His Tyr Tyr Ala Ala Arg Thr Thr Ile Leu Ser Leu Glu
    1250                1255              1260

Met Asp Lys Ser Lys Ser Tyr Glu Lys Ala Ile Asn Thr Ile Asn
    1265                1270              1275

Asn Ile Thr Asp Ser Gly Ile Arg Lys Ile Leu Thr Asn His Leu
    1280                1285              1290

Glu Ala Asn Gly Asn Asp Pro Ser Lys Ala Phe Ser Ala Asp Gly
    1295                1300              1305

Ile Asp Glu Met Asn Lys Asn Ile Ile Leu Leu Asn Gly Gly Lys
    1310                1315              1320

Asn His Lys Pro Ile Tyr Ser Val Arg Lys Tyr Glu Glu Ala Asn
    1325                1330              1335

Lys Phe Ala Val Gly Glu Ile Gly Cys Lys Ser Lys Lys Phe Val
    1340                1345              1350

Glu Ala Asp Lys Gly Gly Asn Leu Tyr Phe Ala Val Tyr Lys Lys
    1355                1360              1365

Asp Asp Asn Ser Arg Ser Phe Arg Thr Ile Pro Leu Asn Glu Val
    1370                1375              1380

Ile Asp Arg Leu Lys Asn Lys Met Ser Pro Val Pro Glu Thr Asp
    1385                1390              1395
```

```
Glu Met Gly Asn Arg Leu Ile Phe Trp Leu Ser Pro Asn Asp Leu
1400                1405                1410

Val Tyr Leu Pro Thr Ala Asp Glu Val Glu Asn Gly Arg Val Thr
    1415                1420                1425

Leu Pro Leu Asp Lys Asp Arg Ile Tyr Lys Met Val Ser Ala Asn
1430                1435                1440

Lys Lys Gln Cys Phe Phe Met Pro Ser Asn Thr Ala Asn Pro Ile
1445                1450                1455

Ile Ser Ile Glu Phe Ser Ser Ser Asn Lys Met Glu Arg Ala Ile
1460                1465                1470

Thr Gly Glu Met Ile Lys Glu Thr Cys Ile Pro Leu Lys Thr Asp
1475                1480                1485

Arg Leu Gly Asn Ile Thr Asp Phe Asp Gly Arg Ile Ser
1490                1495                1500

<210> SEQ ID NO 7
<211> LENGTH: 1211
<212> TYPE: PRT
<213> ORGANISM: Eubacterium rectale

<400> SEQUENCE: 7

Met Glu Asn Tyr Arg Gln Lys His Arg Phe Val Leu Ala Thr Asp Leu
1               5                   10                  15

Gly Ile Gly Ser Asn Gly Trp Ala Ile Ile Asp Leu Asp Ala His Arg
                20                  25                  30

Val Glu Asp Leu Gly Val Gln Ile Phe Glu Ser Gly Glu Glu Gly Ala
            35                  40                  45

Lys Lys Ala Ser Ala Arg Ala Ser Gln Gln Arg Arg Leu Lys Arg Ser
        50                  55                  60

Ala His Arg Leu Asn Arg Arg Lys Gln Arg Lys Glu Ala Leu Ile
65                  70                  75                  80

Lys Phe Leu Gln Glu Ile Glu Phe Pro Asp Leu Val Glu Ile Leu Asn
                85                  90                  95

Ser Phe Lys Lys Gln Lys Asn Pro Asn Asp Ile Leu Ser Leu Arg Val
                100                 105                 110

Lys Gly Leu Asp Asn Lys Leu Ser Pro Leu Glu Leu Phe Ser Ile Leu
            115                 120                 125

Ile Tyr Met Ser Asn Asn Arg Gly Tyr Lys Asp Phe Tyr Asp Asn Asp
        130                 135                 140

Ile Asn Asp Asn Asn Thr Asp Lys Asp Glu Lys Glu Met Glu Lys Ala
145                 150                 155                 160

Lys Ser Thr Ile Glu Lys Leu Phe Ala Ser Asn Ser Tyr Arg Thr Val
                165                 170                 175

Gly Glu Met Ile Ala Thr Asp Pro Thr Phe Ile Val Asp Lys Ser Gly
                180                 185                 190

Ser Lys Lys Val Ile Lys Tyr His Asn Lys Gly Tyr Gln Tyr Leu
            195                 200                 205

Ile Pro Arg Lys Leu Leu Glu Asn Glu Met Ser Leu Ile Leu His Lys
        210                 215                 220

Gln Glu Glu Phe Tyr Asp Cys Leu Ser Ile Asp Asn Ile Thr Ile Ile
225                 230                 235                 240

Leu Asp Lys Ile Phe Phe Gln Arg Asn Phe Glu Asp Gly Pro Gly Pro
                245                 250                 255

Lys Asn Lys Arg Asp Asp Tyr Lys Asn Asn Ser Lys Gly Asn Gln Phe
```

```
                260                 265                 270
Tyr Thr Gly Phe Asn Glu Met Ile Gly Leu Cys Pro Phe Tyr Pro Asn
                    275                 280                 285
Glu Lys Lys Gly Thr Lys Asn Ser Leu Ile Tyr Asp Glu Tyr Tyr Leu
            290                 295                 300
Ile Asn Thr Leu Ser Gln Phe Phe Thr Asp Ser Asn Gly Val Ile
305                 310                 315                 320
Met Ser Phe Ser Lys Ser Leu Leu His Asp Leu Met Leu Tyr Phe Phe
                325                 330                 335
Asp His Lys Gly Glu Leu Thr Asn Lys Glu Leu Ser Ser Phe Leu Leu
                340                 345                 350
Lys His Gly Leu Glu Leu Asn Ser Lys Glu Lys Ser Asn Lys Lys Tyr
            355                 360                 365
Arg Leu Asn Tyr Met Lys Gln Leu Thr Asp Ser Thr Ile Phe Glu Thr
            370                 375                 380
Glu Met Ile Ala Ser Phe Arg Glu Gly Ile Glu Thr Ser Ser Tyr Arg
385                 390                 395                 400
Ser Val Asn Ser Leu Ser Asn Lys Ile Gly Asn Cys Ile Gly Gln Phe
                405                 410                 415
Ile Thr Pro Leu Lys Arg Lys Glu Glu Leu Thr Asn Ile Leu Ile Asp
            420                 425                 430
Thr Asn Tyr Pro Lys Glu Leu Ala Ser Lys Leu Ala Asp Ser Ile Lys
            435                 440                 445
Val Ile Lys Ser Gln Ser Val Ala Asn Ile Ser Asn Lys Tyr Met Leu
        450                 455                 460
Glu Ala Ile His Ala Phe Glu Ser Gly Lys Lys Tyr Gly Asp Phe Gln
465                 470                 475                 480
Ala Glu Phe Asn Glu Thr Arg Glu Leu Glu Asp His His Phe Met Lys
                485                 490                 495
Asn Asn Lys Leu Ile Ala Phe Gln Asp Ser Asp Leu Ile Arg Asn Pro
                500                 505                 510
Val Val Tyr Arg Thr Ile Asn Gln Ser Arg Lys Ile Ile Asn Ala Ala
            515                 520                 525
Ile Asn Lys Tyr Asn Ile Val Arg Ile Asn Ile Glu Val Ala Ser Asp
        530                 535                 540
Val Asn Lys Ser Phe Glu Gln Arg Asp Asn Asp Lys Lys Tyr Gln Asn
545                 550                 555                 560
Asp Asn Tyr Glu Lys Asn Leu Gln Leu Glu Ser Glu Leu Thr Asp Tyr
                565                 570                 575
Ile Asn Lys Glu Asn Leu His Val Asn Val Asn Ser Lys Met Met Glu
            580                 585                 590
Arg Tyr Lys Leu Tyr Leu Ser Gln Asn Lys His Cys Ile Tyr Thr Asn
            595                 600                 605
Thr Pro Leu Thr Met Met Asp Val Ile Tyr Ser Thr Asn Val Gln Val
            610                 615                 620
Asp His Ile Ile Pro Gln Ser Lys Ile Leu Asp Asp Thr Leu Asn Asn
625                 630                 635                 640
Lys Val Leu Val Leu Arg Asp Ala Asn Ser Ile Lys Asn Asn Arg Leu
                645                 650                 655
Pro Leu Glu Ala Phe Asp Glu Met Gln Ile Asn Val Asp Thr Asn Tyr
                660                 665                 670
Thr Lys Lys Asp Tyr Leu Thr Glu Cys Leu His Leu Leu Lys Asn Lys
            675                 680                 685
```

-continued

```
Thr Asn Pro Ile Ser Lys Lys Tyr Gln Tyr Leu Thr Leu Lys Lys
    690             695                 700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                    725                 730                 735

Lys Glu Ser Asp Lys Thr Lys Asn Ile Asp Val Val Thr Ile Lys Gly
                740                 745                 750

Ala Val Thr Ser Arg Phe Arg Lys Arg Trp Leu Thr Thr Tyr Asp Glu
            755                 760                 765

Tyr Gly Tyr His Pro Thr Ile Tyr Ser Leu Glu Asp Lys Gly Arg Asn
    770                 775                 780

Leu Tyr Tyr Tyr His His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810                 815

Ile Lys Ile Asp Arg Asn Leu Ser Lys Glu Gln Lys Gln Arg Asp Ile
                820                 825                 830

Asp Thr Val Ile Lys Asn Thr Val Lys Ser Met Ser Lys Tyr His Gly
            835                 840                 845

Phe Ser Glu Asp Tyr Ile Arg Ser Leu Met Ser Lys Asn His Ile Pro
850                 855                 860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890                 895

Gln Tyr His Tyr Lys Lys Leu Tyr Ile Ala Phe Lys Glu Ala Gln Asn
        900                 905                 910

Ala Leu Lys Glu Lys Glu Thr Leu Glu Lys Glu Leu Ile Glu Arg Phe
            915                 920                 925

Asn Asn Glu Ala Gln Ile Leu Asn Ala Asn Ile Ile Leu Thr Tyr Thr
930                 935                 940

Gly Phe Glu Ser Asn Asn Glu Leu Ile Asp Ile Lys Lys Ala Lys Lys
945                 950                 955                 960

Val Thr Asp Thr Leu Lys Pro Asn Leu Lys Asn Tyr Ile Lys Ala Ile
                965                 970                 975

Asp Ile Leu Thr Gln Glu Glu Tyr Thr Lys Arg Cys Leu Glu Tyr Tyr
                980                 985                 990

Asn Asp Ser Glu Phe Ala Thr Gln Leu Lys Ile Pro Tyr Val Asn Phe
                995                 1000                1005

Lys Ile Asn Lys Arg Phe Arg Gly Lys Ile Gln Gly Ser Glu Asn
    1010                1015                1020

Ala Val Ser Leu Arg Glu Val Leu Lys Lys Thr Lys Leu Asn Ser
    1025                1030                1035

Phe Glu Glu Phe Glu Ser Tyr Leu Lys Ser Glu Asp Gly Ile Lys
    1040                1045                1050

Ser Pro Tyr Tyr Ile Lys Tyr Thr Lys Asn Thr Leu Gly Lys Glu
    1055                1060                1065

Ser Tyr Thr Ile Tyr Glu Ala Asn Ser Tyr Tyr Cys Ala Glu Ile
    1070                1075                1080

Tyr Thr Asp Ser Gln Asn Lys Pro Gln Leu Arg Gly Ile Arg Tyr
    1085                1090                1095
```

```
Val Asp Val Arg Lys Glu Asp Gly Lys Leu Val Leu Leu Lys Pro
    1100                1105                1110

Leu Pro Ser Thr Cys Lys His Ile Thr Tyr Leu Phe His Asn Glu
    1115                1120                1125

Tyr Ile Ala Ile Tyr Lys Asp Ser Asn Tyr Lys Arg Leu Lys Asn
    1130                1135                1140

Asn Gly Phe Gly Ala Tyr Arg Ser Ile Asn Asn Val Asn Val Asn
    1145                1150                1155

Lys Ile Ile Ile Arg Leu Phe Ala Asn Gln Asn Leu Asn Asp Asn
    1160                1165                1170

Asp Val Val Ile Thr Ser Ser Ile Phe Ile Lys Lys Tyr Ser Leu
    1175                1180                1185

Asp Val Phe Gly His Ile Asn Gly Glu Ile Lys Cys Gly Asp Gln
    1190                1195                1200

Ser Leu Phe Thr Ile Lys Lys Arg
    1205                1210

<210> SEQ ID NO 8
<211> LENGTH: 1490
<212> TYPE: PRT
<213> ORGANISM: Eubacterium rectale

<400> SEQUENCE: 8

Met Lys Lys Ile Leu Gly Leu Asp Leu Gly Thr Asn Ser Ile Gly Trp
1               5                   10                  15

Ala Leu Ile Glu His Asn Phe Asp Lys Lys Glu Gly Arg Ile Asp Asp
                20                  25                  30

Leu Gly Val Arg Ile Ile Pro Met Ser Ala Asp Ile Leu Gly Lys Phe
            35                  40                  45

Asp Ala Gly Gln Ser His Ser Gln Thr Ala Glu Arg Thr Gly Tyr Arg
        50                  55                  60

Gly Val Arg Arg Leu Tyr Gln Arg Asp Asn Leu Arg Arg Glu Arg Leu
65                  70                  75                  80

His Arg Val Leu Asn Ile Leu Asp Phe Leu Pro Glu His Tyr Ala Glu
                85                  90                  95

His Ile Asp Phe Glu Lys Arg Leu Gly Gln Phe Lys Glu Gly Lys Glu
                100                 105                 110

Ile Lys Leu Asn Tyr Lys Ser Asn Lys Asp Ser Lys Phe Glu Phe Ile
            115                 120                 125

Phe Lys Ala Ser Tyr Asn Glu Met Leu Ala Ala Phe Lys Lys Tyr Gln
        130                 135                 140

Pro Gly Leu Phe Tyr Val Lys Ala Asn Gly Thr Glu Thr Lys Ile Pro
145                 150                 155                 160

Tyr Asp Trp Thr Ile Tyr Tyr Leu Arg Lys Lys Ala Leu Ser Gln Pro
                165                 170                 175

Leu Thr Lys Gln Glu Leu Ala Trp Ile Ile Leu Asn Phe Asn Gln Lys
            180                 185                 190

Arg Gly Tyr Tyr Gln Leu Arg Gly Glu Glu Ile Asp Asp Asp Lys Asn
        195                 200                 205

Lys Gln Phe Val Gln Leu Lys Val Lys Glu Val Ile Asp Ser Gly Glu
    210                 215                 220

Ala Val Lys Gly Lys Lys Leu Phe Asn Val Ile Phe Glu Asn Gly Trp
225                 230                 235                 240

Lys Tyr Asp Lys Gln Val Val Lys Thr Glu Asp Trp Ile Gly Arg Thr
                245                 250                 255
```

Lys Glu Phe Ile Val Thr Thr Lys Thr Leu Lys Ser Gly Glu Ile Lys
                260                 265                 270

Arg Thr Tyr Lys Ala Val Asp Ser Glu Lys Asp Trp Ala Ala Ile Lys
            275                 280                 285

Ala Lys Thr Glu Gln Asp Ile Glu Arg Ser Asn Lys Thr Val Gly Glu
        290                 295                 300

Phe Ile Tyr Glu Ala Leu Leu Gln Asp Pro Thr Gln Lys Ile Arg Gly
305                 310                 315                 320

Lys Leu Val Lys Thr Ile Glu Arg Lys Phe Tyr Lys Ala Glu Leu Arg
                325                 330                 335

Glu Ile Leu Arg Lys Gln Ile Glu Leu Gln Pro Gln Leu Phe Thr Thr
            340                 345                 350

Lys Leu Tyr Asn Ala Cys Ile Lys Glu Leu Tyr Pro Asn Asn Glu Ala
        355                 360                 365

His Arg Asn Ser Ile Lys Asn Arg Asp Phe Leu Tyr Leu Phe Leu Asp
    370                 375                 380

Asp Ile Ile Phe Tyr Gln Arg Pro Leu Lys Ser Gln Lys Ser Asn Ile
385                 390                 395                 400

Ser Gly Cys His Leu Glu Gln Arg Ile Tyr Thr Lys Ile Asn Pro Val
                405                 410                 415

Ser Gly Lys Lys Glu Glu Val Lys Gln Ala Val Lys Ala Ile Pro Lys
            420                 425                 430

Ser His Pro Ile Phe Gln Glu Phe Arg Ile Trp Gln Trp Leu Gln Asn
        435                 440                 445

Leu Lys Ile Tyr Asp Lys Ile Asn Thr Asp Lys Gly Glu Leu Ala Asp
    450                 455                 460

Val Thr Asn Gln Leu Leu Pro Ser Glu Glu Ser Leu Leu Asp Leu Phe
465                 470                 475                 480

Asp Tyr Leu Gln Thr Lys Lys Glu Leu Asp Gln Ser Gly Phe Ile Lys
                485                 490                 495

Tyr Phe Ile Asp Lys Lys Leu Ile Asn Lys Ser Glu Lys Glu Asn Tyr
            500                 505                 510

Arg Trp Asn Tyr Val Glu Asp Lys Lys Tyr Pro Phe Ala Glu Thr Arg
        515                 520                 525

Ala Gln Phe Ile Ser Arg Leu Asn Lys Val Lys Asn Ile Asn Asn Ile
    530                 535                 540

Ser Glu Phe Leu Asn Lys Lys Thr Arg Leu Gly Glu Lys Glu Ser Ser
545                 550                 555                 560

Pro Phe Val Thr Arg Ile Glu Gln Leu Trp His Ile Ile Tyr Ser Val
                565                 570                 575

Ser Asp Ile Asn Glu Tyr Lys Ser Ala Leu Glu Lys Phe Ala Leu Lys
            580                 585                 590

His Asp Ile Asp Lys Glu Ser Phe Val Ala Asn Phe Ile Lys Phe Pro
        595                 600                 605

Pro Phe Lys Ser Asp Tyr Gly Ser Tyr Ser Lys Lys Ala Leu Ser Lys
    610                 615                 620

Leu Leu Pro Leu Met Arg Arg Gly Lys Tyr Trp Asn Glu Ser Asp Ile
625                 630                 635                 640

Ser Asn Lys Val Lys Gln Arg Val Ser Asp Ile Met Glu Arg Val Asn
                645                 650                 655

Ala Leu Asn Leu Lys Glu Asn Tyr Asn Ala Lys Glu Leu Ala Glu Ala
            660                 665                 670

```
Leu Lys Thr Val Ser Asp Asp Val Lys Lys Gln Leu Ile Lys Ser
            675                 680                 685

Phe Val Pro Phe Lys Asp Lys Asn Pro Leu Lys Gly Leu Asn Thr Tyr
    690                 695                 700

Gln Ala Thr Tyr Leu Val Tyr Gly Arg His Ser Glu Val Gly Asp Ile
705                 710                 715                 720

Gln Ser Trp Lys Thr Pro Glu Asp Ile Asp Thr Tyr Leu Lys Asn Phe
                725                 730                 735

Lys Gln His Ser Leu Arg Asn Pro Ile Val Glu Gln Val Thr Glu
            740                 745                 750

Thr Leu Arg Val Val Arg Asp Ile Trp Ile His Tyr Gly Lys Ser Gln
        755                 760                 765

Leu Asn Phe Phe Asn Glu Ile His Val Glu Leu Gly Arg Glu Met Lys
    770                 775                 780

Asn Pro Ala Asp Lys Arg Lys Gln Ile Ser Asn Arg Asn Ile Glu Asn
785                 790                 795                 800

Glu Asn Thr Asn Asn Arg Ile Arg Glu Ile Leu Lys Asp Leu Lys Asn
                805                 810                 815

Asp Thr Ser Ile Glu Gly Asp Ile Arg Asp Tyr Ser Pro Ser Gln Gln
            820                 825                 830

Asp Leu Leu Lys Ile Tyr Glu Glu Gly Val Tyr Gln Asn Pro Lys Val
        835                 840                 845

Asp Tyr Ser Lys Val Ser Glu Asp Glu Ile Thr Lys Ile Arg Arg Ser
    850                 855                 860

Asn Ser Pro Thr Pro Lys Glu Ile Gln Arg Tyr Arg Leu Trp Leu Glu
865                 870                 875                 880

Gln Gly Tyr Ile Ser Pro Tyr Thr Gly Lys Pro Ile Pro Leu Ser Lys
                885                 890                 895

Leu Phe Thr His Glu Tyr Gln Ile Glu His Ile Ile Pro Gln Ser Arg
            900                 905                 910

Tyr Phe Asp Asn Ser Leu Ser Asn Lys Ile Ile Cys Glu Ser Ala Val
        915                 920                 925

Asn Glu Asp Lys Asp Asn Lys Thr Ala Tyr Glu Tyr Leu Lys Asn Lys
930                 935                 940

Ser Gly Asn Val Ile Asn Gly His Lys Leu Leu Arg Ile Glu Glu Tyr
945                 950                 955                 960

Glu Ala His Val Asn Arg Tyr Phe Lys Asn Asn Arg Gln Lys Leu Lys
                965                 970                 975

Asn Leu Leu Ser Glu Asp Ile Pro Glu Gly Phe Ile Asn Arg Gln Leu
            980                 985                 990

Asn Asp Ser Arg Tyr Ile Ser Lys Leu Ile Lys Gly Leu Leu Ser Asn
        995                 1000                1005

Ile Val Arg Gln Glu Asn Glu Gln Glu Ala Thr Ser Lys Asn Leu
    1010                1015                1020

Ile Pro Val Thr Gly Ala Val Thr Ser Leu Lys Asn Asp Trp
    1025                1030                1035

Gly Leu Asn Asp Lys Trp Asn Glu Leu Ile Leu Pro Arg Phe Glu
    1040                1045                1050

Arg Leu Asn Gln Leu Thr Gln Thr Lys Asn Phe Thr Thr Ser Asn
    1055                1060                1065

Thr Asn Gly Asn Thr Ile Pro Thr Val Pro Asp Asp Leu Leu Lys
    1070                1075                1080

Gly Phe Ser Lys Lys Arg Ile Asp His Arg His His Ala Leu Asp
```

```
              1085                1090                1095
Ala Leu Val Val Ala Cys Cys Thr Arg Asn His Val Gln Tyr Leu
              1100                1105                1110
Asn Ala Leu Asn Ala Glu Lys Ala Asn Tyr Gly Leu Arg Lys Lys
              1115                1120                1125
Leu Leu Ile Val Asn Glu Gln Gly Asp Phe Thr Lys Ile Phe Gln
              1130                1135                1140
Met Pro Trp Lys Gly Phe Thr Ser Glu Ala Lys Asn Gln Leu Glu
              1145                1150                1155
Lys Thr Val Ile Ser Phe Lys Gln Asn Leu Arg Val Ile Asn Lys
              1160                1165                1170
Ala Asn Asn Lys Phe Trp Ser Phe Lys Asp Glu Asn Gly Asn Ile
              1175                1180                1185
Asn Leu Asp Lys Asn Gly Arg Pro Val Lys Lys Leu Arg Lys Gln
              1190                1195                1200
Thr Lys Gly Asp Asn Trp Ala Ile Arg Lys Ala Met His Lys Glu
              1205                1210                1215
Thr Val Ser Gly Lys Ser Asn Ile Glu Thr Pro Lys Gly Lys Ile
              1220                1225                1230
Ala Thr Ala Val Arg Gly Ser Leu Ala Asp Ile Lys Asn Glu Lys
              1235                1240                1245
His Leu Gly Lys Ile Thr Asp Val Gln Ile Arg Glu Val Ile Leu
              1250                1255                1260
Pro Asn His Leu Lys Asn Tyr Val Asp Glu Lys Gly Lys Val Lys
              1265                1270                1275
Phe Asp Leu Ala Phe Asn Asp Glu Gly Ile Glu Asp Leu Asn Lys
              1280                1285                1290
Asn Ile Ile Ala Leu Asn Asn Gly Lys Lys His Gln Pro Ile Arg
              1295                1300                1305
Lys Val Lys Phe Phe Glu Val Gly Ser Lys Phe Ser Ile Ser Glu
              1310                1315                1320
Asn Glu Asn Ser Ala Lys Ser Lys Lys Tyr Val Glu Ala Ala Lys
              1325                1330                1335
Gly Thr Asn Leu Phe Phe Ala Val Tyr Trp Asp Glu Lys Lys Gln
              1340                1345                1350
Lys Arg Asn Tyr Glu Thr Val Pro Leu Asn Glu Val Ile Ala His
              1355                1360                1365
Gln Lys Gln Val Ala His Leu Thr Asn Asn Glu Arg Leu Pro Ile
              1370                1375                1380
Gln Thr Asn Arg Lys Lys Gly Asp Phe Leu Phe Thr Leu Ser Pro
              1385                1390                1395
Asn Asp Leu Val Tyr Val Pro Thr Asp Ala Glu Val Ala Asn Lys
              1400                1405                1410
Gln Pro Ile Asp Phe Lys Asn Leu His Gln Asn Gln Val Asn Arg
              1415                1420                1425
Ile Tyr Lys Met Val Ser Ser Gly Asn Gln Cys Phe Phe Ile
              1430                1435                1440
Lys Asp Lys Ile Ala Thr Ser Ile Trp Asn Lys Asn Glu Phe Ser
              1445                1450                1455
Ser Leu Asn Lys Met Glu Lys Asp Ile Asp Gly Asn Met Ile Lys
              1460                1465                1470
Glu Arg Cys Ile Lys Leu Asn Val Asp Arg Leu Gly Asn Ile Thr
              1475                1480                1485
```

Lys Ala
    1490

<210> SEQ ID NO 9
<211> LENGTH: 1511
<212> TYPE: PRT
<213> ORGANISM: Eubacterium rectale

<400> SEQUENCE: 9

Met Lys Lys Ile Leu Gly Leu Asp Leu Gly Thr Asn Ser Ile Gly Trp
1               5                   10                  15

Ala Val Val Asn Ala Asp Ala Ile Thr Arg Asn Asp Gly Ser Arg Tyr
            20                  25                  30

Leu Lys Pro Asn Ser Ile Ser Ala Ala Gly Ser Arg Ile Ile Pro Met
        35                  40                  45

Ser Ala Asp Val Leu Gly Asn Phe Glu Ser Gly Ile Thr Val Ser Gln
    50                  55                  60

Thr Lys Asp Arg Thr Asp Lys Arg Met Ala Arg Arg Leu His Glu Arg
65                  70                  75                  80

Ala Leu Leu Arg Arg Glu Arg Leu Leu Arg Ile Leu Ser Leu Met Asp
                85                  90                  95

Phe Leu Pro Lys His Phe Ala Ser Lys Ile Asn Arg Tyr Gly Lys Phe
            100                 105                 110

Thr Asp Asp Ser Glu Pro Lys Leu Ala Trp Arg Lys Asn Thr Glu Gly
        115                 120                 125

Lys Tyr Glu Phe Ile Phe Gln Asp Ala Phe Asn Glu Met Leu Ala Glu
    130                 135                 140

Phe Lys Asp Lys Gln Pro Glu Ile Val Lys Glu Gly Lys Lys Ile Pro
145                 150                 155                 160

Tyr Asp Trp Thr Ile Tyr Tyr Leu Arg Lys Lys Ala Leu Glu Lys Ala
                165                 170                 175

Leu Ser Lys Glu Glu Leu Ser Trp Leu Leu Gln Phe Asn Gln Lys
            180                 185                 190

Arg Gly Tyr Tyr Gln Leu Arg Gly Glu Glu Asp Ile Pro Gln Asp
        195                 200                 205

Lys Lys Ile Glu Tyr Leu Ala Gln Lys Val Val Lys Val Glu Ala Thr
    210                 215                 220

Asp Gln Lys Lys Gly Asp Asp Ile Trp Tyr Asn Val Tyr Leu Glu Asn
225                 230                 235                 240

Gly Met Ile Tyr Arg Arg Thr Ser Lys Ala Pro Leu Asp Trp Glu Gly
                245                 250                 255

Lys Ile Lys Glu Phe Ile Val Thr Thr Asp Leu Glu Lys Asp Gly Thr
            260                 265                 270

Pro Lys Lys Asp Lys Glu Gly Asn Ile Lys Arg Ser Phe Arg Ala Pro
        275                 280                 285

Gln Glu Asp Asp Trp Thr Leu Leu Lys Lys Thr Glu Ala Asp Ile
    290                 295                 300

Glu Lys Ser Thr Lys Thr Val Gly Cys Tyr Ile Tyr Asp Ser Leu Leu
305                 310                 315                 320

Asn Asn Pro Lys Gln Lys Ile Ile Gly Lys Leu Val Arg Thr Val Glu
                325                 330                 335

Arg Lys Phe Tyr Lys Glu Glu Leu Thr Gln Ile Leu Lys Lys Gln Val
            340                 345                 350

Glu Leu Ile Pro Glu Leu Arg Asn Asp Asn Leu Tyr Lys Gln Cys Ile

```
                355                 360                 365
Glu Glu Leu Tyr Pro Ile Asn Glu Ala His Arg Asn Thr Ile Ala Lys
    370                 375                 380

Thr Asp Phe Ala Asn Leu Phe Ile Asn Asp Ile Leu Phe Tyr Gln Arg
385                 390                 395                 400

Pro Leu Lys Ser Lys Ser Gln Ile Asp Asn Cys Pro Tyr Glu Glu
                405                 410                 415

His Ile Phe Ile Asp Ser Lys Thr Gly Glu Lys Lys Val Pro Val
            420                 425                 430

Lys Cys Ile Thr Lys Ser Asn Pro Leu Phe Gln Glu Phe Arg Leu Trp
        435                 440                 445

Gln Phe Ile Gln Asn Leu Arg Ile Tyr Gln Arg Glu Lys Glu Ile Asp
    450                 455                 460

Gly Lys Leu Ser Thr Asp Val Asp Ile Thr Ser Glu Cys Leu Lys Ser
465                 470                 475                 480

Glu Glu Asp Tyr Val Arg Leu Phe Asp Trp Leu Asn Asp Arg Glu Ser
                485                 490                 495

Ile Glu Gln Glu Glu Leu Leu Lys Tyr Leu Phe Asn Thr Lys Lys Ser
            500                 505                 510

Lys Asn Lys Glu Asn Pro Tyr Arg Trp Asn Tyr Val Glu Asp Lys Val
        515                 520                 525

Tyr Pro Cys Asn Glu Thr Arg Ala Thr Ile Leu Lys Gly Leu Ser Lys
    530                 535                 540

Cys Gly Ile Asn Ala Ser Val Leu Ser Ser Glu Met Glu Met Ala Leu
545                 550                 555                 560

Trp His Ile Leu Tyr Ser Val Glu Asp Lys Lys Glu Ile Glu Thr Ala
                565                 570                 575

Leu Thr His Phe Ala Gln Lys Gln Gly Trp Asn Gly Glu Phe Ala Ile
            580                 585                 590

Val Phe Ser Lys Leu Lys Pro Phe Lys Lys Asp Tyr Gly Ser Tyr Ser
        595                 600                 605

Glu Lys Ala Ile Lys Lys Leu Leu Ser Leu Met Arg Met Gly Lys Tyr
    610                 615                 620

Trp Asn Gln Asp Asn Ile Asp Lys Asn Thr Leu Asp Arg Ile Asp Lys
625                 630                 635                 640

Ile Ile Asn Gly Glu Tyr Asp Glu Lys Ile Ser Asn Arg Val Arg Asp
                645                 650                 655

Asn Ala Ile Asn Leu Lys Asp Ile Ser Asp Phe Arg Gly Leu Pro Val
            660                 665                 670

Trp Leu Ala Cys Tyr Ile Val Tyr Asp Arg His Ser Glu Ala Lys Asp
        675                 680                 685

Cys Thr Lys Trp Asn Thr Pro Glu Glu Ile Asp Ser Tyr Leu Lys Lys
    690                 695                 700

Phe Lys Gln His Ser Leu Arg Asn Pro Ile Val Glu Gln Val Val Thr
705                 710                 715                 720

Glu Thr Leu Arg Thr Val Arg Asp Ile Trp Lys Gln Glu Gly Gln Ile
                725                 730                 735

Asp Glu Ile His Leu Glu Leu Gly Arg Asp Leu Lys Asn Pro Ala Asp
            740                 745                 750

Lys Arg Lys Lys Met Ser Glu Asn Ile Leu Lys Asn Glu Asn Thr Asn
        755                 760                 765

Leu Arg Ile Lys Ala Met Leu Met Glu Phe Met Asn Pro Gly Met Gly
    770                 775                 780
```

```
Ile Glu Asn Val Arg Pro Tyr Ser Pro Ser Gln Gln Asp Ile Leu Arg
785                 790                 795                 800

Ile Tyr Glu Glu Asn Ala Leu Glu Asn Leu Thr Lys Asp Asp Glu Glu
            805                 810                 815

Phe Asp Phe Ile Ser Lys Ile Ser Lys Gln Ala Gln Pro Thr Lys Ser
            820                 825                 830

Asp Ile Val Arg Tyr Lys Cys Trp Leu Glu Gln Lys Tyr Arg Ser Pro
            835                 840                 845

Tyr Thr Gly Lys Thr Ile Ser Leu Ser Lys Leu Phe Thr Ser Ala Tyr
850                 855                 860

Glu Ile Glu His Ile Ile Pro Gln Ser Arg Tyr Phe Asp Ser Phe
865                 870                 875                 880

Ser Asn Lys Val Ile Cys Glu Ala Glu Val Asn Lys Leu Lys Asp Arg
            885                 890                 895

Gln Leu Gly His Glu Phe Ile Glu Glu His Gly Glu Lys Val Gln
            900                 905                 910

Leu Ser Gln Gly Glu Val Val Glu Ile Leu Ser Val Asp Ala Tyr Glu
            915                 920                 925

Lys Phe Val Lys Glu Asn Tyr Ala Asn Asn Arg Val Lys Met Lys Lys
930                 935                 940

Leu Leu Met Glu Asn Ile Pro Asp Glu Phe Ile Glu Arg Gln Leu Asn
945                 950                 955                 960

Asp Ser Arg Tyr Ile Ser Lys Val Lys Gly Leu Leu Ser Asn Ile
            965                 970                 975

Val Arg Glu Lys Ile Asp Asp Glu Asn Tyr Glu Pro Glu Ala Val Ser
            980                 985                 990

Lys Asn Leu Ile Ser Cys Asn Gly Ala Val Thr Asp Arg Leu Lys Lys
            995                 1000                1005

Asp Trp Gly Met Asn Asp Val Trp Asn Ser Ile Ile Leu Pro Arg
    1010                1015                1020

Phe Ile Arg Met Asn Gln Ile Thr Gly Lys Asp Cys Phe Thr Thr
    1025                1030                1035

Thr Asn Ala Glu Gly His Leu Ile Pro Gln Met Pro Leu Glu Leu
    1040                1045                1050

Gln Lys Gly Phe Asn Lys Lys Arg Ile Asp His Arg His His Ala
    1055                1060                1065

Met Asp Ala Ile Val Ile Ala Cys Thr Thr Arg Asp His Val Asn
    1070                1075                1080

Leu Leu Asn Asn Glu Ala Ala His Ser Lys Phe Asn Ala Thr Arg
    1085                1090                1095

Tyr Gln Leu Gln Arg Lys Leu Arg Cys Phe Glu Lys Ala Met Ile
    1100                1105                1110

Asp Gly Lys Glu Arg Glu Val Ala Lys Glu Phe Leu Lys Pro Trp
    1115                1120                1125

Asp Ser Phe Thr Met Asp Ser Lys Asn Ile Leu Glu Asn Ile Ile
    1130                1135                1140

Val Ser Phe Lys Gln Asn Gln Arg Val Ile Asn Lys Thr Thr Asn
    1145                1150                1155

Thr Phe Gln His Phe Asp Glu Asn Gly Lys Lys Thr Phe Val Lys
    1160                1165                1170

Gln Gly Lys Gly Asn Ser Trp Ala Ile Arg Lys Pro Met His Lys
    1175                1180                1185
```

```
Asp Thr Val Phe Gly Glu Ile Asn Leu Arg Lys Val     Lys Ser Val
    1190                1195                1200

Ser Leu Ser Asp Ala Ile Lys Val Pro Glu Arg Ile     Leu Asn Lys
    1205                1210                1215

Arg Ile Lys Glu Lys Ile Thr Glu Leu Lys Asn Asn     Lys Val Asp
    1220                1225                1230

Ala Lys Asn Ile Lys Lys Tyr Ile Glu Glu Tyr His     Ile Gly Gly
    1235                1240                1245

Tyr Gly Ile Asp Thr Ser Lys Ile Asp Val Phe Tyr     Phe Thr Lys
    1250                1255                1260

Glu Thr Lys Glu Arg Phe Phe Ala Thr Arg Lys Ser     Leu Asp Ser
    1265                1270                1275

Ser Phe Asn Gln Ala Lys Ile Glu Asp Ser Ile Ala     Asp Ser Gly
    1280                1285                1290

Ile Gln Lys Ile Leu Leu Ala His Leu Lys Ser Lys     Asn Gly Asp
    1295                1300                1305

Ala Glu Gln Ala Phe Ser Pro Asp Gly Ile Asp Glu     Met Asn Lys
    1310                1315                1320

Asn Ile Val Glu Leu Asn Asn Gly Lys Phe His Gln     Pro Ile Leu
    1325                1330                1335

Lys Val Arg Val Tyr Glu Lys Ala Asp Lys Phe Ala     Val Gly Gln
    1340                1345                1350

Lys Gly Asn Lys Lys Val Lys Phe Val Glu Ala Ala     Lys Gly Thr
    1355                1360                1365

Asn Leu Phe Phe Ala Val Phe Glu Lys Asp Gly Lys     Arg Ser Tyr
    1370                1375                1380

Leu Thr Ile Pro Leu Asn Val Met Ile Asp Cys Gln     Lys Lys Tyr
    1385                1390                1395

Gly Asn Gln Trp Lys Gln Asn Ile Glu Ser Tyr Leu     Lys Glu Lys
    1400                1405                1410

Asp Leu Val Glu Lys Asp Val Gln Leu Leu Phe Ile     Leu Ser Pro
    1415                1420                1425

Asn Asp Leu Val Tyr Leu Pro Thr Glu Asn Glu Leu     Lys Lys Gly
    1430                1435                1440

Ile Thr Asn Pro Asp Lys Asp Gln Ile Tyr Lys Phe     Val Ser Cys
    1445                1450                1455

Thr Ser Asn Glu Ala His Phe Ile Pro Ser Phe Val     Ala Asn Pro
    1460                1465                1470

Ile Val Gln Thr Thr Glu Leu Gly Ser Asn Asn Lys     Ala Gln Arg
    1475                1480                1485

Ala Trp Asn Asn Lys Met Ile Lys Glu Ile Cys Ile     Pro Ile Glu
    1490                1495                1500

Val Asp Arg Leu Gly Asn Ile Lys
    1505                1510

<210> SEQ ID NO 10
<211> LENGTH: 1048
<212> TYPE: PRT
<213> ORGANISM: Eubacterium rectale

<400> SEQUENCE: 10

Met Val Glu Lys Ile Leu Gly Ile Asp Leu Gly Ile Ser Ser Leu Gly
1               5                   10                  15

Trp Ala Val Val Glu Tyr Asp Lys Asp Asn Asp Glu Asn Asn Lys Ile
                20                  25                  30
```

```
Ile Asp Cys Gly Val Arg Leu Phe Thr Ala Ala Glu Thr Pro Lys Glu
         35                  40                  45

Lys Glu Ser Pro Asn Lys Ala Arg Arg Asp Ala Arg Gly Leu Arg Arg
     50                  55                  60

Val Ile Lys Arg Arg Val Arg Met Asn Thr Ile Lys Asn Leu Leu
 65              70                  75                  80

Ile Thr Tyr Lys Leu Ile Asp Lys Thr Leu Leu Asp Glu Glu Met Gly
                 85                  90                  95

Met Phe His Ser Gln Ser Asn Arg Val Asp Val Trp Lys Leu Arg His
            100                 105                 110

Asp Ala Leu Tyr His Leu Leu Ser Gly Asp Glu Leu Ala Arg Val Leu
            115                 120                 125

Ile His Ile Ala Lys His Arg Gly Tyr Lys Phe Leu Gly Asp Asp Glu
        130                 135                 140

Ser Asp Glu Glu Ser Gly Lys Val Lys Lys Ala Gly Ala Glu Leu Lys
145                 150                 155                 160

Lys Lys Phe Leu Glu Ala Gly Cys Gln Ser Val Gly Glu Trp Leu Trp
                165                 170                 175

Lys Glu Arg Gly Leu Gln Gly Lys Arg Asn Lys Ser Gly Asp Tyr
            180                 185                 190

Glu Ile Ser Ile Pro Arg Asp Phe Leu Val Glu Glu Ile Gln Arg Ile
            195                 200                 205

Phe Glu Thr Gln Gln Lys Phe Gly Ser Thr Phe Ala Thr Ser Glu Leu
    210                 215                 220

Gln Lys Ala Tyr Thr Asp Ile Ala Phe Tyr Val Lys Pro Met Gln Ser
225                 230                 235                 240

Ile Glu Asp Met Val Gly Tyr Cys Thr Phe Tyr Pro Lys Ile Lys Ser
                245                 250                 255

Lys Asn Gln Asp Gly Glu Lys Arg Ala Pro Lys Ala Ser Pro Ser Ala
            260                 265                 270

Glu Gln Phe Val Ile Leu Ser Lys Ile Phe Ser Thr Ile Val Ile Asp
        275                 280                 285

Glu Asn Lys Gln Glu Lys Lys Leu Ile Glu Leu Lys Ser Ile Glu Gln
    290                 295                 300

Leu Ile Gln Ile Ala Arg Ser Lys Glu Thr Leu Lys Tyr Lys Gln Leu
305                 310                 315                 320

Arg Lys Glu Leu Asn Leu Ala Lys Asp Ile Ser Phe Lys Ser Ile Ser
                325                 330                 335

Asp Glu Glu Lys Thr Trp Ile Asn Leu Val Gly Asn Ala Lys Phe Lys
            340                 345                 350

Lys Ile Leu Gly Leu Asn Tyr Glu Thr Phe Leu Lys Asn Thr Glu Ile
        355                 360                 365

Ser Asp Glu Ile Ala Lys Ile Leu Thr Tyr Asp Lys Thr Phe Glu Gln
    370                 375                 380

Lys Glu Thr Lys Leu Lys Asn Leu Leu Val Asn Ile Asp Trp Ile Asp
385                 390                 395                 400

Asn Asn His Ile Ala Glu Leu Ala Lys Leu Ser Phe Ser Gln Phe Asn
                405                 410                 415

Gln Leu Ser Leu Lys Ala Ile Lys Ile Ser Lys Ile Met Ile Glu
            420                 425                 430

Gly Tyr Ala Arg Tyr Asp Glu Ala Val Gln Tyr Ala Phe Glu Asn Asn
            435                 440                 445
```

```
Leu Leu Pro Lys Pro Ser His Glu Lys Ser Ile Leu Pro Pro Leu
450                 455                 460
Lys Glu Thr Asn Ile Ala Ile Leu Asn Pro Thr Val Ile Arg Ala Phe
465                 470                 475                 480
Ala Gln Phe Arg Gln Val Ala Asn Ala Leu Val Ser Lys Tyr Gly Ser
            485                 490                 495
Phe Asp Lys Val His Phe Glu Leu Ala Arg Glu Val Asn Thr Lys Glu
        500                 505                 510
Asp Arg Lys Arg Trp Glu Lys Asp Arg Asp Lys Asn Glu Lys Met His
            515                 520                 525
Arg Gln Ile Thr Glu Lys Leu Val Glu Glu Gly Val Lys Pro Ser Tyr
530                 535                 540
Lys Asn Ile Leu Lys Ser Lys Leu Arg Ser Glu Gln Lys Asp Thr Cys
545                 550                 555                 560
Pro Tyr Cys Gln Lys Asn Leu His Tyr Pro Met Ile Phe Glu Asp Gly
            565                 570                 575
Tyr Ala Glu Ile Asp His Ile Leu Pro Leu Ser Gln Ser Gln Asp Asp
            580                 585                 590
Ser Tyr Val Asn Lys Val Leu Val His Ser Ala Cys Asn Gln Asn Lys
        595                 600                 605
Lys Asn Arg Thr Pro Phe Glu Trp Phe Gln Asp Glu Lys Lys Asp Trp
        610                 615                 620
Asp Thr Phe Lys Ser Tyr Ile Leu Met Glu Ser Thr Leu Gly Glu Lys
625                 630                 635                 640
Lys Arg Asn Tyr Leu Ile Lys Glu Asn Phe Ser Asp Pro Gln Ser Arg
            645                 650                 655
Lys Glu Phe Ile Ser Arg Asn Leu Asn Asp Thr Arg Tyr Met Ser Lys
        660                 665                 670
Ala Ile Lys Thr Tyr Cys Glu Asn His Trp Lys Leu Ser His Asp Asp
        675                 680                 685
Asp Lys Leu Arg Ile Gln Val Arg Ser Gly Lys Leu Thr Ser Thr Leu
        690                 695                 700
Arg His Gln Trp Gly Leu Asp Asn Lys Asn Arg Glu Thr His Thr His
705                 710                 715                 720
His Ala Met Asp Ala Ile Met Ile Ala Phe Ser Thr Gln Gly Met Val
            725                 730                 735
Lys Lys Leu Ser Asp Tyr Phe Ala Lys Lys Glu Ala Lys Val Glu Lys
            740                 745                 750
Asp Lys Pro Val Leu Ile Thr Pro Ile Lys Gln Phe Lys Glu Ala Val
        755                 760                 765
Glu Gln Ala Thr Thr Leu Glu Arg Gln Glu Ser Ile Gln Thr Lys Ala
770                 775                 780
Gly Asp Thr Ile Thr Leu Asn Arg Leu Leu Ile Ser Arg Pro Pro Arg
785                 790                 795                 800
Ala Ser Val Thr Gly Ala Ala His Glu Gln Thr Ala Lys Pro Tyr Pro
            805                 810                 815
Arg Ile Lys Pro Ile Lys Asn Lys Tyr Lys Arg Arg Ile Pro Ile
        820                 825                 830
Asp Glu Asp Lys Phe Glu Leu Phe Arg Asn Asp Lys Val Ala Ser Gly
            835                 840                 845
Asn Asp Lys Asn Phe Tyr Asn Ser Ser Thr Ile Pro Arg Val Asp Ile
850                 855                 860
Tyr Lys Lys Asp Asp Lys Tyr His Val Val Pro Ile Tyr Leu Ser Asp
```

```
865                 870                 875                 880
Met Thr Lys Ala Glu Val Pro Asn Lys Ser Leu Gly Thr Asn Pro Glu
                885                 890                 895
Gly Met Asp Glu Lys Tyr Phe Cys Phe Ser Val Phe Lys Asn Asp Leu
                900                 905                 910
Ile Glu Leu Glu Thr Lys Ala Thr Pro Lys Lys Pro Ser Lys Lys Leu
                915                 920                 925
Leu Gly Tyr Phe Lys Gln Leu Asn Gly Ala Asn Phe Ile Leu Asn Ser
                930                 935                 940
Ile His Asn Gly Ile Ile Asp Gly Phe Val Cys Ser Pro Ile Thr Leu
945                 950                 955                 960
Phe Lys Gln Gln Lys Asp Met Cys Lys Cys Leu Pro Glu Asp Arg
                965                 970                 975
Ala Ile Gly Asn Cys Ser Gln Glu Thr Leu Glu Phe Trp Glu Ala Glu
                980                 985                 990
Asn Ile Lys Val Pro Lys Lys Asp Phe Glu Cys Asp Gln Gly Ile Lys
                995                1000                1005
Phe Ala Ile Ala Val Arg Lys Tyr Thr Ile Asp Pro Leu Gly Tyr
           1010                1015                1020
Tyr His Glu Val Lys Gly Glu Lys Leu Leu Gly Thr Ile Pro Gln
           1025                1030                1035
Gly Ala Lys Lys His Pro Lys Arg Gln Lys
           1040                1045

<210> SEQ ID NO 11
<211> LENGTH: 1337
<212> TYPE: PRT
<213> ORGANISM: Eubacterium rectale

<400> SEQUENCE: 11

Met Lys Lys Asp Tyr Val Ile Gly Leu Asp Ile Gly Thr Asn Ser Val
1               5                  10                  15
Gly Trp Ala Val Met Thr Glu Asp Tyr Gln Leu Val Lys Lys Lys Met
                20                  25                  30
Pro Ile Tyr Gly Asn Thr Glu Lys Lys Ile Lys Lys Asn Phe Trp
                35                  40                  45
Gly Val Arg Leu Phe Glu Glu Gly His Thr Ala Glu Asp Arg Arg Leu
                50                  55                  60
Lys Arg Thr Ala Arg Arg Ile Ser Arg Arg Arg Asn Arg Leu Arg
65                  70                  75                  80
Tyr Leu Gln Ala Phe Phe Glu Glu Ala Met Thr Ala Leu Asp Glu Asn
                85                  90                  95
Phe Phe Ala Arg Leu Gln Glu Ser Phe Leu Val Pro Gly Asp Lys Lys
                100                 105                 110
Trp His Arg His Pro Ile Phe Ala Lys Leu Glu Asp Glu Val Ala Tyr
                115                 120                 125
His Glu Thr Tyr Pro Thr Ile Tyr His Leu Arg Lys Lys Leu Ala Asp
                130                 135                 140
Ser Ser Glu Gln Ala Asp Leu Arg Leu Ile Tyr Leu Ala Leu Ala His
145                 150                 155                 160
Ile Val Lys Tyr Arg Gly His Phe Leu Ile Glu Gly Lys Leu Ser Thr
                165                 170                 175
Glu Asn Ile Ser Val Lys Glu Gln Phe Gln Gln Phe Met Ile Ile Tyr
                180                 185                 190
```

-continued

```
Asn Gln Thr Phe Val Asn Gly Glu Ser Arg Leu Val Ser Ala Pro Leu
            195                 200                 205

Pro Glu Ser Val Leu Ile Glu Glu Leu Thr Glu Lys Ala Ser Arg
    210                 215                 220

Thr Lys Lys Ser Glu Lys Val Leu Gln Gln Phe Pro Gln Lys Ala
225                 230                 235                 240

Asn Gly Leu Phe Gly Gln Phe Leu Lys Leu Met Val Gly Asn Lys Ala
                    245                 250                 255

Asp Phe Lys Lys Val Phe Gly Leu Glu Glu Ala Lys Ile Thr Tyr
            260                 265                 270

Ala Ser Glu Ser Tyr Glu Glu Asp Leu Glu Gly Ile Leu Ala Lys Val
            275                 280                 285

Gly Asp Glu Tyr Ser Asp Val Phe Leu Ala Ala Lys Asn Val Tyr Asp
    290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                    325                 330                 335

Asp Leu Lys Asn Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
            355                 360                 365

Ile Ala His Ala Gly Lys Val Ser Gln Leu Lys Phe Tyr Gln Tyr Val
            370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
                    405                 410                 415

Val Ile Pro His Gln Ile His Leu Ala Glu Leu Gln Ala Ile Ile His
                    420                 425                 430

Arg Gln Ala Ala Tyr Tyr Pro Phe Leu Lys Glu Asn Gln Lys Lys Ile
            435                 440                 445

Glu Gln Leu Val Thr Phe Arg Ile Pro Tyr Tyr Val Gly Pro Leu Ser
    450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
            485                 490                 495

Ala Thr Ala Phe Ile Glu Arg Met Thr Asn Phe Asp Thr Tyr Leu Pro
            500                 505                 510

Ser Glu Lys Val Leu Pro Lys His Ser Leu Leu Tyr Glu Lys Phe Met
    515                 520                 525

Val Phe Asn Glu Leu Thr Lys Ile Ser Tyr Thr Asp Arg Gly Ile
    530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Asp Ile Ile Gln Phe Tyr
                565                 570                 575

Arg Asn Glu Tyr Asn Thr Glu Ile Val Thr Leu Ser Gly Leu Glu Glu
            580                 585                 590

Asp Gln Phe Asn Ala Ser Phe Ser Thr Tyr Gln Asp Leu Leu Lys Cys
            595                 600                 605

Gly Leu Thr Arg Ala Glu Leu Asp His Pro Asp Asn Ala Glu Lys Leu
```

-continued

```
                610                 615                 620
Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Glu Glu Val Leu
                645                 650                 655

Lys Lys Leu Glu Arg Lys His Tyr Thr Gly Trp Gly Arg Leu Ser Lys
                660                 665                 670

Lys Leu Ile Asn Gly Ile Tyr Asp Lys Glu Ser Gly Lys Thr Ile Leu
                675                 680                 685

Asp Tyr Leu Ile Lys Asp Asp Gly Val Ser Lys His Tyr Asn Arg Asn
690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
                725                 730                 735

Asn Glu Leu Ala Gly Ser Pro Ala Ile Lys Lys Gly Ile Tyr Gln Ser
                740                 745                 750

Leu Lys Ile Val Asp Glu Leu Val Ala Ile Met Gly Tyr Ala Pro Lys
                755                 760                 765

Arg Ile Val Val Glu Met Ala Arg Glu Asn Gln Thr Thr Ser Thr Gly
770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
                805                 810                 815

Leu Arg Asp Thr Arg Leu Phe Leu Tyr Tyr Met Gln Asn Gly Lys Asp
                820                 825                 830

Met Tyr Thr Gly Asp Glu Leu Ser Leu His Arg Leu Ser His Tyr Asp
                835                 840                 845

Ile Asp His Ile Ile Pro Gln Ser Phe Met Lys Asp Asp Ser Leu Asp
850                 855                 860

Asn Leu Val Leu Val Gly Ser Thr Glu Asn Arg Gly Lys Ser Asp Asp
865                 870                 875                 880

Val Pro Ser Lys Glu Val Val Lys Lys Met Lys Ala Tyr Trp Glu Lys
                885                 890                 895

Leu Tyr Ala Ala Gly Leu Ile Ser Gln Arg Lys Phe Gln Arg Leu Thr
                900                 905                 910

Lys Gly Glu Gln Gly Gly Leu Thr Leu Glu Asp Lys Ala His Phe Ile
                915                 920                 925

Gln Arg Gln Leu Val Glu Thr Arg Gln Ile Thr Lys Asn Val Ala Gly
                930                 935                 940

Ile Leu Asp Gln Arg Tyr Asn Ala Lys Ser Lys Glu Lys Lys Val Gln
945                 950                 955                 960

Ile Ile Thr Leu Lys Ala Ser Leu Thr Ser Gln Phe Arg Ser Ile Phe
                965                 970                 975

Gly Leu Tyr Lys Val Arg Glu Val Asn Asp Tyr His His Gly Gln Asp
                980                 985                 990

Ala Tyr Leu Asn Cys Val Val Ala Thr Thr Leu Leu Lys Val Tyr Pro
                995                 1000                1005

Asn Leu Ala Pro Glu Phe Val Tyr Gly Glu Tyr Pro Lys Phe Gln
                1010                1015                1020

Ala Phe Lys Glu Asn Lys Ala Thr Ala Lys Ala Ile Ile Tyr Thr
                1025                1030                1035
```

```
Asn Leu Leu Arg Phe Phe Thr Glu Asp Glu Pro Arg Phe Thr Lys
    1040                1045                1050

Asp Gly Glu Ile Leu Trp Ser Asn Ser Tyr Leu Lys Thr Ile Lys
    1055                1060                1065

Lys Glu Leu Asn Tyr His Gln Met Asn Ile Val Lys Lys Val Glu
    1070                1075                1080

Val Gln Lys Gly Gly Phe Ser Lys Glu Ser Ile Lys Pro Lys Gly
    1085                1090                1095

Pro Ser Asn Lys Leu Ile Pro Val Lys Asn Gly Leu Asp Pro Gln
    1100                1105                1110

Lys Tyr Gly Gly Phe Asp Ser Pro Val Val Ala Tyr Thr Val Leu
    1115                1120                1125

Phe Thr His Glu Lys Gly Lys Lys Pro Leu Ile Lys Gln Glu Ile
    1130                1135                1140

Leu Gly Ile Thr Ile Met Glu Lys Thr Arg Phe Glu Gln Asn Pro
    1145                1150                1155

Ile Leu Phe Leu Glu Glu Lys Gly Phe Leu Arg Pro Arg Val Leu
    1160                1165                1170

Met Lys Leu Pro Lys Tyr Thr Leu Tyr Glu Phe Pro Glu Gly Arg
    1175                1180                1185

Arg Arg Leu Leu Ala Ser Ala Lys Glu Ala Gln Lys Gly Asn Gln
    1190                1195                1200

Met Val Leu Pro Glu His Leu Leu Thr Leu Leu Tyr His Ala Lys
    1205                1210                1215

Gln Cys Leu Leu Pro Asn Gln Ser Glu Ser Leu Ala Tyr Val Glu
    1220                1225                1230

Gln His Gln Pro Glu Phe Glu Glu Ile Leu Glu Arg Val Val Asp
    1235                1240                1245

Phe Ala Glu Val His Thr Leu Ala Lys Ser Lys Val Gln Gln Ile
    1250                1255                1260

Val Lys Leu Phe Glu Ala Asn Gln Thr Ala Asp Val Lys Glu Ile
    1265                1270                1275

Ala Ala Ser Phe Ile Gln Leu Met Gln Phe Asn Ala Met Gly Ala
    1280                1285                1290

Pro Ser Thr Phe Lys Phe Phe Gln Lys Asp Ile Glu Arg Ala Arg
    1295                1300                1305

Tyr Thr Ser Ile Lys Glu Ile Phe Asp Ala Thr Ile Ile Tyr Gln
    1310                1315                1320

Ser Thr Thr Gly Leu Tyr Glu Thr Arg Arg Lys Val Val Asp
    1325                1330                1335

<210> SEQ ID NO 12
<211> LENGTH: 1087
<212> TYPE: PRT
<213> ORGANISM: Eubacterium rectale

<400> SEQUENCE: 12

Met Ala Leu Asn Pro Pro Leu Pro Tyr Thr Leu Gly Leu Asp Ile Gly
1               5                   10                  15

Met Ala Ser Val Gly Ala Ala Leu Leu Thr Glu Gln Arg Ile Leu Gly
                20                  25                  30

Leu His Val Arg Ala Phe Asp Lys Ala Glu Thr Ala Lys Glu Gly Asp
            35                  40                  45

Pro Leu Asn Lys Thr Arg Arg Glu Ser Arg Leu Thr Arg Arg Arg Ile
```

-continued

```
                50                  55                  60
Arg Arg Arg Ala His Arg Leu Leu Arg Leu Ala Arg Leu Phe Lys Arg
65                  70                  75                  80

Thr Gly Leu Ile Ala Ala His Pro Glu Ala Phe Ala Leu Pro Gly
                85                  90                  95

Ile Ser Pro Trp Asp Leu Arg Ala Asp Gly Leu Asn Arg Leu Leu Thr
                100                 105                 110

Pro Ala Glu Trp Ala Ala Val Leu Tyr His Leu Val Lys His Arg Gly
                115                 120                 125

Phe Gln Ser Thr Arg Lys Ser Glu Ala Lys Glu Asp Glu Lys Ala Gly
                130                 135                 140

Gln Met Leu Ser Gly Val Ser Ala Asn Gln Gln Arg Met Lys Glu Lys
145                 150                 155                 160

Gly Trp Arg Thr Val Gly Glu Met Ala Ala Arg Asp Glu Ala Phe Ala
                165                 170                 175

Glu Ala Lys Arg Asn Lys Gly Gly Ala Tyr Thr His Thr Phe Ala Arg
                180                 185                 190

Thr Asp Leu Val Ala Glu Leu Lys Leu Leu Phe Lys Gln Gln Ala Gly
                195                 200                 205

Phe Gly Asn Pro His Val Gly Val Asp Phe Glu Asn Asp Val Glu Gln
                210                 215                 220

Leu Leu Leu Ala Arg Arg Pro Ala Leu Ala Gly Asp Ala Leu Leu Lys
225                 230                 235                 240

Leu Val Gly Lys Cys Pro Phe Glu Pro Thr Glu Tyr Arg Ala Pro Lys
                245                 250                 255

Ala Ser Tyr Ser Ala Glu Arg Phe Val Trp Leu Thr Lys Leu Asn Asn
                260                 265                 270

Leu Arg Ile Ser Glu Val Gly Glu Gln Arg Ala Leu Thr Ala Gly Glu
                275                 280                 285

Arg Gln Ile Leu Leu Asn Gln Pro Tyr Leu Leu Ala Lys Phe Thr Tyr
                290                 295                 300

Lys Gln Ala Arg Gln Arg Leu Ser Leu Ala Asp Thr Ala Lys Phe Thr
305                 310                 315                 320

Val Leu Thr Tyr Arg Gly Asp Lys Asp Pro Glu Ser Thr Thr Phe Phe
                325                 330                 335

Glu Ala Lys Ala Tyr His Glu Leu Arg Lys Ala Tyr Glu Lys Ala Gly
                340                 345                 350

Leu Glu Ser Arg Trp Gln Arg Asp Ala Leu Asp Pro Thr Arg Leu Asp
                355                 360                 365

Arg Leu Ala Trp Ala Leu Thr Cys Tyr Lys Thr Asp Asp Asp Ile Arg
                370                 375                 380

Ala His Leu Ala Glu His Gly Val Glu Pro Glu Ile Thr Glu Ala Val
385                 390                 395                 400

Leu Gly Glu Ser Phe Asp Lys Phe Val Gly Leu Ser Leu Lys Ala Leu
                405                 410                 415

Gly Lys Ile Leu Pro Phe Met Glu Gln Gly Gln Arg Tyr Asp Glu Ala
                420                 425                 430

Val Gln Ser Ala Gly Tyr Ala His His Ser Gln Leu Asn Arg Asp Thr
                435                 440                 445

Thr Lys Asn Gln Tyr Leu Pro Pro Asp Lys Asp Gln Ile Arg Asn
                450                 455                 460

Pro Val Val Tyr Arg Ala Leu Asn Gln Ala Arg Lys Leu Val Asn Ala
465                 470                 475                 480
```

```
Ile Val Arg Glu Tyr Gly Ser Pro Ala Ala Ile His Ile Glu Leu Ala
                485                 490                 495

Arg Asp Leu Ser Lys Pro Met Asp Glu Arg Arg Lys Ile Glu Arg Glu
                500                 505                 510

Gln Lys Glu Phe Gln Glu Arg Lys Ala Lys Asp Arg Glu Ala Phe Ile
                515                 520                 525

Glu Gln Phe Ser Phe Asp Pro Lys Gly Leu Asp Leu Gln Lys Tyr Arg
                530                 535                 540

Leu Tyr Arg Glu Gln Met Ser Gln Cys Ala Tyr Ser Gln Lys Ala Ile
545                 550                 555                 560

Asp Val Thr Arg Leu Phe Glu Pro Gly Tyr Ala Glu Ile Asp His Ala
                565                 570                 575

Leu Pro Tyr Ser Arg Ser Tyr Asp Asp Gly Gln Asn Asn Lys Val Leu
                580                 585                 590

Val Leu Thr Ala Glu Asn Arg Asn Lys Gly Asn Arg Thr Pro Tyr Glu
                595                 600                 605

Tyr Leu Asp Gly Ala Ser Asp Ser Pro Gln Trp Gln Arg Phe Glu Ala
                610                 615                 620

Trp Val Leu Gln Asn Lys Ala Tyr Arg Arg Ala Lys Asp Arg Leu
625                 630                 635                 640

Leu Arg Lys His Phe Gly Glu Asp Glu Ala Glu Gly Phe Arg Glu Arg
                645                 650                 655

Asn Leu Ile Asp Thr Arg Tyr Ile Cys Arg Ala Phe Lys Thr Met Val
                660                 665                 670

Glu Asp His Leu Gln Trp His Ala Asp Ser Asp Ala Lys Asn Arg Cys
                675                 680                 685

Val Val Val Ala Gly Gln Leu Thr Ser Leu Leu Arg Ala Arg Trp Gly
                690                 695                 700

Leu Ile Lys Val Arg Glu Asn Gly Asp Leu His His Ala Leu Asp Ala
705                 710                 715                 720

Ala Val Ile Ala Ala Ala Asn Arg Ser Leu Val Lys Arg Met Ala Asp
                725                 730                 735

Tyr Ser Lys Arg Asn Glu Leu Ala Gln Val Arg Asp Arg Tyr Ile Asp
                740                 745                 750

Pro Ala Thr Gly Glu Ile Leu Asp Ile Ala Ala Met Arg Gln Val Glu
                755                 760                 765

Glu His Phe Pro Ser Pro Trp Pro His Phe Arg Ser Glu Leu Leu Ala
                770                 775                 780

Trp Leu Ser Pro Asn Pro Ala His Gly Leu Asp Gly Leu Ala His Tyr
785                 790                 795                 800

Pro Pro Glu Glu Leu Glu His Leu Arg Pro Met Arg Val Ser Arg Ala
                805                 810                 815

Pro Thr Arg Arg Gly Leu Gly Ala Ala His Gln Glu Thr Ile Arg Ser
                820                 825                 830

Val Gly Arg Glu Gly Arg Leu Leu Ala Asp Gly Gln Ser Ala Val Lys
                835                 840                 845

Thr Pro Leu Thr Ala Ile Lys Leu Lys Asp Leu Glu Asn Ile Val Gly
                850                 855                 860

Tyr Ser His Ser His Asn His Ala Met Ile Glu Ala Ile Arg Lys Arg
865                 870                 875                 880

Leu Glu Thr Asn Gly Asn Asp Gly Ala Lys Ala Phe Lys Met Pro Leu
                885                 890                 895
```

```
Phe Lys Pro Ser Ala Thr Asn Gly Tyr Asp Ala Asp Lys Ser His Val
                900                 905                 910

Gly Glu Thr Asp Gln Arg Ala Pro Gln Ile Arg Ser Val Lys Leu Leu
            915                 920                 925

Ala Thr Gln Lys Ser Gly Ile Pro Ile Arg Lys Gly Ile Ala Asn Asn
        930                 935                 940

Gly Ser Met Leu Arg Val Asp Val Phe Gly Lys Gly Lys Phe Tyr
945                 950                 955                 960

Ala Val Pro Val Tyr Val Ala Asp Ala Ala Arg Ala Glu Leu Pro Tyr
                965                 970                 975

Arg Ala Val Ala Ala Phe Lys Pro Glu Asn Glu Trp Pro Glu Met Asp
            980                 985                 990

Glu Lys Gln Phe Met Phe Ser Leu His Pro Asn Asp Trp Val Thr Val
        995                 1000                1005

Lys Leu Lys Ala Glu Thr Ile Ser Gly Tyr Phe Ala Gly Met Asp
    1010                1015                1020

Arg Ser Thr Gly Ala Ile Ser Val Trp Ala His Asp Arg Asn Gln
    1025                1030                1035

Ser Ile Gly Lys Asp Gly Gln Trp Arg Gly Val Gly Met Lys Thr
    1040                1045                1050

Ala Leu Ala Val Glu Lys Tyr His Val Asp Leu Leu Gly Asn Leu
    1055                1060                1065

His Arg Val His Thr Glu Met Arg Leu Pro Leu His Gly Ser Lys
    1070                1075                1080

Ala Ser Lys Asp
    1085

<210> SEQ ID NO 13
<211> LENGTH: 1123
<212> TYPE: PRT
<213> ORGANISM: Eubacterium rectale

<400> SEQUENCE: 13

Met Ser Lys Ile Leu Gly Leu Asp Leu Gly Thr Asn Ser Ile Gly Trp
1               5                   10                  15

Ala Leu Ile Asp Asp Asn Gln Asn Arg Ile Leu Gly Val Gly Ser Arg
                20                  25                  30

Ile Phe Pro Met Gly Val Glu Asn Leu Gly Asp Gly Asp Gly Glu Val
            35                  40                  45

Ser Lys Asn Ala Ser Arg Thr Gly Ala Arg Gly Val Arg Arg Gln Phe
        50                  55                  60

Phe Arg Arg Arg Leu Arg Lys Lys Val Leu Leu Lys Ala Leu Ser Glu
65                  70                  75                  80

His Asn Met Cys Pro Met Val Thr Ile Asp Phe Glu Asp Trp Lys Lys
                85                  90                  95

Ser Lys Gln Phe Pro Ser Glu Lys Leu Ser Asn Trp Phe Ser Leu Asn
            100                 105                 110

Pro Tyr Glu Leu Arg His Lys Ala Leu Ser Glu Lys Leu Thr Leu Glu
        115                 120                 125

Glu Ile Gly Arg Ile Leu Tyr His Leu Ile Gln Arg Arg Gly Phe Leu
    130                 135                 140

Ser Asn Ser Arg Lys Gly Gly Ser Asp Asp Gly Ala Ile Phe Lys Gly
145                 150                 155                 160

Asn Pro Lys Glu Gly Lys Ile Gly Ile Thr Glu Thr Gln Glu Ser Ile
                165                 170                 175
```

```
Gln Asp Lys Ser Leu Gly Ser Tyr Leu Phe Glu Ile Tyr Pro Lys Glu
            180                 185                 190

Asn Gln Pro Phe Glu Gly Gly Leu Glu Arg Ile Arg Asn Arg Tyr Thr
        195                 200                 205

Ile Arg Lys Met Tyr Val Asp Glu Phe Glu Leu Ile Trp Asn Lys Gln
    210                 215                 220

Ser Gln Phe His Ser Ser Leu Asn Asp Asp Leu Lys Thr Leu Leu Gly
225                 230                 235                 240

Gly Arg Lys Leu Asp Gly Tyr Lys Glu Asp Gly Ile Leu Phe His Gln
                245                 250                 255

Arg Pro Leu Arg Ser Gln Lys His Leu Val Gly Asn Cys Ser Phe Glu
            260                 265                 270

Pro Thr Lys Thr Lys Cys Pro Ile Ser Ala Ile Pro Phe Glu Met Phe
        275                 280                 285

Arg Ile Trp Gln Trp Val Asn Thr Leu Glu Tyr Asn Gly Lys Lys Ile
    290                 295                 300

Thr Gln Glu Glu Lys Glu Lys Ile Val Glu Phe Met Cys Ala Asn Glu
305                 310                 315                 320

Lys Pro Asp Phe Lys Arg Ile Arg Lys Val Ile Gly Lys Glu Ser Ala
                325                 330                 335

Glu Phe Lys Phe Asn Tyr Lys Asp Asp Asp Lys Ile Val Gly Thr His
            340                 345                 350

Thr Ile Ser Asn Leu Ser Asn Lys Lys Phe Phe Gly Lys Ala Trp Phe
        355                 360                 365

Asp Phe Ser Glu Lys Glu Gln Glu Asp Ile Trp His Val Leu Tyr Phe
    370                 375                 380

Phe Asp Ser Lys Ser Asn Leu Lys Asp Tyr Ala Ile Lys His Trp Asn
385                 390                 395                 400

Phe Asn Glu Ala Gln Ala Ser Asp Val Ser Lys Phe Asn Val Lys Asp
                405                 410                 415

Gly Tyr Ser Ser Leu Ser Arg Lys Ala Ile Ser Asn Ile Leu Pro Phe
            420                 425                 430

Leu Lys Leu Gly Phe Thr Tyr Asp Val Ser Val Leu Gly Gly Ile
        435                 440                 445

Lys Asn Val Phe Gly Ser Glu Trp Glu Lys Leu Ser Glu Glu Lys Arg
    450                 455                 460

Asn Tyr Leu Ile Asp Asn Val Glu Gly Ile Val Arg Ser Lys Ile Lys
465                 470                 475                 480

Gly Gly Phe Ile Asp Val Ile Lys Gly Ile Leu Arg Asn Asp Tyr Ser
                485                 490                 495

Ile Ser Asp Asn Gln Leu Arg Lys Leu Tyr His His Ser Ala Thr Ile
            500                 505                 510

Asp Ala Val Glu Leu Leu Asp Lys Leu Pro Val Gly Lys Glu Ala Asp
        515                 520                 525

Lys Glu Ile Gln Ala Ile Arg Asn Pro Ile Val Ile Thr Ala Leu Phe
    530                 535                 540

Glu Leu Arg Lys Leu Val Asn Glu Leu Ile Asp Glu His Gly Lys Leu
545                 550                 555                 560

Asp Glu Ile Lys Val Glu Met Ala Arg Asp Leu Lys Ile Ser Lys Ser
                565                 570                 575

Gln Arg Asn Lys Ile Arg Arg Glu Gln Lys Arg Leu Gly Arg Glu Asn
            580                 585                 590
```

```
Asp Arg Val Lys Asp Arg Leu Val Glu Asn Asn Ile Arg Ile Thr His
            595                 600                 605

Asp Asn Ile Leu Leu Tyr Lys Leu Trp Glu Cys Lys Lys Thr Cys
610                 615                 620

Pro Tyr Thr Gly Lys Pro Ile Ser Val Thr Gln Leu Phe Ser Gly Glu
625                 630                 635                 640

Val Gln Ile Glu His Ile His Pro Trp Ser Arg Ser Leu Asn Asp Ser
                645                 650                 655

Phe Ser Asn Lys Thr Leu Cys Tyr Ala Asp Glu Asn Arg Lys Lys Gly
            660                 665                 670

Asn Leu Thr Pro Phe Glu Phe Tyr Gly Ser Asp Glu Thr Asn Trp Ser
        675                 680                 685

Ala Ile Lys Glu Arg Ala Leu Lys Leu Phe Ser Asp Thr Lys Glu Tyr
    690                 695                 700

Pro Asn Ala Tyr Gln Lys Phe Lys Arg Phe Val Gln Val Lys Phe Asp
705                 710                 715                 720

Asp Asp Phe Ser Ser Arg Gln Leu Asn Asp Thr Arg Tyr Ile Ser Lys
                725                 730                 735

Glu Ala Lys Asn Tyr Leu Ser Arg Ile Cys Lys Asn Val Ile Val Ser
            740                 745                 750

Pro Gly Gln Ala Thr Ser Asn Leu Arg Gln Lys Trp Gly Met Asn Asn
        755                 760                 765

Ile Leu Ser Asp Glu Asn Glu Lys Thr Arg Asp Asp His Arg His His
    770                 775                 780

Ala Val Asp Ala Leu Val Met Ala Cys Thr Lys Val Ser Tyr Val Gln
785                 790                 795                 800

Glu Leu Ala Lys Trp Asn Arg Tyr Asn Arg Asn Ser Glu Leu Lys Asn
                805                 810                 815

Phe Pro Leu Pro Trp Glu Thr Phe Arg Phe Asp Ala Glu Lys Ala Val
            820                 825                 830

Glu Lys Ile Leu Ile Ser His Lys Lys Val Ser Asn Asp Ile Thr Val
        835                 840                 845

Arg Thr His Ile Thr Glu Lys Asn Gly Ile Lys Tyr Lys Asn Val Gly
    850                 855                 860

Val Ala Ala Arg Gly Gln Leu His Lys Glu Thr Val Phe Gly Lys Arg
865                 870                 875                 880

Thr Phe Asn Gly Glu Glu Ala Tyr His Val Arg Lys Ser Ile Asp Ser
                885                 890                 895

Leu Glu Thr Ala Lys Gln Ile Glu Lys Val Val Asp Glu Thr Ile Lys
            900                 905                 910

Gln Leu Ile Leu Lys Arg Val Asn Glu Leu Gly Gly Phe Val Lys Asp
        915                 920                 925

Lys Val Pro Ala Asn Thr Phe Phe Ile Val Asp Glu Lys Gly Ile Lys
    930                 935                 940

Gln Pro Gln Leu Phe Leu Pro Asn Lys Asn Gly Gln Pro Ile Pro Val
945                 950                 955                 960

Leu Lys Val Arg Val Lys Glu Ser Val Gly Arg Ala Glu Gln Leu Lys
                965                 970                 975

Ala Asn Val Asn Gln Trp Val Asn Pro Arg Asn Asn His His Val Leu
            980                 985                 990

Ile Tyr Lys Asp Glu His Gly Asn  Leu Lys Glu Asp Val  Val Thr Phe
        995                 1000                1005

Trp Thr Val Val Glu Arg Lys  Arg Thr Gly Gln Ser  Ile Tyr Gln
```

Leu Pro Ile Asn Gly Lys Glu Ile Ile Thr Ser Leu His Thr Asn
    1025                1030                1035

Asp Met Phe Ile Ile Gly Leu Asn Glu Asp Glu Ile Asn Trp Glu
    1040                1045                1050

Leu Ile Asp Phe Asn Leu Ile Asn His His Leu Tyr Arg Val Gln
    1055                1060                1065

Lys Thr Ser Lys Lys Glu Lys Ser Phe Glu Phe Asn Phe Arg Leu
    1070                1075                1080

Gly Ile Ala Ser Ser Leu Asp Asn Lys Ser Gln Glu Ile Ser Ile
    1085                1090                1095

Gln Ser Phe Lys Lys Trp Ile Glu Leu Asn Pro Ile Lys Val Lys
    1100                1105                1110

Ile Ser Val Ser Gly Lys Ile Gln Lys Val
    1115                1120

<210> SEQ ID NO 14
<211> LENGTH: 1322
<212> TYPE: PRT
<213> ORGANISM: Artificial Sequence
<220> FEATURE:
<223> OTHER INFORMATION: Artificially mutated sequence

<400> SEQUENCE: 14

Met Lys Asn Thr Asn Glu Asp Tyr Tyr Leu Gly Leu Ala Ile Gly Thr
1               5                   10                  15

Asp Ser Val Gly Trp Ala Val Thr Asp Lys Glu Tyr Asn Ile Leu Glu
            20                  25                  30

Phe Arg Arg Lys Pro Met Trp Gly Ile His Leu Phe Glu Gly Gly Ser
        35                  40                  45

Thr Ala Gln Lys Thr Arg Val Tyr Arg Thr Ser Arg Arg Arg Leu Lys
    50                  55                  60

Arg Arg Ala Glu Arg Ile Ala Leu Leu Arg Asp Ile Phe Ser Glu Glu
65                  70                  75                  80

Ile Gly Lys Val Asp Pro Gly Phe Phe Glu Arg Leu Asp Glu Ser Asp
                85                  90                  95

Leu His Leu Glu Asp Arg Val Thr Ser Gln Lys Asn Ser Leu Phe Asp
            100                 105                 110

Asp Pro Glu Phe Asn Asp Lys Asp Leu His Lys Arg Phe Pro Thr Ile
        115                 120                 125

Tyr His Leu Arg Arg His Leu Met His Ser Asn Arg Lys Glu Asp Ile
    130                 135                 140

Arg Leu Ile Tyr Leu Ala Ala His His Ile Ile Lys Phe Arg Gly His
145                 150                 155                 160

Phe Leu Tyr Lys Gly Ile Gly Asp Glu Glu Ile Pro Ser Phe Glu Ile
                165                 170                 175

Val Leu Asn Ser Leu Ile Asp Asn Leu Arg Asp Glu Tyr Gly Met Glu
            180                 185                 190

Leu Glu Val Ser Asp Arg Asp Leu Val Lys Ala Leu Leu Ser Asp Phe
        195                 200                 205

Ser Ile Gly Ile Arg Glu Lys Ser Arg Glu Leu Ser Ser Cys Leu Asn
    210                 215                 220

Ala Glu Ser Glu Asn Glu Lys Ala Leu Val Asp Phe Ile Ser Gly Lys
225                 230                 235                 240

Lys Thr Asn Met Lys Lys Leu Phe Asp Asp Glu Ala Leu Asp Lys Met

```
                    245                 250                 255
        Ser Phe Ser Leu Arg Asp Ser Gly Phe Glu Asp Gln Leu Arg Glu Asn
                        260                 265                 270

Glu Gly Val Leu Gly Pro Glu Arg Val His Thr Leu Glu Leu Ser Arg
                        275                 280                 285

Gln Ile Phe Glu Trp Ala Arg Leu Ser Ser Ile Leu Lys Asp Ser Asp
                        290                 295                 300

Ser Ile Ser Glu Ala Lys Ile Lys Asp Tyr Asp Gln His Arg Glu Asp
        305                 310                 315                 320

Leu Arg Met Leu Lys Arg Ala Val Lys Tyr Ala Pro Asp Lys Tyr
                        325                 330                 335

Ser Glu Val Phe Lys Ser Lys Glu His Thr Gly Asn Tyr Cys Ser Tyr
                        340                 345                 350

Val Tyr Val Cys Gly Lys Gly Leu Pro Asp Lys Lys Cys Ser Thr Glu
                        355                 360                 365

Glu Phe Gln Lys Tyr Leu Lys Lys Ile Leu Asp Asp Ser Gly Val Arg
                        370                 375                 380

Asp Asp Glu Glu Phe Lys Thr Leu Ile Gln Arg Leu Asp Ala Gly Ile
        385                 390                 395                 400

Leu Cys Pro Lys Gln Arg Thr Gly Glu Asn Ser Val Ile Pro Tyr Ser
                        405                 410                 415

Val His Arg Lys Glu Leu Ile Gly Ile Leu Asn Asn Ala Ala Glu His
                        420                 425                 430

Tyr Pro Ser Leu Ser Arg Lys Gly Glu Asp Gly Phe Ser Ser Ile Asp
                        435                 440                 445

Lys Ile Leu Met Leu Glu Glu Phe Arg Ile Pro Tyr Tyr Val Gly Pro
        450                 455                 460

Leu Asp Asp Arg Ser Ser Arg Ser Trp Leu Ile Arg Asn Ser Phe Glu
        465                 470                 475                 480

Ala Ile Thr Pro Trp Asn Phe Asn Glu Ile Val Asp Glu Asp Glu Thr
                        485                 490                 495

Ser Glu Arg Phe Ile Gly Asn Leu Thr Ser Met Cys Thr Tyr Leu Gly
                        500                 505                 510

Gly Glu Lys Val Leu Pro Lys Asn Ser Leu Leu Tyr Ser Arg Phe Met
                        515                 520                 525

Leu Tyr Asn Glu Ile Asn Asn Leu Arg Val Gly Gly Glu Lys Ile Pro
                        530                 535                 540

Ala Ala Leu Lys Asn Lys Met Val Ser Glu Leu Phe Ala Asn Arg Ala
        545                 550                 555                 560

Thr Ser Ser Lys Val Thr Leu Lys Glu Leu Lys Ala Phe Leu Lys Gly
                        565                 570                 575

Glu Gly Val Leu Thr Asp Ala Asp Glu Ile Ser Gly Ile Asp Asp Gly
                        580                 585                 590

Val Lys Ser Thr Leu Arg Ser Glu Ile Leu Ile Arg Lys Ile Ile Gly
                        595                 600                 605

Asp Lys Ile Ser Asp Arg Glu Met Ala Glu Ile Val Arg Ile Leu
                        610                 615                 620

Thr Val Phe Gly Asp Glu Arg Arg Ser Lys Ala Lys Leu Lys Lys
        625                 630                 635                 640

Glu Phe Ser Asp Lys Leu Thr Glu Lys Glu Ile Glu Lys Leu Ser Ser
                        645                 650                 655

Leu Lys Phe Asp Gly Trp Gly Arg Leu Ser Glu Lys Phe Leu Thr Gly
                        660                 665                 670
```

```
Leu Arg Gln Glu Val Asn Gly Arg Ser Met Ser Ile Ile Glu Ile Leu
        675                 680                 685

Glu Asp Thr Asn Tyr Asn Leu Gln Glu Thr Leu Ser Lys Tyr Ser Phe
690                 695                 700

Asn Glu Ile Ile Asp Ser Tyr Asn Glu Val Leu Thr Ser Gly Pro Arg
705                 710                 715                 720

Ser Ile Ser Tyr Asp Ile Leu Lys Asp Ser Tyr Leu Ser Pro Ala Val
                725                 730                 735

Lys Arg Gly Val Trp Arg Ala Leu Ser Val Val Lys Asp Ile Leu Lys
                740                 745                 750

Ala Val Gly Arg Pro Pro Lys Lys Ile Phe Val Glu Thr Thr Arg Glu
                755                 760                 765

Glu Arg Glu Lys Lys Arg Thr Glu Ser Arg Lys Asp Ala Leu Met Tyr
770                 775                 780

Leu Tyr Lys Ser Cys Lys Glu Thr Glu Trp Glu Lys Arg Leu Asp Ser
785                 790                 795                 800

Val Glu Glu Ser Ser Leu Arg Asn Arg Ser Leu Tyr Leu Tyr Tyr Thr
                805                 810                 815

Gln Leu Gly Lys Cys Met Tyr Cys Gly Lys Asn Ile Asp Ile Gly Glu
                820                 825                 830

Leu Asn Thr Asp Leu Ala Asp Arg Asp His Ile Tyr Pro Gln Ser Lys
                835                 840                 845

Thr Lys Asp Asp Ser Ile Arg Asn Asn Leu Val Leu Val Cys Arg Gly
850                 855                 860

Cys Asn Gln Ala Lys Gly Asp Arg Tyr Pro Leu Pro Gln Glu Trp Val
865                 870                 875                 880

Ser Arg Met His Ala Phe Trp Thr Met Leu Lys Asp Lys Gly Tyr Ile
                885                 890                 895

Ser Ser Glu Lys Tyr Arg Arg Leu Thr Arg Arg Gly Glu Leu Thr Glu
                900                 905                 910

Glu Glu Phe Gly Ala Phe Ile Asn Arg Gln Leu Val Glu Thr Ser Gln
                915                 920                 925

Ser Ala Lys Ala Val Ile Thr Val Leu Lys Asn Ala Phe Lys Asp Ser
                930                 935                 940

Asp Ile Val Tyr Val Lys Gly Ser Asn Val Ser Asp Phe Arg Ser Ser
945                 950                 955                 960

Tyr Asn Phe Ile Lys Cys Arg Ser Val Asn Asp Tyr His Ala Lys
                965                 970                 975

Asp Ala Tyr Leu Asn Ile Val Val Gly Asn Val Leu Asp Thr Lys Phe
                980                 985                 990

Thr Lys Asn Pro Ser Tyr Val Leu Lys Asn Arg Glu Gln Tyr Asn Ile
                995                 1000                1005

Gly Arg Met Tyr Asp Arg Asn Val Ser Arg Phe Gly Val Asp Ala
        1010                1015                1020

Trp Val Ala Gly Asp Arg Gly Ser Ile Ala Thr Val Arg Lys Tyr
        1025                1030                1035

Met Arg Arg Asn Asn Ile Leu Phe Thr Arg Tyr Ala Thr Lys Ser
        1040                1045                1050

Lys Gly Ala Leu Phe Lys Glu Thr Val His Arg Lys Lys Glu Gly
        1055                1060                1065

Leu Phe Glu Arg Lys Lys Gly Leu Glu Thr Glu Lys Tyr Gly Gly
        1070                1075                1080
```

-continued

Tyr Ser Asp Ile Ser Thr Ser Tyr Leu Thr Leu Leu Glu Tyr Asp
    1085                1090                1095

Lys Gly Lys Lys Arg Ile Arg Ser Leu Glu Ile Val Pro Thr Tyr
    1100                1105                1110

Phe Ala Asn Thr Arg Pro Lys Glu Glu Asp Val Ile Arg Phe Phe
    1115                1120                1125

Ser Glu Thr Arg Gly Leu Ala Asn Val Arg Val Met Pro Glu
    1130                1135                1140

Val Arg Met Lys Ser Leu Phe Glu Tyr Arg Gly Phe Arg Phe His
    1145                1150                1155

Val Thr Gly Ser Asn Gly Lys Gly Arg Phe Trp Ile Ser Ser Ala
    1160                1165                1170

Ile Gln Leu Leu Leu Pro Glu Asn Leu Tyr Ala Tyr Cys Lys Ser
    1175                1180                1185

Ile Glu Asn Asn Glu Lys Asp Ser Gln Arg Arg Ser Glu Lys Pro
    1190                1195                1200

Leu Gln Asn Tyr Gly Phe Ser Ser Glu Met Asn Ile Glu Leu Phe
    1205                1210                1215

Lys Cys Leu Met Asp Lys Ala Ala Lys Pro Pro Tyr Asp Val Lys
    1220                1225                1230

Leu Ser Thr Leu Ser Lys Asn Leu Glu Glu Gly Phe Glu Lys Phe
    1235                1240                1245

Lys Ala Leu Glu Leu Gly Pro Gln Val Lys Val Leu Gln Gln Ile
    1250                1255                1260

Leu Asp Ile Tyr Ser Cys Asp Arg Lys Ser Gly Asp Leu Ser Val
    1265                1270                1275

Leu Gly Ser Ala Arg Asn Ala Gly Arg Leu Asp Met Asn Gly Val
    1280                1285                1290

Leu Ser Glu Ala Asp Gly Glu Gln Val Thr Met Ile Cys Gln Ser
    1295                1300                1305

Pro Ser Gly Leu Phe Glu Lys Arg Val Pro Met Asn Glu Lys
    1310                1315                1320

<210> SEQ ID NO 15
<211> LENGTH: 1322
<212> TYPE: PRT
<213> ORGANISM: Artificial Sequence
<220> FEATURE:
<223> OTHER INFORMATION: Artificially mutated sequence

<400> SEQUENCE: 15

Met Lys Asn Thr Asn Glu Asp Tyr Tyr Leu Gly Leu Asp Ile Gly Thr
1               5                   10                  15

Asp Ser Val Gly Trp Ala Val Thr Asp Lys Glu Tyr Asn Ile Leu Glu
            20                  25                  30

Phe Arg Arg Lys Pro Met Trp Gly Ile His Leu Phe Glu Gly Gly Ser
        35                  40                  45

Thr Ala Gln Lys Thr Arg Val Tyr Arg Thr Ser Arg Arg Leu Lys
    50                  55                  60

Arg Arg Ala Glu Arg Ile Ala Leu Leu Arg Asp Ile Phe Ser Glu Glu
65                  70                  75                  80

Ile Gly Lys Val Asp Pro Gly Phe Phe Glu Arg Leu Asp Glu Ser Asp
                85                  90                  95

Leu His Leu Glu Asp Arg Val Thr Ser Gln Lys Asn Ser Leu Phe Asp
            100                 105                 110

```
Asp Pro Glu Phe Asn Asp Lys Asp Leu His Lys Arg Phe Pro Thr Ile
        115                 120                 125

Tyr His Leu Arg Arg His Leu Met His Ser Asn Arg Lys Glu Asp Ile
130                 135                 140

Arg Leu Ile Tyr Leu Ala Ala His His Ile Ile Lys Phe Arg Gly His
145                 150                 155                 160

Phe Leu Tyr Lys Gly Ile Gly Asp Glu Ile Pro Ser Phe Glu Ile
                165                 170                 175

Val Leu Asn Ser Leu Ile Asp Asn Leu Arg Asp Glu Tyr Gly Met Glu
            180                 185                 190

Leu Glu Val Ser Asp Arg Asp Leu Val Lys Ala Leu Leu Ser Asp Phe
        195                 200                 205

Ser Ile Gly Ile Arg Glu Lys Ser Arg Glu Leu Ser Ser Cys Leu Asn
    210                 215                 220

Ala Glu Ser Glu Asn Glu Lys Ala Leu Val Asp Phe Ile Ser Gly Lys
225                 230                 235                 240

Lys Thr Asn Met Lys Lys Leu Phe Asp Asp Glu Ala Leu Asp Lys Met
                245                 250                 255

Ser Phe Ser Leu Arg Asp Ser Gly Phe Glu Asp Gln Leu Arg Glu Asn
            260                 265                 270

Glu Gly Val Leu Gly Pro Glu Arg Val His Thr Leu Glu Leu Ser Arg
        275                 280                 285

Gln Ile Phe Glu Trp Ala Arg Leu Ser Ser Ile Leu Lys Asp Ser Asp
    290                 295                 300

Ser Ile Ser Glu Ala Lys Ile Lys Asp Tyr Asp Gln His Arg Glu Asp
305                 310                 315                 320

Leu Arg Met Leu Lys Arg Ala Val Lys Lys Tyr Ala Pro Asp Lys Tyr
                325                 330                 335

Ser Glu Val Phe Lys Ser Lys Glu His Thr Gly Asn Tyr Cys Ser Tyr
            340                 345                 350

Val Tyr Val Cys Gly Lys Gly Leu Pro Asp Lys Lys Cys Ser Thr Glu
        355                 360                 365

Glu Phe Gln Lys Tyr Leu Lys Lys Ile Leu Asp Asp Ser Gly Val Arg
    370                 375                 380

Asp Asp Glu Glu Phe Lys Thr Leu Ile Gln Arg Leu Asp Ala Gly Ile
385                 390                 395                 400

Leu Cys Pro Lys Gln Arg Thr Gly Glu Asn Ser Val Ile Pro Tyr Ser
                405                 410                 415

Val His Arg Lys Glu Leu Ile Gly Ile Leu Asn Asn Ala Ala Glu His
            420                 425                 430

Tyr Pro Ser Leu Ser Arg Lys Gly Glu Asp Gly Phe Ser Ser Ile Asp
        435                 440                 445

Lys Ile Leu Met Leu Glu Glu Phe Arg Ile Pro Tyr Tyr Val Gly Pro
    450                 455                 460

Leu Asp Asp Arg Ser Ser Arg Ser Trp Leu Ile Arg Asn Ser Phe Glu
465                 470                 475                 480

Ala Ile Thr Pro Trp Asn Phe Asn Glu Ile Val Asp Glu Asp Glu Thr
                485                 490                 495

Ser Glu Arg Phe Ile Gly Asn Leu Thr Ser Met Cys Thr Tyr Leu Gly
            500                 505                 510

Gly Glu Lys Val Leu Pro Lys Asn Ser Leu Leu Tyr Ser Arg Phe Met
        515                 520                 525

Leu Tyr Asn Glu Ile Asn Asn Leu Arg Val Gly Gly Glu Lys Ile Pro
```

```
                530                 535                 540
Ala Ala Leu Lys Asn Lys Met Val Ser Glu Leu Phe Ala Asn Arg Ala
545                 550                 555                 560

Thr Ser Ser Lys Val Thr Leu Lys Glu Leu Lys Ala Phe Leu Lys Gly
                565                 570                 575

Glu Gly Val Leu Thr Asp Ala Asp Glu Ile Ser Gly Ile Asp Asp Gly
                580                 585                 590

Val Lys Ser Thr Leu Arg Ser Glu Ile Leu Ile Arg Lys Ile Ile Gly
                595                 600                 605

Asp Lys Ile Ser Asp Arg Glu Met Ala Glu Ile Val Arg Ile Leu
                610                 615                 620

Thr Val Phe Gly Asp Glu Arg Arg Ser Lys Ala Lys Leu Lys Lys
625                 630                 635                 640

Glu Phe Ser Asp Lys Leu Thr Glu Lys Glu Ile Glu Lys Leu Ser Ser
                645                 650                 655

Leu Lys Phe Asp Gly Trp Gly Arg Leu Ser Glu Lys Phe Leu Thr Gly
                660                 665                 670

Leu Arg Gln Glu Val Asn Gly Arg Ser Met Ser Ile Ile Glu Ile Leu
                675                 680                 685

Glu Asp Thr Asn Tyr Asn Leu Gln Glu Thr Leu Ser Lys Tyr Ser Phe
                690                 695                 700

Asn Glu Ile Ile Asp Ser Tyr Asn Glu Val Leu Thr Ser Gly Pro Arg
705                 710                 715                 720

Ser Ile Ser Tyr Asp Ile Leu Lys Asp Ser Tyr Leu Ser Pro Ala Val
                725                 730                 735

Lys Arg Gly Val Trp Arg Ala Leu Ser Val Val Lys Asp Ile Leu Lys
                740                 745                 750

Ala Val Gly Arg Pro Pro Lys Lys Ile Phe Val Glu Thr Thr Arg Glu
                755                 760                 765

Glu Arg Glu Lys Lys Arg Thr Glu Ser Arg Lys Asp Ala Leu Met Tyr
                770                 775                 780

Leu Tyr Lys Ser Cys Lys Glu Thr Glu Trp Glu Lys Arg Leu Asp Ser
785                 790                 795                 800

Val Glu Glu Ser Ser Leu Arg Asn Arg Ser Leu Tyr Leu Tyr Tyr Thr
                805                 810                 815

Gln Leu Gly Lys Cys Met Tyr Cys Gly Lys Asn Ile Asp Ile Gly Glu
                820                 825                 830

Leu Asn Thr Asp Leu Ala Asp Arg Asp Ala Ile Tyr Pro Gln Ser Lys
                835                 840                 845

Thr Lys Asp Asp Ser Ile Arg Asn Asn Leu Val Leu Cys Arg Gly
850                 855                 860

Cys Asn Gln Ala Lys Gly Asp Arg Tyr Pro Leu Pro Gln Glu Trp Val
865                 870                 875                 880

Ser Arg Met His Ala Phe Trp Thr Met Leu Lys Asp Lys Gly Tyr Ile
                885                 890                 895

Ser Ser Glu Lys Tyr Arg Arg Leu Thr Arg Arg Gly Glu Leu Thr Glu
                900                 905                 910

Glu Glu Phe Gly Ala Phe Ile Asn Arg Gln Leu Val Glu Thr Ser Gln
                915                 920                 925

Ser Ala Lys Ala Val Ile Thr Val Leu Lys Asn Ala Phe Lys Asp Ser
                930                 935                 940

Asp Ile Val Tyr Val Lys Gly Ser Asn Val Ser Asp Phe Arg Ser Ser
945                 950                 955                 960
```

Tyr Asn Phe Ile Lys Cys Arg Ser Val Asn Asp Tyr His Ala Lys
            965                 970                 975

Asp Ala Tyr Leu Asn Ile Val Val Gly Asn Val Leu Asp Thr Lys Phe
        980                 985                 990

Thr Lys Asn Pro Ser Tyr Val Leu Lys Asn Arg Glu Gln Tyr Asn Ile
        995                 1000                1005

Gly Arg Met Tyr Asp Arg Asn Val Ser Arg Phe Gly Val Asp Ala
        1010                1015                1020

Trp Val Ala Gly Asp Arg Gly Ser Ile Ala Thr Val Arg Lys Tyr
        1025                1030                1035

Met Arg Arg Asn Asn Ile Leu Phe Thr Arg Tyr Ala Thr Lys Ser
        1040                1045                1050

Lys Gly Ala Leu Phe Lys Glu Thr Val His Arg Lys Lys Glu Gly
        1055                1060                1065

Leu Phe Glu Arg Lys Lys Gly Leu Glu Thr Glu Lys Tyr Gly Gly
        1070                1075                1080

Tyr Ser Asp Ile Ser Thr Ser Tyr Leu Thr Leu Leu Glu Tyr Asp
        1085                1090                1095

Lys Gly Lys Lys Arg Ile Arg Ser Leu Glu Ile Val Pro Thr Tyr
        1100                1105                1110

Phe Ala Asn Thr Arg Pro Lys Glu Glu Asp Val Ile Arg Phe Phe
        1115                1120                1125

Ser Glu Thr Arg Gly Leu Ala Asn Val Arg Val Val Met Pro Glu
        1130                1135                1140

Val Arg Met Lys Ser Leu Phe Glu Tyr Arg Gly Phe Arg Phe His
        1145                1150                1155

Val Thr Gly Ser Asn Gly Lys Gly Arg Phe Trp Ile Ser Ser Ala
        1160                1165                1170

Ile Gln Leu Leu Leu Pro Glu Asn Leu Tyr Ala Tyr Cys Lys Ser
        1175                1180                1185

Ile Glu Asn Asn Glu Lys Asp Ser Gln Arg Arg Ser Glu Lys Pro
        1190                1195                1200

Leu Gln Asn Tyr Gly Phe Ser Ser Glu Met Asn Ile Glu Leu Phe
        1205                1210                1215

Lys Cys Leu Met Asp Lys Ala Ala Lys Pro Pro Tyr Asp Val Lys
        1220                1225                1230

Leu Ser Thr Leu Ser Lys Asn Leu Glu Glu Gly Phe Glu Lys Phe
        1235                1240                1245

Lys Ala Leu Glu Leu Gly Pro Gln Val Lys Val Leu Gln Gln Ile
        1250                1255                1260

Leu Asp Ile Tyr Ser Cys Asp Arg Lys Ser Gly Asp Leu Ser Val
        1265                1270                1275

Leu Gly Ser Ala Arg Asn Ala Gly Arg Leu Asp Met Asn Gly Val
        1280                1285                1290

Leu Ser Glu Ala Asp Gly Glu Gln Val Thr Met Ile Cys Gln Ser
        1295                1300                1305

Pro Ser Gly Leu Phe Glu Lys Arg Val Pro Met Asn Glu Lys
        1310                1315                1320

<210> SEQ ID NO 16
<211> LENGTH: 1322
<212> TYPE: PRT
<213> ORGANISM: Artificial Sequence
<220> FEATURE:

<223> OTHER INFORMATION: Artificially mutated sequence

<400> SEQUENCE: 16

```
Met Lys Asn Thr Asn Glu Asp Tyr Tyr Leu Gly Leu Ala Ile Gly Thr
  1               5                  10                  15

Asp Ser Val Gly Trp Ala Val Thr Asp Lys Glu Tyr Asn Ile Leu Glu
             20                  25                  30

Phe Arg Arg Lys Pro Met Trp Gly Ile His Leu Phe Glu Gly Gly Ser
         35                  40                  45

Thr Ala Gln Lys Thr Arg Val Tyr Arg Thr Ser Arg Arg Arg Leu Lys
 50                  55                  60

Arg Arg Ala Glu Arg Ile Ala Leu Leu Arg Asp Ile Phe Ser Glu Glu
 65                  70                  75                  80

Ile Gly Lys Val Asp Pro Gly Phe Phe Glu Arg Leu Asp Glu Ser Asp
                 85                  90                  95

Leu His Leu Glu Asp Arg Val Thr Ser Gln Lys Asn Ser Leu Phe Asp
            100                 105                 110

Asp Pro Glu Phe Asn Asp Lys Asp Leu His Lys Arg Phe Pro Thr Ile
        115                 120                 125

Tyr His Leu Arg Arg His Leu Met His Ser Asn Arg Lys Glu Asp Ile
130                 135                 140

Arg Leu Ile Tyr Leu Ala Ala His Ile Ile Lys Phe Arg Gly His Phe
145                 150                 155                 160

Phe Leu Tyr Lys Gly Ile Gly Asp Glu Glu Ile Pro Ser Phe Glu Ile
                165                 170                 175

Val Leu Asn Ser Leu Ile Asp Asn Leu Arg Asp Glu Tyr Gly Met Glu
            180                 185                 190

Leu Glu Val Ser Asp Arg Asp Leu Val Lys Ala Leu Leu Ser Asp Phe
        195                 200                 205

Ser Ile Gly Ile Arg Glu Lys Ser Arg Glu Leu Ser Ser Cys Leu Asn
    210                 215                 220

Ala Glu Ser Glu Asn Glu Lys Ala Leu Val Asp Phe Ile Ser Gly Lys
225                 230                 235                 240

Lys Thr Asn Met Lys Leu Phe Asp Asp Glu Ala Leu Asp Lys Met
                245                 250                 255

Ser Phe Ser Leu Arg Asp Ser Gly Phe Glu Asp Gln Leu Arg Glu Asn
            260                 265                 270

Glu Gly Val Leu Gly Pro Glu Arg Val His Thr Leu Glu Leu Ser Arg
        275                 280                 285

Gln Ile Phe Glu Trp Ala Arg Leu Ser Ser Ile Leu Lys Asp Ser Asp
    290                 295                 300

Ser Ile Ser Glu Ala Lys Ile Lys Asp Tyr Asp Gln His Arg Glu Asp
305                 310                 315                 320

Leu Arg Met Leu Lys Arg Ala Val Lys Tyr Ala Pro Asp Lys Tyr
                325                 330                 335

Ser Glu Val Phe Lys Ser Lys Glu His Thr Gly Asn Tyr Cys Ser Tyr
            340                 345                 350

Val Tyr Val Cys Gly Lys Gly Leu Pro Asp Lys Lys Cys Ser Thr Glu
        355                 360                 365

Glu Phe Gln Lys Tyr Leu Lys Lys Ile Leu Asp Asp Ser Gly Val Arg
    370                 375                 380

Asp Asp Glu Glu Phe Lys Thr Leu Ile Gln Arg Leu Asp Ala Gly Ile
385                 390                 395                 400
```

```
Leu Cys Pro Lys Gln Arg Thr Gly Glu Asn Ser Val Ile Pro Tyr Ser
                405                 410                 415

Val His Arg Lys Glu Leu Ile Gly Ile Leu Asn Asn Ala Ala Glu His
            420                 425                 430

Tyr Pro Ser Leu Ser Arg Lys Gly Glu Asp Gly Phe Ser Ser Ile Asp
        435                 440                 445

Lys Ile Leu Met Leu Glu Glu Phe Arg Ile Pro Tyr Tyr Val Gly Pro
    450                 455                 460

Leu Asp Asp Arg Ser Arg Ser Trp Leu Ile Arg Asn Ser Phe Glu
465                 470                 475                 480

Ala Ile Thr Pro Trp Asn Phe Asn Glu Ile Val Asp Glu Asp Glu Thr
                485                 490                 495

Ser Glu Arg Phe Ile Gly Asn Leu Thr Ser Met Cys Thr Tyr Leu Gly
            500                 505                 510

Gly Glu Lys Val Leu Pro Lys Asn Ser Leu Leu Tyr Ser Arg Phe Met
        515                 520                 525

Leu Tyr Asn Glu Ile Asn Asn Leu Arg Val Gly Gly Glu Lys Ile Pro
    530                 535                 540

Ala Ala Leu Lys Asn Lys Met Val Ser Glu Leu Phe Ala Asn Arg Ala
545                 550                 555                 560

Thr Ser Ser Lys Val Thr Leu Lys Glu Leu Lys Ala Phe Leu Lys Gly
                565                 570                 575

Glu Gly Val Leu Thr Asp Ala Asp Glu Ile Ser Gly Ile Asp Asp Gly
            580                 585                 590

Val Lys Ser Thr Leu Arg Ser Glu Ile Leu Ile Arg Lys Ile Ile Gly
        595                 600                 605

Asp Lys Ile Ser Asp Arg Glu Met Ala Glu Glu Ile Val Arg Ile Leu
    610                 615                 620

Thr Val Phe Gly Asp Glu Arg Arg Arg Ser Lys Ala Lys Leu Lys Lys
625                 630                 635                 640

Glu Phe Ser Asp Lys Leu Thr Glu Lys Glu Ile Glu Lys Leu Ser Ser
                645                 650                 655

Leu Lys Phe Asp Gly Trp Gly Arg Leu Ser Glu Lys Phe Leu Thr Gly
            660                 665                 670

Leu Arg Gln Glu Val Asn Gly Arg Ser Met Ser Ile Ile Glu Ile Leu
        675                 680                 685

Glu Asp Thr Asn Tyr Asn Leu Gln Glu Thr Leu Ser Lys Tyr Ser Phe
    690                 695                 700

Asn Glu Ile Ile Asp Ser Tyr Asn Glu Val Leu Thr Ser Gly Pro Arg
705                 710                 715                 720

Ser Ile Ser Tyr Asp Ile Leu Lys Asp Ser Tyr Leu Ser Pro Ala Val
                725                 730                 735

Lys Arg Gly Val Trp Arg Ala Leu Ser Val Val Lys Asp Ile Leu Lys
            740                 745                 750

Ala Val Gly Arg Pro Pro Lys Lys Ile Phe Val Glu Thr Thr Arg Glu
        755                 760                 765

Glu Arg Glu Lys Lys Arg Thr Glu Ser Arg Lys Asp Ala Leu Met Tyr
    770                 775                 780

Leu Tyr Lys Ser Cys Lys Glu Thr Glu Trp Lys Arg Leu Asp Ser
785                 790                 795                 800

Val Glu Glu Ser Ser Leu Arg Asn Arg Ser Leu Tyr Leu Tyr Tyr Thr
                805                 810                 815

Gln Leu Gly Lys Cys Met Tyr Cys Gly Lys Asn Ile Asp Ile Gly Glu
```

```
              820                 825                 830
Leu Asn Thr Asp Leu Ala Asp Arg Asp Ala Ile Tyr Pro Gln Ser Lys
            835                 840                 845

Thr Lys Asp Asp Ser Ile Arg Asn Asn Leu Val Leu Val Cys Arg Gly
            850                 855                 860

Cys Asn Gln Ala Lys Gly Asp Arg Tyr Pro Leu Pro Gln Glu Trp Val
865                 870                 875                 880

Ser Arg Met His Ala Phe Trp Thr Met Leu Lys Asp Lys Gly Tyr Ile
            885                 890                 895

Ser Ser Glu Lys Tyr Arg Arg Leu Thr Arg Arg Gly Glu Leu Thr Glu
            900                 905                 910

Glu Glu Phe Gly Ala Phe Ile Asn Arg Gln Leu Val Glu Thr Ser Gln
            915                 920                 925

Ser Ala Lys Ala Val Ile Thr Val Leu Lys Asn Ala Phe Lys Asp Ser
            930                 935                 940

Asp Ile Val Tyr Val Lys Gly Ser Asn Val Ser Asp Phe Arg Ser Ser
945                 950                 955                 960

Tyr Asn Phe Ile Lys Cys Arg Ser Val Asn Asp Tyr His His Ala Lys
            965                 970                 975

Asp Ala Tyr Leu Asn Ile Val Val Gly Asn Val Leu Asp Thr Lys Phe
            980                 985                 990

Thr Lys Asn Pro Ser Tyr Val Leu  Lys Asn Arg Glu Gln  Tyr Asn Ile
            995                 1000                1005

Gly Arg Met Tyr Asp Arg Asn  Val Ser Arg Phe Gly  Val Asp Ala
    1010                1015                1020

Trp Val Ala Gly Asp Arg Gly  Ser Ile Ala Thr Val  Arg Lys Tyr
    1025                1030                1035

Met Arg Arg Asn Asn Ile Leu  Phe Thr Arg Tyr Ala  Thr Lys Ser
    1040                1045                1050

Lys Gly Ala Leu Phe Lys Glu  Thr Val His Arg Lys  Lys Glu Gly
    1055                1060                1065

Leu Phe Glu Arg Lys Lys Gly  Leu Glu Thr Glu Lys  Tyr Gly Gly
    1070                1075                1080

Tyr Ser Asp Ile Ser Thr Ser  Tyr Leu Thr Leu Leu  Glu Tyr Asp
    1085                1090                1095

Lys Gly Lys Lys Arg Ile Arg  Ser Leu Glu Ile Val  Pro Thr Tyr
    1100                1105                1110

Phe Ala Asn Thr Arg Pro Lys  Glu Glu Asp Val Ile  Arg Phe Phe
    1115                1120                1125

Ser Glu Thr Arg Gly Leu Ala  Asn Val Arg Val Val  Met Pro Glu
    1130                1135                1140

Val Arg Met Lys Ser Leu Phe  Glu Tyr Arg Gly Phe  Arg Phe His
    1145                1150                1155

Val Thr Gly Ser Asn Gly Lys  Gly Arg Phe Trp Ile  Ser Ser Ala
    1160                1165                1170

Ile Gln Leu Leu Leu Pro Glu  Asn Leu Tyr Ala Tyr  Cys Lys Ser
    1175                1180                1185

Ile Glu Asn Asn Glu Lys Asp  Ser Gln Arg Arg Ser  Glu Lys Pro
    1190                1195                1200

Leu Gln Asn Tyr Gly Phe Ser  Ser Glu Met Asn Ile  Glu Leu Phe
    1205                1210                1215

Lys Cys Leu Met Asp Lys Ala  Ala Lys Pro Pro Tyr  Asp Val Lys
    1220                1225                1230
```

```
Leu Ser Thr Leu Ser Lys Asn Leu Glu Glu Gly Phe Glu Lys Phe
    1235                1240                1245

Lys Ala Leu Glu Leu Gly Pro Gln Val Lys Val Leu Gln Gln Ile
    1250                1255                1260

Leu Asp Ile Tyr Ser Cys Asp Arg Lys Ser Gly Asp Leu Ser Val
    1265                1270                1275

Leu Gly Ser Ala Arg Asn Ala Gly Arg Leu Asp Met Asn Gly Val
    1280                1285                1290

Leu Ser Glu Ala Asp Gly Glu Gln Val Thr Met Ile Cys Gln Ser
    1295                1300                1305

Pro Ser Gly Leu Phe Glu Lys Arg Val Pro Met Asn Glu Lys
    1310                1315                1320

<210> SEQ ID NO 17
<211> LENGTH: 1211
<212> TYPE: PRT
<213> ORGANISM: Artificial Sequence
<220> FEATURE:
<223> OTHER INFORMATION: Artificially mutated sequence

<400> SEQUENCE: 17

Met Glu Asn Tyr Arg Gln Lys His Arg Phe Val Leu Ala Thr Ala Leu
1               5                   10                  15

Gly Ile Gly Ser Asn Gly Trp Ala Ile Ile Asp Leu Asp Ala His Arg
            20                  25                  30

Val Glu Asp Leu Gly Val Gln Ile Phe Glu Ser Gly Glu Glu Gly Ala
        35                  40                  45

Lys Lys Ala Ser Ala Arg Ala Ser Gln Gln Arg Arg Leu Lys Arg Ser
    50                  55                  60

Ala His Arg Leu Asn Arg Arg Lys Lys Gln Lys Glu Ala Leu Ile
65                  70                  75                  80

Lys Phe Leu Gln Glu Ile Glu Phe Pro Asp Leu Val Glu Ile Leu Asn
                85                  90                  95

Ser Phe Lys Lys Gln Lys Asn Pro Asn Asp Ile Leu Ser Leu Arg Val
            100                 105                 110

Lys Gly Leu Asp Asn Lys Leu Ser Pro Leu Glu Leu Phe Ser Ile Leu
        115                 120                 125

Ile Tyr Met Ser Asn Asn Arg Gly Tyr Lys Asp Phe Tyr Asp Asn Asp
    130                 135                 140

Ile Asn Asp Asn Asn Thr Asp Lys Asp Glu Lys Glu Met Glu Lys Ala
145                 150                 155                 160

Lys Ser Thr Ile Glu Lys Leu Phe Ala Ser Asn Ser Tyr Arg Thr Val
                165                 170                 175

Gly Glu Met Ile Ala Thr Asp Pro Thr Phe Ile Val Asp Lys Ser Gly
            180                 185                 190

Ser Lys Lys Val Ile Lys Tyr His Asn Lys Lys Gly Tyr Gln Tyr Leu
        195                 200                 205

Ile Pro Arg Lys Leu Leu Glu Asn Glu Met Ser Leu Ile Leu His Lys
    210                 215                 220

Gln Glu Glu Phe Tyr Asp Cys Leu Ser Ile Asp Asn Ile Thr Ile Ile
225                 230                 235                 240

Leu Asp Lys Ile Phe Phe Gln Arg Asn Phe Glu Asp Gly Pro Gly Pro
                245                 250                 255

Lys Asn Lys Arg Asp Asp Tyr Lys Asn Asn Ser Lys Gly Asn Gln Phe
            260                 265                 270
```

-continued

Tyr Thr Gly Phe Asn Glu Met Ile Gly Leu Cys Pro Phe Pro Asn
          275                 280                 285

Glu Lys Lys Gly Thr Lys Asn Ser Leu Ile Tyr Asp Glu Tyr Tyr Leu
    290                 295                 300

Ile Asn Thr Leu Ser Gln Phe Phe Thr Asp Ser Asn Gly Val Ile
305                 310                 315                 320

Met Ser Phe Ser Lys Ser Leu Leu His Asp Leu Met Leu Tyr Phe Phe
                325                 330                 335

Asp His Lys Gly Glu Leu Thr Asn Lys Glu Leu Ser Ser Phe Leu Leu
            340                 345                 350

Lys His Gly Leu Glu Leu Asn Ser Lys Glu Lys Ser Asn Lys Lys Tyr
            355                 360                 365

Arg Leu Asn Tyr Met Lys Gln Leu Thr Asp Ser Thr Ile Phe Glu Thr
    370                 375                 380

Glu Met Ile Ala Ser Phe Arg Glu Glu Ile Glu Thr Ser Ser Tyr Arg
385                 390                 395                 400

Ser Val Asn Ser Leu Ser Asn Lys Ile Gly Asn Cys Ile Gly Gln Phe
                405                 410                 415

Ile Thr Pro Leu Lys Arg Lys Glu Glu Leu Thr Asn Ile Leu Ile Asp
            420                 425                 430

Thr Asn Tyr Pro Lys Glu Leu Ala Ser Lys Leu Ala Asp Ser Ile Lys
            435                 440                 445

Val Ile Lys Ser Gln Ser Val Ala Asn Ile Ser Asn Lys Tyr Met Leu
    450                 455                 460

Glu Ala Ile His Ala Phe Glu Ser Gly Lys Lys Tyr Gly Asp Phe Gln
465                 470                 475                 480

Ala Glu Phe Asn Glu Thr Arg Glu Leu Glu Asp His His Phe Met Lys
                485                 490                 495

Asn Asn Lys Leu Ile Ala Phe Gln Asp Ser Asp Leu Ile Arg Asn Pro
            500                 505                 510

Val Val Tyr Arg Thr Ile Asn Gln Ser Arg Lys Ile Ile Asn Ala Ala
    515                 520                 525

Ile Asn Lys Tyr Asn Ile Val Arg Ile Asn Ile Glu Val Ala Ser Asp
    530                 535                 540

Val Asn Lys Ser Phe Glu Gln Arg Asp Asn Asp Lys Lys Tyr Gln Asn
545                 550                 555                 560

Asp Asn Tyr Glu Lys Asn Leu Gln Leu Glu Ser Glu Leu Thr Asp Tyr
            565                 570                 575

Ile Asn Lys Glu Asn Leu His Val Asn Val Asn Ser Lys Met Met Glu
            580                 585                 590

Arg Tyr Lys Leu Tyr Leu Ser Gln Asn Lys His Cys Ile Tyr Thr Asn
    595                 600                 605

Thr Pro Leu Thr Met Met Asp Val Ile Tyr Ser Thr Asn Val Gln Val
610                 615                 620

Asp His Ile Ile Pro Gln Ser Lys Ile Leu Asp Asp Thr Leu Asn Asn
625                 630                 635                 640

Lys Val Leu Val Leu Arg Asp Ala Asn Ser Ile Lys Asn Asn Arg Leu
                645                 650                 655

Pro Leu Glu Ala Phe Asp Glu Met Gln Ile Asn Val Asp Thr Asn Tyr
            660                 665                 670

Thr Lys Lys Asp Tyr Leu Thr Glu Cys Leu His Leu Leu Lys Asn Lys
            675                 680                 685

```
Thr Asn Pro Ile Ser Lys Lys Lys Tyr Gln Tyr Leu Thr Lys Lys
    690             695                 700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                725                 730                 735

Lys Glu Ser Asp Lys Thr Lys Asn Ile Asp Val Val Thr Ile Lys Gly
            740                 745                 750

Ala Val Thr Ser Arg Phe Arg Lys Arg Trp Leu Thr Thr Tyr Asp Glu
                755                 760                 765

Tyr Gly Tyr His Pro Thr Ile Tyr Ser Leu Glu Asp Lys Gly Arg Asn
770                 775                 780

Leu Tyr Tyr Tyr His His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810                 815

Ile Lys Ile Asp Arg Asn Leu Ser Lys Glu Gln Lys Gln Arg Asp Ile
                820                 825                 830

Asp Thr Val Ile Lys Asn Thr Val Lys Ser Met Ser Lys Tyr His Gly
                835                 840                 845

Phe Ser Glu Asp Tyr Ile Arg Ser Leu Met Ser Lys Asn His Ile Pro
850                 855                 860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890                 895

Gln Tyr His Tyr Lys Lys Leu Tyr Ile Ala Phe Lys Glu Ala Gln Asn
                900                 905                 910

Ala Leu Lys Glu Lys Glu Thr Leu Glu Lys Glu Leu Ile Glu Arg Phe
                915                 920                 925

Asn Asn Glu Ala Gln Ile Leu Asn Ala Asn Ile Ile Leu Thr Tyr Thr
930                 935                 940

Gly Phe Glu Ser Asn Asn Glu Leu Ile Asp Ile Lys Lys Ala Lys Lys
945                 950                 955                 960

Val Thr Asp Thr Leu Lys Pro Asn Leu Lys Asn Tyr Ile Lys Ala Ile
                965                 970                 975

Asp Ile Leu Thr Gln Glu Glu Tyr Thr Lys Arg Cys Leu Glu Tyr Tyr
                980                 985                 990

Asn Asp Ser Glu Phe Ala Thr Gln Leu Lys Ile Pro Tyr Val Asn Phe
                995                 1000                1005

Lys Ile Asn Lys Arg Phe Arg Gly Lys Ile Gln Gly Ser Glu Asn
    1010            1015               1020

Ala Val Ser Leu Arg Glu Val Leu Lys Lys Thr Lys Leu Asn Ser
    1025            1030               1035

Phe Glu Glu Phe Glu Ser Tyr Leu Lys Ser Glu Asp Gly Ile Lys
    1040            1045               1050

Ser Pro Tyr Tyr Ile Lys Tyr Thr Lys Asn Thr Leu Gly Lys Glu
    1055            1060               1065

Ser Tyr Thr Ile Tyr Glu Ala Asn Ser Tyr Tyr Cys Ala Glu Ile
    1070            1075               1080

Tyr Thr Asp Ser Gln Asn Lys Pro Gln Leu Arg Gly Ile Arg Tyr
    1085            1090               1095

Val Asp Val Arg Lys Glu Asp Gly Lys Leu Val Leu Leu Lys Pro
```

-continued

```
            1100                1105                1110
Leu Pro Ser Thr Cys Lys His Ile Thr Tyr Leu Phe His Asn Glu
        1115                1120                1125
Tyr Ile Ala Ile Tyr Lys Asp Ser Asn Tyr Lys Arg Leu Lys Asn
        1130                1135                1140
Asn Gly Phe Gly Ala Tyr Arg Ser Ile Asn Asn Val Asn Val Asn
        1145                1150                1155
Lys Ile Ile Ile Arg Leu Phe Ala Asn Gln Asn Leu Asn Asp Asn
        1160                1165                1170
Asp Val Val Ile Thr Ser Ser Ile Phe Ile Lys Lys Tyr Ser Leu
        1175                1180                1185
Asp Val Phe Gly His Ile Asn Gly Glu Ile Lys Cys Gly Asp Gln
        1190                1195                1200
Ser Leu Phe Thr Ile Lys Lys Arg
        1205                1210
```

<210> SEQ ID NO 18
<211> LENGTH: 1211
<212> TYPE: PRT
<213> ORGANISM: Artificial Sequence
<220> FEATURE:
<223> OTHER INFORMATION: Artificially mutated sequence

<400> SEQUENCE: 18

```
Met Glu Asn Tyr Arg Gln Lys His Arg Phe Val Leu Ala Thr Asp Leu
1                5                  10                  15
Gly Ile Gly Ser Asn Gly Trp Ala Ile Ile Asp Leu Asp Ala His Arg
                20                  25                  30
Val Glu Asp Leu Gly Val Gln Ile Phe Glu Ser Gly Glu Glu Gly Ala
            35                  40                  45
Lys Lys Ala Ser Ala Arg Ala Ser Gln Gln Arg Arg Leu Lys Arg Ser
        50                  55                  60
Ala His Arg Leu Asn Arg Arg Lys Lys Gln Arg Lys Glu Ala Leu Ile
65                  70                  75                  80
Lys Phe Leu Gln Glu Ile Glu Phe Pro Asp Leu Val Glu Ile Leu Asn
                85                  90                  95
Ser Phe Lys Lys Gln Lys Asn Pro Asn Asp Ile Leu Ser Leu Arg Val
                100                 105                 110
Lys Gly Leu Asp Asn Lys Leu Ser Pro Leu Glu Leu Phe Ser Ile Leu
            115                 120                 125
Ile Tyr Met Ser Asn Asn Arg Gly Tyr Lys Asp Phe Tyr Asp Asn Asp
        130                 135                 140
Ile Asn Asp Asn Asn Thr Asp Lys Asp Glu Lys Glu Met Glu Lys Ala
145                 150                 155                 160
Lys Ser Thr Ile Glu Lys Leu Phe Ala Ser Asn Ser Tyr Arg Thr Val
                165                 170                 175
Gly Glu Met Ile Ala Thr Asp Pro Thr Phe Ile Val Asp Lys Ser Gly
                180                 185                 190
Ser Lys Lys Val Ile Lys Tyr His Asn Lys Lys Gly Tyr Gln Tyr Leu
            195                 200                 205
Ile Pro Arg Lys Leu Leu Glu Asn Glu Met Ser Leu Ile Leu His Lys
        210                 215                 220
Gln Glu Glu Phe Tyr Asp Cys Leu Ser Ile Asp Asn Ile Thr Ile Ile
225                 230                 235                 240
Leu Asp Lys Ile Phe Phe Gln Arg Asn Phe Glu Asp Gly Pro Gly Pro
```

```
                       245                 250                 255
Lys Asn Lys Arg Asp Asp Tyr Lys Asn Asn Ser Lys Gly Asn Gln Phe
                260                 265                 270

Tyr Thr Gly Phe Asn Glu Met Ile Gly Leu Cys Pro Phe Tyr Pro Asn
            275                 280                 285

Glu Lys Lys Gly Thr Lys Asn Ser Leu Ile Tyr Asp Glu Tyr Tyr Leu
        290                 295                 300

Ile Asn Thr Leu Ser Gln Phe Phe Thr Asp Ser Asn Gly Val Ile
305                 310                 315                 320

Met Ser Phe Ser Lys Ser Leu Leu His Asp Leu Met Leu Tyr Phe Phe
                325                 330                 335

Asp His Lys Gly Glu Leu Thr Asn Lys Glu Leu Ser Ser Phe Leu Leu
            340                 345                 350

Lys His Gly Leu Glu Leu Asn Ser Lys Glu Lys Ser Asn Lys Lys Tyr
        355                 360                 365

Arg Leu Asn Tyr Met Lys Gln Leu Thr Asp Ser Thr Ile Phe Glu Thr
370                 375                 380

Glu Met Ile Ala Ser Phe Arg Glu Ile Glu Thr Ser Ser Tyr Arg
385                 390                 395                 400

Ser Val Asn Ser Leu Ser Asn Lys Ile Gly Asn Cys Ile Gly Gln Phe
                405                 410                 415

Ile Thr Pro Leu Lys Arg Lys Glu Glu Leu Thr Asn Ile Leu Ile Asp
            420                 425                 430

Thr Asn Tyr Pro Lys Glu Leu Ala Ser Lys Leu Ala Asp Ser Ile Lys
        435                 440                 445

Val Ile Lys Ser Gln Ser Val Ala Asn Ile Ser Asn Lys Tyr Met Leu
450                 455                 460

Glu Ala Ile His Ala Phe Glu Ser Gly Lys Lys Tyr Gly Asp Phe Gln
465                 470                 475                 480

Ala Glu Phe Asn Glu Thr Arg Glu Leu Glu Asp His His Phe Met Lys
                485                 490                 495

Asn Asn Lys Leu Ile Ala Phe Gln Asp Ser Asp Leu Ile Arg Asn Pro
            500                 505                 510

Val Val Tyr Arg Thr Ile Asn Gln Ser Arg Lys Ile Ile Asn Ala Ala
        515                 520                 525

Ile Asn Lys Tyr Asn Ile Val Arg Ile Asn Ile Glu Val Ala Ser Asp
530                 535                 540

Val Asn Lys Ser Phe Glu Gln Arg Asp Asn Asp Lys Lys Tyr Gln Asn
545                 550                 555                 560

Asp Asn Tyr Glu Lys Asn Leu Gln Leu Glu Ser Glu Leu Thr Asp Tyr
                565                 570                 575

Ile Asn Lys Glu Asn Leu His Val Asn Val Asn Ser Lys Met Met Glu
            580                 585                 590

Arg Tyr Lys Leu Tyr Leu Ser Gln Asn Lys His Cys Ile Tyr Thr Asn
        595                 600                 605

Thr Pro Leu Thr Met Met Asp Val Ile Tyr Ser Thr Asn Val Gln Val
610                 615                 620

Asp Ala Ile Ile Pro Gln Ser Lys Ile Leu Asp Asp Thr Leu Asn Asn
625                 630                 635                 640

Lys Val Leu Val Leu Arg Asp Ala Asn Ser Ile Lys Asn Asn Arg Leu
                645                 650                 655

Pro Leu Glu Ala Phe Asp Glu Met Gln Ile Asn Val Asp Thr Asn Tyr
            660                 665                 670
```

```
Thr Lys Lys Asp Tyr Leu Thr Glu Cys Leu His Leu Lys Asn Lys
    675                 680                 685

Thr Asn Pro Ile Ser Lys Lys Tyr Gln Tyr Leu Thr Leu Lys Lys
    690                 695                 700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                725                 730                 735

Lys Glu Ser Asp Lys Thr Lys Asn Ile Asp Val Val Thr Ile Lys Gly
                740                 745                 750

Ala Val Thr Ser Arg Phe Arg Lys Arg Trp Leu Thr Thr Tyr Asp Glu
                755                 760                 765

Tyr Gly Tyr His Pro Thr Ile Tyr Ser Leu Glu Asp Lys Gly Arg Asn
    770                 775                 780

Leu Tyr Tyr Tyr His His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810                 815

Ile Lys Ile Asp Arg Asn Leu Ser Lys Glu Gln Lys Gln Arg Asp Ile
                820                 825                 830

Asp Thr Val Ile Lys Asn Thr Val Lys Ser Met Ser Lys Tyr His Gly
                835                 840                 845

Phe Ser Glu Asp Tyr Ile Arg Ser Leu Met Ser Lys Asn His Ile Pro
850                 855                 860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890                 895

Gln Tyr His Tyr Lys Lys Leu Tyr Ile Ala Phe Lys Glu Ala Gln Asn
                900                 905                 910

Ala Leu Lys Glu Lys Glu Thr Leu Glu Lys Glu Leu Ile Glu Arg Phe
                915                 920                 925

Asn Asn Glu Ala Gln Ile Leu Asn Ala Asn Ile Ile Leu Thr Tyr Thr
    930                 935                 940

Gly Phe Glu Ser Asn Asn Glu Leu Ile Asp Ile Lys Lys Ala Lys Lys
945                 950                 955                 960

Val Thr Asp Thr Leu Lys Pro Asn Leu Lys Asn Tyr Ile Lys Ala Ile
                965                 970                 975

Asp Ile Leu Thr Gln Glu Glu Tyr Thr Lys Arg Cys Leu Glu Tyr Tyr
                980                 985                 990

Asn Asp Ser Glu Phe Ala Thr Gln Leu Lys Ile Pro Tyr Val Asn Phe
    995                 1000                1005

Lys Ile Asn Lys Arg Phe Arg Gly Lys Ile Gln Gly Ser Glu Asn
    1010                1015                1020

Ala Val Ser Leu Arg Glu Val Leu Lys Lys Thr Lys Leu Asn Ser
    1025                1030                1035

Phe Glu Glu Phe Glu Ser Tyr Leu Lys Ser Glu Asp Gly Ile Lys
    1040                1045                1050

Ser Pro Tyr Tyr Ile Lys Tyr Thr Lys Asn Thr Leu Gly Lys Glu
    1055                1060                1065

Ser Tyr Thr Ile Tyr Glu Ala Asn Ser Tyr Tyr Cys Ala Glu Ile
    1070                1075                1080
```

```
Tyr Thr Asp Ser Gln Asn Lys Pro Gln Leu Arg Gly Ile Arg Tyr
    1085            1090                1095

Val Asp Val Arg Lys Glu Asp Gly Lys Leu Val Leu Leu Lys Pro
    1100            1105                1110

Leu Pro Ser Thr Cys Lys His Ile Thr Tyr Leu Phe His Asn Glu
    1115            1120                1125

Tyr Ile Ala Ile Tyr Lys Asp Ser Asn Tyr Lys Arg Leu Lys Asn
    1130            1135                1140

Asn Gly Phe Gly Ala Tyr Arg Ser Ile Asn Asn Val Asn Val Asn
    1145            1150                1155

Lys Ile Ile Ile Arg Leu Phe Ala Asn Gln Asn Leu Asn Asp Asn
    1160            1165                1170

Asp Val Val Ile Thr Ser Ser Ile Phe Ile Lys Lys Tyr Ser Leu
    1175            1180                1185

Asp Val Phe Gly His Ile Asn Gly Glu Ile Lys Cys Gly Asp Gln
    1190            1195                1200

Ser Leu Phe Thr Ile Lys Lys Arg
    1205            1210
```

<210> SEQ ID NO 19
<211> LENGTH: 1211
<212> TYPE: PRT
<213> ORGANISM: Artificial Sequence
<220> FEATURE:
<223> OTHER INFORMATION: Artificially mutated sequence

<400> SEQUENCE: 19

```
Met Glu Asn Tyr Arg Gln Lys His Arg Phe Val Leu Ala Thr Ala Leu
1               5                   10                  15

Gly Ile Gly Ser Asn Gly Trp Ala Ile Ile Asp Leu Asp Ala His Arg
            20                  25                  30

Val Glu Asp Leu Gly Val Gln Ile Phe Glu Ser Gly Glu Glu Gly Ala
        35                  40                  45

Lys Lys Ala Ser Ala Arg Ala Ser Gln Gln Arg Arg Leu Lys Arg Ser
    50                  55                  60

Ala His Arg Leu Asn Arg Arg Lys Lys Gln Arg Lys Glu Ala Leu Ile
65                  70                  75                  80

Lys Phe Leu Gln Glu Ile Glu Phe Pro Asp Leu Val Glu Ile Leu Asn
                85                  90                  95

Ser Phe Lys Lys Gln Lys Asn Pro Asn Asp Ile Leu Ser Leu Arg Val
            100                 105                 110

Lys Gly Leu Asp Asn Lys Leu Ser Pro Leu Glu Leu Phe Ser Ile Leu
        115                 120                 125

Ile Tyr Met Ser Asn Asn Arg Gly Tyr Lys Asp Phe Tyr Asp Asn Asp
    130                 135                 140

Ile Asn Asp Asn Asn Thr Asp Lys Asp Glu Lys Glu Met Glu Lys Ala
145                 150                 155                 160

Lys Ser Thr Ile Glu Lys Leu Phe Ala Ser Asn Ser Tyr Arg Thr Val
                165                 170                 175

Gly Glu Met Ile Ala Thr Asp Pro Thr Phe Ile Val Asp Lys Ser Gly
            180                 185                 190

Ser Lys Lys Val Ile Lys Tyr His Asn Lys Lys Gly Tyr Gln Tyr Leu
        195                 200                 205

Ile Pro Arg Lys Leu Leu Glu Asn Glu Met Ser Leu Ile Leu His Lys
    210                 215                 220
```

-continued

```
Gln Glu Glu Phe Tyr Asp Cys Leu Ser Ile Asp Asn Ile Thr Ile Ile
225                 230                 235                 240

Leu Asp Lys Ile Phe Phe Gln Arg Asn Phe Glu Asp Gly Pro Gly Pro
            245                 250                 255

Lys Asn Lys Arg Asp Asp Tyr Lys Asn Asn Ser Lys Gly Asn Gln Phe
        260                 265                 270

Tyr Thr Gly Phe Asn Glu Met Ile Gly Leu Cys Pro Phe Tyr Pro Asn
    275                 280                 285

Glu Lys Lys Gly Thr Lys Asn Ser Leu Ile Tyr Asp Glu Tyr Tyr Leu
290                 295                 300

Ile Asn Thr Leu Ser Gln Phe Phe Thr Asp Ser Asn Gly Val Ile
305                 310                 315                 320

Met Ser Phe Ser Lys Ser Leu Leu His Asp Leu Met Leu Tyr Phe Phe
            325                 330                 335

Asp His Lys Gly Glu Leu Thr Asn Lys Glu Leu Ser Ser Phe Leu Leu
        340                 345                 350

Lys His Gly Leu Glu Leu Asn Ser Lys Glu Lys Ser Asn Lys Lys Tyr
    355                 360                 365

Arg Leu Asn Tyr Met Lys Gln Leu Thr Asp Ser Thr Ile Phe Glu Thr
370                 375                 380

Glu Met Ile Ala Ser Phe Arg Glu Glu Ile Glu Thr Ser Ser Tyr Arg
385                 390                 395                 400

Ser Val Asn Ser Leu Ser Asn Lys Ile Gly Asn Cys Ile Gly Gln Phe
            405                 410                 415

Ile Thr Pro Leu Lys Arg Lys Glu Glu Leu Thr Asn Ile Leu Ile Asp
        420                 425                 430

Thr Asn Tyr Pro Lys Glu Leu Ala Ser Lys Leu Ala Asp Ser Ile Lys
    435                 440                 445

Val Ile Lys Ser Gln Ser Val Ala Asn Ile Ser Asn Lys Tyr Met Leu
450                 455                 460

Glu Ala Ile His Ala Phe Glu Ser Gly Lys Lys Tyr Gly Asp Phe Gln
465                 470                 475                 480

Ala Glu Phe Asn Glu Thr Arg Glu Leu Glu Asp His His Phe Met Lys
            485                 490                 495

Asn Asn Lys Leu Ile Ala Phe Gln Asp Ser Asp Leu Ile Arg Asn Pro
        500                 505                 510

Val Val Tyr Arg Thr Ile Asn Gln Ser Arg Lys Ile Ile Asn Ala Ala
    515                 520                 525

Ile Asn Lys Tyr Asn Ile Val Arg Ile Asn Ile Glu Val Ala Ser Asp
530                 535                 540

Val Asn Lys Ser Phe Glu Gln Arg Asp Asn Asp Lys Lys Tyr Gln Asn
545                 550                 555                 560

Asp Asn Tyr Glu Lys Asn Leu Gln Leu Glu Ser Glu Leu Thr Asp Tyr
            565                 570                 575

Ile Asn Lys Glu Asn Leu His Val Asn Val Asn Ser Lys Met Met Glu
        580                 585                 590

Arg Tyr Lys Leu Tyr Leu Ser Gln Asn Lys His Cys Ile Tyr Thr Asn
    595                 600                 605

Thr Pro Leu Thr Met Met Asp Val Ile Tyr Ser Thr Asn Val Gln Val
610                 615                 620

Asp Ala Ile Ile Pro Gln Ser Lys Ile Leu Asp Asp Thr Leu Asn Asn
625                 630                 635                 640

Lys Val Leu Val Leu Arg Asp Ala Asn Ser Ile Lys Asn Asn Arg Leu
```

-continued

```
                645                 650                 655
Pro Leu Glu Ala Phe Asp Glu Met Gln Ile Asn Val Asp Thr Asn Tyr
            660                 665                 670

Thr Lys Lys Asp Tyr Leu Thr Glu Cys Leu His Leu Leu Lys Asn Lys
        675                 680                 685

Thr Asn Pro Ile Ser Lys Lys Tyr Gln Tyr Leu Thr Leu Lys Lys
        690                 695                 700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                725                 730                 735

Lys Glu Ser Asp Lys Thr Lys Asn Ile Asp Val Val Thr Ile Lys Gly
            740                 745                 750

Ala Val Thr Ser Arg Phe Arg Lys Arg Trp Leu Thr Thr Tyr Asp Glu
                755                 760                 765

Tyr Gly Tyr His Pro Thr Ile Tyr Ser Leu Glu Asp Lys Gly Arg Asn
        770                 775                 780

Leu Tyr Tyr Tyr His His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810                 815

Ile Lys Ile Asp Arg Asn Leu Ser Lys Glu Lys Gln Arg Asp Ile
            820                 825                 830

Asp Thr Val Ile Lys Asn Thr Val Lys Ser Met Ser Lys Tyr His Gly
                835                 840                 845

Phe Ser Glu Asp Tyr Ile Arg Ser Leu Met Ser Lys Asn His Ile Pro
        850                 855                 860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890                 895

Gln Tyr His Tyr Lys Lys Leu Tyr Ile Ala Phe Lys Glu Ala Gln Asn
            900                 905                 910

Ala Leu Lys Glu Lys Thr Leu Glu Lys Glu Leu Ile Glu Arg Phe
        915                 920                 925

Asn Asn Glu Ala Gln Ile Leu Asn Ala Asn Ile Ile Leu Thr Tyr Thr
930                 935                 940

Gly Phe Glu Ser Asn Asn Glu Leu Ile Asp Ile Lys Lys Ala Lys Lys
945                 950                 955                 960

Val Thr Asp Thr Leu Lys Pro Asn Leu Lys Asn Tyr Ile Lys Ala Ile
                965                 970                 975

Asp Ile Leu Thr Gln Glu Tyr Thr Lys Arg Cys Leu Glu Tyr Tyr
            980                 985                 990

Asn Asp Ser Glu Phe Ala Thr Gln Leu Lys Ile Pro Tyr Val Asn Phe
        995                 1000                1005

Lys Ile Asn Lys Arg Phe Arg Gly Lys Ile Gln Gly Ser Glu Asn
        1010                1015                1020

Ala Val Ser Leu Arg Glu Val Leu Lys Lys Thr Lys Leu Asn Ser
        1025                1030                1035

Phe Glu Glu Phe Glu Ser Tyr Leu Lys Ser Glu Asp Gly Ile Lys
        1040                1045                1050

Ser Pro Tyr Tyr Ile Lys Tyr Thr Lys Asn Thr Leu Gly Lys Glu
        1055                1060                1065
```

```
Ser Tyr Thr Ile Tyr Glu Ala Asn Ser Tyr Cys Ala Glu Ile
    1070            1075                1080

Tyr Thr Asp Ser Gln Asn Lys Pro Gln Leu Arg Gly Ile Arg Tyr
1085                1090                1095

Val Asp Val Arg Lys Glu Asp Gly Lys Leu Val Leu Leu Lys Pro
1100                1105                1110

Leu Pro Ser Thr Cys Lys His Ile Thr Tyr Leu Phe His Asn Glu
1115                1120                1125

Tyr Ile Ala Ile Tyr Lys Asp Ser Asn Tyr Lys Arg Leu Lys Asn
    1130            1135                1140

Asn Gly Phe Gly Ala Tyr Arg Ser Ile Asn Asn Val Asn Val Asn
    1145            1150                1155

Lys Ile Ile Ile Arg Leu Phe Ala Asn Gln Asn Leu Asn Asp Asn
    1160            1165                1170

Asp Val Val Ile Thr Ser Ser Ile Phe Ile Lys Lys Tyr Ser Leu
    1175            1180                1185

Asp Val Phe Gly His Ile Asn Gly Glu Ile Lys Cys Gly Asp Gln
    1190            1195                1200

Ser Leu Phe Thr Ile Lys Lys Arg
    1205            1210

<210> SEQ ID NO 20
<211> LENGTH: 36
<212> TYPE: DNA
<213> ORGANISM: Artificial Sequence
<220> FEATURE:
<223> OTHER INFORMATION: REPEAT

<400> SEQUENCE: 20
gtttgagagt gttgtcaaat aagagtcgga ccaatc                           36

<210> SEQ ID NO 21
<211> LENGTH: 97
<212> TYPE: DNA
<213> ORGANISM: Artificial Sequence
<220> FEATURE:
<223> OTHER INFORMATION: TRACR

<400> SEQUENCE: 21
gatagacaaa tgtgtctttg acaacacaag ttcaaataag gcattgccgt aatcgttctt   60
atgaaccccg cagttggcgg gaaaccttct gttgtca                           97

<210> SEQ ID NO 22
<211> LENGTH: 32
<212> TYPE: DNA
<213> ORGANISM: Artificial Sequence
<220> FEATURE:
<223> OTHER INFORMATION: REPEAT

<400> SEQUENCE: 22
gtttgagagt gttgtcaaat aagagtcgga cc                               32

<210> SEQ ID NO 23
<211> LENGTH: 93
<212> TYPE: DNA
<213> ORGANISM: Artificial Sequence
<220> FEATURE:
<223> OTHER INFORMATION: TRACR

<400> SEQUENCE: 23
```

```
gacaaatgtg tctttgacaa cacaagttca aataaggcat tgccgtaatc gttcttatga      60
accccgcagt tggcgggaaa ccttctgttg tca                                  93
```

<210> SEQ ID NO 24
<211> LENGTH: 13
<212> TYPE: DNA
<213> ORGANISM: Artificial Sequence
<220> FEATURE:
<223> OTHER INFORMATION: REPEAT

<400> SEQUENCE: 24

```
gtttgagagt gtt                                                        13
```

<210> SEQ ID NO 25
<211> LENGTH: 67
<212> TYPE: DNA
<213> ORGANISM: Artificial Sequence
<220> FEATURE:
<223> OTHER INFORMATION: TRACR

<400> SEQUENCE: 25

```
aacacaagtt caaataaggc attgccgtaa tcgttcttat gaaccccgca gttggcggga      60
aaccttc                                                               67
```

<210> SEQ ID NO 26
<211> LENGTH: 34
<212> TYPE: DNA
<213> ORGANISM: Artificial Sequence
<220> FEATURE:
<223> OTHER INFORMATION: REPEAT

<400> SEQUENCE: 26

```
gttttagtcg tctgttattt attggtaagg ttat                                 34
```

<210> SEQ ID NO 27
<211> LENGTH: 92
<212> TYPE: DNA
<213> ORGANISM: Artificial Sequence
<220> FEATURE:
<223> OTHER INFORMATION: TRACR

<400> SEQUENCE: 27

```
ataactttac cagtgaatat cagacggcta agataaagct ataagctgtg gggtcgcgca      60
tccccaattt cgcgcacgag cgttagctcg tt                                   92
```

<210> SEQ ID NO 28
<211> LENGTH: 26
<212> TYPE: DNA
<213> ORGANISM: Artificial Sequence
<220> FEATURE:
<223> OTHER INFORMATION: REPEAT

<400> SEQUENCE: 28

```
gttttagtcg tctgttattt attggt                                          26
```

<210> SEQ ID NO 29
<211> LENGTH: 84
<212> TYPE: DNA
<213> ORGANISM: Artificial Sequence
<220> FEATURE:
<223> OTHER INFORMATION: TRACR

<400> SEQUENCE: 29

```
accagtgaat atcagacggc taagataaag ctataagctg tggggtcgcg catccccaat      60
```

```
ttcgcgcacg agcgttagct cgtt                                            84

<210> SEQ ID NO 30
<211> LENGTH: 10
<212> TYPE: DNA
<213> ORGANISM: Artificial Sequence
<220> FEATURE:
<223> OTHER INFORMATION: REPEAT

<400> SEQUENCE: 30
gttttagtcg                                                            10

<210> SEQ ID NO 31
<211> LENGTH: 63
<212> TYPE: DNA
<213> ORGANISM: Artificial Sequence
<220> FEATURE:
<223> OTHER INFORMATION: TRACR

<400> SEQUENCE: 31
cggctaagat aaagctataa gctgtggggt cgcgcatccc caatttcgcg cacgagcgtt     60
agc                                                                   63

<210> SEQ ID NO 32
<211> LENGTH: 14
<212> TYPE: DNA
<213> ORGANISM: Artificial Sequence
<220> FEATURE:
<223> OTHER INFORMATION: REPEAT

<400> SEQUENCE: 32
cctgtgaata gtca                                                       14

<210> SEQ ID NO 33
<211> LENGTH: 78
<212> TYPE: DNA
<213> ORGANISM: Artificial Sequence
<220> FEATURE:
<223> OTHER INFORMATION: TRACR

<400> SEQUENCE: 33
tataaaaaat aattatagaa ccaaactaac caattatgaa aaaatatatta ggacttgact    60 taggaaccaa ctctattg                                                   78

<210> SEQ ID NO 34
<211> LENGTH: 16
<212> TYPE: DNA
<213> ORGANISM: Artificial Sequence
<220> FEATURE:
<223> OTHER INFORMATION: REPEAT

<400> SEQUENCE: 34
cctgtgaata gtcaac                                                     16

<210> SEQ ID NO 35
<211> LENGTH: 80
<212> TYPE: DNA
<213> ORGANISM: Artificial Sequence
<220> FEATURE:
<223> OTHER INFORMATION: TRACR

<400> SEQUENCE: 35
tatataaaaa ataattatag aaccaaacta accaattatg aaaaaaatat taggacttga    60
```

-continued

```
cttaggaacc aactctattg                                          80

<210> SEQ ID NO 36
<211> LENGTH: 12
<212> TYPE: DNA
<213> ORGANISM: Artificial Sequence
<220> FEATURE:
<223> OTHER INFORMATION: REPEAT

<400> SEQUENCE: 36
cctgtgaata gt                                                  12

<210> SEQ ID NO 37
<211> LENGTH: 56
<212> TYPE: DNA
<213> ORGANISM: Artificial Sequence
<220> FEATURE:
<223> OTHER INFORMATION: TRACR

<400> SEQUENCE: 37
taaaaaataa ttatagaacc aaactaacca attatgaaaa aaatattagg acttga   56

<210> SEQ ID NO 38
<211> LENGTH: 15
<212> TYPE: DNA
<213> ORGANISM: Artificial Sequence
<220> FEATURE:
<223> OTHER INFORMATION: REPEAT

<400> SEQUENCE: 38
gttgtgaatt gcttt                                               15

<210> SEQ ID NO 39
<211> LENGTH: 66
<212> TYPE: DNA
<213> ORGANISM: Artificial Sequence
<220> FEATURE:
<223> OTHER INFORMATION: TRACR

<400> SEQUENCE: 39
aaagcaattc acaataagga ttattccgtt gtgaaaacat ttaaggcggt gcgaaagcat 60
cgtcct                                                         66

<210> SEQ ID NO 40
<211> LENGTH: 57
<212> TYPE: DNA
<213> ORGANISM: Artificial Sequence
<220> FEATURE:
<223> OTHER INFORMATION: TRACR

<400> SEQUENCE: 40
aaagcaattc acaataagga ttattccgtt gtgaaaacat ttaaggcggt gcgaaaa    57

<210> SEQ ID NO 41
<211> LENGTH: 12
<212> TYPE: DNA
<213> ORGANISM: Artificial Sequence
<220> FEATURE:
<223> OTHER INFORMATION: REPEAT

<400> SEQUENCE: 41
gttgtgaatt gc                                                  12

<210> SEQ ID NO 42
<211> LENGTH: 61
```

```
<212> TYPE: DNA
<213> ORGANISM: Artificial Sequence
<220> FEATURE:
<223> OTHER INFORMATION: TRACR

<400> SEQUENCE: 42
gcaattcaca ataaggatta ttccgttgtg aaaacattta aggcggtgcg aaagcatcgt        60
c                                                                        61

<210> SEQ ID NO 43
<211> LENGTH: 12
<212> TYPE: DNA
<213> ORGANISM: Artificial Sequence
<220> FEATURE:
<223> OTHER INFORMATION: REPEAT

<400> SEQUENCE: 43
gttttagagc ta                                                            12

<210> SEQ ID NO 44
<211> LENGTH: 61
<212> TYPE: DNA
<213> ORGANISM: Artificial Sequence
<220> FEATURE:
<223> OTHER INFORMATION: TRACR

<400> SEQUENCE: 44
tagcaagtta aaataaggct agtccgttat caacttgaaa aagtggcaca gagtcggtgc        60
t                                                                        61

<210> SEQ ID NO 45
<211> LENGTH: 10
<212> TYPE: DNA
<213> ORGANISM: Artificial Sequence
<220> FEATURE:
<223> OTHER INFORMATION: REPEAT

<400> SEQUENCE: 45
gttttagagc                                                               10

<210> SEQ ID NO 46
<211> LENGTH: 59
<212> TYPE: DNA
<213> ORGANISM: Artificial Sequence
<220> FEATURE:
<223> OTHER INFORMATION: TRACR

<400> SEQUENCE: 46
gcaagttaaa ataaggctag tccgttatca acttgaaaaa gtggcacaga gtcggtgct         59

<210> SEQ ID NO 47
<211> LENGTH: 27
<212> TYPE: DNA
<213> ORGANISM: Artificial Sequence
<220> FEATURE:
<223> OTHER INFORMATION: REPEAT

<400> SEQUENCE: 47
gttttagagt catgttgttt agaatgg                                            27

<210> SEQ ID NO 48
<211> LENGTH: 84
<212> TYPE: DNA
<213> ORGANISM: Artificial Sequence
<220> FEATURE:
```

<223> OTHER INFORMATION: TRACR

<400> SEQUENCE: 48
ccattttaaa cgaaaaactc ctctaaaacg attgcagctt atcgtaaaaa tgaaggaacc    60
tatgattaaa gaaagccgac tgca    84

<210> SEQ ID NO 49
<211> LENGTH: 20
<212> TYPE: DNA
<213> ORGANISM: Artificial Sequence
<220> FEATURE:
<223> OTHER INFORMATION: PRIMER

<400> SEQUENCE: 49
ttgggtaacg ccagggtttt    20

<210> SEQ ID NO 50
<211> LENGTH: 20
<212> TYPE: DNA
<213> ORGANISM: Artificial Sequence
<220> FEATURE:
<223> OTHER INFORMATION: PRIMER

<400> SEQUENCE: 50
tgtgtggaat tgtgagcgga    20

<210> SEQ ID NO 51
<211> LENGTH: 1490
<212> TYPE: PRT
<213> ORGANISM: Artificial Sequence
<220> FEATURE:
<223> OTHER INFORMATION: Artificially mutated sequence

<400> SEQUENCE: 51

Met Lys Lys Ile Leu Gly Leu Ala Leu Gly Thr Asn Ser Ile Gly Trp
1               5                   10                  15

Ala Leu Ile Glu His Asn Phe Asp Lys Lys Glu Gly Arg Ile Asp Asp
            20                  25                  30

Leu Gly Val Arg Ile Ile Pro Met Ser Ala Asp Ile Leu Gly Lys Phe
        35                  40                  45

Asp Ala Gly Gln Ser His Ser Gln Thr Ala Glu Arg Thr Gly Tyr Arg
    50                  55                  60

Gly Val Arg Arg Leu Tyr Gln Arg Asp Asn Leu Arg Arg Glu Arg Leu
65                  70                  75                  80

His Arg Val Leu Asn Ile Leu Asp Phe Leu Pro Glu His Tyr Ala Glu
                85                  90                  95

His Ile Asp Phe Glu Lys Arg Leu Gly Gln Phe Lys Glu Gly Lys Glu
            100                 105                 110

Ile Lys Leu Asn Tyr Lys Ser Asn Lys Asp Ser Lys Phe Glu Phe Ile
        115                 120                 125

Phe Lys Ala Ser Tyr Asn Glu Met Leu Ala Ala Phe Lys Lys Tyr Gln
    130                 135                 140

Pro Gly Leu Phe Tyr Val Lys Ala Asn Gly Thr Glu Thr Lys Ile Pro
145                 150                 155                 160

Tyr Asp Trp Thr Ile Tyr Tyr Leu Arg Lys Lys Ala Leu Ser Gln Pro
                165                 170                 175

Leu Thr Lys Gln Glu Leu Ala Trp Ile Ile Leu Asn Phe Asn Gln Lys
            180                 185                 190

Arg Gly Tyr Tyr Gln Leu Arg Gly Glu Glu Ile Asp Asp Asp Lys Asn

```
            195                 200                 205
Lys Gln Phe Val Gln Leu Lys Val Lys Glu Val Ile Asp Ser Gly Glu
210                 215                 220

Ala Val Lys Gly Lys Lys Leu Phe Asn Val Ile Phe Glu Asn Gly Trp
225                 230                 235                 240

Lys Tyr Asp Lys Gln Val Val Lys Thr Glu Asp Trp Ile Gly Arg Thr
                245                 250                 255

Lys Glu Phe Ile Val Thr Thr Lys Thr Leu Lys Ser Gly Glu Ile Lys
                260                 265                 270

Arg Thr Tyr Lys Ala Val Asp Ser Glu Lys Asp Trp Ala Ala Ile Lys
            275                 280                 285

Ala Lys Thr Glu Gln Asp Ile Glu Arg Ser Asn Lys Thr Val Gly Glu
290                 295                 300

Phe Ile Tyr Glu Ala Leu Leu Gln Asp Pro Thr Gln Lys Ile Arg Gly
305                 310                 315                 320

Lys Leu Val Lys Thr Ile Glu Arg Lys Phe Tyr Lys Ala Glu Leu Arg
                325                 330                 335

Glu Ile Leu Arg Lys Gln Ile Glu Leu Gln Pro Gln Leu Phe Thr Thr
                340                 345                 350

Lys Leu Tyr Asn Ala Cys Ile Lys Glu Leu Tyr Pro Asn Asn Glu Ala
            355                 360                 365

His Arg Asn Ser Ile Lys Asn Arg Asp Phe Leu Tyr Leu Phe Leu Asp
370                 375                 380

Asp Ile Ile Phe Tyr Gln Arg Pro Leu Lys Ser Gln Lys Ser Asn Ile
385                 390                 395                 400

Ser Gly Cys His Leu Glu Gln Arg Ile Tyr Thr Lys Ile Asn Pro Val
                405                 410                 415

Ser Gly Lys Lys Glu Glu Val Lys Gln Ala Val Lys Ala Ile Pro Lys
                420                 425                 430

Ser His Pro Ile Phe Gln Glu Phe Arg Ile Trp Gln Trp Leu Gln Asn
            435                 440                 445

Leu Lys Ile Tyr Asp Lys Ile Asn Thr Asp Lys Gly Glu Leu Ala Asp
450                 455                 460

Val Thr Asn Gln Leu Leu Pro Ser Glu Glu Ser Leu Leu Asp Leu Phe
465                 470                 475                 480

Asp Tyr Leu Gln Thr Lys Lys Glu Leu Asp Gln Ser Gly Phe Ile Lys
                485                 490                 495

Tyr Phe Ile Asp Lys Lys Leu Ile Asn Lys Ser Glu Lys Glu Asn Tyr
                500                 505                 510

Arg Trp Asn Tyr Val Glu Asp Lys Lys Tyr Pro Phe Ala Glu Thr Arg
            515                 520                 525

Ala Gln Phe Ile Ser Arg Leu Asn Lys Val Lys Asn Ile Asn Asn Ile
530                 535                 540

Ser Glu Phe Leu Asn Lys Lys Thr Arg Leu Gly Glu Lys Glu Ser Ser
545                 550                 555                 560

Pro Phe Val Thr Arg Ile Glu Gln Leu Trp His Ile Ile Tyr Ser Val
                565                 570                 575

Ser Asp Ile Asn Glu Tyr Lys Ser Ala Leu Glu Lys Phe Ala Leu Lys
                580                 585                 590

His Asp Ile Asp Lys Glu Ser Phe Val Ala Asn Phe Ile Lys Phe Pro
            595                 600                 605

Pro Phe Lys Ser Asp Tyr Gly Ser Tyr Ser Lys Lys Ala Leu Ser Lys
610                 615                 620
```

```
Leu Leu Pro Leu Met Arg Arg Gly Lys Tyr Trp Asn Glu Ser Asp Ile
625                 630                 635                 640

Ser Asn Lys Val Lys Gln Arg Val Ser Asp Ile Met Glu Arg Val Asn
            645                 650                 655

Ala Leu Asn Leu Lys Glu Asn Tyr Asn Ala Lys Glu Leu Ala Glu Ala
                660                 665                 670

Leu Lys Thr Val Ser Asp Asp Val Lys Lys Gln Leu Ile Lys Ser
        675                 680                 685

Phe Val Pro Phe Lys Asp Lys Asn Pro Leu Lys Gly Leu Asn Thr Tyr
            690                 695                 700

Gln Ala Thr Tyr Leu Val Tyr Gly Arg His Ser Glu Val Gly Asp Ile
705                 710                 715                 720

Gln Ser Trp Lys Thr Pro Glu Asp Ile Asp Thr Tyr Leu Lys Asn Phe
            725                 730                 735

Lys Gln His Ser Leu Arg Asn Pro Ile Val Glu Gln Val Val Thr Glu
                740                 745                 750

Thr Leu Arg Val Val Arg Asp Ile Trp Ile His Tyr Gly Lys Ser Gln
        755                 760                 765

Leu Asn Phe Phe Asn Glu Ile His Val Glu Leu Gly Arg Glu Met Lys
770                 775                 780

Asn Pro Ala Asp Lys Arg Lys Gln Ile Ser Asn Arg Asn Ile Glu Asn
785                 790                 795                 800

Glu Asn Thr Asn Asn Arg Ile Arg Glu Ile Leu Lys Asp Leu Lys Asn
            805                 810                 815

Asp Thr Ser Ile Glu Gly Asp Ile Arg Asp Tyr Ser Pro Ser Gln Gln
                820                 825                 830

Asp Leu Leu Lys Ile Tyr Glu Glu Gly Val Tyr Gln Asn Pro Lys Val
        835                 840                 845

Asp Tyr Ser Lys Val Ser Glu Asp Glu Ile Thr Lys Ile Arg Arg Ser
850                 855                 860

Asn Ser Pro Thr Pro Lys Glu Ile Gln Arg Tyr Arg Leu Trp Leu Glu
865                 870                 875                 880

Gln Gly Tyr Ile Ser Pro Tyr Thr Gly Lys Pro Ile Pro Leu Ser Lys
                885                 890                 895

Leu Phe Thr His Glu Tyr Gln Ile Glu His Ile Ile Pro Gln Ser Arg
                900                 905                 910

Tyr Phe Asp Asn Ser Leu Ser Asn Lys Ile Ile Cys Glu Ser Ala Val
        915                 920                 925

Asn Glu Asp Lys Asp Asn Lys Thr Ala Tyr Glu Tyr Leu Lys Asn Lys
930                 935                 940

Ser Gly Asn Val Ile Asn Gly His Lys Leu Leu Arg Ile Glu Glu Tyr
945                 950                 955                 960

Glu Ala His Val Asn Arg Tyr Phe Lys Asn Asn Arg Gln Lys Leu Lys
                965                 970                 975

Asn Leu Leu Ser Glu Asp Ile Pro Glu Gly Phe Ile Asn Arg Gln Leu
            980                 985                 990

Asn Asp Ser Arg Tyr Ile Ser Lys Leu Ile Lys Gly Leu Leu Ser Asn
        995                 1000                1005

Ile Val Arg Gln Glu Asn Glu Gln Glu Ala Thr Ser Lys Asn Leu
        1010                1015                1020

Ile Pro Val Thr Gly Ala Val Thr Ser Leu Lys Asn Asp Trp
        1025                1030                1035
```

```
Gly Leu Asn Asp Lys Trp Asn Glu Leu Ile Leu Pro Arg Phe Glu
1040                1045                1050

Arg Leu Asn Gln Leu Thr Gln Thr Lys Asn Phe Thr Thr Ser Asn
1055                1060                1065

Thr Asn Gly Asn Thr Ile Pro Thr Val Pro Asp Asp Leu Leu Lys
1070                1075                1080

Gly Phe Ser Lys Lys Arg Ile Asp His Arg His His Ala Leu Asp
1085                1090                1095

Ala Leu Val Val Ala Cys Cys Thr Arg Asn His Val Gln Tyr Leu
1100                1105                1110

Asn Ala Leu Asn Ala Glu Lys Ala Asn Tyr Gly Leu Arg Lys Lys
1115                1120                1125

Leu Leu Ile Val Asn Glu Gln Gly Asp Phe Thr Lys Ile Phe Gln
1130                1135                1140

Met Pro Trp Lys Gly Phe Thr Ser Glu Ala Lys Asn Gln Leu Glu
1145                1150                1155

Lys Thr Val Ile Ser Phe Lys Gln Asn Leu Arg Val Ile Asn Lys
1160                1165                1170

Ala Asn Asn Lys Phe Trp Ser Phe Lys Asp Glu Asn Gly Asn Ile
1175                1180                1185

Asn Leu Asp Lys Asn Gly Arg Pro Val Lys Lys Leu Arg Lys Gln
1190                1195                1200

Thr Lys Gly Asp Asn Trp Ala Ile Arg Lys Ala Met His Lys Glu
1205                1210                1215

Thr Val Ser Gly Lys Ser Asn Ile Glu Thr Pro Lys Gly Lys Ile
1220                1225                1230

Ala Thr Ala Val Arg Gly Ser Leu Ala Asp Ile Lys Asn Glu Lys
1235                1240                1245

His Leu Gly Lys Ile Thr Asp Val Gln Ile Arg Glu Val Ile Leu
1250                1255                1260

Pro Asn His Leu Lys Asn Tyr Val Asp Glu Lys Gly Lys Val Lys
1265                1270                1275

Phe Asp Leu Ala Phe Asn Asp Glu Gly Ile Glu Asp Leu Asn Lys
1280                1285                1290

Asn Ile Ile Ala Leu Asn Asn Gly Lys Lys His Gln Pro Ile Arg
1295                1300                1305

Lys Val Lys Phe Phe Glu Val Gly Ser Lys Phe Ser Ile Ser Glu
1310                1315                1320

Asn Glu Asn Ser Ala Lys Ser Lys Lys Tyr Val Glu Ala Ala Lys
1325                1330                1335

Gly Thr Asn Leu Phe Ala Val Tyr Trp Asp Glu Lys Lys Gln
1340                1345                1350

Lys Arg Asn Tyr Glu Thr Val Pro Leu Asn Glu Val Ile Ala His
1355                1360                1365

Gln Lys Gln Val Ala His Leu Thr Asn Asn Glu Arg Leu Pro Ile
1370                1375                1380

Gln Thr Asn Arg Lys Lys Gly Asp Phe Leu Phe Thr Leu Ser Pro
1385                1390                1395

Asn Asp Leu Val Tyr Val Pro Thr Asp Ala Glu Val Ala Asn Lys
1400                1405                1410

Gln Pro Ile Asp Phe Lys Asn Leu His Gln Asn Gln Val Asn Arg
1415                1420                1425

Ile Tyr Lys Met Val Ser Ser Ser Gly Asn Gln Cys Phe Phe Ile
```

```
                    1430                1435                1440

Lys  Asp  Lys  Ile  Ala  Thr  Ser   Ile  Trp  Asn  Lys  Asn   Glu  Phe  Ser
          1445                1450                     1455

Ser  Leu  Asn  Lys  Met  Glu  Lys   Asp  Ile  Asp  Gly  Asn   Met  Ile  Lys
          1460                1465                     1470

Glu  Arg  Cys  Ile  Lys  Leu  Asn   Val  Asp  Arg  Leu  Gly   Asn  Ile  Thr
          1475                1480                     1485

Lys  Ala
     1490

<210> SEQ ID NO 52
<211> LENGTH: 1490
<212> TYPE: PRT
<213> ORGANISM: Artificial Sequence
<220> FEATURE:
<223> OTHER INFORMATION: Artificially mutated sequence

<400> SEQUENCE: 52

Met  Lys  Lys  Ile  Leu  Gly  Leu  Asp  Leu  Gly  Thr  Asn  Ser  Ile  Gly  Trp
1                   5                   10                      15

Ala  Leu  Ile  Glu  His  Asn  Phe  Asp  Lys  Lys  Glu  Gly  Arg  Ile  Asp  Asp
               20                      25                      30

Leu  Gly  Val  Arg  Ile  Ile  Pro  Met  Ser  Ala  Asp  Ile  Leu  Gly  Lys  Phe
               35                      40                      45

Asp  Ala  Gly  Gln  Ser  His  Ser  Gln  Thr  Ala  Glu  Arg  Thr  Gly  Tyr  Arg
     50                      55                      60

Gly  Val  Arg  Arg  Leu  Tyr  Gln  Arg  Asp  Asn  Leu  Arg  Arg  Glu  Arg  Leu
65                       70                      75                       80

His  Arg  Val  Leu  Asn  Ile  Leu  Asp  Phe  Leu  Pro  Glu  His  Tyr  Ala  Glu
                85                      90                      95

His  Ile  Asp  Phe  Glu  Lys  Arg  Leu  Gly  Gln  Phe  Lys  Glu  Gly  Lys  Glu
                100                     105                     110

Ile  Lys  Leu  Asn  Tyr  Lys  Ser  Asn  Lys  Asp  Ser  Lys  Phe  Glu  Phe  Ile
                115                     120                     125

Phe  Lys  Ala  Ser  Tyr  Asn  Glu  Met  Leu  Ala  Ala  Phe  Lys  Lys  Tyr  Gln
     130                     135                     140

Pro  Gly  Leu  Phe  Tyr  Val  Lys  Ala  Asn  Gly  Thr  Glu  Thr  Lys  Ile  Pro
145                      150                     155                      160

Tyr  Asp  Trp  Thr  Ile  Tyr  Tyr  Leu  Arg  Lys  Lys  Ala  Leu  Ser  Gln  Pro
                165                     170                     175

Leu  Thr  Lys  Gln  Glu  Leu  Ala  Trp  Ile  Ile  Leu  Asn  Phe  Asn  Gln  Lys
                180                     185                     190

Arg  Gly  Tyr  Tyr  Gln  Leu  Arg  Gly  Glu  Glu  Ile  Asp  Asp  Asp  Lys  Asn
                195                     200                     205

Lys  Gln  Phe  Val  Gln  Leu  Lys  Val  Lys  Glu  Val  Ile  Asp  Ser  Gly  Glu
     210                     215                     220

Ala  Val  Lys  Gly  Lys  Lys  Leu  Phe  Asn  Val  Ile  Phe  Glu  Asn  Gly  Trp
225                      230                     235                      240

Lys  Tyr  Asp  Lys  Gln  Val  Val  Lys  Thr  Glu  Asp  Trp  Ile  Gly  Arg  Thr
                245                     250                     255

Lys  Glu  Phe  Ile  Val  Thr  Thr  Lys  Thr  Leu  Lys  Ser  Gly  Glu  Ile  Lys
                260                     265                     270

Arg  Thr  Tyr  Lys  Ala  Val  Asp  Ser  Glu  Lys  Asp  Trp  Ala  Ala  Ile  Lys
                275                     280                     285

Ala  Lys  Thr  Glu  Gln  Asp  Ile  Glu  Arg  Ser  Asn  Lys  Thr  Val  Gly  Glu
```

-continued

```
              290                 295                 300
Phe Ile Tyr Glu Ala Leu Leu Gln Asp Pro Thr Gln Lys Ile Arg Gly
305                 310                 315                 320

Lys Leu Val Lys Thr Ile Glu Arg Lys Phe Tyr Lys Ala Glu Leu Arg
                    325                 330                 335

Glu Ile Leu Arg Lys Gln Ile Glu Leu Gln Pro Gln Leu Phe Thr Thr
                340                 345                 350

Lys Leu Tyr Asn Ala Cys Ile Lys Glu Leu Tyr Pro Asn Asn Glu Ala
            355                 360                 365

His Arg Asn Ser Ile Lys Asn Arg Asp Phe Leu Tyr Leu Phe Leu Asp
        370                 375                 380

Asp Ile Ile Phe Tyr Gln Arg Pro Leu Lys Ser Gln Lys Ser Asn Ile
385                 390                 395                 400

Ser Gly Cys His Leu Glu Gln Arg Ile Tyr Thr Lys Ile Asn Pro Val
                    405                 410                 415

Ser Gly Lys Lys Glu Glu Val Lys Gln Ala Val Lys Ala Ile Pro Lys
                420                 425                 430

Ser His Pro Ile Phe Gln Glu Phe Arg Ile Trp Gln Trp Leu Gln Asn
            435                 440                 445

Leu Lys Ile Tyr Asp Lys Ile Asn Thr Asp Lys Gly Glu Leu Ala Asp
        450                 455                 460

Val Thr Asn Gln Leu Leu Pro Ser Glu Glu Ser Leu Leu Asp Leu Phe
465                 470                 475                 480

Asp Tyr Leu Gln Thr Lys Lys Glu Leu Asp Gln Ser Gly Phe Ile Lys
                    485                 490                 495

Tyr Phe Ile Asp Lys Lys Leu Ile Asn Lys Ser Glu Lys Glu Asn Tyr
                500                 505                 510

Arg Trp Asn Tyr Val Glu Asp Lys Lys Tyr Pro Phe Ala Glu Thr Arg
            515                 520                 525

Ala Gln Phe Ile Ser Arg Leu Asn Lys Val Lys Asn Ile Asn Asn Ile
        530                 535                 540

Ser Glu Phe Leu Asn Lys Lys Thr Arg Leu Gly Glu Lys Glu Ser Ser
545                 550                 555                 560

Pro Phe Val Thr Arg Ile Glu Gln Leu Trp His Ile Ile Tyr Ser Val
                    565                 570                 575

Ser Asp Ile Asn Glu Tyr Lys Ser Ala Leu Glu Lys Phe Ala Leu Lys
                580                 585                 590

His Asp Ile Asp Lys Glu Ser Phe Val Ala Asn Phe Ile Lys Phe Pro
            595                 600                 605

Pro Phe Lys Ser Asp Tyr Gly Ser Tyr Ser Lys Ala Leu Ser Lys
        610                 615                 620

Leu Leu Pro Leu Met Arg Arg Gly Lys Tyr Trp Asn Glu Ser Asp Ile
625                 630                 635                 640

Ser Asn Lys Val Lys Gln Arg Val Ser Asp Ile Met Glu Arg Val Asn
                    645                 650                 655

Ala Leu Asn Leu Lys Glu Asn Tyr Asn Ala Lys Glu Leu Ala Glu Ala
                660                 665                 670

Leu Lys Thr Val Ser Asp Asp Val Lys Lys Gln Leu Ile Lys Ser
            675                 680                 685

Phe Val Pro Phe Lys Asp Lys Asn Pro Leu Lys Gly Leu Asn Thr Tyr
        690                 695                 700

Gln Ala Thr Tyr Leu Val Tyr Gly Arg His Ser Glu Val Gly Asp Ile
705                 710                 715                 720
```

```
Gln Ser Trp Lys Thr Pro Glu Asp Ile Asp Thr Tyr Leu Lys Asn Phe
            725                 730                 735

Lys Gln His Ser Leu Arg Asn Pro Ile Val Glu Gln Val Val Thr Glu
            740                 745                 750

Thr Leu Arg Val Val Arg Asp Ile Trp Ile His Tyr Gly Lys Ser Gln
            755                 760                 765

Leu Asn Phe Phe Asn Glu Ile His Val Glu Leu Gly Arg Glu Met Lys
            770                 775                 780

Asn Pro Ala Asp Lys Arg Lys Gln Ile Ser Asn Arg Asn Ile Glu Asn
785                 790                 795                 800

Glu Asn Thr Asn Asn Arg Ile Arg Glu Ile Leu Lys Asp Leu Lys Asn
            805                 810                 815

Asp Thr Ser Ile Glu Gly Asp Ile Arg Asp Tyr Ser Pro Ser Gln Gln
            820                 825                 830

Asp Leu Leu Lys Ile Tyr Glu Glu Gly Val Tyr Gln Asn Pro Lys Val
            835                 840                 845

Asp Tyr Ser Lys Val Ser Glu Asp Glu Ile Thr Lys Ile Arg Arg Ser
            850                 855                 860

Asn Ser Pro Thr Pro Lys Glu Ile Gln Arg Tyr Arg Leu Trp Leu Glu
865                 870                 875                 880

Gln Gly Tyr Ile Ser Pro Tyr Thr Gly Lys Pro Ile Pro Leu Ser Lys
            885                 890                 895

Leu Phe Thr His Glu Tyr Gln Ile Glu Ala Ile Ile Pro Gln Ser Arg
            900                 905                 910

Tyr Phe Asp Asn Ser Leu Ser Asn Lys Ile Ile Cys Glu Ser Ala Val
            915                 920                 925

Asn Glu Asp Lys Asp Asn Lys Thr Ala Tyr Glu Tyr Leu Lys Asn Lys
            930                 935                 940

Ser Gly Asn Val Ile Asn Gly His Lys Leu Leu Arg Ile Glu Glu Tyr
945                 950                 955                 960

Glu Ala His Val Asn Arg Tyr Phe Lys Asn Asn Arg Gln Lys Leu Lys
            965                 970                 975

Asn Leu Leu Ser Glu Asp Ile Pro Glu Gly Phe Ile Asn Arg Gln Leu
            980                 985                 990

Asn Asp Ser Arg Tyr Ile Ser Lys Leu Ile Lys Gly Leu Leu Ser Asn
            995                 1000                1005

Ile Val Arg Gln Glu Asn Glu Gln Glu Ala Thr Ser Lys Asn Leu
            1010                1015                1020

Ile Pro Val Thr Gly Ala Val Thr Ser Lys Leu Lys Asn Asp Trp
            1025                1030                1035

Gly Leu Asn Asp Lys Trp Asn Glu Leu Ile Leu Pro Arg Phe Glu
            1040                1045                1050

Arg Leu Asn Gln Leu Thr Gln Thr Lys Asn Phe Thr Thr Ser Asn
            1055                1060                1065

Thr Asn Gly Asn Thr Ile Pro Thr Val Pro Asp Asp Leu Leu Lys
            1070                1075                1080

Gly Phe Ser Lys Lys Arg Ile Asp His Arg His His Ala Leu Asp
            1085                1090                1095

Ala Leu Val Val Ala Cys Cys Thr Arg Asn His Val Gln Tyr Leu
            1100                1105                1110

Asn Ala Leu Asn Ala Glu Lys Ala Asn Tyr Gly Leu Arg Lys Lys
            1115                1120                1125
```

Leu Leu Ile Val Asn Glu Gln Gly Asp Phe Thr Lys Ile Phe Gln
1130             1135             1140

Met Pro Trp Lys Gly Phe Thr Ser Glu Ala Lys Asn Gln Leu Glu
1145             1150             1155

Lys Thr Val Ile Ser Phe Lys Gln Asn Leu Arg Val Ile Asn Lys
1160             1165             1170

Ala Asn Asn Lys Phe Trp Ser Phe Lys Asp Glu Asn Gly Asn Ile
1175             1180             1185

Asn Leu Asp Lys Asn Gly Arg Pro Val Lys Lys Leu Arg Lys Gln
1190             1195             1200

Thr Lys Gly Asp Asn Trp Ala Ile Arg Lys Ala Met His Lys Glu
1205             1210             1215

Thr Val Ser Gly Lys Ser Asn Ile Glu Thr Pro Lys Gly Lys Ile
1220             1225             1230

Ala Thr Ala Val Arg Gly Ser Leu Ala Asp Ile Lys Asn Glu Lys
1235             1240             1245

His Leu Gly Lys Ile Thr Asp Val Gln Ile Arg Glu Val Ile Leu
1250             1255             1260

Pro Asn His Leu Lys Asn Tyr Val Asp Glu Lys Gly Lys Val Lys
1265             1270             1275

Phe Asp Leu Ala Phe Asn Asp Glu Gly Ile Glu Asp Leu Asn Lys
1280             1285             1290

Asn Ile Ile Ala Leu Asn Asn Gly Lys Lys His Gln Pro Ile Arg
1295             1300             1305

Lys Val Lys Phe Phe Glu Val Gly Ser Lys Phe Ser Ile Ser Glu
1310             1315             1320

Asn Glu Asn Ser Ala Lys Ser Lys Lys Tyr Val Glu Ala Ala Lys
1325             1330             1335

Gly Thr Asn Leu Phe Phe Ala Val Tyr Trp Asp Glu Lys Lys Gln
1340             1345             1350

Lys Arg Asn Tyr Glu Thr Val Pro Leu Asn Glu Val Ile Ala His
1355             1360             1365

Gln Lys Gln Val Ala His Leu Thr Asn Asn Glu Arg Leu Pro Ile
1370             1375             1380

Gln Thr Asn Arg Lys Lys Gly Asp Phe Leu Phe Thr Leu Ser Pro
1385             1390             1395

Asn Asp Leu Val Tyr Val Pro Thr Asp Ala Glu Val Ala Asn Lys
1400             1405             1410

Gln Pro Ile Asp Phe Lys Asn Leu His Gln Asn Gln Val Asn Arg
1415             1420             1425

Ile Tyr Lys Met Val Ser Ser Gly Asn Gln Cys Phe Phe Ile
1430             1435             1440

Lys Asp Lys Ile Ala Thr Ser Ile Trp Asn Lys Asn Glu Phe Ser
1445             1450             1455

Ser Leu Asn Lys Met Glu Lys Asp Ile Asp Gly Asn Met Ile Lys
1460             1465             1470

Glu Arg Cys Ile Lys Leu Asn Val Asp Arg Leu Gly Asn Ile Thr
1475             1480             1485

Lys Ala
1490

<210> SEQ ID NO 53
<211> LENGTH: 1490
<212> TYPE: PRT

<213> ORGANISM: Artificial Sequence
<220> FEATURE:
<223> OTHER INFORMATION: Artificially mutated sequence

<400> SEQUENCE: 53

```
Met Lys Lys Ile Leu Gly Leu Ala Leu Gly Thr Asn Ser Ile Gly Trp
1               5                   10                  15

Ala Leu Ile Glu His Asn Phe Asp Lys Lys Glu Gly Arg Ile Asp Asp
            20                  25                  30

Leu Gly Val Arg Ile Ile Pro Met Ser Ala Asp Ile Leu Gly Lys Phe
        35                  40                  45

Asp Ala Gly Gln Ser His Ser Gln Thr Ala Glu Arg Thr Gly Tyr Arg
    50                  55                  60

Gly Val Arg Arg Leu Tyr Gln Arg Asp Asn Leu Arg Arg Glu Arg Leu
65                  70                  75                  80

His Arg Val Leu Asn Ile Leu Asp Phe Leu Pro Glu His Tyr Ala Glu
                85                  90                  95

His Ile Asp Phe Glu Lys Arg Leu Gly Gln Phe Lys Glu Gly Lys Glu
            100                 105                 110

Ile Lys Leu Asn Tyr Lys Ser Asn Lys Asp Ser Lys Phe Glu Phe Ile
        115                 120                 125

Phe Lys Ala Ser Tyr Asn Glu Met Leu Ala Ala Phe Lys Lys Tyr Gln
    130                 135                 140

Pro Gly Leu Phe Tyr Val Lys Ala Asn Gly Thr Glu Thr Lys Ile Pro
145                 150                 155                 160

Tyr Asp Trp Thr Ile Tyr Tyr Leu Arg Lys Lys Ala Leu Ser Gln Pro
                165                 170                 175

Leu Thr Lys Gln Glu Leu Ala Trp Ile Ile Leu Asn Phe Asn Gln Lys
            180                 185                 190

Arg Gly Tyr Tyr Gln Leu Arg Gly Glu Glu Ile Asp Asp Asp Lys Asn
        195                 200                 205

Lys Gln Phe Val Gln Leu Lys Val Lys Glu Val Ile Asp Ser Gly Glu
    210                 215                 220

Ala Val Lys Gly Lys Lys Leu Phe Asn Val Ile Phe Glu Asn Gly Trp
225                 230                 235                 240

Lys Tyr Asp Lys Gln Val Val Lys Thr Glu Asp Trp Ile Gly Arg Thr
                245                 250                 255

Lys Glu Phe Ile Val Thr Thr Lys Thr Leu Lys Ser Gly Glu Ile Lys
            260                 265                 270

Arg Thr Tyr Lys Ala Val Asp Ser Glu Lys Asp Trp Ala Ala Ile Lys
        275                 280                 285

Ala Lys Thr Glu Gln Asp Ile Glu Arg Ser Asn Lys Thr Val Gly Glu
    290                 295                 300

Phe Ile Tyr Glu Ala Leu Leu Gln Asp Pro Thr Gln Lys Ile Arg Gly
305                 310                 315                 320

Lys Leu Val Lys Thr Ile Glu Arg Lys Phe Tyr Lys Ala Glu Leu Arg
                325                 330                 335

Glu Ile Leu Arg Lys Gln Ile Glu Leu Gln Pro Gln Leu Phe Thr Thr
            340                 345                 350

Lys Leu Tyr Asn Ala Cys Ile Lys Glu Leu Tyr Pro Asn Asn Glu Ala
        355                 360                 365

His Arg Asn Ser Ile Lys Asn Arg Asp Phe Leu Tyr Leu Phe Leu Asp
    370                 375                 380

Asp Ile Ile Phe Tyr Gln Arg Pro Leu Lys Ser Gln Lys Ser Asn Ile
```

-continued

```
385                 390                 395                 400
Ser Gly Cys His Leu Glu Gln Arg Ile Tyr Thr Lys Ile Asn Pro Val
            405                 410                 415
Ser Gly Lys Lys Glu Glu Val Lys Gln Ala Val Lys Ala Ile Pro Lys
            420                 425                 430
Ser His Pro Ile Phe Gln Glu Phe Arg Ile Trp Gln Trp Leu Gln Asn
            435                 440                 445
Leu Lys Ile Tyr Asp Lys Ile Asn Thr Asp Lys Gly Glu Leu Ala Asp
    450                 455                 460
Val Thr Asn Gln Leu Leu Pro Ser Glu Glu Ser Leu Leu Asp Leu Phe
465                 470                 475                 480
Asp Tyr Leu Gln Thr Lys Lys Glu Leu Asp Gln Ser Gly Phe Ile Lys
                485                 490                 495
Tyr Phe Ile Asp Lys Lys Leu Ile Asn Lys Ser Glu Lys Glu Asn Tyr
            500                 505                 510
Arg Trp Asn Tyr Val Glu Asp Lys Lys Tyr Pro Phe Ala Glu Thr Arg
            515                 520                 525
Ala Gln Phe Ile Ser Arg Leu Asn Lys Val Lys Asn Ile Asn Asn Ile
    530                 535                 540
Ser Glu Phe Leu Asn Lys Lys Thr Arg Leu Gly Glu Lys Glu Ser Ser
545                 550                 555                 560
Pro Phe Val Thr Arg Ile Glu Gln Leu Trp His Ile Ile Tyr Ser Val
                565                 570                 575
Ser Asp Ile Asn Glu Tyr Lys Ser Ala Leu Glu Lys Phe Ala Leu Lys
            580                 585                 590
His Asp Ile Asp Lys Glu Ser Phe Val Ala Asn Phe Ile Lys Phe Pro
            595                 600                 605
Pro Phe Lys Ser Asp Tyr Gly Ser Tyr Ser Lys Lys Ala Leu Ser Lys
    610                 615                 620
Leu Leu Pro Leu Met Arg Arg Gly Lys Tyr Trp Asn Glu Ser Asp Ile
625                 630                 635                 640
Ser Asn Lys Val Lys Gln Arg Val Ser Asp Ile Met Glu Arg Val Asn
                645                 650                 655
Ala Leu Asn Leu Lys Glu Asn Tyr Asn Ala Lys Glu Leu Ala Glu Ala
            660                 665                 670
Leu Lys Thr Val Ser Asp Asp Val Lys Lys Gln Leu Ile Lys Ser
            675                 680                 685
Phe Val Pro Phe Lys Asp Lys Asn Pro Leu Lys Gly Leu Asn Thr Tyr
    690                 695                 700
Gln Ala Thr Tyr Leu Val Tyr Gly Arg His Ser Glu Val Gly Asp Ile
705                 710                 715                 720
Gln Ser Trp Lys Thr Pro Glu Asp Ile Asp Thr Tyr Leu Lys Asn Phe
                725                 730                 735
Lys Gln His Ser Leu Arg Asn Pro Ile Val Glu Gln Val Val Thr Glu
            740                 745                 750
Thr Leu Arg Val Val Arg Asp Ile Trp Ile His Tyr Gly Lys Ser Gln
            755                 760                 765
Leu Asn Phe Phe Asn Glu Ile His Val Glu Leu Gly Arg Glu Met Lys
    770                 775                 780
Asn Pro Ala Asp Lys Lys Gln Ile Ser Asn Arg Asn Ile Glu Asn
785                 790                 795                 800
Glu Asn Thr Asn Asn Arg Ile Arg Glu Ile Leu Lys Asp Leu Lys Asn
                805                 810                 815
```

```
Asp Thr Ser Ile Glu Gly Asp Ile Arg Asp Tyr Ser Pro Ser Gln Gln
            820                 825                 830

Asp Leu Leu Lys Ile Tyr Glu Glu Gly Val Tyr Gln Asn Pro Lys Val
            835                 840                 845

Asp Tyr Ser Lys Val Ser Glu Asp Glu Ile Thr Lys Ile Arg Arg Ser
            850                 855                 860

Asn Ser Pro Thr Pro Lys Glu Ile Gln Arg Tyr Arg Leu Trp Leu Glu
865                 870                 875                 880

Gln Gly Tyr Ile Ser Pro Tyr Thr Gly Lys Pro Ile Pro Leu Ser Lys
                885                 890                 895

Leu Phe Thr His Glu Tyr Gln Ile Glu Ala Ile Pro Gln Ser Arg
            900                 905                 910

Tyr Phe Asp Asn Ser Leu Ser Asn Lys Ile Ile Cys Glu Ser Ala Val
            915                 920                 925

Asn Glu Asp Lys Asp Asn Lys Thr Ala Tyr Glu Tyr Leu Lys Asn Lys
            930                 935                 940

Ser Gly Asn Val Ile Asn Gly His Lys Leu Leu Arg Ile Glu Glu Tyr
945                 950                 955                 960

Glu Ala His Val Asn Arg Tyr Phe Lys Asn Asn Arg Gln Lys Leu Lys
                965                 970                 975

Asn Leu Leu Ser Glu Asp Ile Pro Glu Gly Phe Ile Asn Arg Gln Leu
            980                 985                 990

Asn Asp Ser Arg Tyr Ile Ser Lys Leu Ile Lys Gly Leu Leu Ser Asn
            995                1000                1005

Ile Val Arg Gln Glu Asn Glu Gln Glu Ala Thr Ser Lys Asn Leu
            1010                1015                1020

Ile Pro Val Thr Gly Ala Val Thr Ser Lys Leu Lys Asn Asp Trp
            1025                1030                1035

Gly Leu Asn Asp Lys Trp Asn Glu Leu Ile Leu Pro Arg Phe Glu
            1040                1045                1050

Arg Leu Asn Gln Leu Thr Gln Thr Lys Asn Phe Thr Thr Ser Asn
            1055                1060                1065

Thr Asn Gly Asn Thr Ile Pro Thr Val Pro Asp Asp Leu Leu Lys
            1070                1075                1080

Gly Phe Ser Lys Lys Arg Ile Asp His Arg His His Ala Leu Asp
            1085                1090                1095

Ala Leu Val Val Ala Cys Cys Thr Arg Asn His Val Gln Tyr Leu
            1100                1105                1110

Asn Ala Leu Asn Ala Glu Lys Ala Asn Tyr Gly Leu Arg Lys Lys
            1115                1120                1125

Leu Leu Ile Val Asn Glu Gln Gly Asp Phe Thr Lys Ile Phe Gln
            1130                1135                1140

Met Pro Trp Lys Gly Phe Thr Ser Glu Ala Lys Asn Gln Leu Glu
            1145                1150                1155

Lys Thr Val Ile Ser Phe Lys Gln Asn Leu Arg Val Ile Asn Lys
            1160                1165                1170

Ala Asn Asn Lys Phe Trp Ser Phe Lys Asp Glu Asn Gly Asn Ile
            1175                1180                1185

Asn Leu Asp Lys Asn Gly Arg Pro Val Lys Lys Leu Arg Lys Gln
            1190                1195                1200

Thr Lys Gly Asp Asn Trp Ala Ile Arg Lys Ala Met His Lys Glu
            1205                1210                1215
```

-continued

Thr Val Ser Gly Lys Ser Asn Ile Glu Thr Pro Lys Gly Lys Ile
    1220                1225                1230

Ala Thr Ala Val Arg Gly Ser Leu Ala Asp Ile Lys Asn Glu Lys
    1235                1240                1245

His Leu Gly Lys Ile Thr Asp Val Gln Ile Arg Glu Val Ile Leu
    1250                1255                1260

Pro Asn His Leu Lys Asn Tyr Val Asp Glu Lys Gly Lys Val Lys
    1265                1270                1275

Phe Asp Leu Ala Phe Asn Asp Glu Gly Ile Glu Asp Leu Asn Lys
    1280                1285                1290

Asn Ile Ile Ala Leu Asn Asn Gly Lys Lys His Gln Pro Ile Arg
    1295                1300                1305

Lys Val Lys Phe Phe Glu Val Gly Ser Lys Phe Ser Ile Ser Glu
    1310                1315                1320

Asn Glu Asn Ser Ala Lys Ser Lys Lys Tyr Val Glu Ala Ala Lys
    1325                1330                1335

Gly Thr Asn Leu Phe Phe Ala Val Tyr Trp Asp Glu Lys Lys Gln
    1340                1345                1350

Lys Arg Asn Tyr Glu Thr Val Pro Leu Asn Glu Val Ile Ala His
    1355                1360                1365

Gln Lys Gln Val Ala His Leu Thr Asn Asn Glu Arg Leu Pro Ile
    1370                1375                1380

Gln Thr Asn Arg Lys Lys Gly Asp Phe Leu Phe Thr Leu Ser Pro
    1385                1390                1395

Asn Asp Leu Val Tyr Val Pro Thr Asp Ala Glu Val Ala Asn Lys
    1400                1405                1410

Gln Pro Ile Asp Phe Lys Asn Leu His Gln Asn Gln Val Asn Arg
    1415                1420                1425

Ile Tyr Lys Met Val Ser Ser Gly Asn Gln Cys Phe Phe Ile
    1430                1435                1440

Lys Asp Lys Ile Ala Thr Ser Ile Trp Asn Lys Asn Glu Phe Ser
    1445                1450                1455

Ser Leu Asn Lys Met Glu Lys Asp Ile Asp Gly Asn Met Ile Lys
    1460                1465                1470

Glu Arg Cys Ile Lys Leu Asn Val Asp Arg Leu Gly Asn Ile Thr
    1475                1480                1485

Lys Ala
    1490

<210> SEQ ID NO 54
<211> LENGTH: 1511
<212> TYPE: PRT
<213> ORGANISM: Artificial Sequence
<220> FEATURE:
<223> OTHER INFORMATION: Artificially mutated sequence

<400> SEQUENCE: 54

Met Lys Lys Ile Leu Gly Leu Ala Leu Gly Thr Asn Ser Ile Gly Trp
1               5                   10                  15

Ala Val Val Asn Ala Asp Ala Ile Thr Arg Asn Asp Gly Ser Arg Tyr
                20                  25                  30

Leu Lys Pro Asn Ser Ile Ser Ala Ala Gly Ser Arg Ile Ile Pro Met
            35                  40                  45

Ser Ala Asp Val Leu Gly Asn Phe Glu Ser Gly Ile Thr Val Ser Gln
        50                  55                  60

-continued

```
Thr Lys Asp Arg Thr Asp Lys Arg Met Ala Arg Leu His Glu Arg
 65                  70                  75                  80

Ala Leu Leu Arg Arg Glu Arg Leu Leu Arg Ile Leu Ser Leu Met Asp
                 85                  90                  95

Phe Leu Pro Lys His Phe Ala Ser Lys Ile Asn Arg Tyr Gly Lys Phe
                100                 105                 110

Thr Asp Asp Ser Glu Pro Lys Leu Ala Trp Arg Lys Asn Thr Glu Gly
            115                 120                 125

Lys Tyr Glu Phe Ile Phe Gln Asp Ala Phe Asn Glu Met Leu Ala Glu
130                 135                 140

Phe Lys Asp Lys Gln Pro Glu Ile Val Lys Glu Gly Lys Lys Ile Pro
145                 150                 155                 160

Tyr Asp Trp Thr Ile Tyr Tyr Leu Arg Lys Lys Ala Leu Glu Lys Ala
                165                 170                 175

Leu Ser Lys Glu Glu Leu Ser Trp Leu Leu Leu Gln Phe Asn Gln Lys
            180                 185                 190

Arg Gly Tyr Tyr Gln Leu Arg Gly Glu Glu Asp Ile Pro Gln Asp
        195                 200                 205

Lys Lys Ile Glu Tyr Leu Ala Gln Lys Val Val Lys Val Glu Ala Thr
210                 215                 220

Asp Gln Lys Lys Gly Asp Ile Trp Tyr Asn Val Tyr Leu Glu Asn
225                 230                 235                 240

Gly Met Ile Tyr Arg Arg Thr Ser Lys Ala Pro Leu Asp Trp Glu Gly
                245                 250                 255

Lys Ile Lys Glu Phe Ile Val Thr Thr Asp Leu Glu Lys Asp Gly Thr
            260                 265                 270

Pro Lys Lys Asp Lys Glu Gly Asn Ile Lys Arg Ser Phe Arg Ala Pro
        275                 280                 285

Gln Glu Asp Asp Trp Thr Leu Leu Lys Lys Lys Thr Glu Ala Asp Ile
290                 295                 300

Glu Lys Ser Thr Lys Thr Val Gly Cys Tyr Ile Tyr Asp Ser Leu Leu
305                 310                 315                 320

Asn Asn Pro Lys Gln Lys Ile Ile Gly Lys Leu Val Arg Thr Val Glu
                325                 330                 335

Arg Lys Phe Tyr Lys Glu Leu Thr Gln Ile Leu Lys Lys Gln Val
            340                 345                 350

Glu Leu Ile Pro Glu Leu Arg Asn Asp Asn Leu Tyr Lys Gln Cys Ile
        355                 360                 365

Glu Glu Leu Tyr Pro Ile Asn Glu Ala His Arg Asn Thr Ile Ala Lys
370                 375                 380

Thr Asp Phe Ala Asn Leu Phe Ile Asn Asp Ile Leu Phe Tyr Gln Arg
385                 390                 395                 400

Pro Leu Lys Ser Lys Lys Ser Gln Ile Asp Asn Cys Pro Tyr Glu Glu
                405                 410                 415

His Ile Phe Ile Asp Ser Lys Thr Gly Glu Lys Lys Val Pro Val
            420                 425                 430

Lys Cys Ile Thr Lys Ser Asn Pro Leu Phe Gln Glu Phe Arg Leu Trp
        435                 440                 445

Gln Phe Ile Gln Asn Leu Arg Ile Tyr Gln Arg Glu Lys Glu Ile Asp
450                 455                 460

Gly Lys Leu Ser Thr Asp Val Asp Ile Thr Ser Glu Cys Leu Lys Ser
465                 470                 475                 480

Glu Glu Asp Tyr Val Arg Leu Phe Asp Trp Leu Asn Asp Arg Glu Ser
```

-continued

```
                485                 490                 495
Ile Glu Gln Glu Glu Leu Leu Lys Tyr Leu Phe Asn Thr Lys Lys Ser
            500                 505                 510

Lys Asn Lys Glu Asn Pro Tyr Arg Trp Asn Tyr Val Glu Asp Lys Val
            515                 520                 525

Tyr Pro Cys Asn Glu Thr Arg Ala Thr Ile Leu Lys Gly Leu Ser Lys
            530                 535                 540

Cys Gly Ile Asn Ala Ser Val Leu Ser Ser Glu Met Glu Met Ala Leu
545                 550                 555                 560

Trp His Ile Leu Tyr Ser Val Glu Asp Lys Lys Glu Ile Glu Thr Ala
            565                 570                 575

Leu Thr His Phe Ala Gln Lys Gln Gly Trp Asn Gly Glu Phe Ala Ile
            580                 585                 590

Val Phe Ser Lys Leu Lys Pro Phe Lys Lys Asp Tyr Gly Ser Tyr Ser
            595                 600                 605

Glu Lys Ala Ile Lys Lys Leu Leu Ser Leu Met Arg Met Gly Lys Tyr
            610                 615                 620

Trp Asn Gln Asp Asn Ile Asp Lys Asn Thr Leu Asp Arg Ile Asp Lys
625                 630                 635                 640

Ile Ile Asn Gly Glu Tyr Asp Glu Lys Ile Ser Asn Arg Val Arg Asp
                645                 650                 655

Asn Ala Ile Asn Leu Lys Asp Ile Ser Asp Phe Arg Gly Leu Pro Val
                660                 665                 670

Trp Leu Ala Cys Tyr Ile Val Tyr Asp Arg His Ser Glu Ala Lys Asp
            675                 680                 685

Cys Thr Lys Trp Asn Thr Pro Glu Glu Ile Asp Ser Tyr Leu Lys Lys
            690                 695                 700

Phe Lys Gln His Ser Leu Arg Asn Pro Ile Val Glu Gln Val Val Thr
705                 710                 715                 720

Glu Thr Leu Arg Thr Val Arg Asp Ile Trp Lys Gln Glu Gly Gln Ile
                725                 730                 735

Asp Glu Ile His Leu Glu Leu Gly Arg Asp Leu Lys Asn Pro Ala Asp
            740                 745                 750

Lys Arg Lys Lys Met Ser Glu Asn Ile Leu Lys Asn Glu Asn Thr Asn
            755                 760                 765

Leu Arg Ile Lys Ala Met Leu Met Glu Phe Met Asn Pro Gly Met Gly
            770                 775                 780

Ile Glu Asn Val Arg Pro Tyr Ser Pro Ser Gln Gln Asp Ile Leu Arg
785                 790                 795                 800

Ile Tyr Glu Glu Asn Ala Leu Glu Asn Leu Thr Lys Asp Asp Glu Glu
                805                 810                 815

Phe Asp Phe Ile Ser Lys Ile Ser Lys Gln Ala Gln Pro Thr Lys Ser
            820                 825                 830

Asp Ile Val Arg Tyr Lys Cys Trp Leu Glu Gln Lys Tyr Arg Ser Pro
            835                 840                 845

Tyr Thr Gly Lys Thr Ile Ser Leu Ser Lys Leu Phe Thr Ser Ala Tyr
            850                 855                 860

Glu Ile Glu His Ile Ile Pro Gln Ser Arg Tyr Phe Asp Asp Ser Phe
865                 870                 875                 880

Ser Asn Lys Val Ile Cys Glu Ala Glu Val Asn Lys Leu Lys Asp Arg
            885                 890                 895

Gln Leu Gly His Glu Phe Ile Glu Glu His Gly Glu Lys Val Gln
            900                 905                 910
```

-continued

```
Leu Ser Gln Gly Glu Val Val Glu Ile Leu Ser Val Asp Ala Tyr Glu
        915                 920                 925

Lys Phe Val Lys Glu Asn Tyr Ala Asn Asn Arg Val Lys Met Lys Lys
930                 935                 940

Leu Leu Met Glu Asn Ile Pro Asp Glu Phe Ile Glu Arg Gln Leu Asn
945                 950                 955                 960

Asp Ser Arg Tyr Ile Ser Lys Val Val Lys Gly Leu Leu Ser Asn Ile
                965                 970                 975

Val Arg Glu Lys Ile Asp Asp Glu Asn Tyr Glu Pro Glu Ala Val Ser
            980                 985                 990

Lys Asn Leu Ile Ser Cys Asn Gly Ala Val Thr Asp Arg Leu Lys Lys
                995                 1000                1005

Asp Trp Gly Met Asn Asp Val Trp Asn Ser Ile Ile Leu Pro Arg
        1010                1015                1020

Phe Ile Arg Met Asn Gln Ile Thr Gly Lys Asp Cys Phe Thr Thr
        1025                1030                1035

Thr Asn Ala Glu Gly His Leu Ile Pro Gln Met Pro Leu Glu Leu
        1040                1045                1050

Gln Lys Gly Phe Asn Lys Lys Arg Ile Asp His Arg His His Ala
        1055                1060                1065

Met Asp Ala Ile Val Ile Ala Cys Thr Thr Arg Asp His Val Asn
        1070                1075                1080

Leu Leu Asn Asn Glu Ala Ala His Ser Lys Phe Asn Ala Thr Arg
        1085                1090                1095

Tyr Gln Leu Gln Arg Lys Leu Arg Cys Phe Glu Lys Ala Met Ile
        1100                1105                1110

Asp Gly Lys Glu Arg Glu Val Ala Lys Glu Phe Leu Lys Pro Trp
        1115                1120                1125

Asp Ser Phe Thr Met Asp Ser Lys Asn Ile Leu Glu Asn Ile Ile
        1130                1135                1140

Val Ser Phe Lys Gln Asn Gln Arg Val Ile Asn Lys Thr Thr Asn
        1145                1150                1155

Thr Phe Gln His Phe Asp Glu Asn Gly Lys Lys Thr Phe Val Lys
        1160                1165                1170

Gln Gly Lys Gly Asn Ser Trp Ala Ile Arg Lys Pro Met His Lys
        1175                1180                1185

Asp Thr Val Phe Gly Glu Ile Asn Leu Arg Lys Val Lys Ser Val
        1190                1195                1200

Ser Leu Ser Asp Ala Ile Lys Val Pro Glu Arg Ile Leu Asn Lys
        1205                1210                1215

Arg Ile Lys Glu Lys Ile Thr Glu Leu Lys Asn Asn Lys Val Asp
        1220                1225                1230

Ala Lys Asn Ile Lys Lys Tyr Ile Glu Glu Tyr His Ile Gly Gly
        1235                1240                1245

Tyr Gly Ile Asp Thr Ser Lys Ile Asp Val Phe Tyr Phe Thr Lys
        1250                1255                1260

Glu Thr Lys Glu Arg Phe Phe Ala Thr Arg Lys Ser Leu Asp Ser
        1265                1270                1275

Ser Phe Asn Gln Ala Lys Ile Glu Asp Ser Ile Ala Asp Ser Gly
        1280                1285                1290

Ile Gln Lys Ile Leu Leu Ala His Leu Lys Ser Lys Asn Gly Asp
        1295                1300                1305
```

```
Ala Glu  Gln Ala Phe Ser Pro Asp Gly Ile Asp Glu  Met Asn Lys
    1310             1315                1320

Asn Ile  Val Glu Leu Asn Asn Gly Lys Phe His Gln  Pro Ile Leu
    1325             1330                1335

Lys Val  Arg Val Tyr Glu Lys Ala Asp Lys Phe Ala  Val Gly Gln
    1340             1345                1350

Lys Gly  Asn Lys Lys Val Lys Phe Val Glu Ala Ala  Lys Gly Thr
    1355             1360                1365

Asn Leu  Phe Phe Ala Val Phe Glu Lys Asp Gly Lys  Arg Ser Tyr
    1370             1375                1380

Leu Thr  Ile Pro Leu Asn Val Met Ile Asp Cys Gln  Lys Lys Tyr
    1385             1390                1395

Gly Asn  Gln Trp Lys Gln Asn Ile Glu Ser Tyr Leu  Lys Glu Lys
    1400             1405                1410

Asp Leu  Val Glu Lys Asp Val Gln Leu Leu Phe Ile  Leu Ser Pro
    1415             1420                1425

Asn Asp  Leu Val Tyr Leu Pro Thr Glu Asn Glu Leu  Lys Lys Gly
    1430             1435                1440

Ile Thr  Asn Pro Asp Lys Asp Gln Ile Tyr Lys Phe  Val Ser Cys
    1445             1450                1455

Thr Ser  Asn Glu Ala His Phe Ile Pro Ser Phe Val  Ala Asn Pro
    1460             1465                1470

Ile Val  Gln Thr Thr Glu Leu Gly Ser Asn Asn Lys  Ala Gln Arg
    1475             1480                1485

Ala Trp  Asn Asn Lys Met Ile Lys Glu Ile Cys Ile  Pro Ile Glu
    1490             1495                1500

Val Asp  Arg Leu Gly Asn Ile Lys
    1505             1510

<210> SEQ ID NO 55
<211> LENGTH: 1511
<212> TYPE: PRT
<213> ORGANISM: Artificial Sequence
<220> FEATURE:
<223> OTHER INFORMATION: Artificially mutated sequence

<400> SEQUENCE: 55

Met Lys Lys Ile Leu Gly Leu Asp Leu Gly Thr Asn Ser Ile Gly Trp
1               5                   10                  15

Ala Val Val Asn Ala Asp Ala Ile Thr Arg Asn Asp Gly Ser Arg Tyr
                20                  25                  30

Leu Lys Pro Asn Ser Ile Ser Ala Ala Gly Ser Arg Ile Ile Pro Met
            35                  40                  45

Ser Ala Asp Val Leu Gly Asn Phe Glu Ser Gly Ile Thr Val Ser Gln
        50                  55                  60

Thr Lys Asp Arg Thr Asp Lys Arg Met Ala Arg Arg Leu His Glu Arg
65                  70                  75                  80

Ala Leu Leu Arg Arg Glu Arg Leu Leu Arg Ile Leu Ser Leu Met Asp
                85                  90                  95

Phe Leu Pro Lys His Phe Ala Ser Lys Ile Asn Arg Tyr Gly Lys Phe
            100                 105                 110

Thr Asp Asp Ser Glu Pro Lys Leu Ala Trp Arg Lys Asn Thr Glu Gly
        115                 120                 125

Lys Tyr Glu Phe Ile Phe Gln Asp Ala Phe Asn Glu Met Leu Ala Glu
    130                 135                 140
```

```
Phe Lys Asp Lys Gln Pro Glu Ile Val Lys Glu Gly Lys Lys Ile Pro
145                 150                 155                 160

Tyr Asp Trp Thr Ile Tyr Tyr Leu Arg Lys Lys Ala Leu Glu Lys Ala
            165                 170                 175

Leu Ser Lys Glu Glu Leu Ser Trp Leu Leu Leu Gln Phe Asn Gln Lys
            180                 185                 190

Arg Gly Tyr Tyr Gln Leu Arg Gly Glu Glu Asp Ile Pro Gln Asp
            195                 200                 205

Lys Lys Ile Glu Tyr Leu Ala Gln Lys Val Val Lys Val Glu Ala Thr
        210                 215                 220

Asp Gln Lys Lys Gly Asp Asp Ile Trp Tyr Asn Val Tyr Leu Glu Asn
225                 230                 235                 240

Gly Met Ile Tyr Arg Arg Thr Ser Lys Ala Pro Leu Asp Trp Glu Gly
            245                 250                 255

Lys Ile Lys Glu Phe Ile Val Thr Thr Asp Leu Glu Lys Asp Gly Thr
            260                 265                 270

Pro Lys Lys Asp Lys Glu Gly Asn Ile Lys Arg Ser Phe Arg Ala Pro
        275                 280                 285

Gln Glu Asp Asp Trp Thr Leu Leu Lys Lys Thr Glu Ala Asp Ile
290                 295                 300

Glu Lys Ser Thr Lys Thr Val Gly Cys Tyr Ile Tyr Asp Ser Leu Leu
305                 310                 315                 320

Asn Asn Pro Lys Gln Lys Ile Ile Gly Lys Leu Val Arg Thr Val Glu
            325                 330                 335

Arg Lys Phe Tyr Lys Glu Leu Thr Gln Ile Leu Lys Lys Gln Val
            340                 345                 350

Glu Leu Ile Pro Glu Leu Arg Asn Asp Asn Leu Tyr Lys Gln Cys Ile
            355                 360                 365

Glu Glu Leu Tyr Pro Ile Asn Glu Ala His Arg Asn Thr Ile Ala Lys
        370                 375                 380

Thr Asp Phe Ala Asn Leu Phe Ile Asn Asp Ile Leu Phe Tyr Gln Arg
385                 390                 395                 400

Pro Leu Lys Ser Lys Ser Gln Ile Asp Asn Cys Pro Tyr Glu Glu
            405                 410                 415

His Ile Phe Ile Asp Ser Lys Thr Gly Glu Lys Lys Val Pro Val
            420                 425                 430

Lys Cys Ile Thr Lys Ser Asn Pro Leu Phe Gln Glu Phe Arg Leu Trp
        435                 440                 445

Gln Phe Ile Gln Asn Leu Arg Ile Tyr Gln Arg Glu Lys Glu Ile Asp
450                 455                 460

Gly Lys Leu Ser Thr Asp Val Asp Ile Thr Ser Glu Cys Leu Lys Ser
465                 470                 475                 480

Glu Glu Asp Tyr Val Arg Leu Phe Asp Trp Leu Asn Asp Arg Glu Ser
            485                 490                 495

Ile Glu Gln Glu Glu Leu Leu Lys Tyr Leu Phe Asn Thr Lys Lys Ser
            500                 505                 510

Lys Asn Lys Glu Asn Pro Tyr Arg Trp Asn Tyr Val Glu Asp Lys Val
            515                 520                 525

Tyr Pro Cys Asn Glu Thr Arg Ala Thr Ile Leu Lys Gly Leu Ser Lys
        530                 535                 540

Cys Gly Ile Asn Ala Ser Val Leu Ser Ser Glu Met Glu Met Ala Leu
545                 550                 555                 560

Trp His Ile Leu Tyr Ser Val Glu Asp Lys Lys Glu Ile Glu Thr Ala
```

```
                565                 570                 575
Leu Thr His Phe Ala Gln Lys Gln Gly Trp Asn Gly Glu Phe Ala Ile
            580                 585                 590

Val Phe Ser Lys Leu Lys Pro Phe Lys Asp Tyr Gly Ser Tyr Ser
            595                 600                 605

Glu Lys Ala Ile Lys Lys Leu Leu Ser Leu Met Arg Met Gly Lys Tyr
            610                 615                 620

Trp Asn Gln Asp Asn Ile Asp Lys Asn Thr Leu Asp Arg Ile Asp Lys
625                 630                 635                 640

Ile Ile Asn Gly Glu Tyr Asp Glu Lys Ile Ser Asn Arg Val Arg Asp
                645                 650                 655

Asn Ala Ile Asn Leu Lys Asp Ile Ser Asp Phe Arg Gly Leu Pro Val
            660                 665                 670

Trp Leu Ala Cys Tyr Ile Val Tyr Asp Arg His Ser Glu Ala Lys Asp
            675                 680                 685

Cys Thr Lys Trp Asn Thr Pro Glu Glu Ile Asp Ser Tyr Leu Lys Lys
            690                 695                 700

Phe Lys Gln His Ser Leu Arg Asn Pro Ile Val Glu Gln Val Val Thr
705                 710                 715                 720

Glu Thr Leu Arg Thr Val Arg Asp Ile Trp Lys Gln Glu Gly Gln Ile
                725                 730                 735

Asp Glu Ile His Leu Glu Leu Gly Arg Asp Leu Lys Asn Pro Ala Asp
            740                 745                 750

Lys Arg Lys Lys Met Ser Glu Asn Ile Leu Lys Asn Glu Asn Thr Asn
            755                 760                 765

Leu Arg Ile Lys Ala Met Leu Met Glu Phe Met Asn Pro Gly Met Gly
            770                 775                 780

Ile Glu Asn Val Arg Pro Tyr Ser Pro Ser Gln Gln Asp Ile Leu Arg
785                 790                 795                 800

Ile Tyr Glu Glu Asn Ala Leu Glu Asn Leu Thr Lys Asp Asp Glu Glu
                805                 810                 815

Phe Asp Phe Ile Ser Lys Ile Ser Lys Gln Ala Gln Pro Thr Lys Ser
            820                 825                 830

Asp Ile Val Arg Tyr Lys Cys Trp Leu Glu Gln Lys Tyr Arg Ser Pro
            835                 840                 845

Tyr Thr Gly Lys Thr Ile Ser Leu Ser Lys Leu Phe Thr Ser Ala Tyr
            850                 855                 860

Glu Ile Glu Ala Ile Pro Gln Ser Arg Tyr Phe Asp Asp Ser Phe
865                 870                 875                 880

Ser Asn Lys Val Ile Cys Glu Ala Glu Val Asn Lys Leu Lys Asp Arg
                885                 890                 895

Gln Leu Gly His Glu Phe Ile Glu His His Gly Glu Lys Val Gln
            900                 905                 910

Leu Ser Gln Gly Glu Val Val Glu Ile Leu Ser Val Asp Ala Tyr Glu
            915                 920                 925

Lys Phe Val Lys Glu Asn Tyr Ala Asn Asn Arg Val Lys Met Lys Lys
            930                 935                 940

Leu Leu Met Glu Asn Ile Pro Asp Glu Phe Ile Glu Arg Gln Leu Asn
945                 950                 955                 960

Asp Ser Arg Tyr Ile Ser Lys Val Val Lys Gly Leu Leu Ser Asn Ile
                965                 970                 975

Val Arg Glu Lys Ile Asp Asp Glu Asn Tyr Glu Pro Glu Ala Val Ser
            980                 985                 990
```

```
Lys Asn Leu Ile Ser Cys Asn Gly Ala Val Thr Asp Arg Leu Lys Lys
        995                 1000                    1005

Asp Trp Gly Met Asn Asp Val Trp Asn Ser Ile Ile Leu Pro Arg
    1010                1015                1020

Phe Ile Arg Met Asn Gln Ile Thr Gly Lys Asp Cys Phe Thr Thr
    1025                1030                1035

Thr Asn Ala Glu Gly His Leu Ile Pro Gln Met Pro Leu Glu Leu
    1040                1045                1050

Gln Lys Gly Phe Asn Lys Lys Arg Ile Asp His Arg His His Ala
    1055                1060                1065

Met Asp Ala Ile Val Ile Ala Cys Thr Thr Arg Asp His Val Asn
    1070                1075                1080

Leu Leu Asn Asn Glu Ala Ala His Ser Lys Phe Asn Ala Thr Arg
    1085                1090                1095

Tyr Gln Leu Gln Arg Lys Leu Arg Cys Phe Glu Lys Ala Met Ile
    1100                1105                1110

Asp Gly Lys Glu Arg Glu Val Ala Lys Glu Phe Leu Lys Pro Trp
    1115                1120                1125

Asp Ser Phe Thr Met Asp Ser Lys Asn Ile Leu Glu Asn Ile Ile
    1130                1135                1140

Val Ser Phe Lys Gln Asn Gln Arg Val Ile Asn Lys Thr Thr Asn
    1145                1150                1155

Thr Phe Gln His Phe Asp Glu Asn Gly Lys Lys Thr Phe Val Lys
    1160                1165                1170

Gln Gly Lys Gly Asn Ser Trp Ala Ile Arg Lys Pro Met His Lys
    1175                1180                1185

Asp Thr Val Phe Gly Glu Ile Asn Leu Arg Lys Val Lys Ser Val
    1190                1195                1200

Ser Leu Ser Asp Ala Ile Lys Val Pro Glu Arg Ile Leu Asn Lys
    1205                1210                1215

Arg Ile Lys Glu Lys Ile Thr Glu Leu Lys Asn Asn Lys Val Asp
    1220                1225                1230

Ala Lys Asn Ile Lys Lys Tyr Ile Glu Glu Tyr His Ile Gly Gly
    1235                1240                1245

Tyr Gly Ile Asp Thr Ser Lys Ile Asp Val Phe Tyr Phe Thr Lys
    1250                1255                1260

Glu Thr Lys Glu Arg Phe Phe Ala Thr Arg Lys Ser Leu Asp Ser
    1265                1270                1275

Ser Phe Asn Gln Ala Lys Ile Glu Asp Ser Ile Ala Asp Ser Gly
    1280                1285                1290

Ile Gln Lys Ile Leu Leu Ala His Leu Lys Ser Lys Asn Gly Asp
    1295                1300                1305

Ala Glu Gln Ala Phe Ser Pro Asp Gly Ile Asp Glu Met Asn Lys
    1310                1315                1320

Asn Ile Val Glu Leu Asn Asn Gly Lys Phe His Gln Pro Ile Leu
    1325                1330                1335

Lys Val Arg Val Tyr Glu Lys Ala Asp Lys Phe Ala Val Gly Gln
    1340                1345                1350

Lys Gly Asn Lys Lys Val Lys Phe Val Glu Ala Ala Lys Gly Thr
    1355                1360                1365

Asn Leu Phe Phe Ala Val Phe Glu Lys Asp Gly Lys Arg Ser Tyr
    1370                1375                1380
```

```
Leu Thr Ile Pro Leu Asn Val Met Ile Asp Cys Gln Lys Lys Tyr
    1385                1390                1395

Gly Asn Gln Trp Lys Gln Asn Ile Glu Ser Tyr Leu Lys Glu Lys
    1400                1405                1410

Asp Leu Val Glu Lys Asp Val Gln Leu Leu Phe Ile Leu Ser Pro
    1415                1420                1425

Asn Asp Leu Val Tyr Leu Pro Thr Glu Asn Glu Leu Lys Lys Gly
    1430                1435                1440

Ile Thr Asn Pro Asp Lys Asp Gln Ile Tyr Lys Phe Val Ser Cys
    1445                1450                1455

Thr Ser Asn Glu Ala His Phe Ile Pro Ser Phe Val Ala Asn Pro
    1460                1465                1470

Ile Val Gln Thr Thr Glu Leu Gly Ser Asn Asn Lys Ala Gln Arg
    1475                1480                1485

Ala Trp Asn Asn Lys Met Ile Lys Glu Ile Cys Ile Pro Ile Glu
    1490                1495                1500

Val Asp Arg Leu Gly Asn Ile Lys
    1505                1510

<210> SEQ ID NO 56
<211> LENGTH: 1511
<212> TYPE: PRT
<213> ORGANISM: Artificial Sequence
<220> FEATURE:
<223> OTHER INFORMATION: Artificially mutated sequence

<400> SEQUENCE: 56

Met Lys Lys Ile Leu Gly Leu Ala Leu Gly Thr Asn Ser Ile Gly Trp
1               5                   10                  15

Ala Val Val Asn Ala Asp Ala Ile Thr Arg Asn Asp Gly Ser Arg Tyr
            20                  25                  30

Leu Lys Pro Asn Ser Ile Ser Ala Ala Gly Ser Arg Ile Ile Pro Met
        35                  40                  45

Ser Ala Asp Val Leu Gly Asn Phe Glu Ser Gly Ile Thr Val Ser Gln
    50                  55                  60

Thr Lys Asp Arg Thr Asp Lys Arg Met Ala Arg Arg Leu His Glu Arg
65                  70                  75                  80

Ala Leu Leu Arg Arg Glu Arg Leu Leu Arg Ile Leu Ser Leu Met Asp
                85                  90                  95

Phe Leu Pro Lys His Phe Ala Ser Lys Ile Asn Arg Tyr Gly Lys Phe
            100                 105                 110

Thr Asp Asp Ser Glu Pro Lys Leu Ala Trp Arg Lys Asn Thr Glu Gly
        115                 120                 125

Lys Tyr Glu Phe Ile Phe Gln Asp Ala Phe Asn Glu Met Leu Ala Glu
    130                 135                 140

Phe Lys Asp Lys Gln Pro Glu Ile Val Lys Glu Gly Lys Lys Ile Pro
145                 150                 155                 160

Tyr Asp Trp Thr Ile Tyr Tyr Leu Arg Lys Ala Leu Glu Lys Ala
                165                 170                 175

Leu Ser Lys Glu Glu Leu Ser Trp Leu Leu Leu Gln Phe Asn Gln Lys
            180                 185                 190

Arg Gly Tyr Tyr Gln Leu Arg Gly Glu Glu Asp Ile Pro Gln Asp
        195                 200                 205

Lys Lys Ile Glu Tyr Leu Ala Gln Lys Val Val Lys Val Glu Ala Thr
    210                 215                 220
```

```
Asp Gln Lys Lys Gly Asp Asp Ile Trp Tyr Asn Val Tyr Leu Glu Asn
225                 230                 235                 240

Gly Met Ile Tyr Arg Arg Thr Ser Lys Ala Pro Leu Asp Trp Glu Gly
                245                 250                 255

Lys Ile Lys Glu Phe Ile Val Thr Thr Asp Leu Glu Lys Asp Gly Thr
                260                 265                 270

Pro Lys Lys Asp Lys Glu Gly Asn Ile Lys Arg Ser Phe Arg Ala Pro
                275                 280                 285

Gln Glu Asp Asp Trp Thr Leu Leu Lys Lys Lys Thr Glu Ala Asp Ile
                290                 295                 300

Glu Lys Ser Thr Lys Thr Val Gly Cys Tyr Ile Tyr Asp Ser Leu Leu
305                 310                 315                 320

Asn Asn Pro Lys Gln Lys Ile Ile Gly Lys Leu Val Arg Thr Val Glu
                325                 330                 335

Arg Lys Phe Tyr Lys Glu Glu Leu Thr Gln Ile Leu Lys Lys Gln Val
                340                 345                 350

Glu Leu Ile Pro Glu Leu Arg Asn Asp Asn Leu Tyr Lys Gln Cys Ile
                355                 360                 365

Glu Glu Leu Tyr Pro Ile Asn Glu Ala His Arg Asn Thr Ile Ala Lys
370                 375                 380

Thr Asp Phe Ala Asn Leu Phe Ile Asn Asp Ile Leu Phe Tyr Gln Arg
385                 390                 395                 400

Pro Leu Lys Ser Lys Ser Gln Ile Asp Asn Cys Pro Tyr Glu Glu
                405                 410                 415

His Ile Phe Ile Asp Ser Lys Thr Gly Glu Lys Lys Lys Val Pro Val
                420                 425                 430

Lys Cys Ile Thr Lys Ser Asn Pro Leu Phe Gln Glu Phe Arg Leu Trp
                435                 440                 445

Gln Phe Ile Gln Asn Leu Arg Ile Tyr Gln Arg Glu Lys Glu Ile Asp
                450                 455                 460

Gly Lys Leu Ser Thr Asp Val Asp Ile Thr Ser Glu Cys Leu Lys Ser
465                 470                 475                 480

Glu Glu Asp Tyr Val Arg Leu Phe Asp Trp Leu Asn Asp Arg Glu Ser
                485                 490                 495

Ile Glu Gln Glu Glu Leu Leu Lys Tyr Leu Phe Asn Thr Lys Lys Ser
                500                 505                 510

Lys Asn Lys Glu Asn Pro Tyr Arg Trp Asn Tyr Val Glu Asp Lys Val
                515                 520                 525

Tyr Pro Cys Asn Glu Thr Arg Ala Thr Ile Leu Lys Gly Leu Ser Lys
530                 535                 540

Cys Gly Ile Asn Ala Ser Val Leu Ser Ser Glu Met Glu Met Ala Leu
545                 550                 555                 560

Trp His Ile Leu Tyr Ser Val Glu Asp Lys Lys Glu Ile Glu Thr Ala
                565                 570                 575

Leu Thr His Phe Ala Gln Lys Gln Gly Trp Asn Gly Glu Phe Ala Ile
                580                 585                 590

Val Phe Ser Lys Leu Lys Pro Phe Lys Lys Asp Tyr Gly Ser Tyr Ser
                595                 600                 605

Glu Lys Ala Ile Lys Lys Leu Leu Ser Leu Met Arg Met Gly Lys Tyr
                610                 615                 620

Trp Asn Gln Asp Asn Ile Asp Lys Asn Thr Leu Asp Arg Ile Asp Lys
625                 630                 635                 640

Ile Ile Asn Gly Glu Tyr Asp Glu Lys Ile Ser Asn Arg Val Arg Asp
```

-continued

```
                645                 650                 655
Asn Ala Ile Asn Leu Lys Asp Ile Ser Asp Phe Arg Gly Leu Pro Val
            660                 665                 670
Trp Leu Ala Cys Tyr Ile Val Tyr Asp Arg His Ser Glu Ala Lys Asp
            675                 680                 685
Cys Thr Lys Trp Asn Thr Pro Glu Glu Ile Asp Ser Tyr Leu Lys Lys
            690                 695                 700
Phe Lys Gln His Ser Leu Arg Asn Pro Ile Val Glu Gln Val Val Thr
705                 710                 715                 720
Glu Thr Leu Arg Thr Val Arg Asp Ile Trp Lys Gln Glu Gly Gln Ile
                725                 730                 735
Asp Glu Ile His Leu Glu Leu Gly Arg Asp Leu Lys Asn Pro Ala Asp
                740                 745                 750
Lys Arg Lys Lys Met Ser Glu Asn Ile Leu Lys Asn Glu Asn Thr Asn
                755                 760                 765
Leu Arg Ile Lys Ala Met Leu Met Glu Phe Met Asn Pro Gly Met Gly
            770                 775                 780
Ile Glu Asn Val Arg Pro Tyr Ser Pro Ser Gln Gln Asp Ile Leu Arg
785                 790                 795                 800
Ile Tyr Glu Glu Asn Ala Leu Glu Asn Leu Thr Lys Asp Asp Glu Glu
                805                 810                 815
Phe Asp Phe Ile Ser Lys Ile Ser Lys Gln Ala Gln Pro Thr Lys Ser
                820                 825                 830
Asp Ile Val Arg Tyr Lys Cys Trp Leu Glu Gln Lys Tyr Arg Ser Pro
            835                 840                 845
Tyr Thr Gly Lys Thr Ile Ser Leu Ser Lys Leu Phe Thr Ser Ala Tyr
850                 855                 860
Glu Ile Glu Ala Ile Ile Pro Gln Ser Arg Tyr Phe Asp Ser Phe
865                 870                 875                 880
Ser Asn Lys Val Ile Cys Glu Ala Glu Val Asn Lys Leu Lys Asp Arg
            885                 890                 895
Gln Leu Gly His Glu Phe Ile Glu Glu His His Gly Glu Lys Val Gln
            900                 905                 910
Leu Ser Gln Gly Glu Val Val Glu Ile Leu Ser Val Asp Ala Tyr Glu
        915                 920                 925
Lys Phe Val Lys Glu Asn Tyr Ala Asn Asn Arg Val Lys Met Lys Lys
            930                 935                 940
Leu Leu Met Glu Asn Ile Pro Asp Glu Phe Ile Glu Arg Gln Leu Asn
945                 950                 955                 960
Asp Ser Arg Tyr Ile Ser Lys Val Val Lys Gly Leu Leu Ser Asn Ile
            965                 970                 975
Val Arg Glu Lys Ile Asp Asp Glu Asn Tyr Glu Pro Glu Ala Val Ser
            980                 985                 990
Lys Asn Leu Ile Ser Cys Asn Gly  Ala Val Thr Asp Arg  Leu Lys Lys
            995                 1000                 1005
Asp Trp  Gly Met Asn Asp Val  Trp Asn Ser Ile Ile  Leu Pro Arg
    1010                 1015                 1020
Phe Ile  Arg Met Asn Gln Ile  Thr Gly Lys Asp Cys  Phe Thr Thr
    1025                 1030                 1035
Thr Asn  Ala Glu Gly His Leu  Ile Pro Gln Met Pro  Leu Glu Leu
    1040                 1045                 1050
Gln Lys  Gly Phe Asn Lys Lys  Arg Ile Asp His Arg  His His Ala
    1055                 1060                 1065
```

-continued

```
Met Asp Ala Ile Val Ile Ala Cys Thr Thr Arg Asp His Val Asn
    1070                1075                1080

Leu Leu Asn Asn Glu Ala Ala His Ser Lys Phe Asn Ala Thr Arg
    1085                1090                1095

Tyr Gln Leu Gln Arg Lys Leu Arg Cys Phe Glu Lys Ala Met Ile
    1100                1105                1110

Asp Gly Lys Glu Arg Glu Val Ala Lys Glu Phe Leu Lys Pro Trp
    1115                1120                1125

Asp Ser Phe Thr Met Asp Ser Lys Asn Ile Leu Glu Asn Ile Ile
    1130                1135                1140

Val Ser Phe Lys Gln Asn Gln Arg Val Ile Asn Lys Thr Thr Asn
    1145                1150                1155

Thr Phe Gln His Phe Asp Glu Asn Gly Lys Lys Thr Phe Val Lys
    1160                1165                1170

Gln Gly Lys Gly Asn Ser Trp Ala Ile Arg Lys Pro Met His Lys
    1175                1180                1185

Asp Thr Val Phe Gly Glu Ile Asn Leu Arg Lys Val Lys Ser Val
    1190                1195                1200

Ser Leu Ser Asp Ala Ile Lys Val Pro Glu Arg Ile Leu Asn Lys
    1205                1210                1215

Arg Ile Lys Glu Lys Ile Thr Glu Leu Lys Asn Asn Lys Val Asp
    1220                1225                1230

Ala Lys Asn Ile Lys Lys Tyr Ile Glu Glu Tyr His Ile Gly Gly
    1235                1240                1245

Tyr Gly Ile Asp Thr Ser Lys Ile Asp Val Phe Tyr Phe Thr Lys
    1250                1255                1260

Glu Thr Lys Glu Arg Phe Phe Ala Thr Arg Lys Ser Leu Asp Ser
    1265                1270                1275

Ser Phe Asn Gln Ala Lys Ile Glu Asp Ser Ile Ala Asp Ser Gly
    1280                1285                1290

Ile Gln Lys Ile Leu Leu Ala His Leu Lys Ser Lys Asn Gly Asp
    1295                1300                1305

Ala Glu Gln Ala Phe Ser Pro Asp Gly Ile Asp Glu Met Asn Lys
    1310                1315                1320

Asn Ile Val Glu Leu Asn Asn Gly Lys Phe His Gln Pro Ile Leu
    1325                1330                1335

Lys Val Arg Val Tyr Glu Lys Ala Asp Lys Phe Ala Val Gly Gln
    1340                1345                1350

Lys Gly Asn Lys Lys Val Lys Phe Val Glu Ala Ala Lys Gly Thr
    1355                1360                1365

Asn Leu Phe Phe Ala Val Phe Glu Lys Asp Gly Lys Arg Ser Tyr
    1370                1375                1380

Leu Thr Ile Pro Leu Asn Val Met Ile Asp Cys Gln Lys Lys Tyr
    1385                1390                1395

Gly Asn Gln Trp Lys Gln Asn Ile Glu Ser Tyr Leu Lys Glu Lys
    1400                1405                1410

Asp Leu Val Glu Lys Asp Val Gln Leu Leu Phe Ile Leu Ser Pro
    1415                1420                1425

Asn Asp Leu Val Tyr Leu Pro Thr Glu Asn Glu Leu Lys Lys Gly
    1430                1435                1440

Ile Thr Asn Pro Asp Lys Asp Gln Ile Tyr Lys Phe Val Ser Cys
    1445                1450                1455
```

```
Thr  Ser  Asn  Glu  Ala  His  Phe  Ile  Pro  Ser  Phe  Val  Ala  Asn  Pro
     1460                universe 1465                     1470

Ile  Val  Gln  Thr  Thr  Glu  Leu  Gly  Ser  Asn  Asn  Lys  Ala  Gln  Arg
     1475                     1480                     1485

Ala  Trp  Asn  Asn  Lys  Met  Ile  Lys  Glu  Ile  Cys  Ile  Pro  Ile  Glu
     1490                     1495                     1500

Val  Asp  Arg  Leu  Gly  Asn  Ile  Lys
     1505                     1510

<210> SEQ ID NO 57
<211> LENGTH: 1337
<212> TYPE: PRT
<213> ORGANISM: Artificial Sequence
<220> FEATURE:
<223> OTHER INFORMATION: Artificially mutated sequence

<400> SEQUENCE: 57

Met  Lys  Lys  Asp  Tyr  Val  Ile  Gly  Leu  Ala  Ile  Gly  Thr  Asn  Ser  Val
1                  5                        10                       15

Gly  Trp  Ala  Val  Met  Thr  Glu  Asp  Tyr  Gln  Leu  Val  Lys  Lys  Lys  Met
                   20                       25                       30

Pro  Ile  Tyr  Gly  Asn  Thr  Glu  Lys  Lys  Ile  Lys  Lys  Asn  Phe  Trp
              35                       40                       45

Gly  Val  Arg  Leu  Phe  Glu  Glu  Gly  His  Thr  Ala  Glu  Asp  Arg  Arg  Leu
50                      55                       60

Lys  Arg  Thr  Ala  Arg  Arg  Arg  Ile  Ser  Arg  Arg  Arg  Asn  Arg  Leu  Arg
65                      70                       75                       80

Tyr  Leu  Gln  Ala  Phe  Phe  Glu  Glu  Ala  Met  Thr  Ala  Leu  Asp  Glu  Asn
                   85                       90                       95

Phe  Phe  Ala  Arg  Leu  Gln  Glu  Ser  Phe  Leu  Val  Pro  Glu  Asp  Lys  Lys
                   100                      105                      110

Trp  His  Arg  His  Pro  Ile  Phe  Ala  Lys  Leu  Glu  Asp  Glu  Val  Ala  Tyr
              115                      120                      125

His  Glu  Thr  Tyr  Pro  Thr  Ile  Tyr  His  Leu  Arg  Lys  Lys  Leu  Ala  Asp
     130                     135                      140

Ser  Ser  Glu  Gln  Ala  Asp  Leu  Arg  Leu  Ile  Tyr  Leu  Ala  Leu  Ala  His
145                     150                      155                      160

Ile  Val  Lys  Tyr  Arg  Gly  His  Phe  Leu  Ile  Glu  Gly  Lys  Leu  Ser  Thr
                   165                      170                      175

Glu  Asn  Ile  Ser  Val  Lys  Glu  Gln  Phe  Gln  Gln  Phe  Met  Ile  Ile  Tyr
              180                      185                      190

Asn  Gln  Thr  Phe  Val  Asn  Gly  Glu  Ser  Arg  Leu  Val  Ser  Ala  Pro  Leu
     195                     200                      205

Pro  Glu  Ser  Val  Leu  Ile  Glu  Glu  Leu  Thr  Glu  Lys  Ala  Ser  Arg
210                      215                      220

Thr  Lys  Lys  Ser  Glu  Lys  Val  Leu  Gln  Gln  Phe  Pro  Gln  Glu  Lys  Ala
225                     230                      235                      240

Asn  Gly  Leu  Phe  Gly  Gln  Phe  Leu  Lys  Leu  Met  Val  Gly  Asn  Lys  Ala
                   245                      250                      255

Asp  Phe  Lys  Lys  Val  Phe  Gly  Leu  Glu  Glu  Ala  Lys  Ile  Thr  Tyr
              260                      265                      270

Ala  Ser  Glu  Ser  Tyr  Glu  Glu  Asp  Leu  Glu  Gly  Ile  Leu  Ala  Lys  Val
          275                      280                      285

Gly  Asp  Glu  Tyr  Ser  Asp  Val  Phe  Leu  Ala  Ala  Lys  Asn  Val  Tyr  Asp
     290                      295                      300
```

-continued

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
            325                 330                 335

Asp Leu Lys Asn Phe Lys Arg Phe Ile Arg Glu Asn Cys Pro Asp Glu
        340                 345                 350

Tyr Asp Asn Leu Phe Lys Asn Glu Gln Lys Asp Gly Tyr Ala Gly Tyr
    355                 360                 365

Ile Ala His Ala Gly Lys Val Ser Gln Leu Lys Phe Tyr Gln Tyr Val
370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
            405                 410                 415

Val Ile Pro His Gln Ile His Leu Ala Glu Leu Gln Ala Ile Ile His
        420                 425                 430

Arg Gln Ala Ala Tyr Tyr Pro Phe Leu Lys Glu Asn Gln Lys Lys Ile
    435                 440                 445

Glu Gln Leu Val Thr Phe Arg Ile Pro Tyr Tyr Val Gly Pro Leu Ser
450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
            485                 490                 495

Ala Thr Ala Phe Ile Glu Arg Met Thr Asn Phe Asp Thr Tyr Leu Pro
        500                 505                 510

Ser Glu Lys Val Leu Pro Lys His Ser Leu Leu Tyr Glu Lys Phe Met
    515                 520                 525

Val Phe Asn Glu Leu Thr Lys Ile Ser Tyr Thr Asp Asp Arg Gly Ile
530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Lys Asp Ile Ile Gln Phe Tyr
            565                 570                 575

Arg Asn Glu Tyr Asn Thr Glu Ile Val Thr Leu Ser Gly Leu Glu Glu
        580                 585                 590

Asp Gln Phe Asn Ala Ser Phe Ser Thr Tyr Gln Asp Leu Leu Lys Cys
    595                 600                 605

Gly Leu Thr Arg Ala Glu Leu Asp His Pro Asp Asn Ala Glu Lys Leu
610                 615                 620

Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Glu Glu Val Leu
            645                 650                 655

Lys Lys Leu Glu Arg Lys His Tyr Thr Gly Trp Gly Arg Leu Ser Lys
        660                 665                 670

Lys Leu Ile Asn Gly Ile Tyr Asp Lys Glu Ser Gly Lys Thr Ile Leu
    675                 680                 685

Asp Tyr Leu Ile Lys Asp Gly Val Ser Lys His Tyr Asn Arg Asn
690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val 725                 730                 735
Asn Glu Leu Ala Gly Ser Pro Ala Ile Lys Lys Gly Ile Tyr Gln Ser
                740                 745                 750

Leu Lys Ile Val Asp Glu Leu Val Ala Ile Met Gly Tyr Ala Pro Lys
            755                 760                 765

Arg Ile Val Glu Met Ala Arg Glu Asn Gln Thr Thr Ser Thr Gly
            770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
                805                 810                 815

Leu Arg Asp Thr Arg Leu Phe Leu Tyr Tyr Met Gln Asn Gly Lys Asp
                820                 825                 830

Met Tyr Thr Gly Asp Glu Leu Ser Leu His Arg Leu Ser His Tyr Asp
                835                 840                 845

Ile Asp His Ile Ile Pro Gln Ser Phe Met Lys Asp Asp Ser Leu Asp
850                 855                 860

Asn Leu Val Leu Val Gly Ser Thr Glu Asn Arg Gly Lys Ser Asp Asp
865                 870                 875                 880

Val Pro Ser Lys Glu Val Val Lys Lys Met Lys Ala Tyr Trp Glu Lys
                885                 890                 895

Leu Tyr Ala Ala Gly Leu Ile Ser Gln Arg Lys Phe Gln Arg Leu Thr
                900                 905                 910

Lys Gly Glu Gln Gly Gly Leu Thr Leu Glu Asp Lys Ala His Phe Ile
                915                 920                 925

Gln Arg Gln Leu Val Glu Thr Arg Gln Ile Thr Lys Asn Val Ala Gly
                930                 935                 940

Ile Leu Asp Gln Arg Tyr Asn Ala Lys Ser Lys Glu Lys Lys Val Gln
945                 950                 955                 960

Ile Ile Thr Leu Lys Ala Ser Leu Thr Ser Gln Phe Arg Ser Ile Phe
                965                 970                 975

Gly Leu Tyr Lys Val Arg Glu Val Asn Asp Tyr His His Gly Gln Asp
                980                 985                 990

Ala Tyr Leu Asn Cys Val Val Ala Thr Thr Leu Leu Lys Val Tyr Pro
                995                 1000                1005

Asn Leu Ala Pro Glu Phe Val Tyr Gly Glu Tyr Pro Lys Phe Gln
            1010                1015                1020

Ala Phe Lys Glu Asn Lys Ala Thr Ala Lys Ala Ile Ile Tyr Thr
            1025                1030                1035

Asn Leu Leu Arg Phe Phe Thr Glu Asp Glu Pro Arg Phe Thr Lys
            1040                1045                1050

Asp Gly Glu Ile Leu Trp Ser Asn Ser Tyr Leu Lys Thr Ile Lys
            1055                1060                1065

Lys Glu Leu Asn Tyr His Gln Met Asn Ile Val Lys Lys Val Glu
            1070                1075                1080

Val Gln Lys Gly Gly Phe Ser Lys Glu Ser Ile Lys Pro Lys Gly
            1085                1090                1095

Pro Ser Asn Lys Leu Ile Pro Val Lys Asn Gly Leu Asp Pro Gln
            1100                1105                1110

Lys Tyr Gly Gly Phe Asp Ser Pro Val Val Ala Tyr Thr Val Leu
            1115                1120                1125

Phe Thr His Glu Lys Gly Lys Lys Pro Leu Ile Lys Gln Glu Ile
            1130                1135                1140

```
Leu Gly Ile Thr Ile Met Glu Lys Thr Arg Phe Glu Gln Asn Pro
        1145                1150                1155

Ile Leu Phe Leu Glu Glu Lys Gly Phe Leu Arg Pro Arg Val Leu
        1160                1165                1170

Met Lys Leu Pro Lys Tyr Thr Leu Tyr Glu Phe Pro Glu Gly Arg
        1175                1180                1185

Arg Arg Leu Leu Ala Ser Ala Lys Glu Ala Gln Lys Gly Asn Gln
        1190                1195                1200

Met Val Leu Pro Glu His Leu Leu Thr Leu Leu Tyr His Ala Lys
        1205                1210                1215

Gln Cys Leu Leu Pro Asn Gln Ser Glu Ser Leu Ala Tyr Val Glu
        1220                1225                1230

Gln His Gln Pro Glu Phe Gln Glu Ile Leu Glu Arg Val Val Asp
        1235                1240                1245

Phe Ala Glu Val His Thr Leu Ala Lys Ser Lys Val Gln Gln Ile
        1250                1255                1260

Val Lys Leu Phe Glu Ala Asn Gln Thr Ala Asp Val Lys Glu Ile
        1265                1270                1275

Ala Ala Ser Phe Ile Gln Leu Met Gln Phe Asn Ala Met Gly Ala
        1280                1285                1290

Pro Ser Thr Phe Lys Phe Phe Gln Lys Asp Ile Glu Arg Ala Arg
        1295                1300                1305

Tyr Thr Ser Ile Lys Glu Ile Phe Asp Ala Thr Ile Ile Tyr Gln
        1310                1315                1320

Ser Thr Thr Gly Leu Tyr Glu Thr Arg Lys Val Val Asp
        1325                1330                1335

<210> SEQ ID NO 58
<211> LENGTH: 1337
<212> TYPE: PRT
<213> ORGANISM: Artificial Sequence
<220> FEATURE:
<223> OTHER INFORMATION: Artificially mutated sequence

<400> SEQUENCE: 58

Met Lys Lys Asp Tyr Val Ile Gly Leu Asp Ile Gly Thr Asn Ser Val
1               5                   10                  15

Gly Trp Ala Val Met Thr Glu Asp Tyr Gln Leu Val Lys Lys Lys Met
            20                  25                  30

Pro Ile Tyr Gly Asn Thr Glu Lys Lys Ile Lys Lys Asn Phe Trp
        35                  40                  45

Gly Val Arg Leu Phe Glu Glu Gly His Thr Ala Glu Asp Arg Arg Leu
    50                  55                  60

Lys Arg Thr Ala Arg Arg Arg Ile Ser Arg Arg Asn Arg Leu Arg
65                  70                  75                  80

Tyr Leu Gln Ala Phe Phe Glu Glu Ala Met Thr Ala Leu Asp Glu Asn
                85                  90                  95

Phe Phe Ala Arg Leu Gln Glu Ser Phe Leu Val Pro Glu Asp Lys Lys
            100                 105                 110

Trp His Arg His Pro Ile Phe Ala Lys Leu Glu Asp Glu Val Ala Tyr
        115                 120                 125

His Glu Thr Tyr Pro Thr Ile Tyr His Leu Arg Lys Lys Leu Ala Asp
    130                 135                 140

Ser Ser Glu Gln Ala Asp Leu Arg Leu Ile Tyr Leu Ala Leu Ala His
145                 150                 155                 160
```

```
Ile Val Lys Tyr Arg Gly His Phe Leu Ile Glu Gly Lys Leu Ser Thr
                165                 170                 175

Glu Asn Ile Ser Val Lys Glu Gln Phe Gln Gln Phe Met Ile Ile Tyr
            180                 185                 190

Asn Gln Thr Phe Val Asn Gly Glu Ser Arg Leu Val Ser Ala Pro Leu
        195                 200                 205

Pro Glu Ser Val Leu Ile Glu Glu Leu Thr Glu Lys Ala Ser Arg
210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

Asp Phe Lys Lys Val Phe Gly Leu Glu Glu Ala Lys Ile Thr Tyr
            260                 265                 270

Ala Ser Glu Ser Tyr Glu Glu Asp Leu Glu Gly Ile Leu Ala Lys Val
        275                 280                 285

Gly Asp Glu Tyr Ser Asp Val Phe Leu Ala Ala Lys Asn Val Tyr Asp
    290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                325                 330                 335

Asp Leu Lys Asn Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
        355                 360                 365

Ile Ala His Ala Gly Lys Val Ser Gln Leu Lys Phe Tyr Gln Tyr Val
    370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
                405                 410                 415

Val Ile Pro His Gln Ile His Leu Ala Glu Leu Gln Ala Ile Ile His
            420                 425                 430

Arg Gln Ala Ala Tyr Tyr Pro Phe Leu Lys Glu Asn Gln Lys Lys Ile
        435                 440                 445

Glu Gln Leu Val Thr Phe Arg Ile Pro Tyr Tyr Val Gly Pro Leu Ser
    450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
                485                 490                 495

Ala Thr Ala Phe Ile Glu Arg Met Thr Asn Phe Asp Thr Tyr Leu Pro
            500                 505                 510

Ser Glu Lys Val Leu Pro Lys His Ser Leu Leu Tyr Glu Lys Phe Met
        515                 520                 525

Val Phe Asn Glu Leu Thr Lys Ile Ser Tyr Thr Asp Asp Arg Gly Ile
    530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Lys Asp Ile Ile Gln Phe Tyr
                565                 570                 575
```

```
Arg Asn Glu Tyr Asn Thr Glu Ile Val Thr Leu Ser Gly Leu Glu Glu
            580                 585                 590

Asp Gln Phe Asn Ala Ser Phe Ser Thr Tyr Gln Asp Leu Leu Lys Cys
            595                 600                 605

Gly Leu Thr Arg Ala Glu Leu Asp His Pro Asp Asn Ala Glu Lys Leu
            610                 615                 620

Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Glu Glu Val Leu
            645                 650                 655

Lys Lys Leu Glu Arg Lys His Tyr Thr Gly Trp Gly Arg Leu Ser Lys
            660                 665                 670

Lys Leu Ile Asn Gly Ile Tyr Asp Lys Glu Ser Gly Lys Thr Ile Leu
            675                 680                 685

Asp Tyr Leu Ile Lys Asp Asp Gly Val Ser Lys His Tyr Asn Arg Asn
            690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
            725                 730                 735

Asn Glu Leu Ala Gly Ser Pro Ala Ile Lys Lys Gly Ile Tyr Gln Ser
            740                 745                 750

Leu Lys Ile Val Asp Glu Leu Val Ala Ile Met Gly Tyr Ala Pro Lys
            755                 760                 765

Arg Ile Val Val Glu Met Ala Arg Glu Asn Gln Thr Thr Ser Thr Gly
770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
            805                 810                 815

Leu Arg Asp Thr Arg Leu Phe Leu Tyr Tyr Met Gln Asn Gly Lys Asp
            820                 825                 830

Met Tyr Thr Gly Asp Glu Leu Ser Leu His Arg Leu Ser Ala Tyr Asp
            835                 840                 845

Ile Asp His Ile Ile Pro Gln Ser Phe Met Lys Asp Asp Ser Leu Asp
850                 855                 860

Asn Leu Val Leu Val Gly Ser Thr Glu Asn Arg Gly Lys Ser Asp Asp
865                 870                 875                 880

Val Pro Ser Lys Glu Val Val Lys Lys Met Lys Ala Tyr Trp Glu Lys
            885                 890                 895

Leu Tyr Ala Ala Gly Leu Ile Ser Gln Arg Lys Phe Gln Arg Leu Thr
            900                 905                 910

Lys Gly Glu Gln Gly Gly Leu Thr Leu Glu Asp Lys Ala His Phe Ile
            915                 920                 925

Gln Arg Gln Leu Val Glu Thr Arg Gln Ile Thr Lys Asn Val Ala Gly
            930                 935                 940

Ile Leu Asp Gln Arg Tyr Asn Ala Lys Ser Lys Glu Lys Lys Val Gln
945                 950                 955                 960

Ile Ile Thr Leu Lys Ala Ser Leu Thr Ser Gln Phe Arg Ser Ile Phe
            965                 970                 975

Gly Leu Tyr Lys Val Arg Glu Val Asn Asp Tyr His His Gly Gln Asp
            980                 985                 990

Ala Tyr Leu Asn Cys Val Val Ala  Thr Thr Leu Leu Lys  Val Tyr Pro
```

Asn Leu Ala Pro Glu Phe Val Tyr Gly Glu Tyr Pro Lys Phe Gln
              1010                1015                1020

Ala Phe Lys Glu Asn Lys Ala Thr Ala Lys Ala Ile Ile Tyr Thr
         1025                1030                1035

Asn Leu Leu Arg Phe Phe Thr Glu Asp Glu Pro Arg Phe Thr Lys
         1040                1045                1050

Asp Gly Glu Ile Leu Trp Ser Asn Ser Tyr Leu Lys Thr Ile Lys
         1055                1060                1065

Lys Glu Leu Asn Tyr His Gln Met Asn Ile Val Lys Lys Val Glu
         1070                1075                1080

Val Gln Lys Gly Gly Phe Ser Lys Glu Ser Ile Lys Pro Lys Gly
         1085                1090                1095

Pro Ser Asn Lys Leu Ile Pro Val Lys Asn Gly Leu Asp Pro Gln
         1100                1105                1110

Lys Tyr Gly Gly Phe Asp Ser Pro Val Val Ala Tyr Thr Val Leu
         1115                1120                1125

Phe Thr His Glu Lys Gly Lys Lys Pro Leu Ile Lys Gln Glu Ile
         1130                1135                1140

Leu Gly Ile Thr Ile Met Glu Lys Thr Arg Phe Glu Gln Asn Pro
         1145                1150                1155

Ile Leu Phe Leu Glu Glu Lys Gly Phe Leu Arg Pro Arg Val Leu
         1160                1165                1170

Met Lys Leu Pro Lys Tyr Thr Leu Tyr Glu Phe Pro Glu Gly Arg
         1175                1180                1185

Arg Arg Leu Leu Ala Ser Ala Lys Glu Ala Gln Lys Gly Asn Gln
         1190                1195                1200

Met Val Leu Pro Glu His Leu Leu Thr Leu Leu Tyr His Ala Lys
         1205                1210                1215

Gln Cys Leu Leu Pro Asn Gln Ser Glu Ser Leu Ala Tyr Val Glu
         1220                1225                1230

Gln His Gln Pro Glu Phe Gln Glu Ile Leu Glu Arg Val Val Asp
         1235                1240                1245

Phe Ala Glu Val His Thr Leu Ala Lys Ser Lys Val Gln Gln Ile
         1250                1255                1260

Val Lys Leu Phe Glu Ala Asn Gln Thr Ala Asp Val Lys Glu Ile
         1265                1270                1275

Ala Ala Ser Phe Ile Gln Leu Met Gln Phe Asn Ala Met Gly Ala
         1280                1285                1290

Pro Ser Thr Phe Lys Phe Phe Gln Lys Asp Ile Glu Arg Ala Arg
         1295                1300                1305

Tyr Thr Ser Ile Lys Glu Ile Phe Asp Ala Thr Ile Ile Tyr Gln
         1310                1315                1320

Ser Thr Thr Gly Leu Tyr Glu Thr Arg Arg Lys Val Val Asp
         1325                1330                1335

<210> SEQ ID NO 59
<211> LENGTH: 1337
<212> TYPE: PRT
<213> ORGANISM: Artificial Sequence
<220> FEATURE:
<223> OTHER INFORMATION: Artificially mutated sequence

<400> SEQUENCE: 59

Met Lys Lys Asp Tyr Val Ile Gly Leu Ala Ile Gly Thr Asn Ser Val

-continued

```
  1               5                  10                  15
Gly Trp Ala Val Met Thr Glu Asp Tyr Gln Leu Val Lys Lys Lys Met
             20                  25                  30
Pro Ile Tyr Gly Asn Thr Glu Lys Lys Ile Lys Lys Asn Phe Trp
             35                  40                  45
Gly Val Arg Leu Phe Glu Gly His Thr Ala Glu Asp Arg Arg Leu
 50                  55                  60
Lys Arg Thr Ala Arg Arg Ile Ser Arg Arg Asn Arg Leu Arg
 65                  70                  75                  80
Tyr Leu Gln Ala Phe Phe Glu Glu Ala Met Thr Ala Leu Asp Glu Asn
             85                  90                  95
Phe Phe Ala Arg Leu Gln Glu Ser Phe Leu Val Pro Glu Asp Lys Lys
             100                 105                 110
Trp His Arg His Pro Ile Phe Ala Lys Leu Glu Asp Glu Val Ala Tyr
             115                 120                 125
His Glu Thr Tyr Pro Thr Ile Tyr His Leu Arg Lys Lys Leu Ala Asp
             130                 135                 140
Ser Ser Glu Gln Ala Asp Leu Arg Leu Ile Tyr Leu Ala Leu Ala His
145                 150                 155                 160
Ile Val Lys Tyr Arg Gly His Phe Leu Ile Glu Gly Lys Leu Ser Thr
                    165                 170                 175
Glu Asn Ile Ser Val Lys Glu Gln Phe Gln Gln Phe Met Ile Ile Tyr
             180                 185                 190
Asn Gln Thr Phe Val Asn Gly Glu Ser Arg Leu Val Ser Ala Pro Leu
             195                 200                 205
Pro Glu Ser Val Leu Ile Glu Glu Leu Thr Glu Lys Ala Ser Arg
 210                 215                 220
Thr Lys Lys Ser Glu Lys Val Leu Gln Gln Phe Pro Gln Glu Lys Ala
225                 230                 235                 240
Asn Gly Leu Phe Gly Gln Phe Leu Lys Leu Met Val Gly Asn Lys Ala
                    245                 250                 255
Asp Phe Lys Lys Val Phe Gly Leu Glu Glu Glu Ala Lys Ile Thr Tyr
             260                 265                 270
Ala Ser Glu Ser Tyr Glu Glu Asp Leu Glu Gly Ile Leu Ala Lys Val
             275                 280                 285
Gly Asp Glu Tyr Ser Asp Val Phe Leu Ala Ala Lys Asn Val Tyr Asp
             290                 295                 300
Ala Val Glu Leu Ser Thr Ile Leu Ala Asp Ser Asp Lys Lys Ser His
305                 310                 315                 320
Ala Lys Leu Ser Ser Ser Met Ile Val Arg Phe Thr Glu His Gln Glu
                    325                 330                 335
Asp Leu Lys Asn Phe Lys Arg Phe Ile Arg Glu Asn Cys Pro Asp Glu
             340                 345                 350
Tyr Asp Asn Leu Phe Lys Asn Glu Gln Lys Asp Gly Tyr Ala Gly Tyr
             355                 360                 365
Ile Ala His Ala Gly Lys Val Ser Gln Leu Lys Phe Tyr Gln Tyr Val
             370                 375                 380
Lys Lys Ile Ile Gln Asp Ile Ala Gly Ala Glu Tyr Phe Leu Glu Lys
385                 390                 395                 400
Ile Ala Gln Glu Asn Phe Leu Arg Lys Gln Arg Thr Phe Asp Asn Gly
             405                 410                 415
Val Ile Pro His Gln Ile His Leu Ala Glu Leu Gln Ala Ile Ile His
             420                 425                 430
```

```
Arg Gln Ala Ala Tyr Tyr Pro Phe Leu Lys Glu Asn Gln Lys Ile
        435                 440                 445
Glu Gln Leu Val Thr Phe Arg Ile Pro Tyr Tyr Val Gly Pro Leu Ser
450                 455                 460
Lys Gly Asp Ala Ser Thr Phe Ala Trp Leu Lys Arg Gln Ser Glu Glu
465                 470                 475                 480
Pro Ile Arg Pro Trp Asn Leu Gln Glu Thr Val Asp Leu Asp Gln Ser
                485                 490                 495
Ala Thr Ala Phe Ile Glu Arg Met Thr Asn Phe Asp Thr Tyr Leu Pro
                500                 505                 510
Ser Glu Lys Val Leu Pro Lys His Ser Leu Leu Tyr Glu Lys Phe Met
        515                 520                 525
Val Phe Asn Glu Leu Thr Lys Ile Ser Tyr Thr Asp Arg Gly Ile
        530                 535                 540
Lys Ala Asn Phe Ser Gly Lys Glu Lys Glu Lys Ile Phe Asp Tyr Leu
545                 550                 555                 560
Phe Lys Thr Arg Arg Lys Val Lys Lys Lys Asp Ile Ile Gln Phe Tyr
                565                 570                 575
Arg Asn Glu Tyr Asn Thr Glu Ile Val Thr Leu Ser Gly Leu Glu Glu
                580                 585                 590
Asp Gln Phe Asn Ala Ser Phe Ser Thr Tyr Gln Asp Leu Leu Lys Cys
        595                 600                 605
Gly Leu Thr Arg Ala Glu Leu Asp His Pro Asp Asn Ala Glu Lys Leu
        610                 615                 620
Glu Asp Ile Ile Lys Ile Leu Thr Ile Phe Glu Asp Arg Gln Arg Ile
625                 630                 635                 640
Arg Thr Gln Leu Ser Thr Phe Lys Gly Gln Phe Ser Glu Glu Val Leu
                645                 650                 655
Lys Lys Leu Glu Arg Lys His Tyr Thr Gly Trp Gly Arg Leu Ser Lys
                660                 665                 670
Lys Leu Ile Asn Gly Ile Tyr Asp Lys Glu Ser Gly Lys Thr Ile Leu
        675                 680                 685
Asp Tyr Leu Ile Lys Asp Asp Gly Val Ser Lys His Tyr Asn Arg Asn
        690                 695                 700
Phe Met Gln Leu Ile Asn Asp Ser Gln Leu Ser Phe Lys Asn Ala Ile
705                 710                 715                 720
Gln Lys Ala Gln Ser Ser Glu His Glu Glu Thr Leu Ser Glu Thr Val
                725                 730                 735
Asn Glu Leu Ala Gly Ser Pro Ala Ile Lys Lys Gly Ile Tyr Gln Ser
                740                 745                 750
Leu Lys Ile Val Asp Glu Leu Val Ala Ile Met Gly Tyr Ala Pro Lys
        755                 760                 765
Arg Ile Val Val Glu Met Ala Arg Glu Asn Gln Thr Thr Ser Thr Gly
        770                 775                 780
Lys Arg Arg Ser Ile Gln Arg Leu Lys Ile Val Glu Lys Ala Met Ala
785                 790                 795                 800
Glu Ile Gly Ser Asn Leu Leu Lys Glu Gln Pro Thr Thr Asn Glu Gln
                805                 810                 815
Leu Arg Asp Thr Arg Leu Phe Leu Tyr Tyr Met Gln Asn Gly Lys Asp
                820                 825                 830
Met Tyr Thr Gly Asp Glu Leu Ser Leu His Arg Leu Ser Ala Tyr Asp
        835                 840                 845
```

```
Ile Asp His Ile Ile Pro Gln Ser Phe Met Lys Asp Asp Ser Leu Asp
850                 855                 860

Asn Leu Val Leu Val Gly Ser Thr Glu Asn Arg Gly Lys Ser Asp Asp
865                 870                 875                 880

Val Pro Ser Lys Glu Val Val Lys Met Lys Ala Tyr Trp Glu Lys
                885                 890                 895

Leu Tyr Ala Ala Gly Leu Ile Ser Gln Arg Lys Phe Gln Arg Leu Thr
            900                 905                 910

Lys Gly Glu Gln Gly Gly Leu Thr Leu Glu Asp Lys Ala His Phe Ile
                915                 920                 925

Gln Arg Gln Leu Val Glu Thr Arg Gln Ile Thr Lys Asn Val Ala Gly
930                 935                 940

Ile Leu Asp Gln Arg Tyr Asn Ala Lys Ser Lys Glu Lys Lys Val Gln
945                 950                 955                 960

Ile Ile Thr Leu Lys Ala Ser Leu Thr Ser Gln Phe Arg Ser Ile Phe
                965                 970                 975

Gly Leu Tyr Lys Val Arg Glu Val Asn Asp Tyr His His Gly Gln Asp
            980                 985                 990

Ala Tyr Leu Asn Cys Val Val Ala Thr Thr Leu Leu Lys Val Tyr Pro
            995                 1000                1005

Asn Leu Ala Pro Glu Phe Val Tyr Gly Glu Tyr Pro Lys Phe Gln
        1010            1015            1020

Ala Phe Lys Glu Asn Lys Ala Thr Ala Lys Ala Ile Ile Tyr Thr
        1025            1030            1035

Asn Leu Leu Arg Phe Phe Thr Glu Asp Glu Pro Arg Phe Thr Lys
        1040            1045            1050

Asp Gly Glu Ile Leu Trp Ser Asn Ser Tyr Leu Lys Thr Ile Lys
        1055            1060            1065

Lys Glu Leu Asn Tyr His Gln Met Asn Ile Val Lys Lys Val Glu
        1070            1075            1080

Val Gln Lys Gly Gly Phe Ser Lys Glu Ser Ile Lys Pro Lys Gly
        1085            1090            1095

Pro Ser Asn Lys Leu Ile Pro Val Lys Asn Gly Leu Asp Pro Gln
        1100            1105            1110

Lys Tyr Gly Gly Phe Asp Ser Pro Val Val Ala Tyr Thr Val Leu
        1115            1120            1125

Phe Thr His Glu Lys Gly Lys Lys Pro Leu Ile Lys Gln Glu Ile
        1130            1135            1140

Leu Gly Ile Thr Ile Met Glu Lys Thr Arg Phe Glu Gln Asn Pro
        1145            1150            1155

Ile Leu Phe Leu Glu Glu Lys Gly Phe Leu Arg Pro Arg Val Leu
        1160            1165            1170

Met Lys Leu Pro Lys Tyr Thr Leu Tyr Glu Phe Pro Glu Gly Arg
        1175            1180            1185

Arg Arg Leu Leu Ala Ser Ala Lys Glu Ala Gln Lys Gly Asn Gln
        1190            1195            1200

Met Val Leu Pro Glu His Leu Leu Thr Leu Leu Tyr His Ala Lys
        1205            1210            1215

Gln Cys Leu Leu Pro Asn Gln Ser Glu Ser Leu Ala Tyr Val Glu
        1220            1225            1230

Gln His Gln Pro Glu Phe Glu Ile Leu Glu Arg Val Val Asp
        1235            1240            1245

Phe Ala Glu Val His Thr Leu Ala Lys Ser Lys Val Gln Gln Ile
```

```
            1250                1255                1260

Val Lys Leu Phe Glu Ala Asn Gln Thr Ala Asp Val Lys Glu Ile
        1265                1270                1275

Ala Ala Ser Phe Ile Gln Leu Met Gln Phe Asn Ala Met Gly Ala
        1280                1285                1290

Pro Ser Thr Phe Lys Phe Gln Lys Asp Ile Glu Arg Ala Arg
        1295                1300                1305

Tyr Thr Ser Ile Lys Glu Ile Phe Asp Ala Thr Ile Ile Tyr Gln
        1310                1315                1320

Ser Thr Thr Gly Leu Tyr Glu Thr Arg Arg Lys Val Val Asp
        1325                1330                1335
```

<210> SEQ ID NO 60
<211> LENGTH: 20
<212> TYPE: DNA
<213> ORGANISM: Artificial Sequence
<220> FEATURE:
<223> OTHER INFORMATION: SPACER

<400> SEQUENCE: 60
gtagcggctg aagcactgca                                         20

<210> SEQ ID NO 61
<211> LENGTH: 10
<212> TYPE: DNA
<213> ORGANISM: Artificial Sequence
<220> FEATURE:
<223> OTHER INFORMATION: PAM

<400> SEQUENCE: 61
cgccgtaggt                                                    10

<210> SEQ ID NO 62
<211> LENGTH: 23
<212> TYPE: DNA
<213> ORGANISM: Artificial Sequence
<220> FEATURE:
<223> OTHER INFORMATION: SPACER

<400> SEQUENCE: 62
ggcgtgcagt gcttcagccg cta                                     23

<210> SEQ ID NO 63
<211> LENGTH: 10
<212> TYPE: DNA
<213> ORGANISM: Artificial Sequence
<220> FEATURE:
<223> OTHER INFORMATION: PAM

<400> SEQUENCE: 63
ccccgaccac                                                    10

<210> SEQ ID NO 64
<211> LENGTH: 23
<212> TYPE: DNA
<213> ORGANISM: Artificial Sequence
<220> FEATURE:
<223> OTHER INFORMATION: SPACER

<400> SEQUENCE: 64
gccgctaccc cgaccacatg aag                                     23

<210> SEQ ID NO 65

```
<211> LENGTH: 10
<212> TYPE: DNA
<213> ORGANISM: Artificial Sequence
<220> FEATURE:
<223> OTHER INFORMATION: PAM

<400> SEQUENCE: 65
cagcacgact                                                            10

<210> SEQ ID NO 66
<211> LENGTH: 23
<212> TYPE: DNA
<213> ORGANISM: Artificial Sequence
<220> FEATURE:
<223> OTHER INFORMATION: SPACER

<400> SEQUENCE: 66
ggccagggca cgggcagttt gcc                                             23

<210> SEQ ID NO 67
<211> LENGTH: 10
<212> TYPE: DNA
<213> ORGANISM: Artificial Sequence
<220> FEATURE:
<223> OTHER INFORMATION: PAM

<400> SEQUENCE: 67
ggtggtgcag                                                            10

<210> SEQ ID NO 68
<211> LENGTH: 23
<212> TYPE: DNA
<213> ORGANISM: Artificial Sequence
<220> FEATURE:
<223> OTHER INFORMATION: SPACER

<400> SEQUENCE: 68
gtggtgccca tcctggtcga gct                                             23

<210> SEQ ID NO 69
<211> LENGTH: 10
<212> TYPE: DNA
<213> ORGANISM: Artificial Sequence
<220> FEATURE:
<223> OTHER INFORMATION: PAM

<400> SEQUENCE: 69
ggacggcgac                                                            10

<210> SEQ ID NO 70
<211> LENGTH: 23
<212> TYPE: DNA
<213> ORGANISM: Artificial Sequence
<220> FEATURE:
<223> OTHER INFORMATION: SPACER

<400> SEQUENCE: 70
ggcatcgccc tcgccctcgc cgg                                             23

<210> SEQ ID NO 71
<211> LENGTH: 10
<212> TYPE: DNA
<213> ORGANISM: Artificial Sequence
<220> FEATURE:
<223> OTHER INFORMATION: PAM

<400> SEQUENCE: 71
```
acacgctgaa                                                              10

<210> SEQ ID NO 72
<211> LENGTH: 23
<212> TYPE: DNA
<213> ORGANISM: Artificial Sequence
<220> FEATURE:
<223> OTHER INFORMATION: SPACER

<400> SEQUENCE: 72
gccctcgccg gacacgctga act                                               23

<210> SEQ ID NO 73
<211> LENGTH: 10
<212> TYPE: DNA
<213> ORGANISM: Artificial Sequence
<220> FEATURE:
<223> OTHER INFORMATION: PAM

<400> SEQUENCE: 73
tgtggccgtt                                                              10

<210> SEQ ID NO 74
<211> LENGTH: 23
<212> TYPE: DNA
<213> ORGANISM: Artificial Sequence
<220> FEATURE:
<223> OTHER INFORMATION: SPACER

<400> SEQUENCE: 74
ggtggtcacc aaagtgggcc agg                                               23

<210> SEQ ID NO 75
<211> LENGTH: 10
<212> TYPE: DNA
<213> ORGANISM: Artificial Sequence
<220> FEATURE:
<223> OTHER INFORMATION: PAM

<400> SEQUENCE: 75
gcacgggcag                                                              10

<210> SEQ ID NO 76
<211> LENGTH: 23
<212> TYPE: DNA
<213> ORGANISM: Artificial Sequence
<220> FEATURE:
<223> OTHER INFORMATION: SPACER

<400> SEQUENCE: 76
gtgtccggcg agggcgaggg cga                                               23

<210> SEQ ID NO 77
<211> LENGTH: 10
<212> TYPE: DNA
<213> ORGANISM: Artificial Sequence
<220> FEATURE:
<223> OTHER INFORMATION: PAM

<400> SEQUENCE: 77
tgccacctac                                                              10

<210> SEQ ID NO 78
<211> LENGTH: 23
<212> TYPE: DNA

```
<213> ORGANISM: Artificial Sequence
<220> FEATURE:
<223> OTHER INFORMATION: SPACER

<400> SEQUENCE: 78
gtgagcaagg gcgaggagct gtt                                              23

<210> SEQ ID NO 79
<211> LENGTH: 10
<212> TYPE: DNA
<213> ORGANISM: Artificial Sequence
<220> FEATURE:
<223> OTHER INFORMATION: PAM

<400> SEQUENCE: 79
caccggggtg                                                             10

<210> SEQ ID NO 80
<211> LENGTH: 23
<212> TYPE: DNA
<213> ORGANISM: Artificial Sequence
<220> FEATURE:
<223> OTHER INFORMATION: SPACER

<400> SEQUENCE: 80
gtggtcacca aagtgggcca ggg                                              23

<210> SEQ ID NO 81
<211> LENGTH: 10
<212> TYPE: DNA
<213> ORGANISM: Artificial Sequence
<220> FEATURE:
<223> OTHER INFORMATION: PAM

<400> SEQUENCE: 81
cacgggcagt                                                             10

<210> SEQ ID NO 82
<211> LENGTH: 23
<212> TYPE: DNA
<213> ORGANISM: Artificial Sequence
<220> FEATURE:
<223> OTHER INFORMATION: SPACER

<400> SEQUENCE: 82
gcgagggcga gggcgatgcc acc                                              23

<210> SEQ ID NO 83
<211> LENGTH: 10
<212> TYPE: DNA
<213> ORGANISM: Artificial Sequence
<220> FEATURE:
<223> OTHER INFORMATION: PAM

<400> SEQUENCE: 83
tacggcaagc                                                             10

<210> SEQ ID NO 84
<211> LENGTH: 23
<212> TYPE: DNA
<213> ORGANISM: Artificial Sequence
<220> FEATURE:
<223> OTHER INFORMATION: SPACER

<400> SEQUENCE: 84
gtgctgcttc atgtggtcgg ggt                                              23
```

<210> SEQ ID NO 85
<211> LENGTH: 10
<212> TYPE: DNA
<213> ORGANISM: Artificial Sequence
<220> FEATURE:
<223> OTHER INFORMATION: PAM

<400> SEQUENCE: 85
agcggctgaa                                                          10

<210> SEQ ID NO 86
<211> LENGTH: 23
<212> TYPE: DNA
<213> ORGANISM: Artificial Sequence
<220> FEATURE:
<223> OTHER INFORMATION: SPACER

<400> SEQUENCE: 86
gctgaacttg tggccgttta cgt                                           23

<210> SEQ ID NO 87
<211> LENGTH: 10
<212> TYPE: DNA
<213> ORGANISM: Artificial Sequence
<220> FEATURE:
<223> OTHER INFORMATION: PAM

<400> SEQUENCE: 87
cgccgtccag                                                          10

<210> SEQ ID NO 88
<211> LENGTH: 23
<212> TYPE: DNA
<213> ORGANISM: Artificial Sequence
<220> FEATURE:
<223> OTHER INFORMATION: SPACER

<400> SEQUENCE: 88
gctgaagcac tgcacgccgt agg                                           23

<210> SEQ ID NO 89
<211> LENGTH: 10
<212> TYPE: DNA
<213> ORGANISM: Artificial Sequence
<220> FEATURE:
<223> OTHER INFORMATION: PAM

<400> SEQUENCE: 89
tcagggtggt                                                          10

<210> SEQ ID NO 90
<211> LENGTH: 22
<212> TYPE: DNA
<213> ORGANISM: Artificial Sequence
<220> FEATURE:
<223> OTHER INFORMATION: SPACER

<400> SEQUENCE: 90
gtcaccaaag tgggccaggg ca                                            22

<210> SEQ ID NO 91
<211> LENGTH: 10
<212> TYPE: DNA
<213> ORGANISM: Artificial Sequence
<220> FEATURE:

```
<223> OTHER INFORMATION: PAM

<400> SEQUENCE: 91
cgggcagttt                                                          10

<210> SEQ ID NO 92
<211> LENGTH: 23
<212> TYPE: DNA
<213> ORGANISM: Artificial Sequence
<220> FEATURE:
<223> OTHER INFORMATION: SPACER

<400> SEQUENCE: 92
gtaaacggcc acaagttcag cgt                                           23

<210> SEQ ID NO 93
<211> LENGTH: 10
<212> TYPE: DNA
<213> ORGANISM: Artificial Sequence
<220> FEATURE:
<223> OTHER INFORMATION: PAM

<400> SEQUENCE: 93
gtccggcgag                                                          10

<210> SEQ ID NO 94
<211> LENGTH: 23
<212> TYPE: DNA
<213> ORGANISM: Artificial Sequence
<220> FEATURE:
<223> OTHER INFORMATION: SPACER

<400> SEQUENCE: 94
gtggcatcgc cctcgccctc gcc                                           23

<210> SEQ ID NO 95
<211> LENGTH: 10
<212> TYPE: DNA
<213> ORGANISM: Artificial Sequence
<220> FEATURE:
<223> OTHER INFORMATION: PAM

<400> SEQUENCE: 95
ggacacgctg                                                          10

<210> SEQ ID NO 96
<211> LENGTH: 23
<212> TYPE: DNA
<213> ORGANISM: Artificial Sequence
<220> FEATURE:
<223> OTHER INFORMATION: SPACER

<400> SEQUENCE: 96
ggggtagcgg ctgaagcact gca                                           23

<210> SEQ ID NO 97
<211> LENGTH: 10
<212> TYPE: DNA
<213> ORGANISM: Artificial Sequence
<220> FEATURE:
<223> OTHER INFORMATION: PAM

<400> SEQUENCE: 97
cgccgtaggt                                                          10
```

```
<210> SEQ ID NO 98
<211> LENGTH: 23
<212> TYPE: DNA
<213> ORGANISM: Artificial Sequence
<220> FEATURE:
<223> OTHER INFORMATION: SPACER

<400> SEQUENCE: 98
ggcacgggca gtttgccggt ggt                                          23

<210> SEQ ID NO 99
<211> LENGTH: 10
<212> TYPE: DNA
<213> ORGANISM: Artificial Sequence
<220> FEATURE:
<223> OTHER INFORMATION: PAM

<400> SEQUENCE: 99
gcagatgaac                                                         10

<210> SEQ ID NO 100
<211> LENGTH: 23
<212> TYPE: DNA
<213> ORGANISM: Artificial Sequence
<220> FEATURE:
<223> OTHER INFORMATION: SPACER

<400> SEQUENCE: 100
ggggtggtgc ccatcctggt cga                                          23

<210> SEQ ID NO 101
<211> LENGTH: 10
<212> TYPE: DNA
<213> ORGANISM: Artificial Sequence
<220> FEATURE:
<223> OTHER INFORMATION: PAM

<400> SEQUENCE: 101
gctggacggc                                                         10

<210> SEQ ID NO 102
<211> LENGTH: 23
<212> TYPE: DNA
<213> ORGANISM: Artificial Sequence
<220> FEATURE:
<223> OTHER INFORMATION: SPACER

<400> SEQUENCE: 102
gcgtgcagtg cttcagccgc tac                                          23

<210> SEQ ID NO 103
<211> LENGTH: 10
<212> TYPE: DNA
<213> ORGANISM: Artificial Sequence
<220> FEATURE:
<223> OTHER INFORMATION: PAM

<400> SEQUENCE: 103
cccgaccaca                                                         10

<210> SEQ ID NO 104
<211> LENGTH: 23
<212> TYPE: DNA
<213> ORGANISM: Artificial Sequence
<220> FEATURE:
<223> OTHER INFORMATION: SPACER
```

<400> SEQUENCE: 104
gtcaccaaag tgggccaggg cac                                                23

<210> SEQ ID NO 105
<211> LENGTH: 10
<212> TYPE: DNA
<213> ORGANISM: Artificial Sequence
<220> FEATURE:
<223> OTHER INFORMATION: PAM

<400> SEQUENCE: 105
gggcagtttg                                                               10

<210> SEQ ID NO 106
<211> LENGTH: 23
<212> TYPE: DNA
<213> ORGANISM: Artificial Sequence
<220> FEATURE:
<223> OTHER INFORMATION: SPACER

<400> SEQUENCE: 106
gacggcgacg taaacggcca caa                                                23

<210> SEQ ID NO 107
<211> LENGTH: 10
<212> TYPE: DNA
<213> ORGANISM: Artificial Sequence
<220> FEATURE:
<223> OTHER INFORMATION: PAM

<400> SEQUENCE: 107
gttcagcgtg                                                               10

<210> SEQ ID NO 108
<211> LENGTH: 22
<212> TYPE: DNA
<213> ORGANISM: Artificial Sequence
<220> FEATURE:
<223> OTHER INFORMATION: SPACER

<400> SEQUENCE: 108
gcgtgcagtg cttcagccgc ta                                                 22

<210> SEQ ID NO 109
<211> LENGTH: 10
<212> TYPE: DNA
<213> ORGANISM: Artificial Sequence
<220> FEATURE:
<223> OTHER INFORMATION: PAM

<400> SEQUENCE: 109
ccccgaccac                                                               10

<210> SEQ ID NO 110
<211> LENGTH: 23
<212> TYPE: DNA
<213> ORGANISM: Artificial Sequence
<220> FEATURE:
<223> OTHER INFORMATION: SPACER

<400> SEQUENCE: 110
gccacaagtt cagcgtgtcc ggc                                                23

<210> SEQ ID NO 111
<211> LENGTH: 10

```
<212> TYPE: DNA
<213> ORGANISM: Artificial Sequence
<220> FEATURE:
<223> OTHER INFORMATION: PAM

<400> SEQUENCE: 111
gagggcgagg                                                              10

<210> SEQ ID NO 112
<211> LENGTH: 23
<212> TYPE: DNA
<213> ORGANISM: Artificial Sequence
<220> FEATURE:
<223> OTHER INFORMATION: SPACER

<400> SEQUENCE: 112
gggtggtgcc catcctggtc gag                                               23

<210> SEQ ID NO 113
<211> LENGTH: 10
<212> TYPE: DNA
<213> ORGANISM: Artificial Sequence
<220> FEATURE:
<223> OTHER INFORMATION: PAM

<400> SEQUENCE: 113
ctggacggcg                                                              10

<210> SEQ ID NO 114
<211> LENGTH: 23
<212> TYPE: DNA
<213> ORGANISM: Artificial Sequence
<220> FEATURE:
<223> OTHER INFORMATION: SPACER

<400> SEQUENCE: 114
gtcagggtgg tcaccaaagt ggg                                               23

<210> SEQ ID NO 115
<211> LENGTH: 10
<212> TYPE: DNA
<213> ORGANISM: Artificial Sequence
<220> FEATURE:
<223> OTHER INFORMATION: PAM

<400> SEQUENCE: 115
ccagggcacg                                                              10

<210> SEQ ID NO 116
<211> LENGTH: 23
<212> TYPE: DNA
<213> ORGANISM: Artificial Sequence
<220> FEATURE:
<223> OTHER INFORMATION: SPACER

<400> SEQUENCE: 116
gtgcccatcc tggtcgagct gga                                               23

<210> SEQ ID NO 117
<211> LENGTH: 10
<212> TYPE: DNA
<213> ORGANISM: Artificial Sequence
<220> FEATURE:
<223> OTHER INFORMATION: PAM

<400> SEQUENCE: 117
```
cggcgacgta                                                                       10

<210> SEQ ID NO 118
<211> LENGTH: 23
<212> TYPE: DNA
<213> ORGANISM: Artificial Sequence
<220> FEATURE:
<223> OTHER INFORMATION: SPACER

<400> SEQUENCE: 118
gccgtaggtg gcatcgccct cgc                                                        23

<210> SEQ ID NO 119
<211> LENGTH: 10
<212> TYPE: DNA
<213> ORGANISM: Artificial Sequence
<220> FEATURE:
<223> OTHER INFORMATION: PAM

<400> SEQUENCE: 119
cctcgccgga                                                                       10

<210> SEQ ID NO 120
<211> LENGTH: 23
<212> TYPE: DNA
<213> ORGANISM: Artificial Sequence
<220> FEATURE:
<223> OTHER INFORMATION: SPACER

<400> SEQUENCE: 120
ggcgacgtaa acggccacaa gtt                                                        23

<210> SEQ ID NO 121
<211> LENGTH: 10
<212> TYPE: DNA
<213> ORGANISM: Artificial Sequence
<220> FEATURE:
<223> OTHER INFORMATION: PAM

<400> SEQUENCE: 121
cagcgtgtcc                                                                       10

<210> SEQ ID NO 122
<211> LENGTH: 23
<212> TYPE: DNA
<213> ORGANISM: Artificial Sequence
<220> FEATURE:
<223> OTHER INFORMATION: SPACER

<400> SEQUENCE: 122
gagctggacg gcgacgtaaa cgg                                                        23

<210> SEQ ID NO 123
<211> LENGTH: 10
<212> TYPE: DNA
<213> ORGANISM: Artificial Sequence
<220> FEATURE:
<223> OTHER INFORMATION: PAM

<400> SEQUENCE: 123
ccacaagttc                                                                       10

<210> SEQ ID NO 124
<211> LENGTH: 20
<212> TYPE: DNA
<213> ORGANISM: Artificial Sequence

```
<220> FEATURE:
<223> OTHER INFORMATION: SPACER

<400> SEQUENCE: 124
gtggtgccca tcctggtcga                                                    20

<210> SEQ ID NO 125
<211> LENGTH: 10
<212> TYPE: DNA
<213> ORGANISM: Artificial Sequence
<220> FEATURE:
<223> OTHER INFORMATION: PAM

<400> SEQUENCE: 125
gctggacggc                                                               10

<210> SEQ ID NO 126
<211> LENGTH: 23
<212> TYPE: DNA
<213> ORGANISM: Artificial Sequence
<220> FEATURE:
<223> OTHER INFORMATION: SPACER

<400> SEQUENCE: 126
ggccacaagt tcagcgtgtc cgg                                                23

<210> SEQ ID NO 127
<211> LENGTH: 10
<212> TYPE: DNA
<213> ORGANISM: Artificial Sequence
<220> FEATURE:
<223> OTHER INFORMATION: PAM

<400> SEQUENCE: 127
cgagggcgag                                                               10

<210> SEQ ID NO 128
<211> LENGTH: 23
<212> TYPE: DNA
<213> ORGANISM: Artificial Sequence
<220> FEATURE:
<223> OTHER INFORMATION: SPACER

<400> SEQUENCE: 128
ggtggtcacc aaagtgggcc agg                                                23

<210> SEQ ID NO 129
<211> LENGTH: 10
<212> TYPE: DNA
<213> ORGANISM: Artificial Sequence
<220> FEATURE:
<223> OTHER INFORMATION: PAM

<400> SEQUENCE: 129
gcacgggcag                                                               10

<210> SEQ ID NO 130
<211> LENGTH: 23
<212> TYPE: DNA
<213> ORGANISM: Artificial Sequence
<220> FEATURE:
<223> OTHER INFORMATION: SPACER

<400> SEQUENCE: 130
gtccggcgag ggcgagggcg atg                                                23
```

```
<210> SEQ ID NO 131
<211> LENGTH: 10
<212> TYPE: DNA
<213> ORGANISM: Artificial Sequence
<220> FEATURE:
<223> OTHER INFORMATION: PAM

<400> SEQUENCE: 131
ccacctacgg                                                          10

<210> SEQ ID NO 132
<211> LENGTH: 23
<212> TYPE: DNA
<213> ORGANISM: Artificial Sequence
<220> FEATURE:
<223> OTHER INFORMATION: SPACER

<400> SEQUENCE: 132
gtgcccatcc tggtcgagct gga                                           23

<210> SEQ ID NO 133
<211> LENGTH: 10
<212> TYPE: DNA
<213> ORGANISM: Artificial Sequence
<220> FEATURE:
<223> OTHER INFORMATION: PAM

<400> SEQUENCE: 133
cggcgacgta                                                          10

<210> SEQ ID NO 134
<211> LENGTH: 23
<212> TYPE: DNA
<213> ORGANISM: Artificial Sequence
<220> FEATURE:
<223> OTHER INFORMATION: SPACER

<400> SEQUENCE: 134
gtgtccggcg agggcgaggg cga                                           23

<210> SEQ ID NO 135
<211> LENGTH: 10
<212> TYPE: DNA
<213> ORGANISM: Artificial Sequence
<220> FEATURE:
<223> OTHER INFORMATION: PAM

<400> SEQUENCE: 135
tgccacctac                                                          10

<210> SEQ ID NO 136
<211> LENGTH: 23
<212> TYPE: DNA
<213> ORGANISM: Artificial Sequence
<220> FEATURE:
<223> OTHER INFORMATION: SPACER

<400> SEQUENCE: 136
gggtcagctt gccgtaggtg gca                                           23

<210> SEQ ID NO 137
<211> LENGTH: 10
<212> TYPE: DNA
<213> ORGANISM: Artificial Sequence
<220> FEATURE:
<223> OTHER INFORMATION: PAM
```

<400> SEQUENCE: 137
tcgccctcgc                                                          10

<210> SEQ ID NO 138
<211> LENGTH: 23
<212> TYPE: DNA
<213> ORGANISM: Artificial Sequence
<220> FEATURE:
<223> OTHER INFORMATION: SPACER

<400> SEQUENCE: 138
gccgctaccc cgaccacatg aag                                           23

<210> SEQ ID NO 139
<211> LENGTH: 10
<212> TYPE: DNA
<213> ORGANISM: Artificial Sequence
<220> FEATURE:
<223> OTHER INFORMATION: PAM

<400> SEQUENCE: 139
cagcacgact                                                          10

<210> SEQ ID NO 140
<211> LENGTH: 3633
<212> TYPE: DNA
<213> ORGANISM: Artificial Sequence
<220> FEATURE:
<223> OTHER INFORMATION: HUMANIZED MAD 2007 V1

<400> SEQUENCE: 140
atggaaaatt ataggcaaaa gcacagattc gtcctcgcca cagatctggg aatcggaagc      60
aacggctggg ctatcatcga cctcgacgcc catagagtcg aggatctcgg cgtgcagatc     120
tttgagtccg gagaggaggg agccaagaaa gccagcgcta gagccagcca gcaaagaagg     180
ctcaagagga gcgcccacag actgaataga aggaagaaac aaaggaagga agccctcatc     240
aaattcctcc aagagatcga gtttcccgat ctcgtcgaga ttctcaactc cttcaagaag     300
cagaaaaacc ctaacgacat tctgtctctg agagtcaagg gactcgacaa caagctgtcc     360
cctctggagc tgttcagcat tctgatctac atgagcaaca acagaggata caaagacttc     420
tacgacaatg acattaacga caataatacc gacaaagacg aaaaggagat ggaaaaggcc     480
aagtccacca ttgagaagct cttcgcttcc aatagctaca agccgtgggg agagatgatt     540
gccacagatc taccttttat tgtggacaaa tccggcagca gaaagtcat caagtatcat     600 aacaaaaagg ataccagta tctgattcct agaaagctgc tggagaacga gatgtccctc     660
attctgcaca gcaagagga gttctacgat tgcctcagca tcgacaacat cacaattatt     720
ctggacaaga ttttttttca gagaaacttt gaggatggac ccggccccaa gaacaagagg     780
gatgattata aaataattc caaggaaat cagtttttata ccggattcaa cgagatgatt     840
ggactgtgcc ccttctatcc taacgagaaa aagggcacca gaactctct gatctacgac     900 gagtactacc tcattaatac actctcccag ttctttttca ccgactccaa cggcgtgatt     960
atgagcttca gcaagtctct gctgcatgac ctcatgctgt acttttttga ccataagggc    1020
gaactgacca caaggagct gagcagcttt ctcctcaagc atggactgga gctgaacagc    1080
aaagagaaat ccaataaaaa gtatagactg aattatatga acaactcac agatagcacc    1140 atctttgaga ccgagatgat cgccagcttc agagaggaga tcgagacctc cagctatagg    1200

-continued

```
agcgtgaact ctctgagcaa taagatcggc aactgcatcg gccagttcat taccccctctc     1260 aagagaaagg aggagctgac caacatcctc atcgacacca attacccccaa ggagctggct     1320 tccaagctgg ccgacagcat taaggtgatc aaaagccaga gcgtcgccaa tatttccaac     1380
aaatatatgc tcgaagccat tcacgctttt gagtccggca agaagtacgg cgacttccaa     1440
gccgaattca acgagacaag agagctggag gaccaccatt ttatgaagaa taacaagctg     1500
atcgcctttc aagacagcga tctgatcaga accccgtgg tctatagaac cattaaccaa      1560
tctagaaaaa tcattaacgc cgccatcaat aaatataata ttgtcagaat caacatcgag     1620
gtcgccagcg atgtgaacaa gtccttcgaa caaagagata cgacaagaa gtaccagaac      1680 gacaactatg agaaaaatct gcagctggag tccgagctca ccgactatat caataaggaa     1740
aatctccacg tcaacgtgaa cagcaaaatg atggagagat acaaactgta cctcagccaa     1800
aataagcact gcatctatac aaacaccct ctgacaatga tggacgtgat ctatagcacc      1860
aacgtgcaag tggatcacat cattccccag tccaagattc tggatgacac cctcaacaat     1920
aaggtcctcg tgctcagaga cgccaactcc atcaaaaaca atagactccc tctggaggcc     1980
ttcgatgaga tgcagatcaa tgtggatacc aactacacaa aaaaggacta tctcaccgag     2040
tgcctccatc tgctgaagaa caaaaccaat cccatcagca aaaaaagta tcagtacctc      2100 accctcaaga agctggacga tgagacaatt gagggctta ttagcagaaa tattaacgac      2160
acaaggtaca ttaccagata cattgccaat tatctgaaga ccgctttcaa agagagcgac     2220
aagacaaaga atattgatgt cgtgacaatt aaaggcgccg tgacctctag atttagaaag     2280
aggtggctga ccacatatga cgagtatgga taccacccca ccatctattc tctggaggac     2340
aagggaagga acctctacta ctaccaccac gctatcgacg ccatcattct cgccaacatt     2400
gacaagaggt acattacact ggccaacgcc tacgatacca ttaggctgat taagatcgat     2460
agaaatctgt ccaaggagca gaagcaaagg gacatcgaca cagtcatcaa aaatacagtc     2520
aaaagcatga gcaagtacca tggcttctcc gaggactaca ttagaagcct catgagcaag     2580
aaccacattc ccgccatctg caagaacctc tccgatgaag tgcagatcag aatcccctc     2640 aagttcaaca ccgactatga caacctcggc tacagattca ccgatgacca gtatcactat     2700
aaaaagctgt acattgcctt caaggaggcc cagaatgccc tcaaagaaaa ggaaaccctc     2760
gaaaaggaac tgatcgagag gtttaataac gaggctcaaa tcctcaacgc taatatcatt     2820
ctgacctaca ccggcttcga gtccaacaat gaactgatcg acatcaagaa ggccaagaag     2880
gtgaccgaca cactgaagcc taatctcaag aattacatca aggccattga tatcctcacc     2940
caagaggaat ataccaagag atgtctggag tactataatg actccgagtt cgccacccag     3000
ctcaagattc cttacgtgaa tttcaaaatt aataaaaggt ttaggggcaa gatccaaggc     3060
agcgaaaacg ccgtctctct gagagaggtg ctgaagaaga caaagctgaa cagcttcgaa     3120
gagtttgagt cctatctcaa gagcgaagac ggcattaagt ccccctacta catcaaatat     3180
acaaagaaca cactgggcaa ggagtcctac accatctacg aggctaactc ctactactgt     3240
gccgagatct acaccgatag ccagaataag ccccagctga gaggaattag atacgtcgac     3300
gtgagaaaag aggacggcaa actcgtgctg ctgaagcccc tcccctccac atgcaagcat     3360
atcacctatc tcttccataa tgaatatatt gctatttata agacagcaa ttataagagg      3420 ctcaagaata acggcttcgg agcttataga agcatcaaca acgtgaacgt gaataagatt     3480
attattagac tgtttgccaa tcagaacctc aacgacaacg acgtggtcat caccagcagc     3540
atcttcatca agaagtactc cctcgatgtc ttcggccaca tcaatggcga gatcaagtgc     3600
```

<210> SEQ ID NO 141
<211> LENGTH: 3633
<212> TYPE: DNA
<213> ORGANISM: Artificial Sequence
<220> FEATURE:
<223> OTHER INFORMATION: HUMANIZED MAD2007 V2

<400> SEQUENCE: 141

```
atggagaact accgccagaa gcaccggttt gtgctggcca ccgatctggg catcggcagc      60
aatggctggg ccatcatcga cctggatgca cacagggtgg aggacctggg agtgcagatc     120
ttcgagtctg gcgaggaggg cgccaagaag gccagcgcca gggcctccca gcagcggaga     180
ctgaagagaa gcgcccacag gctgaacagg cgcaagaagc agagaaagga ggccctgatc     240
aagtttctgc aggagatcga gttccccgac ctggtggaga tcctgaactc tttaagaag      300
cagaagaacc ctaatgatat cctgagcctg agggtgaagg gcctggacaa taagctgagc     360
cccctggagc tgttttccat cctgatctac atgtctaaca tcgcggcta aaggatttc       420
tacgacaacg atatcaatga caacaatacc gacaaggatg agaaggagat ggagaaggcc     480
aagtccacca tcgagaagct gtttgccagc aactcctaca ggacagtggg cgagatgatc     540
gccaccgacc caacattcat cgtggataag tctggcagca agaaagtgat caagtatcac     600
aacaagaagg gctatcagta cctgatcccc cgcaagctgc tggagaatga tgtgtctctg     660
atcctgcaca gcaggagga gttttacgac tgcctgagca tcgataatat caccatcatc     720
ctggataaga tcttctttca gcggaatttc gaggacggcc ccggcctaa gaacaagaga      780
gacgattaca gaacaattc taagggcaac cagttttata ccggcttcaa tgagatgatc     840
ggcctgtgcc ctttctaccc aaacgagaag aagggcacaa agaatagcct gatctatgat     900
gagtactatc tgatcaatac cctgagccag ttctttttca gactccaa cggcgtgatc       960
atgtcctttt ctaagagcct gctgcacgac ctgatgctgt acttttcga tcacaagggc     1020
gagctgacca caaggagct gagctccttc ctgctgaagc acggcctgga gctgaattct     1080
aaggagaaga gcaacaagaa gtatcggctg aattacatga gcagctgac cgactccaca     1140
atctttgaga ccgagatgat cgcctctttc agggaggaga tcgagacatc tagctaccgc     1200
agcgtgaact ccctgtctaa taagatcggc aactgcatcg ccagtttat caccccctctg    1260
aagagaaagg aggagctgac caacatcctg atcgataaa attatccaaa ggagctggcc     1320
agcaagctgg ccgacagcat caaagtgatc aagagccagt ccgtggccaa catcagcaat     1380
aagtacatgc tggaggccat ccacgccttc gagtccggca agaagtatgg cgattttcag     1440
gccgagttca cgagaccag ggagctggag gaccaccact ttatgaaaaa caataagctg     1500
atcgccttcc aggactccga tctgatcaga atcctgtgg tgtacaggac aatcaaccag     1560
tctcgcaaga tcatcaatgc cgccatcaac aagtataata tcgtgcggat caacatcgag     1620
gtggcctctg acgtgaataa gagcttcgag cagagagaca cgataagaa gtaccagaac     1680
gataattatg agaagaacct gcagctggag agcgagctga ccgactacat caacaaggag     1740
aatctgcacg tgaacgtgaa tagcaagatg atggagcggg acaagctgta cctgtcccag     1800
aacaagcact gcatctacac caatacaccc ctgaccatga tggatgtgat ctattccaca     1860
aacgtgcagg tggaccacat catccctcag tctaagatcc tggacgatac actgaacaat     1920
aaggtgctgg tgctgcggga tgccaattcc atcaagaaca atagactgcc tctggaggcc     1980
```

```
tttgacgaga tgcagatcaa tgtggatacc aactacacaa agaaggacta tctgaccgag      2040
tgtctgcacc tgctgaagaa caagacaaat ccaatcagca agaagaagta tcagtacctg      2100
accctgaaga agctggacga tgagacaatc gagggcttca tctccagaaa catcaatgac      2160
acccgctata tcacacggta catcgccaac tatctgaaga ccgcctttaa ggagtccgac      2220
aagacaaaga atatcgatgt ggtgaccatc aagggcgccg tgacatctcg gttcagaaag      2280
aggtggctga ccacatacga tgagtatggc taccacccaa ccatctatag cctggaggac      2340
aagggcagga acctgtacta ttaccaccac gccatcgatg ccatcatcct ggccaatatc      2400
gacaagcggt acatcaccct ggccaacgcc tatgatacaa tccggctgat caagatcgac      2460
agaaacctgt ccaaggagca gaagcagcgg gacatcgata ccgtgatcaa gaatacagtg      2520
aagtctatga gcaagtacca cggcttttcc gaggattata tcagatccct gatgtctaag      2580
aatcacatcc cagccatctg caagaacctg tctgacgagg tgcagatcag gatccccctg      2640
aagtttaata ccgactacga taacctgggc tatcgcttca cagacgatca gtatcactac      2700
aagaagctgt acatcgcctt caaggaggcc cagaacgccc tgaaggagaa ggagaccctg      2760
gagaaggagc tgatcgagcg gtttaacaat gaggcccaga tcctgaacgc caatatcatc      2820
ctgacctata caggcttcga gagcaacaat gagctgatcg atatcaagaa ggccaagaag      2880
gtgaccgaca cactgaagcc aaacctgaag aattacatca aggccatcga tatcctgacc      2940
caggaggagt atacaaagcg tgtgtctgag tattacaacg actccgagtt cgccacccag      3000
ctgaagatcc cctacgtgaa cttcaagatc aacaagcggt tccggggcaa gatccagggc      3060
tccgagaacg ccgtgtctct gagagaggtg ctgaagaaga caaagctgaa ttcttttgag      3120
gagttcgagt cctacctgaa gtctgaggat ggcatcaaga gccctatta tcatcaagtat       3180 accaagaata cactgggcaa ggagtcttat accatctacg aggccaacag ctattactgc      3240
gccgagatct acacagactc ccagaataag cctcagctga gaggcatcag atatgtggac      3300
gtgagaaagg aggatggcaa gctggtgctg ctgaagccac tgccctctac ctgtaagcac      3360
atcacatacc tgtttcacaa tgagtacatc gccatctata aggacagcaa ctacaagagg      3420
ctgaagaaca atggctttgg cgccatcgc tccatcaaca atgtgaacgt gaataagatc      3480
atcatcaggc tgttcgccaa ccagaatctg aacgacaatg acgtggtcat cacctcctct      3540
atctttatca agaagtacag cctggacgtg ttcggccaca tcaacggcga gatcaagtgt      3600
ggcgaccaga gcctgttcac catcaagaag cgg                                    3633
```

<210> SEQ ID NO 142
<211> LENGTH: 1211
<212> TYPE: PRT
<213> ORGANISM: Sharpea azabuensis

<400> SEQUENCE: 142

```
Met Glu Asn Tyr Arg Gln Lys His Arg Phe Val Leu Ala Thr Asp Leu
1               5                   10                  15

Gly Ile Gly Ser Asn Gly Trp Ala Ile Ile Asp Leu Asp Ala His Arg
            20                  25                  30

Val Glu Asp Leu Gly Val Gln Ile Phe Glu Ser Gly Glu Glu Gly Ala
        35                  40                  45

Lys Lys Ala Ser Ala Arg Ala Ser Gln Gln Arg Arg Leu Lys Arg Ser
    50                  55                  60

Ala His Arg Leu Asn Arg Arg Lys Lys Gln Arg Lys Glu Ala Leu Ile
65                  70                  75                  80
```

```
Lys Phe Leu Gln Glu Ile Glu Phe Pro Asp Leu Val Glu Ile Leu Asn
                85                  90                  95
Ser Phe Lys Lys Gln Lys Asn Pro Asn Asp Ile Leu Ser Leu Arg Val
            100                 105                 110
Lys Gly Leu Asp Asn Lys Leu Ser Pro Leu Glu Leu Phe Ser Ile Leu
        115                 120                 125
Ile Tyr Met Ser Asn Asn Arg Gly Tyr Lys Asp Phe Tyr Asp Asn Asp
    130                 135                 140
Ile Asn Asp Asn Asn Thr Asp Asn Asp Glu Lys Glu Met Gln Lys Ala
145                 150                 155                 160
Lys Ser Thr Ile Glu Lys Leu Phe Ala Ser Asn Ser Tyr Arg Thr Val
            165                 170                 175
Gly Glu Met Ile Ala Thr Asp Pro Thr Phe Ile Val Asp Lys Ser Gly
        180                 185                 190
Ser Lys Lys Val Ile Lys Tyr His Asn Lys Lys Gly Tyr Gln Tyr Leu
    195                 200                 205
Ile Pro Arg Lys Leu Leu Glu Asn Glu Met Ser Leu Ile Leu His Lys
210                 215                 220
Gln Glu Glu Phe Tyr Asp Cys Leu Ser Ile Asp Asn Ile Thr Ile Ile
225                 230                 235                 240
Leu Asp Lys Ile Phe Phe Gln Arg Asn Phe Glu Asp Gly Pro Gly Pro
            245                 250                 255
Lys Asn Lys Arg Asp Asp Tyr Lys Asn Asn Ser Lys Gly Asn Gln Phe
        260                 265                 270
Tyr Thr Gly Phe Asn Glu Met Ile Gly Leu Cys Pro Phe Tyr Pro Asn
    275                 280                 285
Glu Lys Lys Gly Thr Lys Asn Ser Leu Ile Tyr Asp Glu Tyr Tyr Leu
290                 295                 300
Ile Asn Thr Leu Ser Gln Phe Phe Thr Asp Ser Asn Gly Val Ile
305                 310                 315                 320
Met Ser Phe Ser Lys Ser Leu Leu His Asp Leu Met Leu Tyr Phe Phe
            325                 330                 335
Asp His Lys Gly Glu Ile Thr Asn Lys Glu Leu Ser Ser Phe Leu Leu
        340                 345                 350
Lys His Gly Leu Glu Leu Asn Ser Lys Glu Lys Ser Asn Lys Lys Tyr
    355                 360                 365
Lys Leu Asn Tyr Met Lys Gln Leu Thr Asp Ser Thr Ile Phe Glu Thr
370                 375                 380
Glu Met Ile Ala Ser Phe Arg Glu Glu Ile Glu Thr Ser Ser Tyr Arg
385                 390                 395                 400
Ser Val Asn Ser Leu Ser Asn Lys Ile Gly Asn Cys Ile Gly Gln Phe
            405                 410                 415
Ile Thr Pro Ser Lys Arg Lys Glu Glu Leu Thr Asn Ile Leu Ile Asp
        420                 425                 430
Thr Asn Tyr Pro Lys Glu Leu Ala Ser Lys Leu Ala Asp Ser Ile Lys
    435                 440                 445
Val Ile Lys Ser Gln Ser Val Ala Asn Ile Ser Asn Lys Tyr Met Leu
450                 455                 460
Glu Ala Ile His Ala Phe Glu Ser Gly Lys Lys Tyr Gly Asp Phe Gln
465                 470                 475                 480
Ala Glu Phe Asn Glu Thr Arg Glu Leu Glu Asp His His Phe Met Lys
            485                 490                 495
Asn Asn Lys Leu Ile Ala Ile Gln Asp Ser Asp Leu Ile Arg Asn Pro
```

```
            500             505                 510
Val Val Tyr Arg Thr Ile Asn Gln Ser Arg Lys Ile Ile Asn Ala Ala
            515                 520             525

Ile Asn Lys Tyr Asn Ile Val Arg Ile Asn Ile Glu Val Ala Ser Asp
            530                 535             540

Val Asn Lys Ser Phe Glu Gln Arg Asp Asn Asp Lys Lys Tyr Gln Asn
545                 550                 555                 560

Asp Asn Tyr Glu Lys Asn Leu Gln Leu Glu Ser Glu Leu Thr Asp Tyr
                565                 570             575

Ile Asn Lys Glu Asn Leu His Val Asn Val Asn Ser Lys Met Met Glu
            580                 585             590

Arg Tyr Lys Leu Tyr Leu Ser Gln Asn Lys His Cys Ile Tyr Thr Asn
            595                 600             605

Thr Pro Leu Thr Met Met Asp Val Ile Tyr Gly Thr Asn Val Gln Val
            610                 615             620

Asp His Ile Ile Pro Gln Ser Lys Ile Leu Asp Asp Thr Leu Asn Asn
625                 630                 635                 640

Lys Val Leu Val Leu Arg Asp Ala Asn Ser Ile Lys Asn Asn Arg Leu
                645                 650             655

Pro Leu Glu Ala Phe Asp Glu Met Gln Ile Asn Val Asp Thr Asn Tyr
                660                 665             670

Thr Lys Lys Asp Tyr Leu Thr Glu Cys Leu His Leu Leu Lys Asn Lys
            675                 680             685

Thr Asn Pro Ile Ser Lys Lys Lys Tyr Gln Tyr Leu Thr Leu Lys Lys
            690                 695             700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                725                 730             735

Lys Glu Ser Asp Lys Thr Lys Asn Ile Asp Val Val Thr Ile Lys Gly
                740                 745             750

Ala Val Thr Ser Arg Phe Arg Lys Arg Trp Leu Thr Thr Tyr Asp Glu
            755                 760             765

Tyr Gly Tyr His Pro Thr Ile Tyr Ser Leu Glu Asp Lys Gly Arg Asn
            770                 775             780

Leu Tyr Tyr Tyr His His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810             815

Ile Lys Ile Asp Arg Asn Leu Ser Lys Glu Gln Lys Gln Arg Asp Ile
                820                 825             830

Asp Thr Val Ile Lys Asn Thr Val Lys Ser Met Ser Lys Tyr His Gly
            835                 840             845

Phe Ser Glu Asp Tyr Ile Arg Ser Leu Met Ser Lys Asn His Ile Pro
            850                 855             860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890             895

Gln Tyr His Tyr Lys Lys Leu Tyr Ile Ala Phe Lys Glu Ala Gln Asn
                900                 905             910

Ala Leu Lys Glu Lys Glu Ile Leu Glu Lys Glu Leu Thr Glu Arg Phe
            915                 920             925
```

```
Asn Asn Glu Ala Gln Ile Leu Asn Ala Asn Ile Ile Leu Thr Tyr Thr
        930                 935                 940

Gly Phe Glu Ser Asn Asn Glu Leu Ile Asp Ile Lys Ala Lys Lys
945                 950                 955                 960

Val Ile Asp Thr Leu Lys Pro Asp Leu Lys Asn Tyr Ile Lys Ala Ile
            965                 970                 975

Asp Ile Leu Thr Gln Glu Glu Tyr Thr Lys Arg Cys Leu Glu Tyr Tyr
            980                 985                 990

Asn Asp Ser Glu Phe Ala Glu Gln Leu Lys Ile Pro Tyr Val Asn Phe
            995                 1000                1005

Lys Ile Asn Lys Arg Phe Arg Gly Lys Ile Gln Gly Ser Glu Asn
    1010                1015                1020

Ala Val Ser Leu Arg Glu Val Leu Lys Lys Thr Lys Leu Asn Ser
    1025                1030                1035

Phe Glu Glu Phe Glu Ser Tyr Leu Lys Ser Glu Asp Gly Ile Lys
    1040                1045                1050

Ser Pro Tyr Tyr Ile Lys Tyr Thr Lys Asn Thr Leu Gly Lys Glu
    1055                1060                1065

Ser Tyr Thr Ile Tyr Glu Ala Asn Ser Tyr Tyr Cys Ala Glu Ile
    1070                1075                1080

Tyr Thr Asp Ser Gln Asn Lys Pro Gln Leu Arg Gly Ile Arg Tyr
    1085                1090                1095

Val Asp Val Arg Lys Glu Asp Gly Lys Leu Val Leu Leu Lys Pro
    1100                1105                1110

Leu Pro Ser Thr Cys Lys His Ile Thr Tyr Leu Phe His Asn Glu
    1115                1120                1125

Tyr Ile Ala Ile Tyr Lys Asp Ser Asn Tyr Lys Arg Leu Lys Asn
    1130                1135                1140

Asn Gly Phe Gly Ala Tyr Arg Ser Ile Lys Asn Val Asn Val Asn
    1145                1150                1155

Lys Ile Ile Ile Arg Leu Phe Ala Asn Gln Asn Leu Asn Asp Asn
    1160                1165                1170

Asp Val Val Ile Thr Ser Ser Ile Phe Ile Lys Lys Tyr Ser Leu
    1175                1180                1185

Asp Val Phe Gly His Ile Asn Gly Glu Ile Lys Cys Gly Asp Gln
    1190                1195                1200

Ser Leu Phe Thr Ile Lys Lys Arg
    1205                1210

<210> SEQ ID NO 143
<211> LENGTH: 1211
<212> TYPE: PRT
<213> ORGANISM: Sharpea azabuensis

<400> SEQUENCE: 143

Met Glu Asn Tyr Arg Gln Lys His Arg Phe Val Leu Ala Thr Asp Leu
1               5                   10                  15

Gly Ile Gly Ser Asn Gly Trp Ala Ile Ile Asp Leu Asp Ala His Arg
            20                  25                  30

Val Glu Asp Leu Gly Val Gln Ile Phe Glu Ser Gly Glu Gly Ala
        35                  40                  45

Lys Lys Ala Ser Ala Arg Ala Ser Gln Gln Arg Leu Lys Arg Ser
    50                  55                  60

Ala His Arg Leu Asn Arg Arg Lys Lys Gln Arg Lys Glu Ser Leu Ile
```

```
                65                  70                  75                  80
Lys Phe Leu Gln Glu Ile Glu Phe Pro Asp Leu Asn Asn Ile Leu Asp
                    85                  90                  95

Ser Phe Lys Lys Gln Lys Asn Pro Asn Asp Ile Leu Ser Leu Arg Val
                    100                 105                 110

Lys Gly Leu Asp Asn Lys Leu Ser Pro Leu Glu Leu Phe Ser Val Leu
                    115                 120                 125

Ile Tyr Met Ser Asn Asn Arg Gly Tyr Lys Asp Phe Tyr Asp Asn Asp
            130                 135                 140

Ile Asn Glu Asp Lys Lys Asp Ser Asp Glu Lys Glu Met Gln Lys Ala
145                 150                 155                 160

Lys Ser Thr Ile Glu Lys Leu Phe Ala Ser Asn Ser Tyr Arg Thr Val
                    165                 170                 175

Gly Glu Met Ile Ala Thr Asp Pro Thr Phe Ile Val Asp Lys Ser Gly
                180                 185                 190

Ser Lys Lys Val Ile Lys Tyr His Asn Lys Lys Gly Tyr Gln Tyr Leu
                195                 200                 205

Ile Pro Arg Lys Leu Leu Glu Asn Glu Met Ser Leu Ile Leu His Lys
            210                 215                 220

Gln Glu Glu Phe Tyr Asp Cys Leu Ser Ile Asp Asn Ile Thr Ile Ile
225                 230                 235                 240

Leu Asp Lys Ile Phe Phe Gln Arg Asn Phe Glu Asp Gly Pro Gly Pro
                    245                 250                 255

Lys Asn Lys Arg Asp Asp Tyr Lys Asn Asn Ser Lys Gly Asn Gln Phe
                260                 265                 270

Tyr Thr Gly Phe Asn Glu Met Ile Gly Leu Cys Pro Phe Tyr Pro Asn
            275                 280                 285

Glu Lys Lys Gly Thr Lys Asn Ser Leu Ile Tyr Asp Glu Tyr Tyr Leu
                290                 295                 300

Ile Asn Thr Leu Ser Gln Phe Phe Thr Asp Ser Asn Gly Val Ile
305                 310                 315                 320

Met Ser Phe Ser Lys Ser Leu Leu His Asp Leu Met Leu Tyr Phe Phe
                    325                 330                 335

Asp His Lys Gly Glu Leu Thr Asn Lys Glu Leu Ser Ser Phe Leu Leu
                340                 345                 350

Lys His Gly Leu Glu Leu Asn Ser Lys Glu Lys Ser Asn Lys Lys Tyr
            355                 360                 365

Arg Leu Asn Tyr Met Lys Gln Leu Thr Asp Ser Thr Ile Phe Glu Thr
    370                 375                 380

Glu Met Ile Ala Ser Phe Arg Glu Glu Ile Glu Thr Ser Ser Tyr Arg
385                 390                 395                 400

Ser Val Asn Ser Leu Ser Asn Lys Ile Gly Asn Cys Ile Gly Gln Phe
                    405                 410                 415

Ile Thr Pro Leu Lys Arg Lys Glu Glu Leu Thr Asn Ile Leu Ile Asp
                420                 425                 430

Thr Asn Tyr Pro Lys Glu Leu Ala Ser Lys Leu Ala Asp Ser Ile Lys
            435                 440                 445

Val Ile Lys Ser Gln Ser Val Ala Asn Ile Ser Asn Lys Tyr Met Leu
    450                 455                 460

Glu Ala Ile His Ala Phe Glu Ser Gly Lys Lys Tyr Gly Asp Phe Gln
465                 470                 475                 480

Ala Glu Phe Asn Glu Thr Arg Glu Leu Glu Asp His His Phe Met Lys
                    485                 490                 495
```

```
Asn Asn Lys Leu Ile Ala Phe Gln Asp Ser Asp Leu Ile Arg Asn Pro
                500                 505                 510

Val Val Tyr Arg Thr Ile Asn Gln Ser Arg Lys Ile Ile Asn Ala Ala
            515                 520                 525

Ile Asn Lys Tyr Asn Ile Val Arg Ile Asn Ile Glu Val Ala Ser Asp
        530                 535                 540

Val Asn Lys Ser Phe Glu Gln Arg Asp Asn Asp Lys Lys Tyr Gln Asn
545                 550                 555                 560

Asp Asn Tyr Glu Lys Asn Leu Gln Leu Glu Ser Glu Leu Thr Asp Tyr
                565                 570                 575

Ile Asn Lys Glu Asn Leu His Val Asn Val Asn Ser Lys Met Met Glu
            580                 585                 590

Arg Tyr Lys Leu Tyr Leu Ser Gln Asn Lys His Cys Ile Tyr Thr Asn
        595                 600                 605

Thr Pro Leu Thr Met Met Asp Val Ile Tyr Gly Thr Asn Val Gln Val
    610                 615                 620

Asp His Ile Ile Pro Gln Ser Lys Ile Leu Asp Asp Thr Leu Asn Asn
625                 630                 635                 640

Lys Val Leu Val Leu Arg Asp Ala Asn Ser Ile Lys Asn Asn Arg Leu
                645                 650                 655

Pro Leu Glu Ala Phe Asp Glu Met Gln Ile Asn Val Asp Thr Asn Tyr
            660                 665                 670

Thr Lys Lys Asp Tyr Leu Thr Glu Cys Leu His Leu Leu Lys Asn Lys
        675                 680                 685

Thr Asn Pro Ile Ser Lys Lys Tyr Gln Tyr Leu Thr Leu Lys Lys
    690                 695                 700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                725                 730                 735

Lys Glu Ser Asp Lys Thr Lys Asn Ile Asp Val Val Thr Ile Lys Gly
            740                 745                 750

Ala Val Thr Ser Arg Phe Arg Lys Arg Trp Leu Thr Thr Tyr Asp Glu
        755                 760                 765

Tyr Gly Tyr His Pro Thr Ile Tyr Ser Leu Glu Asp Lys Gly Arg Asn
    770                 775                 780

Leu Tyr Tyr Tyr His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810                 815

Ile Lys Ile Asp Arg Asn Leu Ser Lys Glu Lys Gln Arg Asp Ile
            820                 825                 830

Asp Thr Val Ile Lys Asn Thr Val Lys Ser Met Ser Lys Tyr His Gly
        835                 840                 845

Phe Ser Glu Asp Tyr Ile Arg Ser Leu Met Ser Lys Asn His Ile Pro
    850                 855                 860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890                 895

Gln Tyr His Tyr Lys Lys Leu Tyr Ile Ala Phe Lys Glu Ala Gln Asn
            900                 905                 910
```

```
Ala Leu Lys Glu Lys Glu Ile Leu Glu Lys Glu Leu Thr Glu Arg Phe
        915                 920                 925

Asn Asn Glu Ala Gln Ile Leu Asn Ala Asn Ile Ile Leu Thr Tyr Thr
        930                 935                 940

Gly Phe Glu Ser Asn Asn Glu Leu Ile Asp Ile Lys Lys Ala Lys Lys
945                 950                 955                 960

Val Ile Asp Thr Leu Lys Pro Asp Leu Lys Asn Tyr Ile Lys Ala Ile
            965                 970                 975

Asp Ile Leu Thr Gln Glu Glu Tyr Thr Lys Arg Cys Leu Glu Tyr Tyr
        980                 985                 990

Asn Asp Ser Glu Phe Ala Glu Gln Leu Lys Ile Pro Tyr Val Asn Phe
        995                 1000                1005

Lys Ile Asn Lys Arg Phe Arg Gly Lys Ile Gln Gly Ser Glu Asn
    1010                1015                1020

Ala Val Ser Leu Arg Glu Val Leu Lys Lys Thr Lys Leu Asn Ser
    1025                1030                1035

Phe Glu Glu Phe Glu Ser Tyr Leu Lys Ser Glu Asp Gly Ile Lys
    1040                1045                1050

Ser Pro Tyr Tyr Ile Lys Tyr Thr Lys Asn Thr Leu Gly Lys Glu
    1055                1060                1065

Ser Tyr Thr Ile Tyr Glu Ala Asn Ser Tyr Tyr Cys Ala Glu Ile
    1070                1075                1080

Tyr Thr Asp Ser Gln Asn Lys Pro Gln Leu Arg Gly Ile Arg Tyr
    1085                1090                1095

Val Asp Val Arg Lys Glu Asp Gly Lys Leu Val Leu Leu Lys Pro
    1100                1105                1110

Leu Pro Ser Thr Cys Lys His Ile Thr Tyr Leu Phe His Asn Glu
    1115                1120                1125

Tyr Ile Ala Ile Tyr Lys Asp Ser Asn Tyr Lys Arg Leu Lys Asn
    1130                1135                1140

Asn Gly Phe Gly Ala Tyr Arg Ser Ile Lys Asn Val Asn Val Asn
    1145                1150                1155

Lys Ile Ile Ile Arg Leu Phe Ala Asn Gln Asn Leu Asn Asp Asn
    1160                1165                1170

Asp Val Val Ile Thr Ser Ser Ile Phe Ile Lys Lys Tyr Ser Leu
    1175                1180                1185

Asp Val Phe Gly His Ile Asn Gly Glu Ile Lys Cys Gly Asp Gln
    1190                1195                1200

Ser Leu Phe Thr Ile Lys Lys Arg
    1205                1210

<210> SEQ ID NO 144
<211> LENGTH: 1211
<212> TYPE: PRT
<213> ORGANISM: Sharpea azabuensis

<400> SEQUENCE: 144

Met Glu Asn Tyr Arg Gln Lys His Arg Phe Val Leu Ala Thr Asp Leu
1               5                   10                  15

Gly Ile Gly Ser Asn Gly Trp Ala Ile Ile Asp Leu Asp Ala His Arg
            20                  25                  30

Val Glu Asp Leu Gly Val Gln Ile Phe Glu Ser Gly Glu Glu Gly Ala
        35                  40                  45

Lys Lys Ala Ser Ala Arg Ala Ser Gln Gln Arg Arg Leu Lys Arg Ser
    50                  55                  60
```

```
Ala His Arg Leu Asn Arg Arg Lys Lys Gln Arg Lys Glu Ala Leu Ile
 65                  70                  75                  80

Lys Phe Leu Gln Glu Ile Glu Phe Pro Asp Leu Val Glu Ile Leu Asn
                 85                  90                  95

Ser Phe Lys Lys Gln Lys Asn Pro Asn Asp Ile Leu Ser Leu Arg Val
            100                 105                 110

Lys Gly Leu Asp Asn Lys Leu Ser Pro Leu Glu Leu Phe Ser Val Leu
        115                 120                 125

Ile Tyr Met Ser Asn Asn Arg Gly Tyr Lys Asp Phe Tyr Asp Asn Asp
    130                 135                 140

Ile Asn Glu Asp Lys Lys Asp Ser Asp Gly Lys Glu Met Gln Lys Ala
145                 150                 155                 160

Lys Ser Thr Ile Glu Lys Leu Phe Ala Ser Asn Ser Tyr Arg Thr Val
                165                 170                 175

Gly Glu Met Ile Ala Thr Asp Pro Thr Phe Ile Val Asp Lys Ser Gly
            180                 185                 190

Ser Lys Lys Val Ile Lys Tyr His Asn Lys Lys Gly Tyr Gln Tyr Leu
        195                 200                 205

Ile Pro Arg Lys Leu Leu Glu Asn Glu Met Ser Leu Ile Leu His Lys
    210                 215                 220

Gln Glu Glu Phe Tyr Asp Cys Leu Ser Ile Asp Asn Val Thr Ile Ile
225                 230                 235                 240

Leu Asp Lys Ile Phe Phe Gln Arg Asn Phe Glu Asp Gly Pro Gly Pro
                245                 250                 255

Lys Asn Lys Arg Asp Asp Tyr Lys Asn Asn Ser Lys Gly Asn Gln Phe
            260                 265                 270

Tyr Thr Gly Phe Asn Glu Met Ile Gly Leu Cys Pro Phe Tyr Pro Asn
        275                 280                 285

Glu Lys Lys Gly Thr Lys Asn Ser Leu Ile Tyr Asp Glu Tyr Tyr Leu
    290                 295                 300

Ile Asn Thr Leu Ser Gln Phe Phe Thr Asp Ser Asn Gly Val Ile
305                 310                 315                 320

Met Ser Phe Ser Lys Ser Leu Leu His Asp Leu Met Leu Tyr Phe Phe
                325                 330                 335

Asp His Lys Gly Glu Leu Thr Tyr Lys Glu Leu Ser Ser Phe Leu Leu
            340                 345                 350

Lys His Gly Leu Glu Leu Asn Ser Lys Glu Lys Ser Asn Lys Lys Tyr
        355                 360                 365

Arg Leu Asn Tyr Met Lys Gln Leu Thr Asp Ser Thr Ile Phe Glu Thr
    370                 375                 380

Glu Met Ile Ala Ser Phe Arg Glu Glu Ile Glu Thr Ser Ser Tyr Arg
385                 390                 395                 400

Ser Val Asn Ser Leu Ser Asn Lys Ile Gly Asn Cys Ile Gly Gln Phe
                405                 410                 415

Ile Thr Pro Leu Lys Arg Lys Glu Glu Leu Thr Asn Ile Leu Ile Asp
            420                 425                 430

Thr Asn Tyr Pro Lys Glu Leu Ala Ser Lys Leu Ala Asp Ser Ile Lys
        435                 440                 445

Val Ile Lys Ser Gln Ser Val Ala Asn Ile Ser Asn Lys Tyr Met Leu
    450                 455                 460

Glu Ala Ile His Ala Phe Glu Ser Gly Lys Lys Tyr Gly Asp Phe Gln
465                 470                 475                 480
```

-continued

```
Ala Glu Phe Asn Glu Thr Arg Glu Leu Glu Asp His His Phe Met Lys
                485                 490                 495

Asn Asn Lys Leu Ile Ala Phe Gln Asp Ser Asp Leu Ile Arg Asn Pro
            500                 505                 510

Val Val Tyr Arg Thr Ile Asn Gln Ser Arg Lys Ile Ile Asn Ala Ala
        515                 520                 525

Ile Asn Lys Tyr Asn Ile Val Arg Ile Asn Ile Glu Val Ala Ser Asp
    530                 535                 540

Val Asn Lys Ser Phe Glu Gln Arg Asp Asn Asp Lys Lys Tyr Gln Asn
545                 550                 555                 560

Asp Asn Tyr Glu Lys Asn Leu Gln Leu Glu Ser Glu Leu Thr Asp Tyr
                565                 570                 575

Ile Asn Lys Glu Asn Leu His Val Asn Val Asn Ser Lys Met Met Glu
            580                 585                 590

Arg Tyr Lys Leu Tyr Leu Ser Gln Asn Lys His Cys Ile Tyr Thr Asn
        595                 600                 605

Thr Pro Leu Thr Met Met Asp Val Ile Tyr Ser Thr Asn Val Gln Val
    610                 615                 620

Asp His Ile Ile Pro Gln Ser Lys Ile Leu Asp Asp Thr Leu Asn Asn
625                 630                 635                 640

Lys Val Leu Val Leu Arg Asp Ala Asn Ser Ile Lys Asn Asn Arg Leu
                645                 650                 655

Pro Leu Glu Ala Phe Asp Glu Met Gln Ile Asn Val Asp Thr Asn Tyr
            660                 665                 670

Thr Lys Lys Asp Tyr Leu Thr Glu Cys Leu His Leu Leu Lys Asn Lys
        675                 680                 685

Thr Asn Pro Ile Ser Lys Lys Lys Tyr Gln Tyr Leu Thr Leu Lys Lys
    690                 695                 700

Leu Asp Asp Glu Thr Ile Glu Gly Phe Ile Ser Arg Asn Ile Asn Asp
705                 710                 715                 720

Thr Arg Tyr Ile Thr Arg Tyr Ile Ala Asn Tyr Leu Lys Thr Ala Phe
                725                 730                 735

Lys Glu Ser Asp Lys Thr Lys Asn Ile Asp Val Val Thr Ile Lys Gly
            740                 745                 750

Ala Val Thr Ser Arg Phe Arg Lys Arg Trp Leu Thr Thr Tyr Asp Glu
        755                 760                 765

Tyr Gly Tyr His Pro Thr Ile Tyr Ser Leu Glu Asp Lys Gly Arg Asn
    770                 775                 780

Leu Tyr Tyr Tyr His Ala Ile Asp Ala Ile Ile Leu Ala Asn Ile
785                 790                 795                 800

Asp Lys Arg Tyr Ile Thr Leu Ala Asn Ala Tyr Asp Thr Ile Arg Leu
                805                 810                 815

Ile Lys Ile Asp Arg Asn Leu Ser Lys Glu Lys Gln Arg Asp Ile
            820                 825                 830

Asp Thr Val Ile Lys Asn Thr Val Lys Ser Met Ser Lys Tyr His Gly
        835                 840                 845

Phe Ser Glu Asp Tyr Ile Arg Ser Leu Met Ser Lys Asn His Ile Pro
    850                 855                 860

Ala Ile Cys Lys Asn Leu Ser Asp Glu Val Gln Ile Arg Ile Pro Leu
865                 870                 875                 880

Lys Phe Asn Thr Asp Tyr Asp Asn Leu Gly Tyr Arg Phe Thr Asp Asp
                885                 890                 895

Gln Tyr His Tyr Lys Lys Leu Tyr Ile Ala Phe Lys Glu Ala Gln Asn
```

```
                    900                 905                 910
Ala Leu Lys Glu Lys Glu Thr Leu Glu Lys Glu Leu Ile Glu Arg Phe
            915                 920                 925

Asn Asn Glu Ala Gln Ile Leu Asn Ala Asn Ile Ile Leu Thr Tyr Thr
            930                 935                 940

Gly Phe Glu Ser Asn Asn Glu Leu Ile Asp Ile Lys Lys Ala Lys Lys
945                 950                 955                 960

Val Thr Asp Thr Leu Lys Pro Asn Leu Lys Asn Tyr Ile Lys Ala Ile
                965                 970                 975

Asp Ile Leu Thr Gln Glu Glu Tyr Thr Lys Arg Cys Leu Glu Tyr Tyr
            980                 985                 990

Asn Asp Ser Glu Phe Ala Thr Gln Leu Lys Ile Pro Tyr Val Asn Phe
            995                 1000                1005

Lys Ile Asn Lys Arg Phe Arg Gly Lys Ile Gln Gly Ser Glu Asn
            1010                1015                1020

Ala Val Ser Leu Arg Glu Val Leu Lys Lys Thr Lys Leu Asn Ser
            1025                1030                1035

Phe Glu Glu Phe Glu Ser Tyr Leu Lys Ser Glu Asp Gly Ile Lys
            1040                1045                1050

Ser Pro Tyr Tyr Ile Lys Tyr Thr Lys Asn Thr Leu Gly Lys Glu
            1055                1060                1065

Ser Tyr Thr Ile Tyr Glu Ala Asn Ser Tyr Tyr Cys Ala Glu Ile
            1070                1075                1080

Tyr Thr Asp Ser Gln Asn Lys Pro Gln Leu Arg Gly Ile Arg Tyr
            1085                1090                1095

Val Asp Val Arg Lys Glu Asp Gly Lys Leu Val Leu Leu Lys Pro
            1100                1105                1110

Leu Pro Ser Thr Cys Lys His Ile Thr Tyr Leu Phe His Asn Glu
            1115                1120                1125

Tyr Ile Ala Ile Tyr Lys Asp Ser Asn Tyr Lys Arg Leu Lys Asn
            1130                1135                1140

Asn Gly Phe Gly Ala Tyr Arg Ser Ile Asn Asn Val Asn Val Asn
            1145                1150                1155

Lys Ile Ile Ile Arg Leu Phe Ala Asn Gln Asn Leu Asn Asp Asn
            1160                1165                1170

Asp Val Val Ile Thr Ser Ser Ile Phe Ile Lys Lys Tyr Ser Leu
            1175                1180                1185

Asp Val Phe Gly His Ile Asn Gly Glu Ile Lys Cys Gly Asp Gln
            1190                1195                1200

Ser Leu Phe Thr Ile Lys Lys Arg
            1205                1210
```

MAD NUCLEASES

RELATED CASES

This application is a continuation of U.S. Ser. No. 17,084,522, filed 29 Oct. 2020; which is a continuation of U.S. Ser. No. 16/837,212, filed 1 Apr. 2020, now U.S. Pat. No. 10,883,095; which claims priority to U.S. Ser. No. 62/946,282, filed 10 Dec. 2019, entitled "Novel MAD Nucleases."

FIELD OF THE INVENTION

This invention relates to new nucleic acid-guided nucleases for making rational, directed edits to live cells.

INCORPORATION BY REFERENCE

Submitted with the present application is an electronically filed sequence listing via EFS-Web as an ASCII formatted sequence listing, entitled "INSC036US3_seqlist_20210308", created Mar. 8, 2021, and 381,982 bytes in size. The sequence listing is part of the specification filed Mar. 12, 2021 and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have beer identified that allow manipulation of gene sequence; hence, gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and PAM length requirements for different nucleic acid-guided nucleases vary; however, PAMs typically are 2-7 base-pair sequences adjacent or in proximity to the target sequence and, depending on the nuclease, can be 5' or 3' to the target sequence. Engineering nucleic acid-guided nucleases or mining for new nucleic acid-guided nucleases may provide nucleases with altered PAM preferences and/or altered activity or fidelity; all changes that may increase the versatility of a nucleic acid-guided nuclease for certain editing tasks.

There is thus a need in the art of nucleic acid-guided nuclease gene editing for novel nucleases with varied PAM preferences, varied activity in cells from different organisms such as mammals and/or altered enzyme fidelity. The novel MAD-series nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides mined MAD-series nucleases (e.g., RNA-guided nucleases or RGNs) with varied PAM preferences, and/or varied activity in mammalian cells.

Thus, in one embodiment there are provided MAD-series nuclease systems that perform nucleic acid-guided nuclease editing including a MAD2001 system comprising SEQ ID Nos. 1 (MAD2001 nuclease), 20 (gRNA repeat sequence) and 21 (gRNA tracr sequence); a MAD2001 system comprising SEQ ID Nos. 1 (MAD2001 nuclease), 22 (gRNA repeat sequence) and 23 (gRNA tracr sequence); a MAD2001 system comprising SEQ ID Nos. 1 (MAD2001 nuclease), 24 (gRNA repeat sequence) and 25 (gRNA tracr sequence); a MAD2007 system comprising SEQ ID Nos. 7 (MAD2007 nuclease), 26 (gRNA repeat sequence) and 27 (gRNA tracr sequence); a MAD2007 system comprising SEQ ID Nos. 7 (MAD2007 nuclease), 28 (gRNA repeat sequence) and 29 (gRNA tracr sequence); a MAD2007 system comprising SEQ ID Nos. 7 (MAD2007 nuclease), 30 (gRNA repeat sequence) and 31 (gRNA tracr sequence); a MAD2008 system comprising SEQ ID Nos. 8 (MAD2008 nuclease), 32 (gRNA repeat sequence) and 33 (gRNA tracr sequence); a MAD2008 system comprising SEQ ID Nos. 8 (MAD2008 nuclease), 34 (gRNA repeat sequence) and 35 (gRNA tracr sequence); a MAD2008 system comprising SEQ ID Nos. 8 (MAD2008 nuclease), 36 (gRNA repeat sequence) and 37 (gRNA tracr sequence); a MAD2009 system comprising SEQ ID Nos. 9 (MAD2009 nuclease), 38 (gRNA repeat sequence) and 39 (gRNA tracr sequence); a MAD2009 system comprising SEQ ID Nos. 9 (MAD2009 nuclease), 38 (gRNA repeat sequence) and 40 (gRNA tracr sequence); a MAD2009 system comprising SEQ ID Nos. 9 (MAD2009 nuclease), 41 (gRNA repeat sequence) and 42 (gRNA tracr sequence); a MAD2011 system comprising SEQ ID Nos. 11 (MAD2011 nuclease), 43 (gRNA repeat sequence) and 44 (gRNA tracr sequence); a MAD2011 system comprising SEQ ID Nos. 11 (MAD2011 nuclease), 45 (gRNA repeat sequence) and 46 (gRNA tracr sequence); and a MAD2011 system comprising SEQ ID Nos. 11 (MAD2011 nuclease), 47 (gRNA repeat sequence) and 48 (gRNA tracr sequence). In some aspects, the MAD-series system components are delivered as sequences to be transcribed (in the case of the gRNA components) and transcribed and translated (in the case of the MAD-series nuclease), and in some aspects, the coding sequence for the MAD-series nuclease and the gRNA component sequences are on the same vector. In other aspects, the coding sequence for the MAD-series nuclease and the gRNA component sequences are on a different vector and in some aspects, the gRNA component sequences are located in an editing cassette which also comprises a donor DNA (e.g., homology arm). In other aspects, the MAD-series nuclease is delivered to the cells as a peptide or the MAD-series nuclease and gRNA components are delivered to the cells as a ribonuclease complex.

Additionally there are provided nickases comprising a MAD2001 nickase 1 [SEQ ID No. 14]; a MAD2001 nickase 2 [SEQ ID No. 15]; a dead MAD2001 [SEQ ID No. 16]; a MAD2007 nickase 1 [SEQ ID No. 17]; a MAD2007 nickase 2 [SEQ ID No. 18]; a dead MAD2007 [SEQ ID No. 19]; a MAD2008 nickase 1 [SEQ ID No. 51]; a MAD2008 nickase 2 [SEQ ID No. 52]; a dead MAD2008 [SEQ ID No. 53]; a MAD2009 nickase 1 [SEQ ID No. 54]; a MAD2009 nickase 2 [SEQ ID No. 55]; a dead MAD2009 [SEQ ID No. 56]; a MAD 2011 nickase 1 [SEQ ID No. 57]; a MAD2011 nickase 2 [SEQ ID No. 58]; and a dead MAD2011 [SEQ ID No. 2859].

In addition, there are provided spacer sequence and PAM sequence pairs for MAD2007, including SEQ ID Nos. 60 and 61; SEQ ID Nos. 62 and 63; SEQ ID Nos. 64 and 65; SEQ ID Nos. 66 and 67; SEQ ID Nos. 68 and 69; SEQ ID Nos. 70 and 71; SEQ ID Nos. 72 and 73; SEQ ID Nos. 74 and 75; SEQ ID Nos. 76 and 77; SEQ ID Nos. 78 and 79; SEQ ID Nos. 80 and 81; SEQ ID Nos. 82 and 83; SEQ ID Nos. 84 and 85; SEQ ID Nos. 86 and 87; SEQ ID Nos. 88 and 89; SEQ ID Nos. 90 and 91; SEQ ID Nos. 92 and 93; SEQ ID Nos. 94 and 95; SEQ ID Nos. 96 and 97; SEQ ID Nos. 98 and 99; SEQ ID Nos. 100 and 101; SEQ ID Nos. 102 and 103; SEQ ID Nos. 104 and 105; SEQ ID Nos. 106 and 107; SEQ ID Nos. 108 and 109; SEQ ID Nos. 110 and 111; SEQ ID Nos. 112 and 113; SEQ ID Nos. 114 and 115; SEQ ID Nos. 116 and 117; SEQ ID Nos. 118 and 119; SEQ ID Nos. 120 and 121; SEQ ID Nos. 122 and 123; SEQ ID Nos. 124 and 125; and SEQ ID Nos. 126 and 127. Also, there are provided spacer sequence and PAM sequence pairs for MAD2001, including SEQ ID Nos. 128 and 129; SEQ ID Nos. 130 and 131; SEQ ID Nos. 132 and 133; SEQ ID Nos. 134 and 135; SEQ ID Nos. 136 and 137; and SEQ ID Nos. 138 and 139.

In yet another embodiment, there is provided additional MAD2007 sequences from *Sharpea azabuensis* comprising SEQ ID No. 142; SEQ ID No. 143; and SEQ ID No. 144.

These aspects and other features and advantages of the invention are described below in more detail.

DETAILED DESCRIPTION

Figure 1:
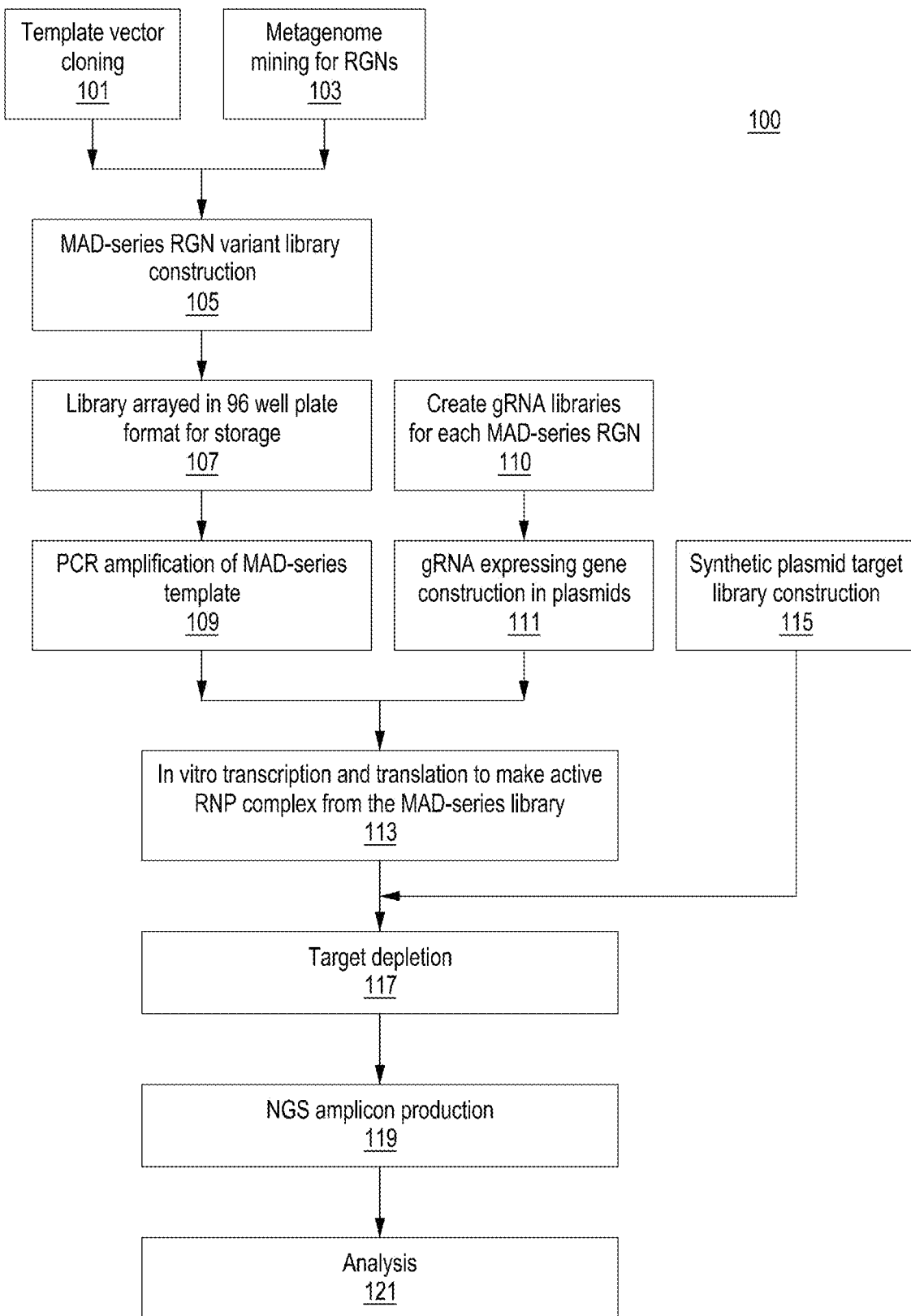
FIG. 1 is an exemplary workflow for creating and screening mined MAD-series nucleases or RGNs.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* 3$^{rd}$ Ed., W. H. Freeman Pub., New York, N.Y.; Berg et al. (2002) *Biochemistry*, 5$^{th}$ Ed., W.H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, "*Directed Evolution: An Approach to Engineer Enzymes*", Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides. Terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region— the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease (see, e.g., FIG. 1).

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments-particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

RNA-guided nucleases (RGNs) have rapidly become the foundational tools for genome engineering of prokaryotes and eukaryotes. Clustered Rapidly Interspaced Short Palindromic Repeats (CRISPR) systems are an adaptive immunity system which protect prokaryotes against mobile genetic elements (MGEs). RGNs are a major part of this defense system because they identify and destroy MGEs. RGNs can be repurposed for genome editing in various organisms by reprogramming the CRISPR RNA (crRNA) that guides the RGN to a specific target DNA. A number of different RGNs have been identified to date for various applications; however, there are various properties that make some RGNs more desirable than others for specific applications. RGNs can be used for creating specific double strand breaks (DSBs), specific nicks of one strand of DNA, or guide another moiety to a specific DNA sequence.

The ability of an RGN to specifically target any genomic sequence is perhaps the most desirable feature of RGNs; however, RGNs can only access their desired target if the target DNA also contains a short motif called PAM (protospacer adjacent motif) that is specific for every RGN. Type V RGNs such as MAD7, AsCas12a and LbCas12a tend to access DNA targets that contain YTTN/TTTN on the 5' end whereas type II RGNs target DNA sequences containing a specific short motif on the 3' end. An example well known in the art for a type II RGN is SpCas9 which requires an NGG on the 3' end of the target DNA. Type II RGNs have substantially different domain architecture relative to type V RGNs. Further, type II RGNs also require a transactivating RNA (tracrRNA) in addition to a crRNA for optimal function. Compared to type V RGNs, the type II RGNs create a double-strand break closer to the PAM sequence, which is highly desirable for precise genome editing applications.

A number of type II RGNs have been discovered so far; however, their use in widespread applications is limited by restrictive PAMs. For example, the PAM of SpCas9 occurs less frequently in AT-rich regions of the genome. New RGNs with new and less restrictive PAMs are beneficial for the field. Further, not all type II nucleases are active in multiple organisms. For example, a number of RGNs have been discussed in the scientific literature but only a few have been demonstrated to be active in vitro and fewer still are active in cells, particularly in mammalian cells. The present disclosure identifies multiple RGNs that have novel PAMs and are active in mammalian cells.

In performing nucleic acid-guided nuclease editing, the mined MAD-series nucleases or RGNs may be delivered to cells to be edited as a polypeptide; alternatively, a polynucleotide sequence encoding the mined MAD-series nucleases are transformed or transfected into the cells to be edited. The polynucleotide sequence encoding the mined MAD-series nuclease may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the mined MAD-series nuclease to be employed depends on many factors, such as what type of edit is to be made in the target sequence and whether an appropriate PAM is located close to the desired target sequence. The mined MAD-series nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA) complexes with a compatible nucleic acid-guided nuclease and can then hybridize with a target sequence, thereby directing the nuclease to the target sequence. With the MAD-series enzymes described herein, the nucleic acid-guided nuclease editing system uses two separate guide nucleic acid components that combine and function as a guide nucleic acid; that is, a CRISPR RNA (crRNA) and a transactivating CRISPR RNA (tracrRNA). The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below.

A guide nucleic acid comprises a guide polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the components of the guide nucleic acid is provided as a sequence to be expressed from a plasmid or vector and comprises both the guide sequence and the scaffold sequence as a single transcript under the control of a promoter, and in some embodiments, an inducible promoter. In general, to generate an edit in a target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

As mentioned previously, the range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the mined MAD-series nucleases disclosed herein may recognize different PAMs, the mined MAD-series nucleases increase the number of target sequences that can be targeted for editing; that is, mined MAD-series nucleases decrease the regions of "PAM deserts" in the genome. Thus, the mined MAD-series nucleases expand the scope of target sequences that may be edited by increasing the number (variety) of PAM sequences recognized. Moreover, cocktails of mined MAD-series nucleases may be delivered to cells such that target sequences adjacent to several different PAMs may be edited in a single editing run.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). For cassettes of this type, see U.S. Pat. No. 10,240,167; 10,266,849; 9,982,278; 10,351,877; 10,364,442; 10,435,715; and 10,465,207. The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments the promoter driving transcription of the gRNA and the donor nucleic acid (or driving more than one gRNA/donor nucleic acid pair) is an inducible promoter. Inducible editing is advantageous in that isolated cells can be grown for several to many cell doublings to establish colonies before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Pat. No. 10,533,152; 10,550,363; 10,532,324; and U.S. Ser. No. 16/597,826, filed 9 Oct. 2019; Ser. No. 16/597,831, filed 9 Oct. 2019; Ser. No. 16/693,630, filed 25 Nov. 2019; Ser. No. 16/687,640, filed 18 Nov. 2019; and Ser. No. 16/686,066, filed 15 Nov. 2019. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes one or more nuclear localization sequences (NLSs), such as about or more than about 1, 2, 3, 4, 5, 6, 7, 8, 9, 10, or more NLSs. In some embodiments, the nuclease comprises NLSs at or near the amino-terminus of the mined MAD-series RGN, NLSs at or near the carboxy-terminus of the mined MAD-series RGN, or a combination.

The engine and editing vectors comprise control sequences operably linked to the component sequences to be transcribed. As stated above, the promoters driving transcription of one or more components of the mined MAD-series nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the mined MAD-series nuclease (e.g., the cells may have already been transformed with an engine vector or the coding sequence for the mined MAD-series nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Pat. No. 10,435,713; 10,443,074; 10,323,258; and 10,415,058.

After the cells are transformed with the components necessary to perform nucleic acid-guided nuclease editing, the cells are cultured under conditions that promote editing. For example, if constitutive promoters are used to drive transcription of the mined MAD-series nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

FIG. 1 shows an exemplary workflow 100 for creating and for in vitro screening of mined MAD-series enzymes. In a first step 101, a vector was prepared and cloned to make a template vector into which the coding sequences for the mined MAD-series RGNs are inserted. In another step 103, metagenome mining was performed to identify putative RGNs of interest based on, e.g., sequence, potential PAM and likelihood of activity. Once putative RGNs of interest were identified in silico, cassettes were constructed 105 and cloned into the vector backbone and then transformed into cells, thereby generating a library of mined MAD-series RGNs. The cells transformed with the mined MAD-series RGNs were arrayed in 96-well plates 107 for storage.

At step 109, an aliquot of the cells from each well was taken, and the mined MAD-series RGNs were amplified from each aliquot. In parallel, gRNA libraries were amplified 110 for each mined MAD-series RGN. At step 111, amplified PCR fragment expressing the gRNA libraries were combined with the amplified mined MAD-series RGNs to perform in vitro transcription and translation to make active ribonuclease protein complexes 113. A synthetic target library was constructed 115 in which to test target depletion 117 for each of the mined MAD-series RGNs. After target depletion, amplicons were produced for analysis using next-gen sequencing 119 and sequencing data analysis was performed 121 to determine target depletion.

Example 2: Metagenome Mining

Figure 2:
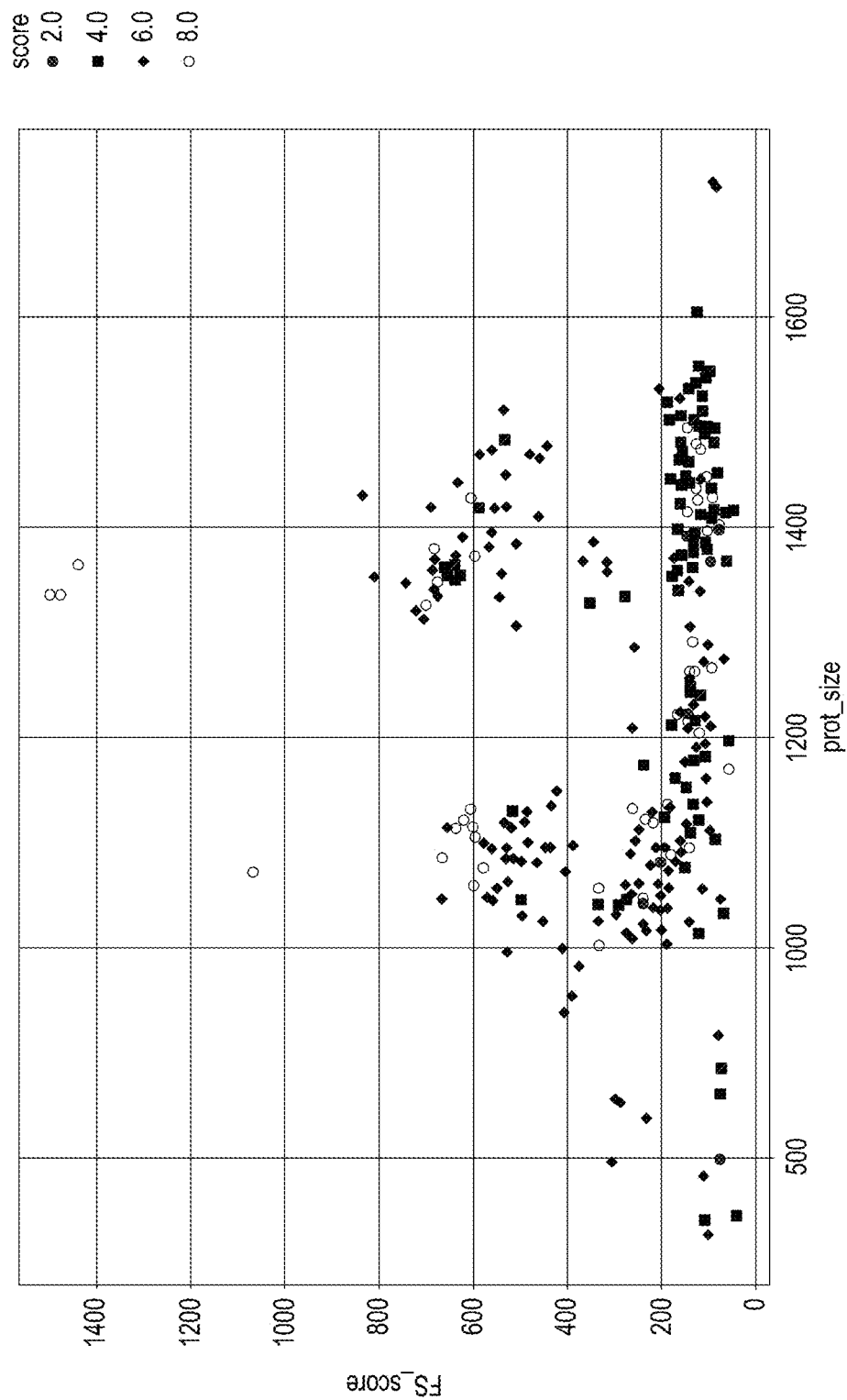
FIG. 2 is a plot of protein size vs. search score for the novel nucleases discovered.

Metagenome-assembled genomes (MAG's) from various sources including Genbank Bioproject accession numbers PRJNA348753, PRJNA385857, PRJNA432584 and PRJNA434545 were used to search for novel, putative CRISPR nucleases using HMMER hidden Markov model searches. Hundreds of potential nucleases were identified. FIG. 2 shows the novel RGNs found, plotting protein size vs. HMMER search score. For each MAG with a nuclease present, putative CRISPR arrays were identified and spacer sequences extracted. These spacers were then used as queries to search the JGI IMG/VR viral metagenome database (Paez-Espino et al, Nucleic Acids Res. 2017 Jan. 4; 45(D1): D457-D465) and predict putative PAM sequences based on viral sequences adjacent to spacer hits. Based on the sequence, potential PAM and confidence that the nuclease is likely active, 13 nucleases were identified (Table 1) for in vitro validation. The sequence of each of the 13 nucleases is shown in Table 2.

TABLE 1

| Mined MAD-series Name | Source | Predicted PAM | Protein size (aas) | Active | Measured PAM |
|---|---|---|---|---|---|
| MAD2001 | Methaomassiliicoccaceae archaeon UBA75 | | 1322 | yes | NNRC |
| MAD2002 | Alphaproteobacteria bacterium UBA756 | | 997 | | |
| MAD2003 | *Butyicimonas virosa* | CGGTT | 1392 | | |
| MAD2004 | *Mariprofundus* sp. UVA 1536 | | 1133 | | |
| MAD2005 | *Micavibrio* sp. UBA2341 | | 1049 | | |
| MAD2006 | Bacteroidales bacterium UBA3382 | ATTTNN | 1501 | | |
| MAD2007 | *Kandleria* sp. UBA3674 | NNCCART | 1211 | yes | NNNSR |
| MAD2008 | Flavobacteriaceae bacterium UBA3591 | | 1490 | yes | NNAA |
| MAD2009 | *Fibrobacter* sp. UBA4297 | CNAAAG | 1511 | yes | NNAA |
| MAD2010 | *Sulfurospirillum* sp. UBA5727 | | 1048 | | |
| MAD2011 | *Enterococcus faecalis* | | 1337 | yes | NGG |
| MAD2012 | *Thiobacillus denitrificans* | | 1087 | | |
| MAD2013 | *Flavobacterium* sp. UBA6135 | NANNGT | 1123 | | |

TABLE 2

| Mined MAD-series Name | SEQ ID No. | Sequence |
|---|---|---|
| MAD2001 | 1 | MKNTNEDYYLGLDIGTDSVGWAVTDKEYNILEFRRKPMWGIHLFEGG<br>STAQKTRVYRTSRRRLKRRAERIALLRDIFSEEIGKVDPGFFERLDESDL<br>HLEDRVTSQKNSLFDDPEFNDKDLHKRFPTIYHLRRHLMHSNRKEDIR<br>LIYLAAHHIIKFRGHFLYKGIGDEEIPSFEIVLNSLIDNLRDEYGMELEVS<br>DRDLVKALLSDFSIGIREKSRELSSCLNAESENEKALVDFISGKKTNMK<br>KLFDDEALDKMSFSLRDSGFEDQLRENEGVLGPERVHTLELSRQIFEW<br>ARLSSILKDSDSISEAKIKDYDQHREDLRMLKRAVKKYAPDKYSEVFK<br>SKEHTGNYCSYVYVCGKGLPDKKCSTEEFQKYLKKILDDSGVRDDEE<br>FKTLIQRLDAGILCPKQRTGENSVIPYSVHRKELIGILNNAAEHYPSLSR<br>KGEDGFSSIDKILMLEEFRIPYYVGPLDDRSSRSWLIRNSFEAITPWNFN<br>EIVDEDETSERFIGNLTSMCTYLGGEKVLPKNSLLYSRFMLYNEINNLR<br>VGGEKIPAALKNKMVSELFANRATSSKVTLKELKAFLKGEGVLTDAD<br>EISGIDDGVKSTLRSEILIRKIIGDKISDREMAEEIVRILTVFGDERRRSKA<br>KLKKEFSDKLTEKEIEKLSSLKFDGWGRLSEKFLTGLRQEVNGRSMSII<br>EILEDTNYNLQETLSKYSFNEIIDSYNEVLTSGPRSISYDILKDSYLSPAV<br>KRGVWRALSVVKDILKAVGRPPKKIFVETTREEREKKRTESRKDALM<br>YLYKSCKETEWEKRLDSVEESSLRNRSLYLYYTQLGKCMYCGKNIDIG<br>ELNTDLADRDHIYPQSKTKDDSIRNNLVLVCRGCNQAKGDRYPLPQE<br>WVSRMHAFWTMLKDKGYISSEKYRRLTRRGELTEEEFGAFINRQLVE<br>TSQSAKAVITVLKNAFKDSDIVYVKGSNVSDFRSSYNFIKCRSVNDYH<br>HAKDAYLNIVVGNVLDTKFTKNPSYVLKNREQYNIGRMYDRNVSRFG<br>VDAWVAGDRGSIATVRKYMRRNNILFTRYATKSKGALFKETVHRKKE<br>GLFERKKGLETEKYGGYSDISTSYLTLLEYDKGKKRIRSLEIVPTYFAN<br>TRPKEEDVIRFFSETRGLANVRVVMPEVRMKSLFEYRGFRFHVTGSNG<br>KGRFWISSAIQLLLPENLYAYCKSIENNEKDSQRRSEKPLQNYGFSSEM<br>NIELFKCLMDKAAKPPYDVKLSTLSKNLEEGFEKFKALELGPQVKVL<br>QQILDIYSCDRKSGDLSVLGSARNAGRLDMNGVLSEADGEQVTMICQS<br>PSGLFEKRVPMNEK |
| MAD2002 | 2 | MKKRIFGFDIGIASLGWAVVDFDDTADPENDIYPTGEIVKSGVRCFPVA<br>ENPKDGSSLAQPRRQKRLLRRLCRRKARRMAGIKNLFVANGLIGKDA<br>LFNEKSNIYKARDNADVWDLRVKALTDKLTTIEFIRVLTHLAKHRGFK<br>SYRIAAEKADAESGKVLEAVKANRALLENGKTLAQIIVEKGGQKRNRE<br>KMIVKNGKTEKQASYENSIPRDEIERETRLIFEKQRAFGLEAANEKLQ<br>RDFEKIAFRFREIKSKNIEKMIGKCEFEKDEPRAPKNAPSAEFFVAWTKI<br>NNCRVREPDGKIRFLTQEEKENVFNLLKDQKEVKYSALKKALFAKRP<br>DVQFTDIEYNPKPVYDKKTGEIIEKTENPENQKFFSLKGWHDLKSVIDV<br>SSYPVETLDKIATVIATKKNDTDIAKGLKELNLPDAEIEKLTSLSFSKFIR<br>LSLKALYKILPEMQKGMKYNEACDAVGYDFKSTGESFAAQKGK<br>FLPPIPEALATTVPVVNRAMTQFRKVYNALAREYGTPDQINIELARDV<br>YNTHDERKKIADKQKEYGEERKKARDLAQEKMEIENISGRDLLKFRLY<br>EQQDGKCIYSGETLDLRRLTEQDYCDVDHIIPYSRSLDNSQNNKVLCLS<br>RENRRKSDKTPLEYIIDPVKQAEFIARVKSMKGLSAPKRDRLLIRDFKE<br>KELEFRDRNINDTRYMARYIMKYLDDCIDFSGSQTDIKDHVQSRIG<br>SLTDFLRHQWGLHKDRNENDRHHAQDAIVIACATNGYTQYLAHLSKI<br>FENKQAYANKYGQPWYKAFKQHVKQPWDGFYQDVQASLAEIFVSRP<br>PRKNATGEVHQDTIRTLNPNKPQYSEKDVKSGIKLRGGLANNGDMLR<br>VDVFSKKNAKGKEQFYLVPIYLADRIKPELPNKAIVANKSESEWIIMDA<br>TYSFKFSLYMDDLVSVIKGDKKIFGYYKGTSRSTASITIEGHDRNFIQPS<br>IGVKTVDNIKKYQIDPLGRYVEVKSEIRLPLNIKKRKS |
| MAD2003 | 3 | MKKVLGLDLGSSSIGWAYVHEAENEAELGSSKIIKLGVRVNPLTVDEQ<br>RNFEQGKSITTNASRTLKRCMRRNLQRYKLRRENLIEVLKKHGFISDAS<br>ILSEQGNYTTFETYRLRAKAAVAEISLEELARVLLMINKKRGYKSSRKN<br>RGGDEGKFIDGISVAKQLYDRGITPGQFSLELLKEGKRHLPDYYRSDLQ<br>NELDRIWNFQQSFYPEILTQNFREQIRDKGQKNTSQIFLREYQIYTADN<br>KGADKLSRALQWRVEGLSRKLSVEELAFVMSDLNGSISGSSGYLGAIG<br>DRSKELYLGKQTVGQYLMEKLNTNPNGSLKSKVFYRQDYLDEFERIW<br>ETQAGFHKELTLELKKEIRDIIIFYQRSLKSQKGLISFCELESKLVEIEVN<br>GKMRRKVVGSRVCPKSSPLFQEFKIWSILNNICVWSVDKSKSSEARKM<br>DERDKEPNLNQEEKEILFKELSLKEKLSKRDVLELLFEDARKLDMNYE<br>KVEGNRTQATLFKAYQEIIARSGHGEYDFTRMLSSEILEIVSGVFDGLG<br>YNTDILYFNSEGELDQQPLYRLWHLLYSFEGDKSNSGNENLINKITNLY<br>GFDREYAVILADVVFPPDYGNLSAKAIHKILPYLKDGNKYSLACEYAG<br>FRHSKNSLTKEEREKRVLKERLDILPKNTLRNPVVEKILNQMVHVVNG<br>VINKYGKPDEIRIELARELKKNAKEREEWTRAINKSTIENEKLRSVLKK<br>EFGFGTQVSRNDIVRYKLYLELESRGFKTLYSNTYIPLEKLFFKEFDIEHII<br>PQSRLFDDSFSNKTIELRSVNQEKDNQTAYDYVSGKGGEAGLQEYLER<br>VEDLFKGGYINKAKYNKLRMTGKDIPDDFIDRDLRDTQYIARRAKAM<br>LEEVVGNVVSTSGAVTDRLREDWQLVDVMKELNWNKYERLGLTEIV<br>EDRDGRKIRRIKGWTKRNDRHHAMDALTIAFTKPKYVQYLNNLNAR<br>GDKSSSVYGIERDELSRDSKGKLRFNSPMPLKEFRMEAKLHLENVLVS<br>TKAKNKVITPNVNKSKKRGGMNQKVQLTPRGQLHQETIYGSIKQYVT<br>KEVKVGSAFNMEMILKVANKAYREALLKRLNAFDQDAKKAFTGKNS<br>LEKNPIFINDSHTCKVPEKVKVVSFETVYTIRKEIGPDLKVDKVIDKRV |

TABLE 2-continued

| Mined MAD-series Name | SEQ ID No. | Sequence |
|---|---|---|
| | | RDILETRLVEFGGDSKLAFTNLDENPIWLNKEKGIDIKRVTISGVSNVIA LHDKLDKDGKLVLDEHGQPQPVDFVCSGNNHHVVVYRDPEGKIQDD VVSFFEATVRAKEGLPVIDREYKKQEGWEFLFSMKQNEYFVFPNEETG FDPKEVDLMNPDNYALISPNLFRVQTMSRVMYGNQVVRDYKFRHHLE TTVKDCKELKDIAYKQYKSLDFASQIVKVRIDHIGQIVHVGEY |
| MAD2004 | 4 | MADKEKLKETYTIGLDIGIASVGWAILGENRIIDLGVRCFDKAETAKEG ESLNLSRRMARLMRRRLRRRAWRLTKLARLLKRVGLIADVGVLKQPP SKGFQTPNLWQLRVEGLDRKLGDDEWARVIYHLCKHRGFHWISKAEA KAADSDKEGGKVKQGLAGTKRLMQEKSYRTAAEMVLAEFPDAQRNK QGEYSKALSRELLCEELKELFKQQRAFGHTHADDKLETNILGNGDKKS GLFWVQKPSLSGEALLKMLGKCTFEKDEYRAAKACFTAERHVLLTRI NNLRIVENGKMRGLTADERRIALWQPYQQAGDFTFKQLGSALEKHGS LLKGGYKFAGLTYPRETDEKAKNPETATLVKIPAWQELKKTLIGVGLE REWQGMADAALNGKPDLLDKIGWVLSVYKEDDEVELELGKLQLAAN VIHALQTVRFDKFSNLSLLALCKILPQMENGMRYDEACKEAGYQHSM PDMQDLEAKVRYLPPFYSGREKDGRLKFNEDMDIPRNPVVLRALNQA RKVVNALIRKYGSPHAVHIEMARDLSRPIDERRKIERDQADYRTKNED ARKAFASDFGFEPKGRQFEKYMLYREQQAKCAYSLAPLDLNRVLNDQ GYAEVDHALPYSRSFDDGKNNRVLVLTSENRNKGNQTPYEYLDGTS DSEKWRLFESFVSGNKAYSQAKRNLLKKDFGVKETQDFKERNLNDT RYICRFFKNYVEQYLQLHEESDAKRCVVVSGQLTSLLRFRWGINKIRSE SDRHHALDAAVVAACSHGLVKRMSDYSRRKELGQVRDRIEKVDKKT GEIIDHFPSPWAHFRQELLARLHIDDANELRAVVENLGTYPPEALESLT PLFVSRAPQRRNSGAAHKETIYAQPEAMKEKGSVTQKVAVTSLKPAD VDKLIDPERNVKLYAYLRKWLAGKDEREKRAKAIEASAGRGKEKRDL TPEEKIEIERLRALPQKPDKQGKPTGPIVRAVTMVIDKLSGIPVRGGIAK NDTMLRVDMFSKAKRYYLVTVYVFHSVAKELPSRAIVAHKDEDDWT VISEDFEFCFSMYPNDFIRISQKKETFMGYYAGCDRGSGNVNLWSHDR NSQIGKSGMIRGIGVKTAVNVEKFNVDVLGNIYPAPPEIRRELA |
| MAD2005 | 5 | MGYILGIDIGIASIGFAGVNHDLKKILFSGVHIFEAAENPKTGASLAEPR RTARGQRRVIHRRAQRKNAIRQLLLRHGLNCLSVVDKKYEPTGKNTPP ISPWDLRRTALDRKLTDEELVRILFHIGKHRGFQSNKKSQSNEGDDGK ALKGAGDLEQKWIQSGEKTIGAYLSTQSKKRNGNESYDNFIKRDWLR EEIKVIFEAQRKFNQIKATEVLRLEYAGTGEKAKRNTPEGDGIAFYQRP LQSSEKLIGDCTFEKGEKRAPKFSYTAELFVLWSRLNNTKIKIQNGDER FLTQDEKNKLVNLAHKNKGGVSYTQARKEIGLNESERFNISYRQLDKG DNSWEKIRNEAEKSNFLKLSGFHALHEALDTGSATDWQKWIGSDRDK LDEVAYITSFIEDGKIIREKYQKLGLNEDQIKKLCEIKNFSKTVDLSLKA LRNILPELEKGLRYDEACKALNYNNQPENKGLSKVPKFEDVRNPVVN RALGQTRKVINACIREYGLPDTIVVELAREVGKNFRDRKDIEKEQKTN EARRNTAKTHIAEILGIIEDNVTGEDILKYRLWKEQDCFCPYSGAYITPE MLRDSTSVQIDHIIPYSRSWDNSYMNKVLVLTTENQKKKNDTPFEYLG KTNRWEALEVFARQLPPKKAERLLTENFDDKKAGEWKDRALNDTRY MARLLKTHLEQSLDLGKGNRVQTRNGSLTAHLRGAWGFPDKNRRN DRHHALDAIVIACSTQSMVQGLTNWNKYEARRKNPAERPLPPKPWES FREDAKESVNSIFVSRMPVRTISGAAHEDTIRSIRKSDGKIIQRIKLKDFK KDTLENMVDKARNIKLYDILKERLDAHGGDAKKAFATPVYMPVNDPS KPAPRINSVRILTNEKSGIEINHGLASNGDMRVDVFKKDNKFWLVPIY VHHFAEDKLPNKAIMQGKDEREWEEMNDDDFMFSLYRNDLIKVTTK KETMLVYFGGLDRATGNISIKAHDRDPSFGTNGENRTGVKTAINFEKF SVNYFGRKHKIEKEKRLGVAHSDDSERGAAIPEQGTGAAAE |
| MAD2006 | 6 | MKRILGLDLGTNSIGWAVINQDNINDKDILTGIECTGSRIIPMDAATLG DFDRGNAQSQTADRTKRRSARRLIERSHIRRERLNRVLMTMGWLPEH YSDSLDRYGKLSKGTEQKIAWKKSGNGNYEFIFKDSFNEMLDDPKNE HPDFAQRGLKIPYDWTIYYLRKKALTHPKRVTVTNQELAWILHSFNQKRGY YQRGEEEQQPDKKIEYIPLKVKEIRETGETKGADKWFELILENDLVYK RTFKEMPDWKGKTLELIVTTDLDKDGNPVIKDGKAKYSIRAPKEDDW TLVKVRTQSDIRKSGKTVGCYIYDALIRKPDIKIRGKLVRTIEREFYREE LEQILKKQKEFNQDLRDKELYNECIGVLYPNNDTHRKEIANRDDFAYL FINDIIFYQRPLKSKKSLISDCPYEERIYKDKSTGQKLTSAIKCIPKSHPTY QEFRLWQFLSYLKIYEKERTEIGKIQTDIDITDILLPDNESYAALFKKLN DEAEIKQDKILKYFPQLKKNIKNFRWNYPEDKTYPGNTTRAEMLKRLK KANIGSDFLTTEQETALWHILYSVNDKAELEKALSTFANKHGIEEEPFL NEFVKFPPFKSDYGAYSFKATNKLLSLMRRGCYWDEENIDCNTKERIE KIISGEYDPEINDRVREKTINLNGISDFQGLPTWLACYVVYGRHSEIKDI TKWEKPSDIDNYLKLFKQHSLRNPIVEQVVLETLRTVRDIWKQVGRID EIHIELGREMKNSASERKRIAEQISKNENTNLRIKAMLTEFLNPEFEIDN VRPYSPTQQEILKIYEEGVLNSGIEIDEKVKNFLKSFDKAENRPTRAEFL KYKLWLDQKYISPYTGQPIPLSKLFTSEYEIEHIIPQSRFFDDSLSNKVIC EAKVNSEKGARLGHEFIKGCHEQIIDLGFGKTVKILSIEAYEEHVRKNY GHNKAKQKKLMLDEIPDTFIERQLNDSRYISKLVKTLLSNIVREDDEAE AISKNVITCTGQITDRLKHDWGVNDVWNGIILPRFQRMEKLQPGKRFT |

TABLE 2-continued

| Mined MAD-series Name | SEQ ID No. | Sequence |
|---|---|---|
| | | ATNTNGKLIPYMPLEYQKGFSSKRIDHRHHAMDAIVIACANRNIVNYL<br>NNESARSDAKISRYDLRNLLCDKKQDDAGNHTWTMKIPWNTFIRDM<br>RKALEGIIVSFKQNLRVINKSSNHITKYVDGQKKRVPQSEGDNRSIRKS<br>LHKDTVFGLVNLREKKTVSLSEALKKPDRIVDKALKHRIKEFKTAGKT<br>DTDIKKLLKNGPDKVEIYYFSEEKSIGKDKARHYYAARTTILSLEMDKS<br>KSYEKAINTINNITDSGIRKILTNHLEANGNDPSKAFSADGIDEMNKNII<br>LLNGGKNHKPIYSVRKYEEANKFAVGEIGCKSKKFVEADKGGNLYFA<br>VYKKDDNSRSFRTIPLNEVIDRLKNKMSPVPETDEMGNRLIFWLSPND<br>LVYLPTADEVENGRVTLPLDKDRIYKMVSANKKQCFFMPSNTANPIISI<br>EFSSSNKMERAITGEMIKETCIPLKTDRLGNITDFDGRIS |
| MAD2007 | 7 | MENYRQKHRFVLATDLGIGSNGWAIIDLDAHRVEDLGVQIFESGEEGA<br>KKASARASQQRRLKRSAHRLNRRKKQRKEALIKFLQEIEFPDLVEILNS<br>FKKQKNPNDILSLRVKGLDNKLSPLELFSILIYMSNNRGYKDFYNDIN<br>DNNTDKDEKEMEKAKSTIEKLFASNSYRTVGEMIATDPTFIVDKSGSK<br>KVIKYHNKKGYQYLIPRKLLENEMSLILHKQEEFYDCLSIDNITIILDKIF<br>FQRNFEDGPGPKNKRDDYKNNSKGNQFYTGFNEMIGLCPFYPNEKKG<br>TKNSLIYDEYYLINTLSQFFFTDSNGVIMSFSKSLLHDLMLYFFDHKGE<br>LTNKELSSFLLKHGLELNSKEKSNKKYRLNYMKQLTDSTIFETEMIASF<br>REEIETSSYRSVNSLSNKIGNCIGQFITPLKRKEELTNILIDTNYPKELAS<br>KLADSIKVIKSQSVANISNKYMLEAIHAFESGKKYGDFQAEFNETRELE<br>DHHFPMKNNKLIAFQDSDLIRNPVVYRTINQSRKIINAAINKYNIVRINIE<br>VASDVNKSFEQRDNDKKYQNDNYEKNLQLESELTDYINKENLHVNVN<br>SKMMERYKLYLSQNKHCIYTNTPLTMMDVIYSTNVQVDHIIPQSKILD<br>DTLNNKVLVLRDANSIKNNRLPLEAFDEMQINVDTNYTKKDYLTECL<br>HLLKNKTNPISKKKYQYLTLKKLDDETIEGFISRNINDTRYITRYIANYL<br>KTAFKESDKTKNIDVVTIKGAVTSRFRKRWLTTYDEYGYHPTIYSLED<br>KGRNLYYYHHAIDAIILANIDKRYITLANAYDTIRLIKIDRNLSKEQKQR<br>DIDTVIKNTVKSMSKYHGFSEDYIRSLMSKNHIPAICKNLSDEVQIRIPL<br>KFNTDYDNLGYRFTDDQYHYKKLYIAPFKEAQNALKEKETLEKELIERF<br>NNEAQILNANIILTYTGFESNNELIDIKKAKKVTDTLKPNLKNYIKAIDI<br>LTQEEYTKRCLEYYNDSEFATQLKIPYVNFKINKRFRGKIQGSENAVSL<br>REVLKKTKLNSFEEFESYLKSEDGIKSPYYIKYTKNTLGKESYTIYEANS<br>YYCAEIYTDSQNKPQLRGIRYVDVRKEDGKLVLLKPLPSTCKHITYLFH<br>NEYIAIYKDSNYKRLKNNGFGAYRSINNVNVNKIIIRLFANQNLNDND<br>VVITSSIFIKKYSLDVFGHINGEIKCGDQSLFTIKKR |
| MAD2008 | 8 | MKKILGLDLGTNSIGWALIEHNFDKKEGRIDDLGVRIIPMSADILGKFD<br>AGQSHSQTAERTGYRGVRRLYQRDNLRRERLHRVLNILDFLPEHYAE<br>HIDFEKRLGQFKEGKEIKLNYKSNKDSKFEFIFKASYNEMLAAFKKYQ<br>PGLFYVKANGTETKIPYDWTIYYLRKKALSQPLTKQELAWIILNFNQK<br>RGYYQLRGEEIDDDKNKQFVQLKVKEVIDSGEAVKGKKLFNVIFENG<br>WKYDKQVVKTEDWIGRTKEFIVTTKTLKSGEIKRTYKAVDSEKDWAA<br>IKAKTEQDIERSNKTVGEFIYEALLQDPTQKIRGKLVKTIERKFYKAELR<br>EILRKQIELQPQLFTTKLYNACIKELYPNNEAHRNSIKNRDFLYLFLDDII<br>FYQRPLKSQKSNISGCHLEQRIYTKINPVSGKKEEVKQAVKAIPKSHPIF<br>QEFRIWQWLQNLKIYDKINTDKGELADVTNQLLPSEESLLDLFDYLQT<br>KKELDQSGFIKYFIDKKLINKSEKENYRWNYVEDKKYPFAETRAQFISR<br>LNKVKNINNISEFLNKKTRLGEKESSPFVTRIEQLWHIIYSVSDINEYKS<br>ALEKFALKHDIDKESFVANFIKFPPPFKSDYGSYSKKALSKLLPLMRRGK<br>YWNESDISNKVKQRVSDIMERVNALNLKENYNAKELAEALKTVSDDD<br>VKKQLIKSFVPFKDKNPLKGLNTYQATYLVYGRHSEVGDIQSWKTPED<br>IDTYLKNFKQHSLRNPIVEQVVTETLRVVRDIWIHYGKSQLNFFNEIHV<br>ELGREMKNPADKRKQISNRNIENENTNNRIREILKDLKNDTSIEGDIRD<br>YSPSQQDLLKIYEEGVYQNPKVDYSKVSEDEITKIRRSNSPTPKEIQRYR<br>LWLEQGYISPYTGKPIPLSKLFTHEYQIEHIIPQSRYFDNSLSNKIICESAV<br>NEDKDNKTAYEYLKNKSGNVINGHKLLRIEEYEAHVNRYFKNNRQKL<br>KNLLSEDIPEGFINRQLNDSRYISKLIKGLLSNIVRQENEQEATSKNLIPV<br>TGAVTSKLKNDWGLNDKWNELILPRFERLNQLTQTKNFTTSNTNGNTI<br>PTVPDDLLKGFSKKRIDHRHHALDALVVACCTRNHVQYLNALNAEKA<br>NYGLRKKLLIVNEQGDFTKIFQMPWKGFTSEAKNQLEKTVISFKQNLR<br>VINKANNKFWSFKDENGNINLDKNGRPVKKLRKQTKGDNWAIRKAM<br>HKETVSGKSNIETPKGKIATAVRGSLADIKNEKHLGKITDVQIREVILPN<br>HLKNYVDEKGKVKFDLAFNDEGIEDLNKNIIALNNGKKHQPIRKVKFF<br>EVGSKFSISENENSAKSKKYVEAAKGTNLFFAVYWDEKKQKRNYETV<br>PLNEVIAHQKQVAHLTNNERLPIQTNRKKGDFLFTLSPNDLVYVPTDA<br>EVANKQPIDFKNLHQNQVNRIYKMVSSSGNQCFFIKDKIATSIWNKNE<br>FSSSLNKMEKDIDGNMIKERCIKLNVDRLGNITKA |
| MAD2009 | 9 | MKKILGLDLGTNSIGWAVVNADAITRNDGSRYLKPNSISAAGSRIIPMS<br>ADVLGNFESGITVSQTKDRTDKRMARRLHERALLRRERLLRILSLMDF<br>LPKHFASKINRYGKFTDDSEPKLAWRKNTEGKYEFIFQDAFNEMLAEF<br>KDKQPEIVKEGKKIPYDWTIYYLRKKALEKALSKEELSWLLLQFNQKR<br>GYYQLRGEEEDIPQDKKIEYLAQKVVKVEATDKKGDDIWYNVYLEN<br>GMIYRRTSKAPLDWEGKIKEFIVTTDLEKDGTPKKDKEGNIKRSFRAPQ |

TABLE 2-continued

| Mined MAD-series Name | SEQ ID No. | Sequence |
|---|---|---|
| | | EDDWTLLKKKTEADIEKSTKTVGCYIYDSLLNNPKQKIIGKLVRTVER<br>KFYKEELTQILKKQVELIPELRNDNLYKQCIEELYPINEAHRNTIAKTDF<br>ANLFINDILFYQRPLKSKKSQIDNCPYEEHIFIDSKTGEKKKVPVKCITK<br>SNPLFQEFRLWQFIQNLRIYQREKEIDGKLSTDVDITSECLKSEEDYVRL<br>FDWLNDRESIEQEELLKYLFNTKKSKNKENPYRWNYVEDKVYPCNET<br>RATILKGLSKCGINASVLSSEMEMALWHILYSVEDKKEIETALTHFAQK<br>QGWNGEFAIVFSKLKPFKKDYGSYSEKAIKKLLSLMRMGKYWNQDNI<br>DKNTLDRIDKIINGEYDEKISNRVRDNAINLKDISDFRGLPVWLACYIV<br>YDRHSEAKDCTKWNTPEEIDSYLKKFKQHSLRNPIVEQVVTETLRTVR<br>DIWKQEGQIDEIHLELGRDLKNPADKRKKMSENILKNENTNLRIKAML<br>MEFMNPGMGIENVRPYSPSQQDILRIYEENALENLTKDDEEFDFISKISK<br>QAQPTKSDIVRYKCWLEQKYRSPYTGKTISLSKLFTSAYEIEHIIPQSRY<br>FDDSFSNKVICEAEVNKLKDRQLGHEFIEEHHGEKVQLSQGEVVEILSV<br>DAYEKFVKENYANNRVKMKKLLMENIPDEFIERQLNDSRYISKVVKG<br>LLSNIVREKIDDENYEPEAVSKNLISCNGAVTDRLKKDWGMNDVWNSI<br>ILPRFIRMNQITGKDCFTTTNAEGHLIPQMPLELQKGFNKKRIDHRHHA<br>MDAIVIACTTRDHVNLLNNEAAHSKFNATRYQLQRKLRCFEKAMIDG<br>KEREVAKEFLKPWDSFTMDSKNILENIIVSFKQNQRVINKTTNTFQHFD<br>ENGKKTFVKQGKGNSWAIRKPMHKDTVFGEINLRKVKSVSLSDAIKV<br>PERILNKRIKEKITELKNNKVDAKNIKKYIEEYHIGGYGIDTSKIDVFY<br>FTKETKERFFATRKSLDSSFNQAKIEDSIADSGIQKILLAHLKSKNGDAE<br>QAFSPDGIDEMNKNIVELNNGKFHQPILKVRVYEKADKFAVGQKGNK<br>KVKFVEAAKGTNLFFAVFEKDGKRSYLTIPLNVMIDCQKKYGNQWKQ<br>NIESYLKEKDLVEKDVQLLFILSPNDLVYLPTENELKKGITNPDKDQIY<br>KFVSCTSNEAHFIPSFVANPIVQTTELGSNNKAQRAWNNKMIKEICI<br>PIEVDRLGNIK |
| MAD2010 | 10 | MVEKILGIDLGISSLGWAVVEYDKDNDENNKIIDCGVRLFTAAETPKE<br>KESPNKARRDARGLRRVIKRRRVRMNTIKNLLITYKLIDKTLLDEEMG<br>MFHSQSNRVDVWKLRHDALYHLLSGDELARVLIHIAKHRGYKFLGDD<br>ESDEESGKVKKAGAELKKKFLEAGCQSVGEWLWKERGLQGKKRNKS<br>GDYEISIPRDFLVEEIQRIFETQQKFGSTFATSELQKAYTDIAFYVKPMQ<br>SIEDMVGYCTFYPKIKSKNQDGEKRAPKASPSAEQFVILSKIFSTIVIDE<br>NKQEKKLIELKSIEQLIQIARSKETLKYKQLRKELNLAKDISFKSISDEEK<br>TWINLVGNAKFKKILGLNYETFLKNTEISDEIAKILTYDKTFEQKETKL<br>KNLLVNIDWIDNNHIAELAKLSFSQFNQLSLKAIKIISKIMIEGYARYDE<br>AVQYAFENNLLPKPSHEKSILLPPLKETNIAILNPTVIRAFAQFRQVANA<br>LVSKYGSFDKVHFELAREVNTKEDRKRWEKDRDKNEKMHRQITEKL<br>VEEGVKPSYKNILKSKLRSEQKDTCPYCQKNLHYPMIFEDGYAEIDHIL<br>PLSQSQDDSYVNKVLVHSACNQNKKNRTPFEWFQDEKKDWDTFKSYI<br>LMESTLGEKKRNYLIKENFSDPQSRKEFISRNLNDTRYMSKAIKTYCEN<br>HWKLSHDDDKLRIQVRSGKLTSTLRHQWGLDNKNRETHTHHAMDAI<br>MIAFSTQGMVKKLSDYFAKKEAKVEKDKPVLITPIKQFKEAVEQATTL<br>ERQESIQTKAGDTITLNRLLISRPPRASVTGAAHEQTAKPYPRIKPIKNK<br>YKRRRIPIDEDKFELFRNDKVASGNDKNFYNSSTIPRVDIYKKDDKYH<br>VVPIYLSDMTKAEVPNKSLGTNPEGMDEKYFCFSVFKNDLIELETKAT<br>PKKPSKKLLGYFKQLNGANFILNSIHNGIIDGFVCSPITLFKQQKDMCK<br>KCLPEDRAIGNCSQETLEFWEAENIKVPKKDFECDQGIKFAIAVRKYTI<br>DPLGYYHEVKGEKLLGTIPQGAKKHPKRQK |
| MAD2011 | 11 | MKKDYVIGLDIGTNSVGWAVMTEDYQLVKKKMPIYGNTEKKKIKKN<br>FWGVRLFEEGHTAEDRRLKRTARRRISRRRNRLRYLQAFFEEAMTALD<br>ENFFARLQESFLVPEDKKWHRHPIFAKLEDEVAYHETYPTIYHLRKKL<br>ADSSEQADLRLIYLALAHIVKYRGHFLIEGKLSTENISVKEQFQQFMIIY<br>NQTFVNGESRLVSAPLPESVLIEEEELTEKASRTKKSEKVLQQFPQEKAN<br>GLFGQFLKLMVGNKADFKKVFGLEEEAKITYASESYEEDLEGILAKVG<br>DEYSDVFLAAKNVYDAVELSTILADSDKKSHAKLSSSMIVRFTEHQED<br>LKNFKRFIRENCPDEYDNLFKNEQKDGYAGYIAHAGKVSQLKFYQYV<br>KKIIQDIAGAEYFLEKIAQENFLRKQRTFDNGVIPHQIHLAELQAIIHRQ<br>AAYYPFLKENQKKIEQLVTFRIPYYVGPLSKGDASTFAWLKRQSEEPIR<br>PWNLQETVDLDQSATAFIERMTNFDTYLPSEKVLPKHSLLYEKPMVFN<br>ELTKISYTDDRGIKANFSGKEKEKIFDYLFKTRRKVKKKDIIQFYRNEY<br>NTEIVTLSGLEEDQFNASFSTYQDLLKCGLTRAELDHPDNAEKLEDIIKI<br>LTIFEDRQRIRTQLSTFKGQFSEEVLKKLERKHYTGWGRLSKKLINGIY<br>DKESGKTILDYLIKDDGVSKHYNRNFMQLINDSQLSFKNAIQKAQSSE<br>HEETLSETVNELAGSPAIKKGIYQSLKIVDELVAIMGYAPKRIVVEMAR<br>ENQTTSTGKRRSIQRLKIVEKAMAEIGSNLLKEQPTTNEQLRDTRLFLY<br>YMQNGKDMYTGDELSLHRLSHYDIDHIIPQSFMKDDSLDNLVLVGSTE<br>NRGKSDDVPSKEVVKKMKAYWEKLYAAGLISQRKFQRLTKGEQGGL<br>TLEDKAHFIQRQLVETRQIITKNVAGILDQRYNAKSKEKKVQIITLKASL<br>TSQFRSIFGLYKVREVNDYHHGQDAYLNCVVATTLLKVYPNLAPEFV<br>YGEYPKFQAFKENKATAKAIIYTNLLRFFTEDEPRFTKDGEILWSNSYL<br>KTIKKELNYHQMNIVKKVEVQKGGFSKESIKPGPSNKLIPVKNGLDP<br>QKYGGFDSPVVAYTVLFTHEKGKKPLIKQEILGITIMEKTRFEQNPILFL<br>EEKGFLRPRVLMKLPKYTLYEFPEGRRRLLASAKEAQKGNQMVLPEH |

TABLE 2-continued

| Mined MAD-series Name | SEQ ID No. | Sequence |
|---|---|---|
| | | LLTLLYHAKQCLLPNQSESLAYVEQHQPEFQEILERVVDFAEVHTLAK SKVQQIVKLFEANQTADVKEIAASFIQLMQFNAMGAPSTFKFFQKDIER ARYTSIKEIFDATIIYQSTTGLYETRRKVVD |
| MAD2012 | 12 | MALNPPLPYTLGLDIGMASVGAALLTEQRILGLHVRAFDKAETAKEGD PLNKTRRESRLTRRRIRRRAHRLLRLARLFKRTGLIAAAHPEAFALPGIS PWDLRADGLNRLLTPAEWAAVLYHLVKHRGFQSTRKSEAKEDEKAG QMLSGVSANQQRMKEKGWRTVGEMAARDEAFAEAKRNKGGAYTHT FARTDLVAELKLLFKQQAGFGNPHVGVDFENDVEQLLLARRPALAGD ALLKLVGKCPFEPTEYRAPKASYSAERFVWLTKLNNLRISEVGEQRAL TAGERQILLNQPYLLAKFTYKQARQRLSLADTAKFTVLTYRGDKDPES TTFFEAKAYHELRKAYEKAGLESRWQRDALDPTRLDRLAWALTCYKT DDDIRAHLAEHGVEPEITEAVLGESFDKFVGLSLKALGKILPFMEQGQR YDEAVQSAGYAHHSQLNRDTTKNQYLPPPDKDQIRNPVVYRALNQAR KLVNAIVREYGSPAAIHIELARDLSKPMDERRKIEREQKEFQERKAKDR EAFIEQFSFDPKGLDLQKYRLYREQMSQCAYSQKAIDVTRLFEPGYAEI DHALPYSRSYDDGQNNKVLVLTAENRNKGNRTPYEYLDGASDSPQW QRFEAWVLQNKAYRRAKRDRLLRKHFGEDEAEGFRERNLIDTRYICR AFKTMVEDHLQWHADSDAKNRCVVVAGQLTSLLRARWGLIKVRENG DLHHALDAAVIAAANRSLVKRMADYSKRNELAQVRDRYIDPATGEIL DIAAMRQVEEHFPSPWPHFRSELLAWLSPNPAHGLDGLAHYPPEELEH LRPMRVSRAPTRRGLGAAHQETIRSVGREGRLLADGQSAVKTPLTAIK LKDLENIVGYSHSHNHAMIEAIRKRLETNGNDGAKAFKMPLFKPSATN GYDADKSHVGETDQRAPQIRSVKLLATQKSGIPIRKGIANNGSMLRVD VFGKGGKFYAVPVYVADAARAELPYRAVAAFKPENEWPEMDEKQFM FSLHPNDWVTVKLKAETISGYFAGMDRSTGAISVWAHDRNQSIGKDG QWRGVGMKTALAVEKYHVDLLGNLHRVHTEMRLPLHGSKASKD |
| MAD2013 | 13 | MSKILGLDLGTNSIGWALIDDNQNRILGVGSRIFPMGVENLGDGDGEV SKNASRTGARGVRRQFFRRRLRKKVLLKALSEHNMCPMVTIDFEDWK KSKQFPSEKLSNWFSLNPYELRHKALSEKLTLEEIGRILYHLIQRRGFLS NSRKGGSDDGAIFKGNPKEGKIGITETQESIQDKSLGSYLFEIYPKENQP FEGGLERIRNRYTIRKMYVDEFELIWNKQSQFHSSLNDDLKTLLGGRK LDGYKEDGILFHQRPLRSQKHLVGNCSFEPTKTKCPISAIPFEMFRIWQ WVNTLEYNGKKITQEEKEKIVEFMCANEKPDFKRIRKVIGKESAEFKF NYKDDDKIVGTHTISNLSNKKFFGKAWFDFSEKEQEDIWHVLYFFDSK SNLKDYAIKHWNFNEAQASDVSKFNVKDGYSSLSRKAISNILPFLKLGF TYDVSVVLGGIKNVFGSEWEKLSEEKRNYLIDNVEGIVRSKIKGGFIDV IKGILRNDYSISDNQLRKLYHHSATIDAVELLDKLPVGKEADKEIQAIR NPIVITALFELRKLVNELIDEHGKLDEIKVEMARDLKISKSQRNKIRREQ KRLERENDRVKDRLVENNIRITHDNILLYKLWEECKKTCPYTGKPISVT QLFSGEVQIEHIHPWSRSLNDSFSNKTLCYADENRKKGNLTPFEFYGSD ETNWSAIKERALKLFSDTKEYPNAYQKFKRFVQVKFDDDFSSRQLNDT RYISKEAKNYLSRICKNVIVSPGQATSNLRQKWGMNNILSDENEKTRD DHRHHAVDALVMACTKVSYVQELAKWNRYNRNSELKNFPLPWETFR FDAEKAVEKILISHKKVSNDITVRTHITEKNGIKYKNVGVAARGQLHK ETVFGKRTFNGEEAYHVRKSIDSLETAKQIEKVVDETIKQLILKRVNEL GGFVKDKVPANTFFIVDEKGIKQPQLFLPNKNGQPIPVLKVRVKESVG RAEQLKANVNQWVNPRNNHHVLIYKDEHGNLKEDVVTFWTVVERKR TGQSIYQLPINGKEIITSLHTNDMFIIGLNEDEINWELIDFNLINHHLYRV QKTSKKEKSFEFNFRLGIASSLDNKSQEISIQSFKKWIELNPIKVKISVSG KIQKV |

Example 3: Vector Cloning, MAD-Series RGN Library Construction and PCR

The mined MAD-series RGN coding sequences were cloned into a pUC57 vector with T7-promoter sequence attached to the 5'-end of the coding sequence and a T7-terminator sequence attached to the 3'-end of the coding sequence. 100 ng of the plasmid mixture was transformed into E.cloni® SUPREME electrocompetent solo cells (Lucigen, Middleton, Wis.)). After the cells were recovered in 5 mL of recovery medium at 37° C. for 1 hr in a shaking incubator, 1 mL of 50% glycerol was added and the cells were stored at −80° C. as 100 μL aliquots.

The stored cells were diluted in phosphate buffered saline and spread on LB agar plates with 100 μg/mL of carbenicillin. The cells were then grown overnight at 37° C. in an incubator. Colonies were picked and inoculated into 1 mL of LB medium (100 μg/mL of carbenicillin) in 96-well culture blocks. Cultures were grown overnight in a shaking incubator at 37° C. Next, 1 μL of the cells were diluted into 500 μL of PCR grade water, and 25 μl aliquots of diluted cultures were boiled for 5 min at 95° C. using a thermal cycler. The cells were used to PCR amplify the different mined MAD-series RGN coding sequences. The rest of the cultures were stored at −80° C. with added glycerol at 10% v/v concentration.

First, Q5 Hot Start 2× master mix reagent (NEB, Ipswich, Mass.) was used to amplify the mined MAD-series RGN sequences using the boiled cells as a source of mined MAD-series RGN templates. The forward primer 5'-TTGGGTAACGCCAGGGTTTT [SEQ ID No. 49] and reverse primer 5'-TGTGTGGAATTGTGAGCGGA [SEQ ID No. 50] amplified the sequences flanking the mined MAD-series RGN in the pUC57 vector including the T7-promoter and T7-terminator components at the 5'- and 3'-end of the mined MAD-series RGNs, respectively. 1 M primers were used in a 10 μL PCR reaction using 3.3 μL boiled cell samples as templates in 96 well PCR plates. The PCR conditions shown in Table 3 were used:

TABLE 3

| STEP | TEMPERATURE | TIME |
| --- | --- | --- |
| DENATURATION | 98° C. | 30 SEC |
| 30 CYCLES | 98° C. | 10 SEC |
| | 66° C. | 30 SEC |
| | 72° C. | 2.5 MIN |
| FINAL EXTENSION | 72° C. | 2 MIN |
| HOLD | 12° C. | |

Example 4: gRNA Library Construction

Figure 3:
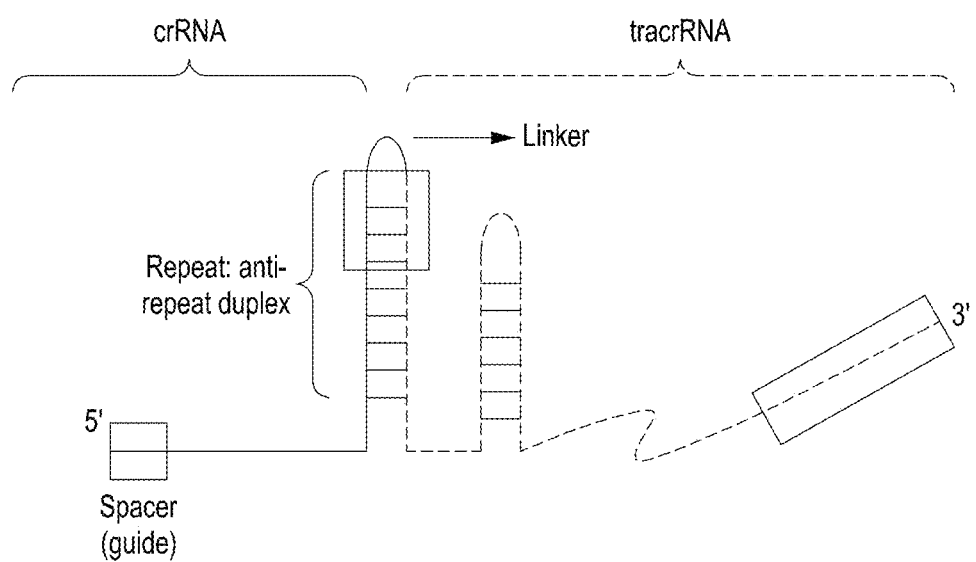
FIG. 3 is a schematic of gRNA designs for new MAD nucleases.

The functional gRNAs associated with each RGN can be difficult to predict since multiple RNAs may be needed for the RGN to function and the length of transcribed RNA can also be highly variable. Therefore, a 384-member library of gRNAs was created for each RGN. The gRNA consisted of a variable spacer sequence, a CRISPR repeat sequence, a linker sequence, and the tracrRNA sequence. FIG. 3 is a schematic of gRNA designs for the mined MAD-series RGNs. The tracrRNA was found by identifying the anti-repeat sequence. The crRNA was covalently linked to the tracrRNA using a GAAA linker. The initial gRNA design was optimized by creating a library of gRNAs by truncating the 5' region, the 3' region and the repeat/anti-repeat duplex. To find the optimal gRNA length, different lengths of spacer, repeat:anti-repeat duplex and 3' end of the tracrRNA were included. The library also was subdivided into six pools based on the overall length of the gRNA. This enabled identification of the shortest gRNA that is optimal for nuclease activity. These gRNAs were then cloned downstream of the T7 promoter.

The target library was designed based on an assumption that the PAMs of these nucleases will reside on the 3' end. Two artificial protospacers were selected with different GC content. Since PAM sequences can range from 3-7 or 3-10 nucleotides in length, three different PAM target libraries were prepared for each protospacer. Library 1 contained the PAM NNNNATGC; library 2 consisted of the PAM ATNNNNGC; and library 3 contained the PAM ATGCNNNN. The sliding PAM library ensures that PAMs ranging from 4 nt to 8 nt are captured. The target libraries were cloned into a target plasmid that contains thesequences necessary for next generation sequencing of uncut targets.

Example 5: In Vitro Transcription and Translation for Production of MAD-Series Nucleases and gRNAs The MAD-series RGNs were tested for activity by in vitro transcription and translation (txtl). Both the gRNA plasmid and nuclease plasmid were included in each txtl reaction. A PURExpress® In Vitro Protein Synthesis Kit (NEB, Ipswich, Mass.) was used to produce mined MAD-series RGNs from the PCR-amplified MAD-series RGN library and also to produce the gRNA libraries. In each well in a 96-well plate, the reagents listed in Table 4 were mixed to start the production of mined MAD-series RGNs and gRNAs:

TABLE 4

| | REAGENTS | VOLUME (μl) |
| --- | --- | --- |
| 1 | SolA (NEB kit) | 3.3 |
| 2 | SolB (NEB kit) | 2.5 |
| 3 | PCR amplified gRNA subpool | 1 |
| 4 | Murine RNase inhibitor (NEB) | 0.2 |
| 5 | Water | 0.3 |
| 6 | PCR amplified T7 MAD-series RGNs | 1.0 |

A master mix with all reagents was mixed on ice with the exception of the PCR-amplified T7-MAD-series RGNs to cover enough 96-well plates for the assay. After 7.3 L of the master mix was distributed in each well in 96 well plates, 1 μL of the PCR amplified MAD-series RGNs under the control of T7 promoter was added. The 96-well plates were sealed and incubated for 4 hrs at 37° C. in a thermal cycler. The plates were kept at room temperature until the target pool was added to perform the target depletion reaction.

After 4 hours incubation to allow production of the mined MAD-series RGNs and gRNAs, 4 μL of the target library pool (10 ng/μL) was added to the in vitro transcription/translation reaction mixture and allowed to deplete for 30 min, 3 hrs or overnight at 37° C. The target depletion reaction mixtures were diluted into PCR-grade water that contains RNAse A and then boiled for 5 min at 95° C. The mixtures were then amplified and sequenced. The PCR conditions are shown in Table 5:

TABLE 5

| STEP | TEMPERATURE | TIME |
| --- | --- | --- |
| DENATURATION | 98° C. | 30 SEC |
| 6 CYCLES | 98° C. | 10 SEC |
| | 61° C. | 30 SEC |
| | 72° C. | 10 SEC |
| 22 CYCLES | 98° C. | 10 SEC |
| | 72° C. | 10 SEC |
| FINAL EXTENSION | 72° C. | 2 MINUTES |
| HOLD | 12° C. | |

Example 5: Results

Figure 4:
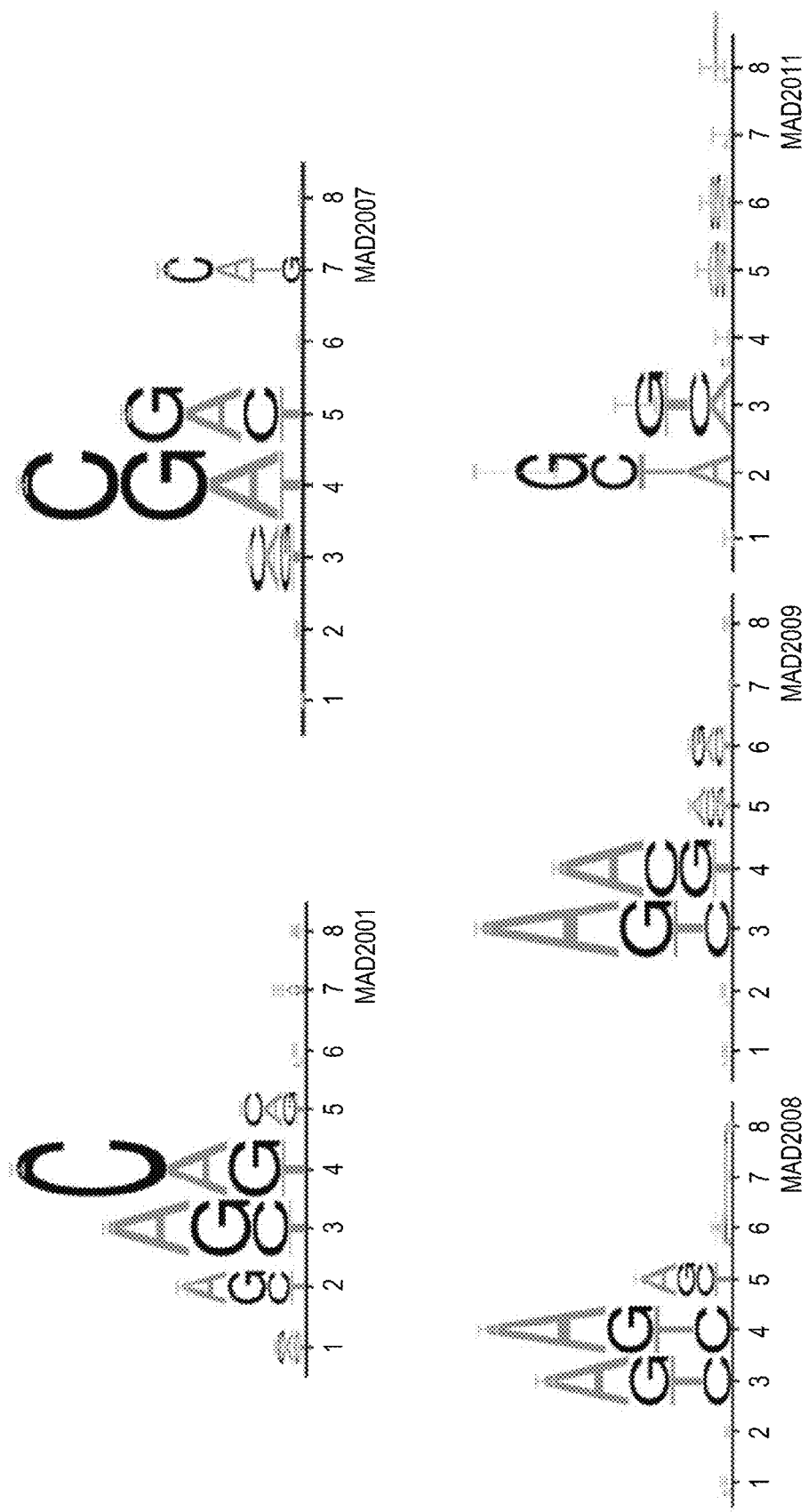
FIG. 4 shows the enrichment of targets cleaved by the mined MAD-series nucleases in the form of a sequence logo.
Figure 5:
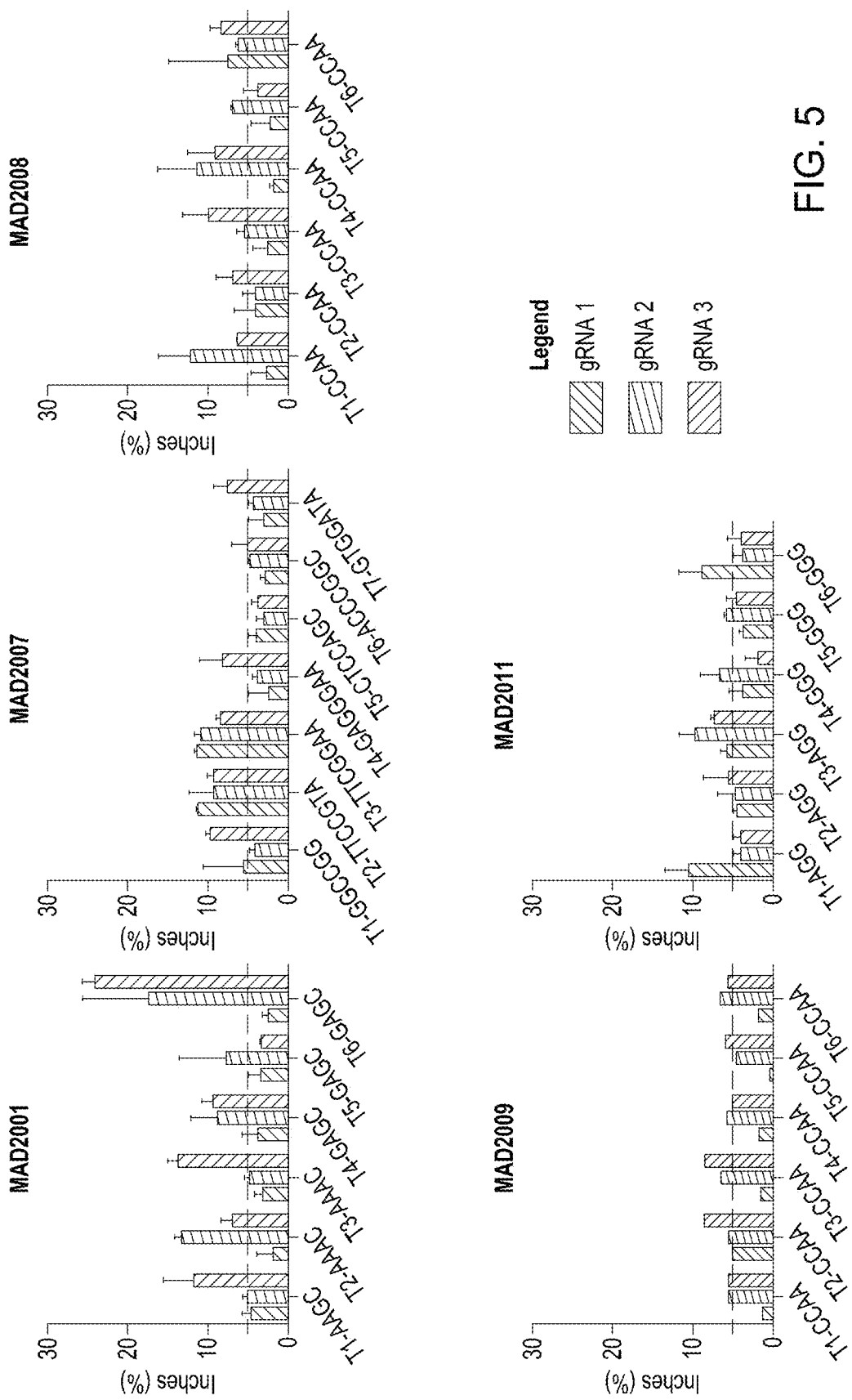
FIG. 5 is a series of bar graphs showing the activity of MAD2001, MAD2007, MAD2008, MAD2009 and MAD2011 in HEK293T cells.
Figure 6:
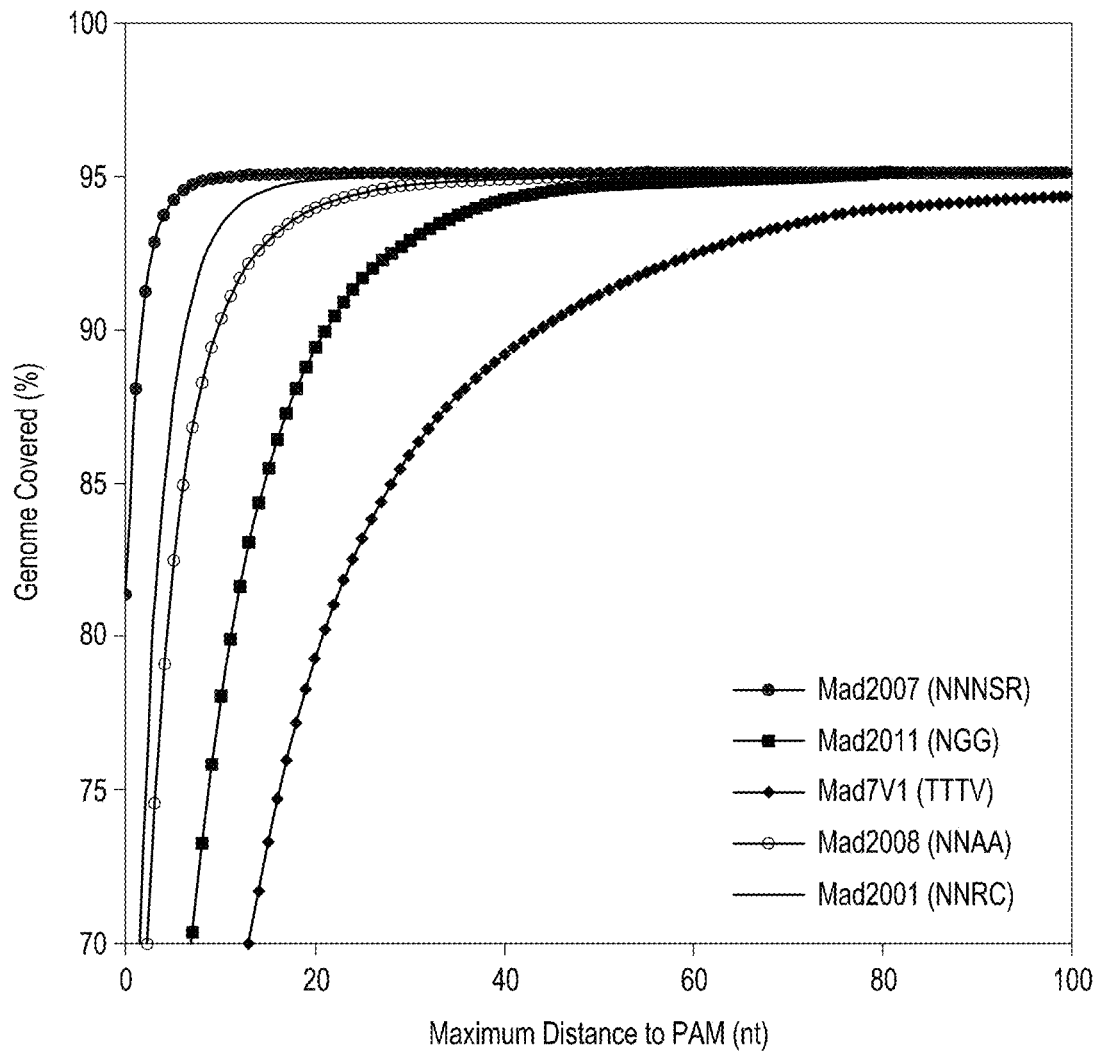
FIG. 6 shows human genome coverage of MAD2001, MAD2007, MAD2008, MAD2009 and MAD2011.
Figure 7:
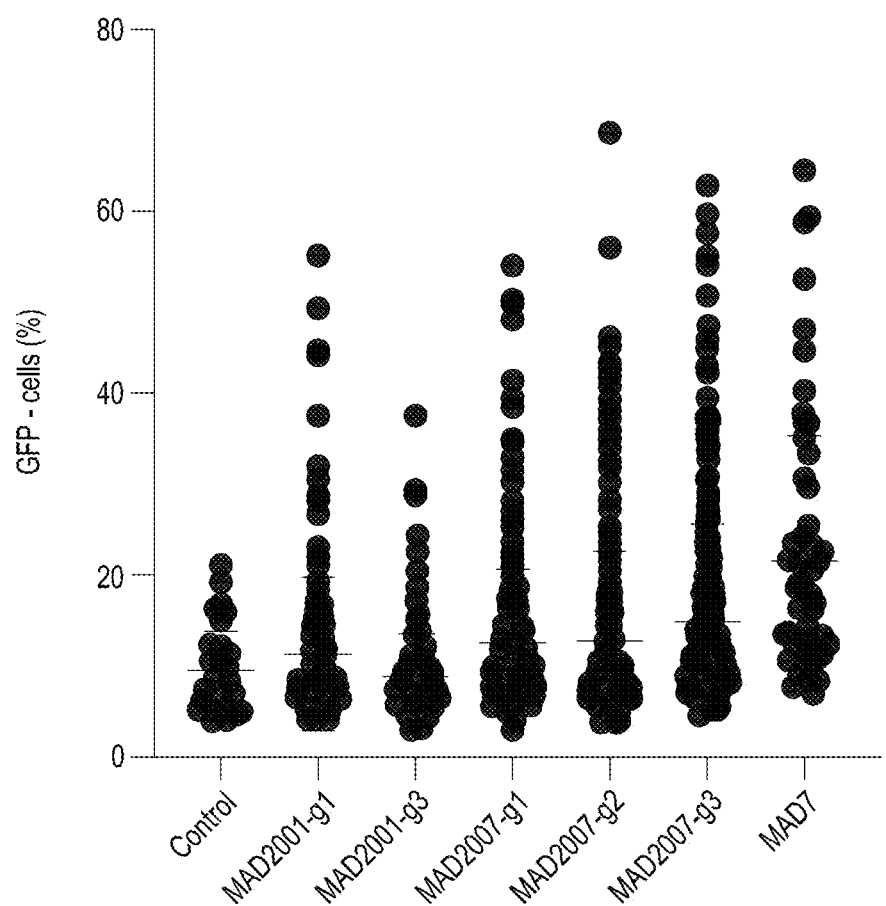
FIG. 7 shows the percentage of GFP⁻ HEK293T cells relative to a negative control.
Figure 8:
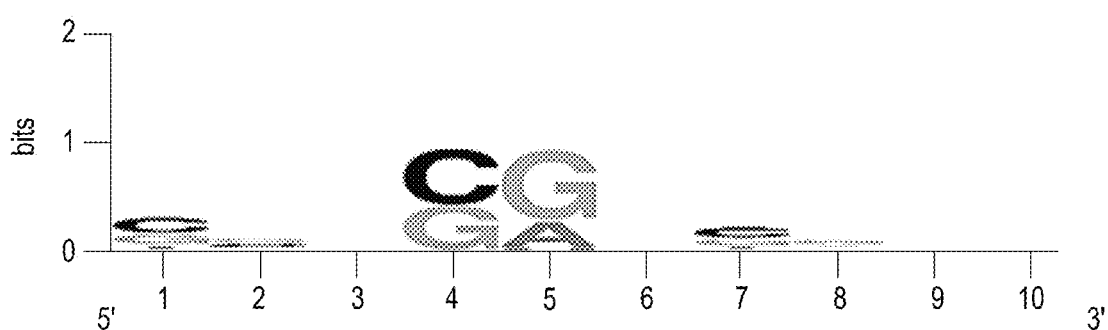
FIG. 8 is a sequence logo for the PAM of MAD2007 in HEK293T cells.
Figure 9:
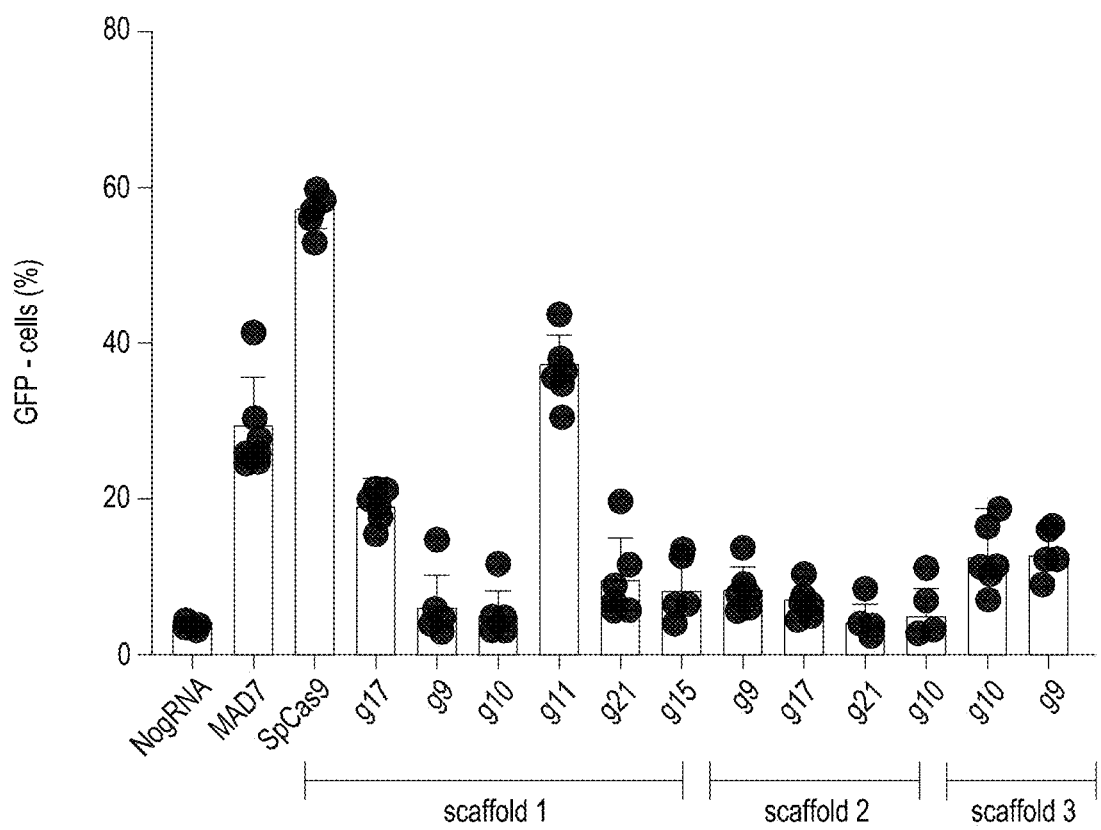
FIG. 9 shows the percentage of GFP⁻ HEK293T cells relative to a negative control.

The screen was performed on three target pools containing NNNNATGC, ATNNNGC and ATGCNNNN PAMs. FIG. 4 shows the depletion map of MAD2001 on targets containing NNNNATGC 3' PAMs as measured in vitro; FIG. 5 shows the depletion map of MAD2007 on targets containing NNNNATGC 3' PAMs (top) and ATNNNNGC 3' PAMs (bottom) as measured in vitro; FIG. 6 shows the depletion map of MAD2008 on targets containing the NNN-NATGC 3' PAMs as measured in vitro; FIG. 7 shows the depletion map of MAD2008 on targets containing the NNN-NATGC 3' PAMs as measured in vitro; FIG. 8 shows the depletion map of MAD2011 on targets containing the NNN-NATGC 3' PAMs as measured in vitro; and FIG. 9 shows the enrichment of targets cleaved by MADs shown in the form of a sequence logo, summarizing the PAMs of the mined MAD-series RGNs that were active in the in vitro screen. Thus, as seen in FIGS. 4-9, the MAD2001, MAD2007, MAD2008, MAD2009 and MAD2011 nucleases were active. MAD2001 cut targets containing the NNRC PAMs, MAD2007 preferred NNNSR PAMs, MAD2008 and MAD2009 depleted targets with NNAA PAMs. PAMs NNNNATGC, ATNNNGC and ATGCNNNN are substantially less restrictive than either a NGG or TTTV PAM (see FIG. 11) for human genome editing. Lastly, MAD2011 has an NGG PAM similar to SpCas9. The gRNA subpools that were most active were identified. Since each gRNA subpool contained 64 different combinations of gRNAs, we tested each gRNA within the most active or shortest subpool to identify the optimal gRNA sequence. The three gRNAs that showed the highest depletion in the in vitro assay were identified. These sequences are listed in table 6.

TABLE 6

| gRNA | Spacer | Repeat | Linker | tracrRNA |
|---|---|---|---|---|
| MAD2001-gRNAv1 | 23 | GTTTGAGAGTGTTGTCAAATAAGAGTCGGACCAATC [SEQ ID No. 20] | GAAA | GATAGACAAATGTGTCTTTGACAACACAAGTTCAAATAAGGCATTGCCGTAATCGTTCTTATGAACCCCGCAGTTGGCGGGAAACCTTCTGTTGTCA [SEQ ID No. 21] |
| MAD2001-gRNAv2 | 23 | GTTTGAGAGTGTTGTCAAATAAGAGTCGGACC [SEQ ID No. 22] | GAAA | GACAAATGTGTCTTTGACAACACAAGTTCAAATAAGGCATTGCCGTAATCGTTCTTATGAACCCCGCAGTTGGCGGGAAACCTTCTGTTGTCA [SEQ ID No. 23] |
| MAD2001-gRNAv3 | 23 | GTTTGAGAGTGTT [SEQ ID No. 24] | GAAA | AACACAAGTTCAAATAAGGCATTGCCGTAATCGTTCTTATGAACCCCGCAGTTGGCGGGAAACCTTC [SEQ ID No. 25] |
| MAD2007-gRNAv1 | 23 | GTTTTAGTCGTCTGTTATTTATTGGTAAGGTTAT [SEQ ID No. 26] | GAAA | ATAACTTTACCAGTGAATATCAGACGGCTAAGATAAAGCTATAAGCTGTGGGGTCGCGCATCCCCAATTTCGCGCACGAGCGTTAGCTCGTT [SEQ ID No. 27] |
| MAD2007-gRNAv2 | 23 | GTTTTAGTCGTCTGTTATTTATTGGT [SEQ ID No. 28] | GAAA | ACCAGTGAATATCAGACGGCTAAGATAAAGCTATAAGCTGTGGGGTCGCGCATCCCCAATTTCGCGCACGAGCGTTAGCTCGTT [SEQ ID No. 29] |
| MAD2007-gRNAv3 | 23 | GTTTTAGTCG [SEQ ID No. 30] | GAAA | CGGCTAAGATAAAGCTATAAGCTGTGGGGTCGCGCATCCCCAATTTCGCGCACGAGCGTTAGC [SEQ ID No. 31] |
| MAD2008-gRNAv1 | 23 | CCTGTGAATAGTCA [SEQ ID No. 32] | GAAA | TATAAAAATAATTATAGAACCAAACTAACCAATTATGAAAAAAATATTAGGACTTGACTTAGGAACCAACTCTATTG [SEQ ID No. 33] |
| MAD2008-gRNAv2 | 23 | CCTGTGAATAGTCAAC [SEQ ID No. 34] | GAAA | TATATAAAAATAATTATAGAACCAAACTAACCAATTATGAAAAAAATATTAGGACTTGACTTAGGAACCAACTCTATTG [SEQ ID No. 35] |
| MAD2008-gRNAv3 | 23 | CCTGTGAATAGT [SEQ ID No. 36] | GAAA | TAAAAAATAATTATAGAACCAAACTAACCAATTATGAAAAAAATATTAGGACTTGA [SEQ ID No. 37] |
| MAD2009-gRNAv1 | 23 | GTTGTGAATTGCTTT [SEQ ID No. 38] | GAAA | AAAGCAATTCACAATAAGGATTATTCCGTTGTGAAAACATTTAAGGCGGTGCGAAAGCATCGTCCT [SEQ ID No. 39] |
| MAD2009-gRNAv2 | 23 | GTTGTGAATTGCTTT [SEQ ID No. 38] | GAAA | AAAGCAATTCACAATAAGGATTATTCCGTTGTGAAAACATTTAAGGCGGTGCGAAAA [SEQ ID No. 40] |
| MAD2009-gRNAv3 | 23 | GTTGTGAATTGC [SEQ ID No. 41] | GAAA | GCAATTCACAATAAGGATTATTCCGTTGTGAAAACATTTAAGGCGGTGCGAAAGCATCGTC [SEQ ID No. 42] |
| MAD2011-gRNAv1 | 23 | GTTTTAGAGCTA [SEQ ID No. 43] | GAAA | TAGCAAGTTAAAATAAGGCTAGTCCGTTATCAACTTGAAAAAGTGGCACAGAGTCGGTGCT [SEQ ID No. 44] |
| MAD2011-gRNAv2 | 23 | GTTTTAGAGC [SEQ ID No. 45] | GAAA | GCAAGTTAAAATAAGGCTAGTCCGTTATCAACTTGAAAAAGTGGCACAGAGTCGGTGCT [SEQ ID No. 46] |
| MAD2011-gRNAv3 | 23 | GTTTTAGAGTCATGTTGTTTAGAATGG [SEQ ID No. 47] | GAAA | CCATTTTAAACGAAAAACTCCTCTAAAACGATTGCAGCTTATCGTAAAAATGAAGGAACCTATGATTAAAGAAAGCCGACTGCA [SEQ ID No. 48] |

Figure 10:
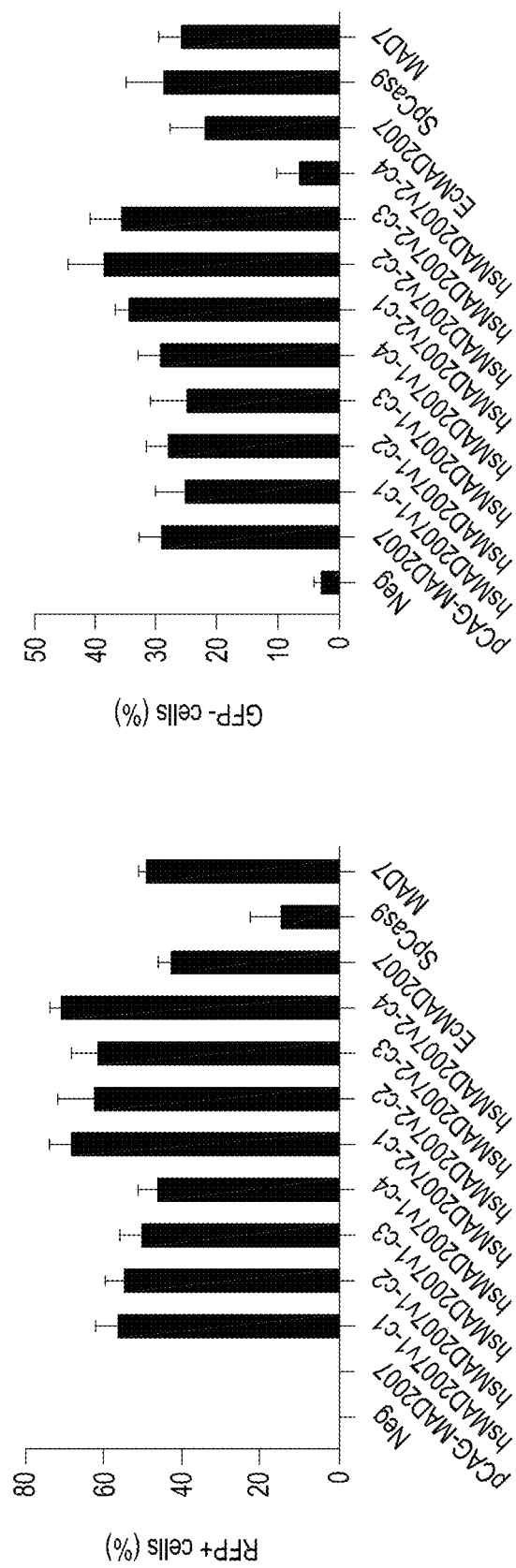
FIG. 10 shows the percentage of loss of function in HEK293T cells for two different human codon optimized MAD2007 nucleases.

Using the PAM information and top three gRNA designs, the activity of MAD2001, MAD2007, MAD2008, MAD2009 and MAD2011 was tested in HEK293T cells. The cells were co-transfected with the nuclease plasmid and gRNA plasmid. The nucleases were expressed from a strong CAG promoter whereas gRNAs were expressed from a U6 promoter. The cells were analyzed for indels by a T7E1 assay. As shown in FIG. 10, four out of the five MADs showed activity. MAD2001 was active on multiple endogenous targets, showing up to 20% indels on a target containing GAGC PAM. This is the first demonstration of an archaeal CRISPR nuclease that is active in mammalian cells. MAD2007, MAD2008 and MAD2011 show lower and variable level of indels on the targets tested. FIG. 11 illustrates the human genome coverage of the newly-discovered nucleases for precise editing, providing coverage for precise editing in human cells.

In addition, nickase and nuclease dead variants of MAD-series nucleases, namely MAD2001, MAD2007, MAD2008, MAD2009 and MAD2011, were also identified where these nickases and dead variants are used for various nickase based precise editing applications. The sequences of the nickase and nuclease dead variants are listed in Table 7 below, where the amino acid residues that vary from the wildtype MAD2001 [SEQ ID NO. 1] nuclease amino acid sequence (for SEQ ID Nos. 14-16) and MAD2007 [SEQ ID No. 7] nuclease amino acid sequence (for SEQ ID Nos. 17-19) are highlighted and bolded.

TABLE 7

| Mined MAD-series Name | SEQ ID No. | Sequence |
| --- | --- | --- |
| MAD2001 Nickase 1 | 14 | MKNTNEDYYLGLAIGTDSVGWAVTDKEYNILEFRRKPMWGIHLFEGG STAQKTRVYRTSRRRLKRRAERIALLRDIFSEEIGKVDPGFFERLDESDL HLEDRVTSQKNSLFDDPEFNDKDLHKRFPTIYHLRRHLMHSNRKEDIR LIYLAAHHIIKFRGHFLYKGIGDEEIPSFEIVLNSLIDNLRDEYGMELEVS DRDLVKALLSDFSIGIREKSRELSSCLNAESENEKALVDFISGKKTNMK KLFDDEALDKMSFSLRDSGFEDQLRENEGVLGPERVHTLELSRQIFEW ARLSSILKDSDSISEAKIKDYDQHREDLRMLKRAVKKYAPDKYSEVFK SKEHTGNYCSYVYVCGKGLPDKKCSTEEFQKYLKKILDDSGVRDDEE FKTLIQRLDAGILCPKQRTGENSVIPYSVHRKELIGILNNAAEHYPSLSR KGEDGFSSIDKILMLEEFRIPYYVGPLDDRSSRSWLIRNSFEAITPWNFN EIVDEDETSERFIGNLTSMCTYLGGEKVLPKNSLLYSRFMLYNEINNLR VGGEKIPAALKNKMVSELFANRATSSKVTLKELKAFLKGEGVLTDAD EISGIDDGVKSTLRSEILIRKIIGDKISDREMAEEIVRILTVFGDERRRSKA KLKKEFSDKLTEKEIEKLSSLKFDGWGRLSEKFLTGLRQEVNGRSMSII EILEDTNYNLQETLSKYSFNEIIDSYNEVLTSGPRSISYDILKDSYLSPAV KRGVWRALSVVKDILKAVGRPPKKIFVETTREEREKKRTESRKDALM YLYKSCKETEWEKRLDSVEESSLRNRSLYLYYTQLGKCMYCGKNIDIG ELNTDLADRDHIYPQSKTKDDSIRNNLVLVCRGCNQAKGDRYPLPQE WVSRMHAFWTMLKDKGYISSEKYRRLTRRGELTEEEFGAFINRQLVE TSQSAKAVITVLKNAFKDSDIVYVKGSNVSDFRSSYNFIKCRSVNDYH HAKDAYLNIVVGNVLDTKFTKNPSYVLKNREQYNIGRMYDRNVSRFG VDAWVAGDRGSIATVRKYMRRNNILFTRYATKSKGALFKETVHRKKE GLFERKKGLETEKYGGYSDISTSYLTLLEYDKGKKRIRSLEIVPTYFAN TRPKEEDVIRFFSETRGLANVRVVMPEVRMKSLFEYRGFRFHVTGSNG KGRFWISSAIQLLLPENLYAYCKSIENNEKDSQRRSEKPLQNYGFSSEM NIELFKCLMDKAAKPPYDVKLSTLSKNLEEGFEKFKALELGPQVKVLQ QILDIYSCDRKSGDLSVLGSARNAGRLDMNGVLSEADGEQVTMICQSP SGLFEKRVPMNEK |
| MAD2001 Nickase 2 | 15 | MKNTNEDYYLGLDIGTDSVGWAVTDKEYNILEFRRKPMWGIHLFEGG STAQKTRVYRTSRRRLKRRAERIALLRDIFSEEIGKVDPGFFERLDESDL HLEDRVTSQKNSLFDDPEFNDKDLHKRFPTIYHLRRHLMHSNRKEDIR LIYLAAHHIIKFRGHFLYKGIGDEEIPSFEIVLNSLIDNLRDEYGMELEVS DRDLVKALLSDFSIGIREKSRELSSCLNAESENEKALVDFISGKKTNMK KLFDDEALDKMSFSLRDSGFEDQLRENEGVLGPERVHTLELSRQIFEW ARLSSILKDSDSISEAKIKDYDQHREDLRMLKRAVKKYAPDKYSEVFK SKEHTGNYCSYVYVCGKGLPDKKCSTEEFQKYLKKILDDSGVRDDEE FKTLIQRLDAGILCPKQRTGENSVIPYSVHRKELIGILNNAAEHYPSLSR KGEDGFSSIDKILMLEEFRIPYYVGPLDDRSSRSWLIRNSFEAITPWNFN EIVDEDETSERFIGNLTSMCTYLGGEKVLPKNSLLYSRFMLYNEINNLR VGGEKIPAALKNKMVSELFANRATSSKVTLKELKAFLKGEGVLTDAD EISGIDDGVKSTLRSEILIRKIIGDKISDREMAEEIVRILTVFGDERRRSKA KLKKEFSDKLTEKEIEKLSSLKFDGWGRLSEKFLTGLRQEVNGRSMSII EILEDTNYNLQETLSKYSFNEIIDSYNEVLTSGPRSISYDILKDSYLSPAV KRGVWRALSVVKDILKAVGRPPKKIFVETTREEREKKRTESRKDALM YLYKSCKETEWEKRLDSVEESSLRNRSLYLYYTQLGKCMYCGKNIDIG ELNTDLADRDAIYPQSKTKDDSIRNNLVLVCRGCNQAKGDRYPLPQE WVSRMHAFWTMLKDKGYISSEKYRRLTRRGELTEEEFGAFINRQLVE TSQSAKAVITVLKNAFKDSDIVYVKGSNVSDFRSSYNFIKCRSVNDYH HAKDAYLNIVVGNVLDTKFTKNPSYVLKNREQYNIGRMYDRNVSRFG VDAWVAGDRGSIATVRKYMRRNNILFTRYATKSKGALFKETVHRKKE GLFERKKGLETEKYGGYSDISTSYLTLLEYDKGKKRIRSLEIVPTYFAN TRPKEEDVIRFFSETRGLANVRVVMPEVRMKSLFEYRGFRFHVTGSNG KGRFWISSAIQLLLPENLYAYCKSIENNEKDSQRRSEKPLQNYGFSSEM NIELFKCLMDKAAKPPYDVKLSTLSKNLEEGFEKFKALELGPQVKVLQ QILDIYSCDRKSGDLSVLGSARNAGRLDMNGVLSEADGEQVTMICQSP SGLFEKRVPMNEK |

TABLE 7-continued

| Mined MAD-series Name | SEQ ID No. | Sequence |
|---|---|---|
| dMAD2001 | 16 | MKNTNEDYYLGLAIGTDSVGWAVTDKEYNILEFRRKPMWGIHLFEGG<br>STAQKTRVYRTSRRRLKRRAERIALLRDIFSEEIGKVDPGFFERLDESDL<br>HLEDRVTSQKNSLFDDPEFNDKDLHKRFPTIYHLRRHLMHSNRKEDIR<br>LIYLAAHHIIKFRGHFLYKGIGDEEIPSFEIVLNSLIDNLRDEYGMELEVS<br>DRDLVKALLSDFSIGIREKSRELSSCLNAESENEKALVDFISGKKTNMK<br>KLFDDEALDKMSFSLRDSGFEDQLRENEGVLGPERVHTLELSRQIFEW<br>ARLSSILKDSDSISEAKIKDYDQHREDLRMLKRAVKKYAPDKYSEVFK<br>SKEHTGNYCSYVYVCGKGLPDKKCSTEEFQKYLKKILDDSGVRDDEE<br>FKTLIQRLDAGILCPKQRTGENSVIPYSVHRKELIGILNNAAEHYPSLSR<br>KGEDGFSSIDKILMLEEFRIPYYVGPLDDRSSRSWLIRNSFEAITPWNFN<br>EIVDEDETSERFIGNLTSMCTYLGGEKVLPKNSLLYSRFMLYNEINNLR<br>VGGEKIPAALKNKMVSELFANRATSSKVTLKELKAFLKGEGVLTDAD<br>EISGIDDGVKSTLRSEILIRKIIGDKISDREMAEEIVRILTVFGDERRRSKA<br>KLKKEFSDKLTEKEIEKLSSLKFDGWGRLSEKFLTGLRQEVNGRSMSII<br>EILEDTNYNLQETLSKYSFNEIIDSYNEVLTSGPRSISYDILKDSYLPSAV<br>KRGVWRALSVVKDILKAVGRPPKKIFVETTREEREKKRTESRKDALM<br>YLYKSCKETEWEKRLDSVEESSLRNRSLYLYYTQLGKCMYCGKNIDIG<br>ELNTDLADRDAIYPQSKTKDDSIRNNLVLVCRGCNQAKGDRYPLPQE<br>WVSRMHAFWTMLKDKGYISSEKYRRLTRRGELTEEEFGAFINRQLVE<br>TSQSAKAVITVLKNAFKDSDIVYVKGSNVSDFRSSYNFIKCRSVNDYH<br>HAKDAYLNIVVGNVLDTKFTKNPSYVLKNREQYNIGRMYDRNVSRFG<br>VDAWVAGDRGSIATVRKYMRRNNILFTRYATKSKGALFKETVHRKKE<br>GLFERKKGLETEKYGGYSDISTSYLTLLEYDKGKKIRSLEIVPTYFAN<br>TRPKEEDVIRFFSETRGLANVRVVMPEVRMKSLFEYRGFRHVTGSNG<br>KGRFWISSAIQLLLPENLYAYCKSIENNEKDSQRRSEKPLQNYGFSSEM<br>NIELFKCLMDKAAKPPYDVKLSTLSKNLEEGFEKFKALELGPQVKVLQ<br>QILDIYSCDRKSGDLSVLGSARNAGRLDMNGVLSEADGEQVTMICQSP<br>SGLFEKRVPMNEK |
| MAD2007 Nickase 1 | 17 | MENYRQKHRFVLATALGIGSNGWAIIDLDAHRVEDLGVQIFESGEEGA<br>KKASARASQQRRLKRSAHRLNRRKKQRKEALIKFLQEIEFPDLVEILNS<br>FKKQKNPNDILSLRVKGLDNKLSPLELFSILIYMSNNRGYKDFYDNDIN<br>DNNTDKDEKEMEKAKSTIEKLFASNSYRTVGEMIATDPTFIVDKSGSK<br>KVIKYHNKKGYQYLIPRKLLENEMSLILHKQEEFYDCLSIDNITIILDKIF<br>FQRNFEDGPGPKNKRDDYKNNSKGNQFYTGFNEMIGLCPFYPNEKKG<br>TKNSLIYDEYYLINTLSQFFFTDSNGVIMSFSKSLLHDLMLYFFDHKGE<br>LTNKELSSFLLKHGLELNSKEKSNKKYRLNYMKQLTDSTIFETEMIASF<br>REEIETSSYRSVNSLSNKIGNCIGQFITPLKRKEELTNILIDTNYPKELAS<br>KLADSIKVIKSQSVANISNKYMLEAIHAFESGKKYGDFQAEFNETRELE<br>DHHFMKNNKLIAFQDSDLIRNPVVYRTINQSRKIINAAINKYNIVRINIE<br>VASDVNKSFEQRDNDKKYQNDNYEKNLQLESELTDYINKENLHVVN<br>SKMMERYKLYLSQNKHCIYTNTPLTMMDVIYSTNVQVDHIIPQSKILD<br>DTLNNKVLVLRDANSIKNNRLPLEAFDEMQINVDTNYTKKDYLTECL<br>HLLKNKTNPISKKKYQYLTLKKLDDETIEGFISRNINDTRYITRYIANYL<br>KTAFKESDKTKNIDVVTIKGAVTSRFRKRWLTTYDEYGYHPTIYSLED<br>KGRNLYYYHHAIDAIILANIDKRYITLANAYDTIRLIKIDRNLSKEQKQR<br>DIDTVIKNTVKSMSKYHGFSEDYIRSLMSKNHIPAICKNLSDEVQIRIPL<br>KFNTDYDNLGYRFTDDQYHYKKLYIAFKEAQNALKEKETLEKELIERF<br>NNEAQILNANIILTYTGFESNNELIDIKKAKKVTDTLKPNLKNYIKAIDI<br>LTQEEYTKRCLEYYNDSEFATQLKIPYVNFKINKRFRGKIQGSENAVSL<br>REVLKKTKLNSFEEFESYLKSEDGIKSPYYIKYTKNTLGKESYTIYEANS<br>YYCAEIYTDSQNKPQLRGIRYVDVRKEDGKLVLLKPSTCKHITYLFH<br>NEYIAIYKDSNYKRLKNNGFGAYRSINNVNVNKIIIRLFANQNLNDND<br>VVITSSIFIKKYSLDVFGHINGEIKCGDQSLFTIKKR |

TABLE 7-continued

| Mined MAD-series Name | SEQ ID No. | Sequence |
|---|---|---|
| MAD2007 Nickase 2 | 18 | MENYRQKHRFVLATDLGIGSNGWAIIDLDAHRVEDLGVQIFESGEEGA<br>KKASARASQQRRLKRSAHRLNRRKKQRKEALIKFLQEIEFPDLVEILNS<br>FKKQKNPNDILSLRVKGLDNKLSPLELFSILIYMSNNRGYKDFYDNDIN<br>DNNTDKDEKEMEKAKSTIEKLFASNSYRTVGEMIATDPTFIVDKSGSK<br>KVIKYHNKKGYQYLIPRKLLENEMSLILHKQEEFYDCLSIDNITIILDKIF<br>FQRNFEDGPGPKNKRDDYKNNSKGNQFYTGFNEMIGLCPFYPNEKKG<br>TKNSLIYDEYYLINTLSQFFFTDSNGVIMSFSKSLLHDLMLYFFDHKGE<br>LTNKELSSFLLKHGLELNSKEKSNKKYRLNYMKQLTDSTIFETEMIASF<br>REEIETSSYRSVNSLSNKIGNCIGQFITPLKRKEELTNILIDTNYPKELAS<br>KLADSIKVIKSQSVANISNKYMLEAIHAFESGKKYGDFQAEFNETRELE<br>DHHFMKNNKLIAFQDSDLIRNPVVYRTINQSRKIINAAINKYNIVRINIE<br>VASDVNKSFEQRDNDKKYQNDNYEKNLQLESELTDYINKENLHVNVN<br>SKMMERYKLYLSQNKHCIYTNTPLTMMDVIYSTNVQVDAIIPQSKILD<br>DTLNNKVLVLRDANSIKNNRLPLEAFDEMQINVDTNYTKKDYLTECL<br>HLLKNKTNPISKKKYQYLTLKKLDDETIEGFISRNINDTRYITRYIANYL<br>KTAFKESDKTKNIDVVTIKGAVTSRFRKRWLTTYDEYGYHPTIYSLED<br>KGRNLYYYHHAIDAIILANIDKRYITLANAYDTIRLIKIDRNLSKEQKQR<br>DIDTVIKNTVKSMSKYHGFSEDYIRSLMSKNHIPAICKNLSDEVQIRIPL<br>KFNTDYDNLGYRFTDDQYHYKKLYIAFKEAQNALKEKETLEKELIERF<br>NNEAQILNANIILTYTGFESNNELIDIKKAKKVTDTLKPNLKNYIKAIDI<br>LTQEEYTKRCLEYYNDSEFATQLKIPYVNFKINKRFRGKIQGSENAVSL<br>REVLKKTKLNSFEEFESYLKSEDGIKSPYYIKYTKNTLGKESYTIYEANS<br>YYCAEIYTDSQNKPQLRGIRYVDVRKEDGKLVLLKPLPSTCKHITYLFH<br>NEYIAIYKDSNYKRLKNNGFGAYRSINNVNVNKIIIRLFANQNLNDND<br>VVITSSIFIKKYSLDVFGHINGEIKCGDQSLFTIKKR |
| dMAD2007 | 19 | MENYRQKHRFVLATALGIGSNGWAIIDLDAHRVEDLGVQIFESGEEGA<br>KKASARASQQRRLKRSAHRLNRRKKQRKEALIKFLQEIEFPDLVEILNS<br>FKKQKNPNDILSLRVKGLDNKLSPLELFSILIYMSNNRGYKDFYDNDIN<br>DNNTDKDEKEMEKAKSTIEKLFASNSYRTVGEMIATDPTFIVDKSGSK<br>KVIKYHNKKGYQYLIPRKLLENEMSLILHKQEEFYDCLSIDNITIILDKIF<br>FQRNFEDGPGPKNKRDDYKNNSKGNQFYTGFNEMIGLCPFYPNEKKG<br>TKNSLIYDEYYLINTLSQFFFTDSNGVIMSFSKSLLHDLMLYFFDHKGE<br>LTNKELSSFLLKHGLELNSKEKSNKKYRLNYMKQLTDSTIFETEMIASF<br>REEIETSSYRSVNSLSNKIGNCIGQFITPLKRKEELTNILIDTNYPKELAS<br>KLADSIKVIKSQSVANISNKYMLEAIHAFESGKKYGDFQAEFNETRELE<br>DHHFMKNNKLIAFQDSDLIRNPVVYRTINQSRKIINAAINKYNIVRINIE<br>VASDVNKSFEQRDNDKKYQNDNYEKNLQLESELTDYINKENLHVNVN<br>SKMMERYKLYLSQNKHCIYTNTPLTMMDVIYSTNVQVDAIIPQSKILD<br>DTLNNKVLVLRDANSIKNNRLPLEAFDEMQINVDTNYTKKDYLTECL<br>HLLKNKTNPISKKKYQYLTLKKLDDETIEGFISRNINDTRYITRYIANYL<br>KTAFKESDKTKNIDVVTIKGAVTSRFRKRWLTTYDEYGYHPTIYSLED<br>KGRNLYYYHHAIDAIILANIDKRYITLANAYDTIRLIKIDRNLSKEQKQR<br>DIDTVIKNTVKSMSKYHGFSEDYIRSLMSKNHIPAICKNLSDEVQIRIPL<br>KFNTDYDNLGYRFTDDQYHYKKLYIAFKEAQNALKEKETLEKELIERF<br>NNEAQILNANIILTYTGFESNNELIDIKKAKKVTDTLKPNLKNYIKAIDI<br>LTQEEYTKRCLEYYNDSEFATQLKIPYVNFKINKRFRGKIQGSENAVSL<br>REVLKKTKLNSFEEFESYLKSEDGIKSPYYIKYTKNTLGKESYTIYEANS<br>YYCAEIYTDSQNKPQLRGIRYVDVRKEDGKLVLLKPLPSTCKHITYLFH<br>NEYIAIYKDSNYKRLKNNGFGAYRSINNVNVNKIIIRLFANQNLNDND<br>VVITSSIFIKKYSLDVFGHINGEIKCGDQSLFTIKKR |

TABLE 7-continued

| Mined MAD-series Name | SEQ ID No. | Sequence |
|---|---|---|
| MAD2008 Nickase 1 | 51 | MKKILGLALGTNSIGWALIEHNFDKKEGRIDDLGVRIIPMSADILGKFD
AGQSHSQTAERTGYRGVRRLYQRDNLRRERLHRVLNILDFLPEHYAE
HIDFEKRLGQFKEGKEIKLNYKSNKDSKFEFIFKASYNEMLAAFKKYQ
PGLFYVKANGTETKIPYDWTIYYLRKKALSQPLTKQELAWIILNFNQK
RGYYQLRGEEIDDDKNKQFVQLKVKEVIDSGEAVKGKKLFNVIFENG
WKYDKQVVKTEDWIGRTKEFIVTTKTLKSGEIKRTYKAVDSEKDWAA
IKAKTEQDIERSNKTVGEFIYEALLQDPTQKIRGKLVKTIERKFYKAELR
EILRKQIELQPQLFTTKLYNACIKELYPNNEAHRNSIKNRDFLYLFLDDII
FYQRPLKSQKSNISGCHLEQRIYTKINPVSGKKEEVKQAVKAIPKSHPIF
QEFRIWQWLQNLKIYDKINTDKGELADVTNQLLPSEESLLDLFDYLQT
KKELDQSGFIKYFIDKKLINKSEKENYRWNYVEDKKYPFAETRAQFISR
LNKVKNINNISEFLNKKTRLGEKESSPFVTRIEQLWHIIYSVSDINEYKS
ALEKFALKHDIDKESFVANFIKFPPPFKSDYGSYSKKALSKLLPLMRRGK
YWNESDISNKVKQRVSDIMERVNALNLKENYNAKELAEALKTVSDDD
VKKQLIKSFVPFKDKNPLKGLNTYQATYLVYGRHSEVGDIQSWKTPED
IDTYLKNFKQHSLRNPIVEQVVTETLRVVRDIWIHYGKSQLNFFNEIHV
ELGREMKNPADKRKQISNRNIENENTNNRIREILKDLKNDTSIEGDIRD
YSPSQQDLLKIYEEGVYQNPKVDYSKVSEDEITKIRRSNSPTPKEIQRYR
LWLEQGYISPYTGKPIPLSKLFTHEYQIEHIIPQSRYFDNSLSNKIICESAV
NEDKDNKTAYEYLKNKSGNVINGHKLLRIEEYEAHVNRYFKNNRQKL
KNLLSEDIPEGFINRQLNDSRYISKLIKGLLSNIVRQENEQEATSKNLIPV
TGAVTSKLKNDWGLNDKWNELILPRFERLNQLTQTKNFTTSNTNGNTI
PTVPDDLLKGFSKKRIDHRHHALDALVVACCTRNHVQYLNALNAEKA
NYGLRKKLLIVNEQGDFTKIFQMPWKGFTSEAKNQLEKTVISFKQNLR
VINKANNKFWSFKDENGNINLDKNGRPVKKLRKQTKGDNWAIRKAM
HKETVSGKSNIETPKGKIATAVRGSLADIKNEKHLGKITDVQIREVILPN
HLKNYVDEKGKVKFDLAFNDEGIEDLNKNIIALNNGKKHQPIRKVKFF
EVGSKFSISENENSAKSKKYVEAAKGTNLFFAVYWDEKKQKRNYETV
PLNEVIAHQKQVAHLTNNERLPIQTNRKKGDFLFTLSPNDLVYVPTDA
EVANKQPIDFKNLHQNQVNRIYKMVSSSGNQCFFIKDKIATSIWNKNE
FSSLNKMEKDIDGNMIKERCIKLNVDRLGNITKA |
| MAD2008 Nickase 2 | 52 | MKKILGLDLGTNSIGWALIEHNFDKKEGRIDDLGVRIIPMSADILGKFD
AGQSHSQTAERTGYRGVRRLYQRDNLRRERLHRVLNILDFLPEHYAE
HIDFEKRLGQFKEGKEIKLNYKSNKDSKFEFIFKASYNEMLAAFKKYQ
PGLFYVKANGTETKIPYDWTIYYLRKKALSQPLTKQELAWIILNFNQK
RGYYQLRGEEIDDDKNKQFVQLKVKEVIDSGEAVKGKKLFNVIFENG
WKYDKQVVKTEDWIGRTKEFIVTTKTLKSGEIKRTYKAVDSEKDWAA
IKAKTEQDIERSNKTVGEFIYEALLQDPTQKIRGKLVKTIERKFYKAELR
EILRKQIELQPQLFTTKLYNACIKELYPNNEAHRNSIKNRDFLYLFLDDII
FYQRPLKSQKSNISGCHLEQRIYTKINPVSGKKEEVKQAVKAIPKSHPIF
QEFRIWQWLQNLKIYDKINTDKGELADVTNQLLPSEESLLDLFDYLQT
KKELDQSGFIKYFIDKKLINKSEKENYRWNYVEDKKYPFAETRAQFISR
LNKVKNINNISEFLNKKTRLGEKESSPFVTRIEQLWHIIYSVSDINEYKS
ALEKFALKHDIDKESFVANFIKFPPPFKSDYGSYSKKALSKLLPLMRRGK
YWNESDISNKVKQRVSDIMERVNALNLKENYNAKELAEALKTVSDDD
VKKQLIKSFVPFKDKNPLKGLNTYQATYLVYGRHSEVGDIQSWKTPED
IDTYLKNFKQHSLRNPIVEQVVTETLRVVRDIWIHYGKSQLNFFNEIHV
ELGREMKNPADKRKQISNRNIENENTNNRIREILKDLKNDTSIEGDIRD
YSPSQQDLLKIYEEGVYQNPKVDYSKVSEDEITKIRRSNSPTPKEIQRYR
LWLEQGYISPYTGKPIPLSKLFTHEYQIEAIIPQSRYFDNSLSNKIICESAV
NEDKDNKTAYEYLKNKSGNVINGHKLLRIEEYEAHVNRYFKNNRQKL
KNLLSEDIPEGFINRQLNDSRYISKLIKGLLSNIVRQENEQEATSKNLIPV
TGAVTSKLKNDWGLNDKWNELILPRFERLNQLTQTKNFTTSNTNGNTI
PTVPDDLLKGFSKKRIDHRHHALDALVVACCTRNHVQYLNALNAEKA
NYGLRKKLLIVNEQGDFTKIFQMPWKGFTSEAKNQLEKTVISFKQNLR
VINKANNKFWSFKDENGNINLDKNGRPVKKLRKQTKGDNWAIRKAM
HKETVSGKSNIETPKGKIATAVRGSLADIKNEKHLGKITDVQIREVILPN
HLKNYVDEKGKVKFDLAFNDEGIEDLNKNIIALNNGKKHQPIRKVKFF
EVGSKFSISENENSAKSKKYVEAAKGTNLFFAVYWDEKKQKRNYETV
PLNEVIAHQKQVAHLTNNERLPIQTNRKKGDFLFTLSPNDLVYVPTDA
EVANKQPIDFKNLHQNQVNRIYKMVSSSGNQCFFIKDKIATSIWNKNE
FSSLNKMEKDIDGNMIKERCIKLNVDRLGNITKA |

TABLE 7-continued

| Mined MAD-series Name | SEQ ID No. | Sequence |
|---|---|---|
| dMAD2008 | 53 | MKKILGLALGTNSIGWALIEHNFDKKEGRIDDLGVRIIPMSADILGKFD AGQSHSQTAERTGYRGVRRLYQRDNLRRERLHRVLNILDFLPEHYAE HIDFEKRLGQFKEGKEIKLNYKSNKDSKFEFIFKASYNEMLAAFKKYQ PGLFYVKANGTETKIPYDWTIYYLRKKALSQPLTKQELAWIILNFNQK RGYYQLRGEEIDDDKNKQFVQLKVKEVIDSGEAVKGKKLFNVIFENG WKYDKQVVKTEDWIGRTKEFIVTTKTLKSGEIKRTYKAVDSEKDWAA IKAKTEQDIERSNKTVGEFIYEALLQDPTQKIRGKLVKTIERKFYKAELR EILRKQIELQPQLFTTKLYNACIKELYPNNEAHRNSIKNRDFLYLFLDDII FYQRPLKSQKSNISGCHLEQRIYTKINPVSGKKEEVKQAVKAIPKSHPIF QEFRIWQWLQNLKIYDKINTDKGELADVTNQLLPSEESLLDLFDYLQT KKELDQSGFIKYFIDKKLINKSEKENYRWNYVEDKKYPFAETRAQFISR LNKVKNINNISEFLNKKTRLGEKESSPFVTRIEQLWHIIYSVSDINEYKS ALEKFALKHDIDKESFVANFIKFPPFKSDYGSYSKKALSKLLPLMRRGK YWNESDISNKVKQRVSDIMERVNALNLKENYNAKELAEALKTVSDDD VKKQLIKSFVPFKDKNPLKGLNTYQATYLVYGRHSEVGDIQSWKTPED IDTYLKNFKQHSLRNPIVEQVVTETLRVVRDIWIHYGKSQLNFFNEIHV ELGREMKNPADKRKQISNRNIENENTNNRIREILKDLKNDTSIEGDIRD YSPSQQDLLKIYEEGVYQNPKVDYSKVSEDEITKIRRSNSPTPKEIQRYR LWLEQGYISPYTGKPIPLSKLFTHEYQIEAIIPQSRYFDNSLSNKIICESAV NEDKDNKTAYEYLKNKSGNVINGHKLLRIEEYEAHVNRYFKNNRQKL KNLLSEDIPEGFINRQLNDSRYISKLIKGLLSNIVRQENEQEATSKNLIPV TGAVTSKLKNDWGLNDKWNELILPRFERLNQLTQTKNFTTSNTNGNTI PTVPDDLLKGFSKKRIDHRHHALDALVVACCTRNHVQYLNALNAEKA NYGLRKKLLIVNEQGDFTKIFQMPWKGFTSEAKNQLEKTVISFKQNLR VINKANNKFWSFKDENGNINLDKNGRPVKKLRKQTKGDNWAIRKAM HKETVSGKSNIETPKGKIATAVRGSLADIKNEKHLGKITDVQIREVILPN HLKNYVDEKGKVKFDLAFNDEGIEDLNKNIIALNNGKKHQPIRKVKFF EVGSKFSISENENSAKSKKYVEAAKGTNLFFAVYWDEKKQKRNYETV PLNEVIAHQKQVAHLTNNERLPIQTNRKKGDFLFTLSPNDLVYVPTDA EVANKQPIDFKNLHQNVNRIYKMVSSSGNQCFFIKDKIATSIWNKNE FSSLNKMEKDIDGNMIKERCIKLNVDRLGNITKA |
| MAD2009 Nickase 1 | 54 | MKKILGLALGTNSIGWAVVNADAITRNDGSRYLKPNSISAAGSRIIPMS ADVLGNFESGITVSQTKDRTDKRMARRLHERALLRRERLLRILSLMDF LPKHFASKINRYGKFTDDSEPKLAWRKNTEGKYEFIFQDAFNEMLAEF KDKQPEIVKEGKKIPYDWTIYYLRKKALEKALSKEELSWLLLQFNQKR GYYQLRGEEEDIPQDKKIEYLAQKVVKEATDQKKGDDIWYNVYLEN GMIYRRTSKAPLDWEGKIKEFIVTTDLEKDGTPKKDKEGNIKRSFRAPQ EDDWTLLKKKTEADIEKSTKTVGCYIYDSLLNNPKQKIIGKLVRTVER KFYKEELTQILKKQVELIPELRNDNLYKQCIEELYPINEAHRNTIAKTDF ANLFINDILFYQRPLKSKKSQIDNCPYEEHIFIDSKTGEKKKVPVKCITK SNPLFQEFRLWQFIQNLRIYQREKEIDGKLSTDVDITSECLKSEEDYVRL FDWLNDRESIEQEELLKYLFNTKKSKNKENPYRWNYVEDKVYPCNET RATILKGLSKCGINASVLSSEMEMALWHILYSVEDKKEIETALTHFAQK QGWNGEFAIVFSKLKPFKKDYGSYSEKAIKKLLSLMRMGKYWNQDNI DKNTLDRIDKIINGEYDEKISNRVRDNAINLKDISDFRGLPVWLACYIV YDRHSEAKDCTKWNTPEEIDSYLKKFKQHSLRNPIVEQVVTETLRTVR DIWKQEGQIDEIHLELGRDLKNPADKRKKMSENILKNENTNLRIKAML MEFMNPGMGIENVRPYSPSQQDILRIYEENALENLTKDDEEFDFISKISK QAQPTKSDIVRYKCWLEQKYRSPYTGKTISLSKLFTSAYEIEHIIPQSRY FDDSFSNKVICEAEVNLKDRQLGHEFIEEHHGEKVQLSQGEVVEILSV DAYEKFVKENYANNRVMKKLLMENIPDEFIERQLNDSRYISKVVKG LLSNIVREKIDDENYEPEAVSKNLISCNGAVTDRLKKDWGMNDVWNSI ILPRFIRMNQITGKDCFTTTNAEGHLIPQMPLELQKGFNKKRIDHRHHA MDAIVIACTTRDHVNLLNNEAAHSKFNATRYQLQRKLRCFEKAMIDG KEREVAKEFLKPWDSFTMDSKNILENIIVSFKQNRVINKTNTFQHFD ENGKKTFVKQGKGNSWAIRKPMHKDTVFGEINLRKVKSVSLSDAIKV PERILNKRIKEKITELKNNKVDAKNIKKYIEEYHIGGYGIDTSKIDVFY FTKETKERFFATRKSLDSSFNQAKIEDSIADSGIQKILLAHLKSKNGDAE QAFSPDGIDEMNKNIVELNNGKHFQPILKVRVYEKADKFAVGQKGNK KVKFVEAAKGTNLFFAVFEKDGKRSYLTIPLNVMIDCQKKYGNQWKQ NIESYLKEKDLVEKDVQLLFILSPNDLVYLPTENELKKGITNPDKDQIY KFVSCTSNEAHFIPSFVANPIVQTTELGSNNKAQRAWNNKMIKEICI PIEVDRLGNIK |

TABLE 7-continued

| Mined MAD-series Name | SEQ ID No. | Sequence |
|---|---|---|
| MAD2009 Nickase 2 | 55 | MKKILGLDLGTNSIGWAVVNADAITRNDGSRYLKPNSISAAGSRIIPMS<br>ADVLGNFESGITVSQTKDRTDKRMARRLHERALLRRERLLRILSLMDF<br>LPKHFASKINRYGKFTDDSEPKLAWRKNTEGKYEFIFQDAFNEMLAEF<br>KDKQPEIVKEGKKIPYDWTIYYLRKKALEKALSKEELSWLLLQFNQKR<br>GYYQLRGEEEDIPQDKKIEYLAQKVVKVEATDQKKGDDIWYNVYLEN<br>GMIYRRTSKAPLDWEGKIKEFIVTTDLEKDGTPKKDKEGNIKRSFRAPQ<br>EDDWTLLKKKTEADIEKSTKTVGCYIYDSLLNNPKQKIIGKLVRTVER<br>KFYKEELTQILKKQVELIPELRNDNLYKQCIEELYPINEAHRNTIAKTDF<br>ANLFINDILFYQRPLKSKKSQIDNCPYEEHIFIDSKTGEKKKVPVKCITK<br>SNPLFQEFRLWQFIQNLRIYQREKEIDGKLSTDVDITSECLKSEEDYVRL<br>FDWLNDRESIEQEELLKYLFNTKKSKNKENPYRWNYVEDKVYPCNET<br>RATILKGLSKCGINASVLSSEMEMALWHILYSVEDKKEIETALTHFAQK<br>QGWNGEFAIVFSKLKPFKKDYGSYSEKAIKKLLSLMRMGKYWNQDNI<br>DKNTLDRIDKIINGEYDEKISNRVRDNAINLKDISDFRGLPVWLACYIV<br>YDRHSEAKDCTKWNTPEEIDSYLKKFKQHSLRNPIVEQVVTETLRTVR<br>DIWKQEGQIDEIHLELGRDLKNPADKRKKMSENILKNENTNLRIKAML<br>MEFMNPGMGIENVRPYSPSQQDILRIYEENALENLTKDDEEFDFISKISK<br>QAQPTKSDIVRYKCWLEQKYRSPYTGKTISLSKLFTSAYEIEÄIIPQSRY<br>FDDSFSNKVICEAEVNKLKDRQLGHEFIEEHHGEKVQLSQGEVVEILSV<br>DAYEKFVKENYANNRVKMKKELMENIPDEFIERQLNDSRYISKVVKG<br>LLSNIVREKIDDENYEPEAVSKNLISCNGAVTDRLKKDWGMNDVWNSI<br>ILPRFIRMNQITGKDCFTTTNAEGHLIPQMPLELQKGFNKKRIDHRHHA<br>MDAIVIACTTRDHVNLLNNEAAHSKFNATRYQLRKERCFEKAMIDG<br>KEREVAKEFLKPWDSFTMDSKNILENIIVSFKQNQRVINKTTNTFQHFD<br>ENGKKTFVKQGKGNSWAIRKPMHKDTVFGEINLRKVKSVSLSDAIKV<br>PERILNKRIKEKITELKNNKVDAKNIKKYIEEYHIGGYGIDTSKIDVFY<br>FTKETKERFFATRKSLDSSFNQAKIEDSIADSGIQKILLAHLKSKNGDAE<br>QAFSPDGIDEMNKNIVELNNGKFHQPILKVRVYEKADKFAVGQKGNK<br>KVKFVEAAKGTNLFFAVFEKDGKRSYLTIPLNVMIDCQKKYGNQWKQ<br>NIESYLKEKDLVEKDVQLLFILSPNDLVYLPTENELKKGITNPDKDQIY<br>KFVSCTSNEAHFIPSFVANPIVQTTELGSNNKAQRAWNNKMIKEICI<br>PIEVDRLGNIK |
| dMAD2009 | 56 | MKKILGLÄLGTNSIGWAVVNADAITRNDGSRYLKPNSISAAGSRIIPMS<br>ADVLGNFESGITVSQTKDRTDKRMARRLHERALLRRERLLRILSLMDF<br>LPKHFASKINRYGKFTDDSEPKLAWRKNTEGKYEFIFQDAFNEMLAEF<br>KDKQPEIVKEGKKIPYDWTIYYLRKKALEKALSKEELSWLLLQFNQKR<br>GYYQLRGEEEDIPQDKKIEYLAQKVVKVEATDQKKGDDIWYNVYLEN<br>GMIYRRTSKAPLDWEGKIKEFIVTTDLEKDGTPKKDKEGNIKRSFRAPQ<br>EDDWTLLKKKTEADIEKSTKTVGCYIYDSLLNNPKQKIIGKLVRTVER<br>KFYKEELTQILKKQVELIPELRNDNLYKQCIEELYPINEAHRNTIAKTDF<br>ANLFINDILFYQRPLKSKKSQIDNCPYEEHIFIDSKTGEKKKVPVKCITK<br>SNPLFQEFRLWQFIQNLRIYQREKEIDGKLSTDVDITSECLKSEEDYVRL<br>FDWLNDRESIEQEELLKYLFNTKKSKNKENPYRWNYVEDKVYPCNET<br>RATILKGLSKCGINASVLSSEMEMALWHILYSVEDKKEIETALTHFAQK<br>QGWNGEFAIVFSKLKPFKKDYGSYSEKAIKKLLSLMRMGKYWNQDNI<br>DKNTLDRIDKIINGEYDEKISNRVRDNAINLKDISDFRGLPVWLACYIV<br>YDRHSEAKDCTKWNTPEEIDSYLKKFKQHSLRNPIVEQVVTETLRTVR<br>DIWKQEGQIDEIHLELGRDLKNPADKRKKMSENILKNENTNLRIKAML<br>MEFMNPGMGIENVRPYSPSQQDILRIYEENALENLTKDDEEFDFISKISK<br>QAQPTKSDIVRYKCWLEQKYRSPYTGKTISLSKLFTSAYEIEÄIIPQSRY<br>FDDSFSNKVICEAEVNKLKDRQLGHEFIEEHHGEKVQLSQGEVVEILSV<br>DAYEKFVKENYANNRVKMKKLLMENIPDEFIERQLNDSRYISKVVKG<br>LLSNIVREKIDDENYEPEAVSKNLISCNGAVTDRLKKDWGMNDVWNSI<br>ILPRFIRMNQITGKDCFTTTNAEGHLIPQMPLELQKGFNKKRIDHRHHA<br>MDAIVIACTTRDHVNLLNNEAAHSKFNATRYQLRKLRCFEKAMIDG<br>KEREVAKEFLKPWDSFTMDSKNILENIIVSFKQNQRVINKTTNTFQHFD<br>ENGKKTFVKQGKGNSWAIRKPMHKDTVFGEINLRKVKSVSLSDAIKV<br>PERILNKRIKEKITELKNNKVDAKNIKKYIEEYHIGGYGIDTSKIDVFY<br>FTKETKERFFATRKSLDSSFNQAKIEDSIADSGIQKILLAHLKSKNGDAE<br>QAFSPDGIDEMNKNIVELNNGKFHQPILKVRVYEKADKFAVGQKGNK<br>KVKFVEAAKGTNLFFAVFEKDGKRSYLTIPLNVMIDCQKKYGNQWKQ<br>NIESYLKEKDLVEKDVQLLFILSPNDLVYLPTENELKKGITNPDKDQIY<br>KFVSCTSNEAHFIPSFVANPIVQTTELGSNNKAQRAWNNKMIKEICI<br>PIEVDRLGNIK |

TABLE 7-continued

| Mined MAD-series Name | SEQ ID No. | Sequence |
|---|---|---|
| MAD2011 Nickase 1 | 57 | MKKDYVIGLAIGTNSVGWAVMTEDYQLVKKKMPIYGNTEKKKIKKN<br>FWGVRLFEEGHTAEDRRLKRTARRRISRRRNRLRYLQAFFEEAMTALD<br>ENFFARLQESFLVPEDKKWHRHPIFAKLEDEVAYHETYPTIYHLRKKL<br>ADSSEQADLRLIYLALAHIVKYRGHFLIEGKLSTENISVKEQFQQFMIIY<br>NQTFVNGESRLVSAPLPESVLIEEELTEKASRTKKSEKVLQQFPQEKAN<br>GLFGQFLKLMVGNKADFKKVFGLEEEAKITYASESYEEDLEGILAKVG<br>DEYSDVFLAAKNVYDAVELSTILADSDKKSHAKLSSSMIVRFTEHQED<br>LKNFKRFIRENCPDEYDNLFKNEQKDGYAGYIAHAGKVSQLKFYQYV<br>KKIIQDIAGAEYFLEKIAQENFLRKQRTFDNGVIPHQIHLAELQAIIHRQ<br>AAYYPFLKENQKKIEQLVTFRIPYYVGPLSKGDASTFAWLKRQSEEPIR<br>PWNLQETVDLDQSATAFIERMTNFDTYLPSEKVLPKHSLLYEKFMVFN<br>ELTKISYTDDRGIKANFSGKEKEKIFDYLFKTRRKVKKKDIIQFYRNEY<br>NTEIVTLSGLEEDQFNASFSTYQDLLKCGLTRAELDHPDNAEKLEDIIKI<br>LTIFEDRQRIRTQLSTFKGQFSEEVLKKLERKHYTGWGRLSKKLINGIY<br>DKESGKTILDYLIKDDGVSKHYNRNFMQLINDSQLSFKNAIQKAQSSE<br>HEETLSETVNELAGSPAIKKGIYQSLKIVDELVAIMGYAPKRIVVEMAR<br>ENQTTSTGKRRSIQRLKIVEKAMAEIGSNLLKEQPTTNEQLRDTRLFLY<br>YMQNGKDMYTGDELSLHRLSHYDIDHIIPQSFMKDDSLDNLVLVGSTE<br>NRGKSDDVPSKEVVKKMKAYWEKLYAAGLISQRKFQRLTKGEQGGL<br>TLEDKAHFIQRQLVETRQITKNVAGILDQRYNAKSKEKKVQIITLKASL<br>TSQFRSIFGLYKVREVNDYHHGQDAYLNCVVATTLLKVYPNLAPEFV<br>YGEYPKFQAFKENKATAKAIIYTNLLRFFTEDEPRFTKDGEILWSNSYL<br>KTIKKELNYHQMNIVKKVEVQKGGFSKESIKPKGPSNKLIPVKNGLDP<br>QKYGGFDSPVVAYTVLFTHEKGKKPLIKQEILGITIMEKTRFEQNPILFL<br>EEKGFLRPVLMKLPKYTLYEFPEGRRRLLASAKEAQKGNQMVLPEH<br>LLTLLYHAKQCLLPNQSESLAYVEQHQPEFQEILERVVDFAEVHTLAK<br>SKVQQIVKLFEANQTADVKEIAASFIQLMQFNAMGAPSTFKFFQKDIER<br>ARYTSIKEIFDATIIYQSTTGLYETRRKVVD |
| MAD2011 Nickase 2 | 58 | MKKDYVIGLDIGTNSVGWAVMTEDYQLVKKKMPIYGNTEKKKIKKN<br>FWGVRLFEEGHTAEDRRLKRTARRRISRRRNRLRYLQAFFEEAMTALD<br>ENFFARLQESFLVPEDKKWHRHPIFAKLEDEVAYHETYPTIYHLRKKL<br>ADSSEQADLRLIYLALAHIVKYRGHFLIEGKLSTENISVKEQFQQFMIIY<br>NQTFVNGESRLVSAPLPESVLIEEELTEKASRTKKSEKVLQQFPQEKAN<br>GLFGQFLKLMVGNKADFKKVFGLEEEAKITYASESYEEDLEGILAKVG<br>DEYSDVFLAAKNVYDAVELSTILADSDKKSHAKLSSSMIVRFTEHQED<br>LKNFKRFIRENCPDEYDNLFKNEQKDGYAGYIAHAGKVSQLKFYQYV<br>KKIIQDIAGAEYFLEKIAQENFLRKQRTFDNGVIPHQIHLAELQAIIHRQ<br>AAYYPFLKENQKKIEQLVTFRIPYYVGPLSKGDASTFAWLKRQSEEPIR<br>PWNLQETVDLDQSATAFIERMTNFDTYLPSEKVLPKHSLLYEKFMVFN<br>ELTKISYTDDRGIKANFSGKEKEKIFDYLFKTRRKVKKKDIIQFYRNEY<br>NTEIVTLSGLEEDQFNASFSTYQDLLKCGLTRAELDHPDNAEKLEDIIKI<br>LTIFEDRQRIRTQLSTFKGQFSEEVLKKLERKHYTGWGRLSKKLINGIY<br>DKESGKTILDYLIKDDGVSKHYNRNFMQLINDSQLSFKNAIQKAQSSE<br>HEETLSETVNELAGSPAIKKGIYQSLKIVDELVAIMGYAPKRIVVEMAR<br>ENQTTSTGKRRSIQRLKIVEKAMAEIGSNLLKEQPTTNEQLRDTRLFLY<br>YMQNGKDMYTGDELSLHRLSAYDIDHIIPQSFMKDDSLDNLVLVGSTE<br>NRGKSDDVPSKEVVKKMKAYWEKLYAAGLISQRKFQRLTKGEQGGL<br>TLEDKAHFIQRQLVETRQITKNVAGILDQRYNAKSKEKKVQIITLKASL<br>TSQFRSIFGLYKVREVNDYHHGQDAYLNCVVATTLLKVYPNLAPEFV<br>YGEYPKFQAFKENKATAKAIIYTNLLRFFTEDEPRFTKDGEILWSNSYL<br>KTIKKELNYHQMNIVKKVEVQKGGFSKESIKPKGPSNKLIPVKNGLDP<br>QKYGGFDSPVVAYTVLFTHEKGKKPLIKQEILGITIMEKTRFEQNPILFL<br>EEKGFLRPVLMKLPKYTLYEFPEGRRRLLASAKEAQKGNQMVLPEH<br>LLTLLYHAKQCLLPNQSESLAYVEQHQPEFQEILERVVDFAEVHTLAK<br>SKVQQIVKLFEANQTADVKEIAASFIQLMQFNAMGAPSTFKFFQKDIER<br>ARYTSIKEIFDATIIYQSTTGLYETRRKVVD |

TABLE 7-continued

| Mined MAD-series Name | SEQ ID No. | Sequence |
|---|---|---|
| dMAD2011 | 59 | MKKDYVIGLÄIGTNSVGWAVMTEDYQLVKKKMPIYGNTEKKKIKKN FWGVRLFEEGHTAEDRRLKRTARRRISRRRNRLRYLQAFFEEAMTALD ENFFARLQESFLVPEDKKWHRHPIFAKLEDEVAYHETYPTIYHLRKKL ADSSEQADLRLIYLALAHIVKYRGHFLIEGKLSTENISVKEQFQQFMIIY NQTFVNGESRLVSAPLPESVLIEEELTEKASRTKKSEKVLQQFPQEKAN GLFGQFLKLMVGNKADFKKVFGLEEEAKITYASESYEEDLEGILAKVG DEYSDVFLAAKNVYDAVELSTILADSDKKSHAKLSSSMIVRFTEHQED LKNFKRFIRENCPDEYDNLFKNEQKDGYAGYIAHAGKVSQLKFYQYV KKIIQDIAGAEYFLEKIAQENFLRKQRTFDNGVIPHQIHLAELQAIIHRQ AAYYPFLKENQKKIEQLVTFRIPYYVGPLSKGDASTFAWLKRQSEEPIR PWNLQETVDLDQSATAFIERMTNFDTYLPSEKVLPKHSLLYEKFMVFN ELTKISYTDDRGIKANFSGKEKEKIFDYLFKTRRKVKKKDIIQFYRNEY NTEIVTLSGLEEDQFNASFSTYQDLLKCGLTRAELDHPDNAEKLEDIIKI LTIFEDRQRIRTQLSTFKGQFSEEVLKKLERKHYTGWGRLSKKLINGIY DKESGKTILDYLIKDDGVSKHYNRNFMQLINDSQLSFKNAIQKAQSSE HEETLSETVNELAGSPAIKKGIYQSLKIVDELVAIMGYAPKRIVVEMAR ENQTTSTGKRRSIQRLKIVEKAMAEIGSNLLKEQPTTNEQLRDTRLFLY YMQNGKDMYTGDELSLHRLSÄYDIDHIIPQSFMKDDSLDNLVLVGST ENRGKSDDVPSKEVVKKMKAYWEKLYAAGLISQRKFQRLTKGEQGG LTLEDKAHFIQRQLVETRQITKNVAGILDQRYNAKSKEKKVQIITLKAS LTSQFRSIFGLYKVREVNDYHHGQDAYLNCVVATTLLKVYPNLAPEFV YGEYPKFQAFKENKATAKAIIYTNLLRFFTEDEPRFTKDGEILWSNSYL KTIKKELNYHQMNIVKKVEVQKGGFSKESIKPKGPSNKLIPVKNGLDP QKYGGFDSPVVAYTVLFTHEKGKKPLIKQEILGITIMEKTRFEQNPILFL EEKGFLRPRVLMKLPKYTLYEFPEGRRRLLASAKEAQKGNQMVLPEH LLTLLYHAKQCLLPNQSESLAYVEQHQPEFQEILERVVDFAEVHTLAK SKVQQIVKLFEANQTADVKEIAASFIQLMQFNAMGAPSTFKFFQKDIER ARYTSIKEIFDATIIYQSTTGLYETRRKVVD |

Example 6: Screening for Active MAD2001 and MAD2007 Spacers in HEK293T-GFP Cells by Measuring GFP Loss of Function In order to test if MAD2007 and MAD2001 are active in mammalian cells, a library of spacers targeting the GFP locus in HEK293t-GFP cells was designed. For MAD2001, 23 spacers targeting NNRC PAMs were designed in two gRNA scaffolds (g1 and g3). For MAD2007, 43 spacers targeting NNNSR PAMs were designed in 3 gRNA scaffolds (g1, g2 and g3). The gRNAs were cloned into a pComplete plasmid (CMV-MAD200x-U6-gRNA) and transformed into E. coli (NEB5 alpha strain). The resulting colonies were picked into 96-well midwell plates and grown overnight. The E. coli culture was used as a PCR template to amplify a 7 kb fragment that contains CMV promoter driven MAD2007/MAD2001 and U6 driven gRNA. The 150 ng of unpurified PCR reactions were used to transfect 20,000 HEK293T-GFP cells in 96 wells with 1 μL of PolyFect transfection reagent. The cells were then incubated at 37° C. for 96 hours followed by flow cytometry. Using flow cytometry, GFP-cells and GFP+cells in each well were measured. The percentage of GFP-cells in each well was plotted (see FIG. 7). Relative to the negative control, a number of gRNA spacers for MAD2001 and MAD2007 were found to be functional. Overall, 6 out of 23 designed spacers for MAD2001 were functional. Whereas 34/43 spacers designed for MAD2007 were functional. The spacer and PAM sequences identified using this GFP screen are shown in Table 8.

TABLE 8

| Spacer ("hit") name | Spacer Sequence | SEQ ID No. | PAM Sequence | SEQ ID No. |
|---|---|---|---|---|
| MAD2007-g1 | GTAGCGGCTGAAGCACTGCA | 60 | cgccgtaggt | 61 |
| MAD2007-g2 | GGCGTGCAGTGCTTCAGCCGCTA | 62 | ccccgaccac | 63 |
| MAD2007-g3 | GCCGCTACCCCGACCACATGAAG | 64 | cagcacgact | 65 |
| MAD2007-g4 | GGCCAGGGCACGGGCAGTTTGCC | 66 | ggtggtgcag | 67 |
| MAD2007-g5 | GTGGTGCCCATCCTGGTCGAGCT | 68 | ggacggcgac | 69 |
| MAD2007-g8 | GGCATCGCCCTCGCCCTCGCCGG | 70 | acacgctgaa | 71 |
| MAD2007-g9 | GCCCTCGCCGGACACGCTGAACT | 72 | tgtggccgtt | 73 |
| MAD2007-g10 | GGTGGTCACCAAAGTGGGCCAGG | 74 | gcacgggcag | 75 |
| MAD2007-g11 | GTGTCCGGCGAGGGCGAGGGCGA | 76 | tgccacctac | 77 |
| MAD2007-g12 | GTGAGCAAGGGCGAGGAGCTGTT | 78 | caccggggtg | 79 |
| MAD2007-g13 | GTGGTCACCAAAGTGGGCCAGGG | 80 | cacgggcagt | 81 |

TABLE 8-continued

| Spacer ("hit") name | Spacer Sequence | SEQ ID No. | PAM Sequence | SEQ ID No. |
|---|---|---|---|---|
| MAD2007-g14 | GCGAGGGCGAGGGCGATGCCACC | 82 | tacggcaagc | 83 |
| MAD2007-g15 | GTGCTGCTTCATGTGGTCGGGGT | 84 | agcggctgaa | 85 |
| MAD2007-g16 | GCTGAACTTGTGGCCGTTTACGT | 86 | cgccgtccag | 87 |
| MAD2007-g17 | GCTGAAGCACTGCACGCCGTAGG | 88 | tcagggtggt | 89 |
| MAD2007-g18 | GTCACCAAAGTGGGCCAGGGCA | 90 | cgggcagttt | 91 |
| MAD2007-g19 | GTAAACGGCCACAAGTTCAGCGT | 92 | gtccggcgag | 93 |
| MAD2007-g20 | GTGGCATCGCCCTCGCCCTCGCC | 94 | ggacacgctg | 95 |
| MAD2007-g21 | GGGGTAGCGGCTGAAGCACTGCA | 96 | cgccgtaggt | 97 |
| MAD2007-g22 | GGCACGGGCAGTTTGCCGGTGGT | 98 | gcagatgaac | 99 |
| MAD2007-g23 | GGGGTGGTGCCCATCCTGGTCGA | 100 | gctggacggc | 101 |
| MAD2007-g24 | GCGTGCAGTGCTTCAGCCGCTAC | 102 | cccgaccaca | 103 |
| MAD2007-g25 | GTCACCAAAGTGGGCCAGGGCAC | 104 | gggcagtttg | 105 |
| MAD2007-g26 | GACGGCGACGTAAACGGCCACAA | 106 | gttcagcgtg | 107 |
| MAD2007-g27 | GCGTGCAGTGCTTCAGCCGCTA | 108 | ccccgaccac | 109 |
| MAD2007-g28 | GCCACAAGTTCAGCGTGTCCGGC | 110 | gagggcgagg | 111 |
| MAD2007-g29 | GGGTGGTGCCCATCCTGGTCGAG | 112 | ctggacggcg | 113 |
| MAD2007-g30 | GTCAGGGTGGTCACCAAAGTGGG | 114 | ccagggcacg | 115 |
| MAD2007-g31 | GTGCCCATCCTGGTCGAGCTGGA | 116 | cggcgacgta | 117 |
| MAD2007-g32 | GCCGTAGGTGGCATCGCCCTCGC | 118 | cctcgccgga | 119 |
| MAD2007-g33 | GGCGACGTAAACGGCCACAAGTT | 120 | cagcgtgtcc | 121 |
| MAD2007-g34 | GAGCTGGACGGCGACGTAAACGG | 122 | ccacaagttc | 123 |
| MAD2007-g35 | GTGGTGCCCATCCTGGTCGA | 124 | gctggacggc | 125 |
| MAD2007-g36 | GGCCACAAGTTCAGCGTGTCCGG | 126 | cgagggcgag | 127 |
| MAD2001-g1 | GGTGGTCACCAAAGTGGGCCAGG | 128 | gcacgggcag | 129 |
| MAD2001-g2 | GTCCGGCGAGGGCGAGGGCGATG | 130 | ccacctacgg | 131 |
| MAD2001-g4 | GTGCCCATCCTGGTCGAGCTGGA | 132 | cggcgacgta | 133 |
| MAD2001-g5 | GTGTCCGGCGAGGGCGAGGGCGA | 134 | tgccacctac | 135 |
| MAD2001-g6 | GGGTCAGCTTGCCGTAGGTGGCA | 136 | tcgccctcgc | 137 |
| MAD2001-g7 | GCCGCTACCCCGACCACATGAAG | 138 | cagcacgact | 139 |

Additionally, the PAM regions of the 34 MAD2007 spacers that were functional in HEF293T cells were used to generate a sequence logo, which is shown in FIG. 8. The results show that the PAM of MAD2007 in HEK293T cells is NNNSR.

Next, some of the MAD2007 spacer hits identified in the screen were tested using plasmid transfections in HEK293T-GFP cells for validation. The results are shown in FIG. 9. Relative to the no gRNA control, the hits were found to be active. However, there were varying levels of activities depending on the spacer sequence. The activity of MAD2007 is comparable to MAD7 and but lower than SpCas9.

Example 7: Codon Optimization of MAD2007

All the data discussed thus far was generated using E. coli codon optimized MAD2007. MAD2007 was optimized for human cells and two codon optimized versions (hsMAD2007v1 [SEQ ID NO. 140] and hsMAD2007v2 [SEQ ID No. 141]) were designed. The designs were then cloned into pComplete vector which contains CMV driven MAD2007-T2A-dsRed and U6 driven gRNA (g11 with scaffold 1 from above). For each design, 4 separate clones (c1, c2, c3 and c4) were picked and tested in HEK293T-GFP cells for GFP loss of function. The results are shown in FIG. 9. Based on dsRed expression, hsMAD2007v2 showed higher expression relative to EcMAD2007. Furthermore, based on the percentage of GFP-, hsMAD2007v2 showed higher activity relative to EcMAD2007.

Example 8: MAD2007 Homologs

A bioinformatic search for MAD2007-like protein sequences was performed in the public databases and three sequences from *Sharpea azabuensis* were identified that are >98% identical to MAD2007. These sequences are shown in Table 9.

TABLE 9

| MAD2007 homolog | Protein Sequence |
| --- | --- |
| MAD2007 [SEQ ID No. 7] | MENYRQKHRFVLATDLGIGSNGWAIIDLDAHRVEDLGVQIFESG EEGAKKASARASQQRREKRSAHRENRRKKQRKEALIKFLQEIEF PDLVEILNSFKKQKNPNDILSLRVKGLDNKLSPLELFSILIYMSNN RGYKDFYDNDINDNNTDKDEKEMEKAKSTIEKLFASNSYRTVG EMIATDPTFIVDKSGSKKVIKYHNKKGYQYLIPRKLLENEMSLIL HKQEEFYDCLSIDNITIILDKIFFQRNFEDGPGPKNKRDDYKNNS KGNQFYTGFNEMIGLCPFYPNEKKGTKNSLIYDEYYLINTLSQFF FTDSNGVIMSFSKSLLHDLMLYFFDHKGELTNKELSSFLLKHGLE LNSKEKSNKKYRLNYMKQLTDSTIFETEMIASFREEIETSSYRSV NSLSNKIGNCIGQFITPLKRKEELTNILIDTNYPKELASKLADSIKV IKSQSVANISNKYMLEAIHAFESGKKYGDFQAEFNETRELEDHH FMKNNKLIAFQDSDLIRNPVVYRTINQSRKIINAAINKYNIVRINI EVASDVNKSFEQRDNDKKYQNDNYEKNLQLESELTDYINKENL HVNVNSKMMERYKLYLSQNKHCIYTNTPLTMMDVIYSTNVQV DHIIPQSKILDDTLNNKVLVLRDANSIKNNRLPLEAFDEMQINVD TNYTKKDYLTECLHLLKNKTNPISKKKYQYLTLKKLDDETIEGFI SRNINDTRYITRYIANYLKTAFKESDKTKNIDVVTIKGAVTSRFR KRWLTTYDEYGYHPTIYSLEDKGRNLYYYHHAIDAIILANIDKR YITLANAYDTIRLIKIDRNLSKEQKQRDIDTVIKNTVKSMSKYHG FSEDYIRSLMSKNHIPAICKNLSDEVQIRIPLKFNTDYDNLGYRFT DDQYHYKKLYIAFKEAQNALKEKETLEKELIERFNNEAQILNAN IILTYTGFESNNELIDIKKAKKVTDTLKPNLKNYIKAIDILTQEEYT KRCLEYYNDSEFATQLKIPYVNFKINKRFRGKIQGSENAVSLREV LKKTKLNSFEEFESYLKSEDGIKSPYYIKYTKNTLGKESYTIYEA NSYYCAEIYTDSQNKPQLRGIRYVDVRKEDGKLVLLKPLPSTCK HITYLFHNEYIAIYKDSNYKRLKNNGFGAYRSINNVNVNKIIIRLF ANQNLNDNDVVITSSIFIKKYSLDVFGHINGEIKCGDQSLFTIKKR |
| MAD2007-like protein 1 (WP_033162146) [SEQ ID No. 142] | MENYRQKHRFVLATDLGIGSNGWAIIDLDAHRVEDLGVQIFESG EEGAKKASARASQQRRLKRSAHRLNRRKKQRKEALIKFLQEIEF PDLVEILNSFKKQKNPNDILSLRVKGLDNKLSPLELFSILIYMSNN RGYKDFYDNDINDNNTDNDEKEMQKAKSTIEKLFASNSYRTVG EMIATDPTFIVDKSGSKKVIKYHNKKGYQYLIPRKLLENEMSLIL HKQEEFYDCLSIDNITIILDKIFFQRNFEDGPGPKNKRDDYKNNS KGNQFYTGFNEMIGLCPFYPNEKKGTKNSLIYDEYYLINTLSQFF FTDSNGVIMSFSKSLLHDLMLYFFDHKGEITNKELSSFLLKHGLE LNSKEKSNKKYKLNYMKQLTDSTIFETEMIASFREEIETSSYRSV NSLSNKIGNCIGQFITPSKRKEELTNILIDTNYPKELASKLADSIKV IKSQSVANISNKYMLEAIHAFESGKKYGDFQAEFNETRELEDHH FMKNNKLIAIQDSDLIRNPVVYRTINQSRKIINAAINKYNIVRINIE VASDVNKSFEQRDNDKKYQNDNYEKNLQLESELTDYINKENLH VNVNSKMMERYKLYLSQNKHCIYTNTPLTMMDVIYGTNVQVD HIIPQSKILDDTLNNKVLVLRDANSIKNNRLPLEAFDEMQINVDT NYTKKDYLTECLHLLKNKTNPISKKKYQYLTLKKLDDETIEGFIS RNINDTRYITRYIANYLKTAFKESDKTKNIDVVTIKGAVTSRFRK RWLTTYDEYGYHPTIYSLEDKGRNLYYYHHAIDAIILANIDKRYI TLANAYDTIRLIKIDRNLSKEQKQRDIDTVIKNTVKSMSKYHGFS EDYIRSLMSKNHIPAICKNLSDEVQIRIPLKFNTDYDNLGYRFTD DQYHYKKLYIAFKEAQNALKEKEILEKELTERFNNEAQILNANII LTYTGFESNNELIDIKKAKKVIDTLKPDLKNYIKAIDILTQEEYTK RCLEYYNDSEFAEQLKIPYVNFKINKRFRGKIQGSENAVSLREVL KKTKLNSFEEFESYLKSEDGIKSPYYIKYTKNTLGKES YTIYEAN SYYCAEIYTDSQNKPQLRGIRYVDVRKEDGKLVLLKPLPSTCKHI TYLFHNEYIAIYKDSNYKRLKNNGFGAYRSIKNVNVNKIIIRLFA NQNLNDNDVVITSSIFIKKYSLDVFGHINGEIKCGDQSLFTIKKR |
| MAD2007-like protein 2 (WP_074732643) [SEQ ID No. 143] | MENYRQKHRFVLATDLGIGSNGWAIIDLDAHRVEDLGVQIFESG EEGAKKASARASQQRRLKRSAHRLNRRKKQRKESLIKFLQEIEF PDLNNILDSFKKQKNPNDILSLRVKGLDNKLSPLELFSVLIYMSN NRGYKDFYDNDINEDKKDSDEKEMQKAKSTIEKLFASNSYRTV GEMIATDPTFIVDKSGSKKVIKYHNKKGYQYLIPRKLLENEMSLI LHKQEEFYDCLSIDNITIILDKIFFQRNFEDGPGPKNKRDDYKNNS KGNQFYTGFNEMIGLCPFYPNEKKGTKNSLIYDEYYLINTLSQFF FTDSNGVIMSFSKSLLHDLMLYFFDHKGELTNKELSSFLLKHGLE LNSKEKSNKKYRLNYMKQLTDSTIFETEMIASFREEIETSSYRSV NSLSNKIGNCIGQFITPLKRKEELTNILIDTNYPKELASKLADSIKV IKSQSVANISNKYMLEAIHAFESGKKYGDFQAEFNETRELEDHH FMKNNKLIAFQDSDLIRNPVVYRTINQSRKIINAAINKYNIVRINI |

TABLE 9-continued

| MAD2007 homolog | Protein Sequence |
|---|---|
| | EVASDVNKSFEQRDNDKKYQNDNYEKNLQLESELTDYINKENL
HVNVNSKMMERYKLYLSQNKHCIYTNTPLTMMDVIYGTNVQV
DHIIPQSKILDDTLNNKVLVLRDANSIKNNRLPLEAFDEMQINVD
TNYTKKDYLTECLHLLKNKTNPISKKKYQYLTLKKLDDETIEGFI
SRNINDTRYITRYIANYLKTAFKESDKTKNIDVVTIKGAVTSRFR
KRWLTTYDEYGYHPTIYSLEDKGRNLYYYHHAIDAIILANIDKR
YITLANAYDTIRLIKIDRNLSKEQKQRDIDTVIKNTVKSMSKYHG
FSEDYIRSLMSKNHIPAICKNLSDEVQIRIPLKFNTDYDNLGYRFT
DDQYHYKKLYIAFKEAQNALKEKEILEKELTERFNNEAQILNAN
IILTYTGFESNNELIDIKKAKKVIDTLKPDLKNYIKAIDILTQEEYT
KRCLEYYNDSEFAEQLKIPYVNFKINKRFRGKIQGSENAVSLREV
LKKTKLNSFEEFESYLKSEDGIKSPYYIKYTKNTLGKESYTIYEA
NSYYCAEIYTDSQNKPQLRGIRYVDVRKEDGKLVLLKPLPS TCK
HITYLFHNEYIAIYKDSNYKRLKNNGFGAYRSIKNVNVNKIIIRLF
ANQNLNDNDVVITSSIFIKKYSLDVFGHINGEIKCGDQSLFTIKKR |
| MAD2007-like protein 3 (WP_164121414) [SEQ ID No. 144] | MENYRQKHRFVLATDLGIGSNGWAIIDLDAHRVEDLGVQIFESG
EEGAKKASARASQQRRLKRSAHRLNRRKKQRKEALIKFLQEIEF
PDLVEILNSFKKQKNPNDILSLRVKGLDNKLSPLELFSVLIYMSN
NRGYKDFYDNDINEDKKDSDEKEMQKAKSTIEKLFASNSYRTV
GEMIATDPTFIVDKSGSKKVIKYHNKKGYQYLIPRKLLENEMSLI
LHKQEEFYDCLSIDNVTIILDKIFFQRNFEDGPGPKNKRDDYKNN
SKGNQFYTGFNEMIGLCPFYPNEKKGTKNSLIYDEYYLINTLSQF
FPTDSNGVIMSFSKSLLHDLMLYFFDHKGELTYKELSSFLLKHGL
ELNSKEKSNKKYRLNYMKQLTDSTIFETEMIASFREEIETSSYRS
VNSLSNKIGNCIGQFITPLKRKEELTNILIDTNYPKELASKLADSIK
VIKSQSVANISNKYMLEAIHAFESGKKYGDFQAEFNETRELEDH
HFMKNNKLIAFQDSDLIRNPVVYRTINQSRKIINAAINKYNIVRIN
IEVASDVNKSFEQRDNDKKYQNDNYEKNLQLESELTDYINKENL
HVNVNSKMMERYKLYLSQNKHCIYTNTPLTMMDVIYSTNVQV
DHIIPQSKILDDTLNNKVLVLRDANSIKNNRLPLEAFDEMQINVD
TNYTKKDYLTECLHLLKNKTNPISKKKYQYLTLKKLDDETIEGFI
SRNINDTRYITRYIANYLKTAFKESDKTKNIDVVTIKGAVTSRFR
KRWLTTYDEYGYHPTIYSLEDKGRNLYYYHHAIDAIILANIDKR
YITLANAYDTIRLIKIDRNLSKEQKQRDIDTVIKNTVKSMSKYHG
FSEDYIRSLMSKNHIPAICKNLSDEVQIRIPLKFNTDYDNLGYRFT
DDQYHYKKLYIAFKEAQNALKEKETLEKELIERFNNEAQILNAN
IILTYTGFESNNELIDIKKAKKVTDTLKPNLKNYIKAIDILTQEEYT
KRCLEYYNDSEFATQLKIPYVNFKINKRFRGKIQGSENAVSLREV
LKKTKLNSFEEFESYLKSEDGIKSPYYIKYTKNTLGKESYTIYEA
NSYYCAEIYTDSQNKPQLRGIRYVDVRKEDGKLVLLKPLPSTCK
HITYLFHNEYIAIYKDSNYKRLKNNGFGAYRSINNVNVNKIIIRLF
ANQNLNDNDVVITSSIFIKKYSLDVFGHINGEIKCGDQSLFTIKKR |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A nuclease system capable of performing nucleic acid-guided nuclease editing, wherein the nuclease system is selected from a nuclease system comprising SEQ ID NO: 8, SEQ ID NO: 32 and SEQ ID NO: 33; a nuclease system comprising SEQ ID NO: 8, SEQ ID NO: 34 and SEQ ID NO: 35; and a nuclease system comprising SEQ ID NO: 8, SEQ ID NO: 36 and SEQ ID NO: 37.

2. The nuclease system of claim 1 comprising SEQ ID NO: 8, SEQ ID NO: 32 and SEQ ID NO: 33.

3. The nuclease system of claim 1 comprising SEQ ID NO: 8, SEQ ID NO: 34 and SEQ ID NO: 35.

4. The nuclease system of claim 1 comprising SEQ ID NO: 8, SEQ ID NO: 36 and SEQ ID NO: 37.

5. A nickase having an amino acid sequence selected from SEQ ID NO: 51 and SEQ ID NO: 52.

6. A dead nuclease having the amino acid sequence of SEQ ID NO: 53.

* * * * *